US011787839B2

(12) United States Patent
Pan

(10) Patent No.: US 11,787,839 B2
(45) Date of Patent: Oct. 17, 2023

(54) TARGETING α2δ-1-BOUND GLUTAMATE RECEPTORS FOR TREATING DISEASES AND DISORDERS

(71) Applicant: Board of Regents, The University of Texas System, Austin, TX (US)

(72) Inventor: Hui-lin Pan, Houston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 527 days.

(21) Appl. No.: 16/639,076

(22) PCT Filed: Aug. 14, 2018

(86) PCT No.: PCT/US2018/046770
§ 371 (c)(1),
(2) Date: Feb. 13, 2020

(87) PCT Pub. No.: WO2019/036511
PCT Pub. Date: Feb. 21, 2019

(65) Prior Publication Data
US 2020/0181201 A1 Jun. 11, 2020

Related U.S. Application Data

(60) Provisional application No. 62/545,342, filed on Aug. 14, 2017.

(51) Int. Cl.
| | |
|---|---|
| *A61K 38/16* | (2006.01) |
| *C07K 14/705* | (2006.01) |
| *C07K 14/00* | (2006.01) |
| *A61P 23/00* | (2006.01) |
| *A61K 9/00* | (2006.01) |
| *A61K 31/485* | (2006.01) |
| *A61K 45/06* | (2006.01) |
| *C07K 7/06* | (2006.01) |
| *C07K 7/08* | (2006.01) |
| *C07K 14/005* | (2006.01) |
| *C12N 7/00* | (2006.01) |
| *C12N 15/113* | (2010.01) |
| *G01N 33/50* | (2006.01) |
| *A61K 38/00* | (2006.01) |

(52) U.S. Cl.
CPC ............ *C07K 14/00* (2013.01); *A61K 9/0019* (2013.01); *A61K 31/485* (2013.01); *A61K 45/06* (2013.01); *A61P 23/00* (2018.01); *C07K 7/06* (2013.01); *C07K 7/08* (2013.01); *C07K 14/005* (2013.01); *C12N 7/00* (2013.01); *C12N 15/1138* (2013.01); *G01N 33/5041* (2013.01); *A61K 38/00* (2013.01); *C07K 2319/10* (2013.01); *C12N 2740/15043* (2013.01)

(58) Field of Classification Search
None
See application file for complete search history.

(56) References Cited

U.S. PATENT DOCUMENTS

| | | |
|---|---|---|
| 2005/0059804 A1 | 3/2005 | Brown et al. |
| 2005/0208044 A1 | 9/2005 | Barclay et al. |
| 2011/0104181 A1 | 5/2011 | Eroglu et al. |
| 2015/0231203 A1 | 8/2015 | Garcia-Caballero et al. |

FOREIGN PATENT DOCUMENTS

| | | |
|---|---|---|
| WO | WO 2001/020336 | 3/2001 |
| WO | WO 2016/154559 | 9/2016 |

OTHER PUBLICATIONS

Bauer et al., "A new look at calcium channel α2δ subunits," *Current Opinion in Neurobiology*, 20(5):563-571, 2010.
Brawek et al., "Differential modulation of K(+)-evoked (3)H-neurotransmitter release from human neocortex by gabapentin and pregabalin," *Naunyn-Schmiedeberg's Arch Pharmacol.*, 376(5):301-307, 2008.
Hara et al., "Inhibitory effect of gabapentin on N-methyl-D-aspartate receptors expressed in Xenopus oocytes," *Acta Anaesthesiol Scand.*, 51(1):122-128, 2007.
Meloni et al., "Neuroprotective peptides fused to arginine-rich cell penetrating peptides: neuroprotective mechanism likely mediated by peptide endocytic properties," *Pharmacology and Therapeutics*, 153:36-54, 2015.
Partial Supplementary European Search Report issued in European Application No. 18845742.8, dated Mar. 24, 2021.
Yamamoto et al., "Oxaliplatin administration increases expression of the voltage-dependent calcium channel α2δ-1 subunit in the rat spinal cord," *Journal of Pharmacological Sciences*, 130(2): 117-122, 2016.
Cole et al., "Differential distribution of voltage-gated calcium channel alpha-2 delta (alpha2delta) subunit mRNA-containing cells in the rat central nervous system and the dorsal root ganglia," *J Comp Neurol*, 491:246-269, 2005.
Dolphin, "Calcium channel auxiliary α2δ and β subunits: trafficking and one step beyond," *Nat Rev Neurosci*, 13:542-555, 2012.
Dolphin, "Calcium channel α2δ subunits in epilepsy and as targets for antiepileptic drugs," *Jasper's Basic Mechanisms of the Epilepsies*, Fourth Edition, 2012.
Dolphin, "The α2δ subunits of voltage-gated calcium channels," *Biochimica et Biophysica Acta*, 1828:1541-1549, 2013.
Eroglu et al., "Gabapentin receptor α2δ-1 is a neuronal thrombospondin receptor responsible for excitatory CNS synaptogenesis," *Cell*, 139(2):380-392, 2009.
Field et al., "Identification of the alpha2-delta-1 subunit of voltage-dependent calcium channels as a molecular target for pain mediating the analgesic actions of pregabalin," *Proc Natl Acad Sci U S A*, 103(46):17537-17542, 2006.

(Continued)

*Primary Examiner* — Christine J Saoud
*Assistant Examiner* — Jon M Lockard
(74) *Attorney, Agent, or Firm* — Parker Highlander PLLC

(57) ABSTRACT

The present disclosure provides α2δ-1 C-terminal domain mimetics for the treatment of pain, epilepsy or other disorders in a subject. Further provided is an α2δ-1 C-terminal domain peptide which blocks binding of α2δ-1 to the glutamate receptors NMDAR and AMPAR.

17 Claims, 52 Drawing Sheets

Specification includes a Sequence Listing.

(56) References Cited

OTHER PUBLICATIONS

Fuller-Bicer et al., "Targeted disruption of the voltage-dependent calcium channel alpha2/delta-1 -subunit," *Am J Physiol Heart Circ Physiol*, 297:H117-H124, 2009.

Kordasiewicz et al., "C-termini of P/Q-type $Ca^{2+}$ channel α1A subunits translocate to nuclei and promote polyglutamine-mediated toxicity," *Human Molecular Genetics*, 15(10): 1587-1599, 2006.

Lana et al., "Thrombospondin-4 reduces binding affinity of [(3)H]-gabapentin to calcium-channel α2δ-1-subunit but does not interact with α2δ-1 on the cell-surface when coexpressed," *Sci Rep*, 6:24531, 2016.

Li et al., "Chloride Homeostasis Critically Regulates Synaptic NMDA Receptor Activity in Neuropathic Pain," *Cell Rep*, 15:1376-1383, 2016.

Patel et al., "α2δ-1 gene deletion affects somatosensory neuron function and delays mechanical hypersensitivity in response to peripheral nerve damage," *J Neurosci*, 33:16412-16426, 2013.

PCT International Search Report and Written Opinion issued in International Application No. PCT/US2018/046770, dated Dec. 7, 2018.

Turner et al., "Cell-penetrating peptide conjugates of peptide nucleic acids (PNA) as inhibitors of HIV-1 Tat-dependent trans-activation in cells," *Nucleic Acids Research*, 33(21):6837-6849, 2005.

Wu et al., "Role of Tat-mediated PDZ peptide delivery in pain therapy," *Journal of Biomaterials and Nanobiotechnology*, 2:596-600, 2011.

Yu et al., "NMDA receptor activation mediates neuropathic pain states induced by calcium channel α2δ1 subunit," *Korean J Pain*, 22(3):210-215, 2009.

Zhou et al., "N-methyl-D-aspartate receptor- and calpain-mediated proteolytic cleavage of K+-Cl-cotransporter-2 impairs spinal chloride homeostasis in neuropathic pain," *J Biol Chem*, 287:33853-33864, 2012.

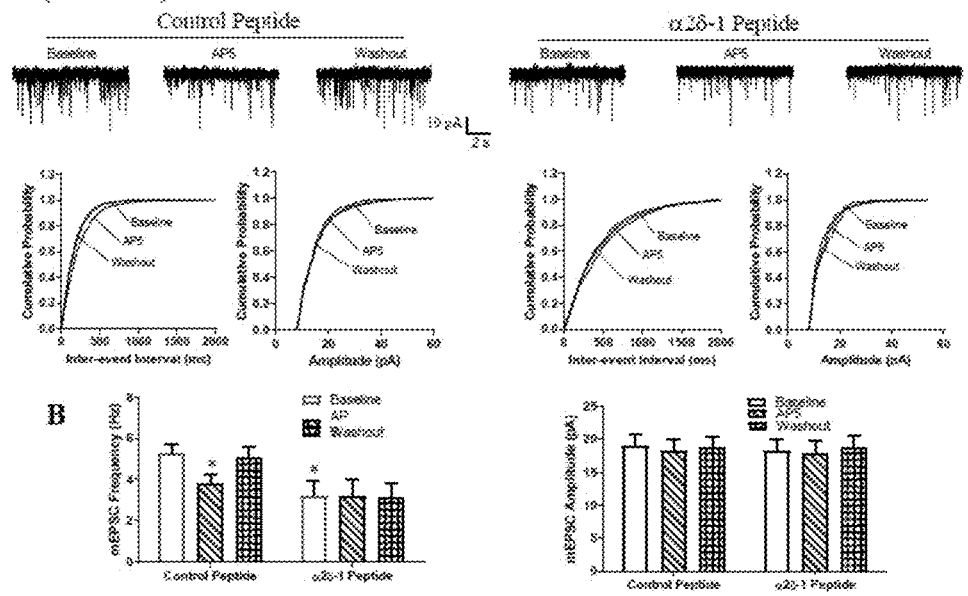
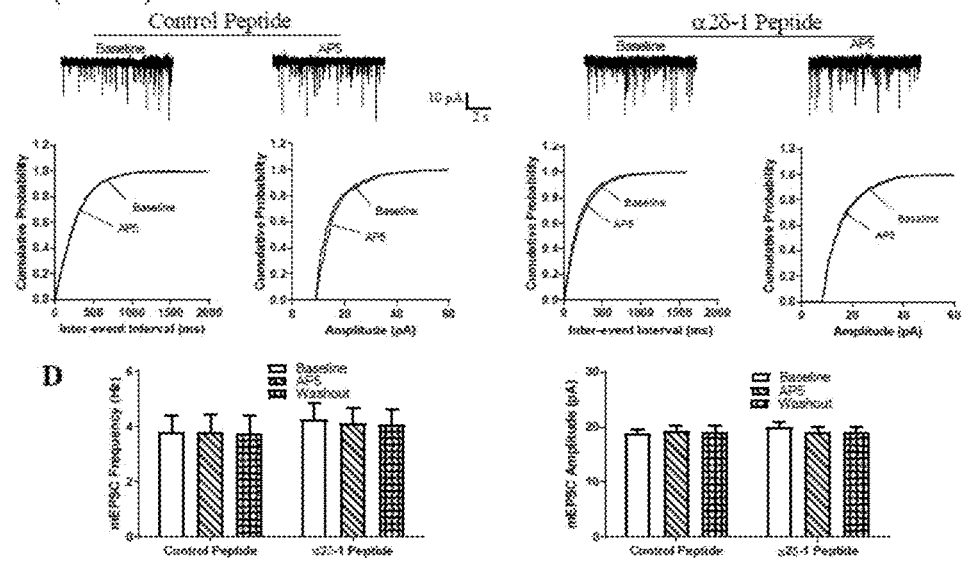
FIGS. 34A-34D

TARGETING α2δ-1-BOUND GLUTAMATE RECEPTORS FOR TREATING DISEASES AND DISORDERS

The present application is a national phase application under 35 U.S.C. § 371 of International Application No. PCT/US2018/046770, filed Aug. 14, 2018, which claims the priority benefit of U.S. Provisional Application Ser. No. 62/545,342, filed Aug. 14, 2017, the entire contents of each of which are hereby incorporated by reference.

This invention was made with government support under grant numbers R01 NS073935 and R01 GM120844 awarded by the National Institutes of Health. The government has certain rights in the invention.

INCORPORATION OF SEQUENCE LISTING

The sequence listing that is contained in the file named "UTSCP1300US.txt", which is 17,499 bytes (as measured in Microsoft Windows) and was created on Jan. 6, 2020, is filed herewith by electronic submission and is incorporated by reference herein.

BACKGROUND

1. Field

The present invention relates generally to the fields of molecular biology and medicine. More particularly, it concerns methods and compositions for uncoupling α2δ-1-NMDA receptor binding for the treatment of pain and epilepsy.

2. Description of Related Art

Chronic neuropathic pain is a major medical problem that remains difficult to treat. α2δ-1 is expressed in the dorsal root ganglion (DRG) and spinal superficial dorsal horn neurons (Cole et al., 2005), and nerve injury increases α2δ-1 expression levels in both locations (Luo et al., 2001). Although α2δ-1 plays a key role in neuropathic pain (Patel et al., 2013; Li et al., 2004), it is unclear exactly how α2δ-1 causes neuropathic pain. α2δ-1 is commonly known to be a subunit of voltage-activated calcium ($Ca^{2+}$) channels (VACCs) (Dolphin et al., 2012), but quantitative proteomic analysis indicates that α2δ-1 is not a core subunit of VACCs (Muller et al., 2010). α2δ-1 is also the binding site of gabapentinoids, including gabapentin and pregabalin (Gee et al., 1996; Fuller-bicer et al., 2009; Marais et al., 2009), which are widely used to treat neuropathic pain and epilepsy (Dworkin et al., 2010; Rowbotham et al., 1998; Anhut et al., 1994). However, gabapentinoids have little effect on VACC activity (Rock et al., 1993; Schumachet et al., 1998) or VACC-mediated neurotransmitter release at presynaptic terminals (Hoppa et al., 2012; Brown and Randall, 2005). Alternatively, gabapentin may reduce α2δ-1 interaction with thrombospondin, an astrocyte-secreted protein, and inhibit new synapse formation (but not already-formed synapses) (Eroglu et al., 2016). Nevertheless, this action cannot fully account for the relatively rapid onset of gabapentinoid effects on pain hypersensitivity. A recent study suggests that the association between α2δ-1 and thrombospondin is rather weak and that there is no α2δ-1-thrombospondin interaction on the cell surface (Lana et al., 2016). Thus, the molecular mechanisms responsible for the therapeutic effects of gabapentinoids remain a long-standing puzzle. Because α2δ-1 is a single-pass transmembrane protein and does not affect neuronal function independently (Wiser et al., 1996), it is critically important to identify the relevant interacting proteins that involve it in neuropathic pain and gabapentinoid actions in order to develop methods for treating neuropathic pain.

SUMMARY

In a first embodiment, the present disclosure provides isolated peptides comprising an amino acid sequence with at least 90% (e.g., 91, 92, 93, 94, 95, 96, 97, 98, 99 or 100%) sequence identity with SEQ ID NO:1, wherein said peptides are fused to a cell-penetrating peptide. In some aspects, the peptide is further defined as a linear peptide or a cyclic peptide. In certain aspects, the cell penetrating peptide is TAT. In particular aspects, the cell-penetrating peptide comprises the sequence of SEQ ID NO:2.

In some aspects, the peptide comprises at least 15, 20, 25, 30, 35, 40, 45 or 50 residues. In certain aspects, the peptide contains no more than 15, 16, 17, 18, 19, 20, 25, 30, 35, 40, 45 or 50 residues.

In some aspects, the peptide comprises the sequence of SEQ ID NO:1. In some aspects, the peptide comprises the sequence of SEQ ID NO:4. In certain aspects, the peptide consists of the sequence of SEQ ID NO:4.

In particular aspects, peptide acts as an α2δ-1 C-terminal domain mimetic and blocks binding of α2δ-1 to a glutamate receptor. In some aspects, the glutamate receptor is NMDA receptor or AMPA receptor.

Further provided herein are isolated nucleic acids encoding the peptides of the embodiments (e.g., α2δ-1 C-terminal domain mimetic). Also provided herein are vectors comprising a contiguous sequence consisting of the nucleic acid of the embodiments. In some aspects, the vector is a viral vector, such as a lentiviral vector.

In another embodiment, there are provided pharmaceutical compositions comprising (a) a peptide that acts as an α2δ-1 C-terminal domain mimetic and blocks binding of α2δ-1 to a glutamate receptor and (b) a pharmaceutically acceptable carrier, buffer or diluent. In particular aspects, the peptide is a peptide according to the embodiments (e.g., α2δ-1 C-terminal domain mimetic).

A further embodiment provides a method for treating pain and/or epileptic seizures in a subject comprising administering an effective amount of a α2δ-1 C-terminal domain inhibitor (e.g., an α2δ-1 C-terminal domain mimetic) to the subject, wherein the α2δ-1 C-terminal domain inhibitor blocks binding of α2δ-1 to a glutamate receptor. In some aspects, the α2δ-1 C-terminal domain mimetic is a peptide according to the embodiments (e.g, α2δ-1 C-terminal domain mimetic). In some aspects, the α2δ-1 C-terminal domain inhibitor is RNA, such as shRNA targeting the α2δ-1 C-terminal domain. In some aspects, the α2δ-1 C-terminal domain inhibitor comprises guide RNA. In some aspects, the guide RNA is administered in combination with a Cas enzyme. In certain aspects, the glutamate receptor is NMDA receptor or AMPA receptor. In particular aspects, the subject is a human.

In some aspects, the pain is neuropathic pain. In specific aspects, the neuropathic pain is chronic. In some aspects, the chronic neuropathic pain is chemotherapy-induced neuropathic pain.

In certain aspects, administering comprises intravenous, intrathecal, intra-arterial, intra-tumoral, subcutaneous, topical or intraperitoneal administration. In particular aspects, administering comprises local, regional, systemic, or continual administration.

In additional aspects, the method further comprises administering to said subject a second therapy. In some aspects, the second therapy is an anticonvulsant. In particular aspects, the anticonvulsant is a barbiturate, benzodiazepine, bromide, carbamate, or carboxamide. In some aspects, the second therapy is administered prior to the α2δ-1 C-terminal domain mimetic. In other aspects, second therapy is administered after the α2δ-1 C-terminal domain mimetic. In particular aspects, second therapy is administered at the same time as the α2δ-1 C-terminal domain mimetic.

In some aspects, the α2δ-1 C-terminal domain mimetic administered daily. In particular aspects, the α2δ-1 C-terminal domain mimetic is administered daily for 7 days, 2 weeks, 3 weeks, 4 weeks, one month, 6 weeks, 8 weeks, two months, 12 weeks, or 3 months.

In particular aspects, the α2δ-1 C-terminal domain mimetic decreases protein levels of α2δ-1 in the subject. In some aspects, the α2δ-1 C-terminal domain mimetic decreases protein levels of NMDAR subunits GluN1, GluN2A, and/or GluN2B in the subject.

A further embodiment provides a method for treating and/or preventing brain injury in a subject comprising administering an effective amount of a α2δ-1 C-terminal domain inhibitor (e.g., an α2δ-1 C-terminal domain mimetic) to the subject, wherein the α2δ-1 C-terminal domain inhibitor blocks binding of α2δ-1 to a glutamate receptor. In some aspects, the α2δ-1 C-terminal domain mimetic is a peptide according to the embodiments (e.g, α2δ-1 C-terminal domain mimetic). In some aspects, the α2δ-1 C-terminal domain inhibitor is RNA, such as shRNA targeting the α2δ-1 C-terminal domain. In some aspects, the α2δ-1 C-terminal domain inhibitor comprises guide RNA. In some aspects, the guide RNA is administered in combination with a Cas enzyme. In certain aspects, the glutamate receptor is NMDA receptor or AMPA receptor. In particular aspects, the subject is a human.

In some aspects, the focal cerebral ischemia and/or reperfusion is associated with ischemic stroke. In certain aspects, the α2δ-1 C-terminal domain inhibitor results in a neuroprotective effect.

In certain aspects, administering comprises intravenous, intrathecal, intra-arterial, intra-tumoral, subcutaneous, topical or intraperitoneal administration. In particular aspects, administering comprises local, regional, systemic, or continual administration.

In additional aspects, the method further comprises administering to said subject a second therapy. In some aspects, the second therapy is an anticonvulsant. In particular aspects, the anticonvulsant is a barbiturate, benzodiazepine, bromide, carbamate, or carboxamide. In some aspects, the second therapy is administered prior to the α2δ-1 C-terminal domain mimetic. In other aspects, second therapy is administered after the α2δ-1 C-terminal domain mimetic. In particular aspects, second therapy is administered at the same time as the α2δ-1 C-terminal domain mimetic.

In some aspects, the α2δ-1 C-terminal domain mimetic administered daily. In particular aspects, the α2δ-1 C-terminal domain mimetic is administered daily for 7 days, 2 weeks, 3 weeks, 4 weeks, one month, 6 weeks, 8 weeks, two months, 12 weeks, or 3 months.

In particular aspects, the α2δ-1 C-terminal domain mimetic decreases protein levels of α2δ-1 in the subject. In some aspects, the α2δ-1 C-terminal domain mimetic decreases protein levels of NMDAR subunits GluN1, GluN2A, and/or GluN2B in the subject.

A further embodiment provides a method for treating neurogenic hypertension in a subject comprising administering an effective amount of a α2δ-1 C-terminal domain inhibitor (e.g., an α2δ-1 C-terminal domain mimetic) to the subject, wherein the α2δ-1 C-terminal domain inhibitor blocks binding of α2δ-1 to a glutamate receptor. In some aspects, the α2δ-1 C-terminal domain mimetic is a peptide according to the embodiments (e.g, α2δ-1 C-terminal domain mimetic). In some aspects, the α2δ-1 C-terminal domain inhibitor is RNA, such as shRNA targeting the α2δ-1 C-terminal domain. In some aspects, the α2δ-1 C-terminal domain inhibitor comprises guide RNA. In some aspects, the guide RNA is administered in combination with a Cas enzyme. In certain aspects, the glutamate receptor is NMDA receptor or AMPA receptor. In particular aspects, the subject is a human. In some aspects, the α2δ-1 C-terminal domain inhibitor results in inhibition of angiotensin II.

In certain aspects, administering comprises intravenous, intrathecal, intra-arterial, intra-tumoral, subcutaneous, topical or intraperitoneal administration. In particular aspects, administering comprises local, regional, systemic, or continual administration.

In additional aspects, the method further comprises administering to said subject a second therapy. In some aspects, the second therapy is administered prior to the α2δ-1 C-terminal domain mimetic. In other aspects, second therapy is administered after the α2δ-1 C-terminal domain mimetic. In particular aspects, second therapy is administered at the same time as the α2δ-1 C-terminal domain mimetic.

In some aspects, the α2δ-1 C-terminal domain mimetic administered daily. In particular aspects, the α2δ-1 C-terminal domain mimetic is administered daily for 7 days, 2 weeks, 3 weeks, 4 weeks, one month, 6 weeks, 8 weeks, two months, 12 weeks, or 3 months.

In particular aspects, the α2δ-1 C-terminal domain mimetic decreases protein levels of α2δ-1 in the subject. In some aspects, the α2δ-1 C-terminal domain mimetic decreases protein levels of NMDAR subunits GluN1, GluN2A, and/or GluN2B in the subject.

A further embodiment provides a method for treating opioid-induced analgesic tolerance and/or hyperalgesia in a subject comprising administering an effective amount of a α2δ-1 C-terminal domain inhibitor (e.g., an α2δ-1 C-terminal domain mimetic) to the subject, wherein the α2δ-1 C-terminal domain inhibitor blocks binding of α2δ-1 to a glutamate receptor. In some aspects, the α2δ-1 C-terminal domain mimetic is a peptide according to the embodiments (e.g, α2δ-1 C-terminal domain mimetic). In some aspects, the α2δ-1 C-terminal domain inhibitor is RNA, such as shRNA targeting the α2δ-1 C-terminal domain. In some aspects, the α2δ-1 C-terminal domain inhibitor comprises guide RNA. In some aspects, the guide RNA is administered in combination with a Cas enzyme. In certain aspects, the glutamate receptor is NMDA receptor or AMPA receptor. In particular aspects, the subject is a human. In some aspects, the opioid is morphine.

In certain aspects, administering comprises intravenous, intrathecal, intra-arterial, intra-tumoral, subcutaneous, topical or intraperitoneal administration. In particular aspects, administering comprises local, regional, systemic, or continual administration.

In additional aspects, the method further comprises administering to said subject a second therapy. In some aspects, the second therapy is an anticonvulsant. In some aspects, the second therapy is administered prior to the α2δ-1 C-terminal domain mimetic. In other aspects, second therapy is administered after the α2δ-1 C-terminal domain mimetic. In particular aspects, second therapy is administered at the same time as the α2δ-1 C-terminal domain mimetic.

In some aspects, the α2δ-1 C-terminal domain mimetic is administered daily. In particular aspects, the α2δ-1 C-terminal domain mimetic is administered daily for 7 days, 2 weeks, 3 weeks, 4 weeks, one month, 6 weeks, 8 weeks, two months, 12 weeks, or 3 months.

In particular aspects, the α2δ-1 C-terminal domain mimetic decreases protein levels of α2δ-1 in the subject. In some aspects, the α2δ-1 C-terminal domain mimetic decreases protein levels of NMDAR subunits GluN1, GluN2A, and/or GluN2B in the subject.

In another embodiment, there is provided an in vitro method for identifying a α2δ-1 C-terminal domain mimetic comprising contacting a cell with calcium indicator dye, wherein the cell expresses a glutamate receptor and α2δ-1; culturing the cell in the presence of a glutamate receptor agonist and a test compound for a sufficient period of time; and measuring calcium signaling in the cell, wherein a decrease in calcium signaling as compared to a control identifies a α2δ-1 C-terminal domain mimetic.

In some aspects, the calcium indicator dye is Fluo-3, Fluo-4, calcium green, Indo-1, or Fura2. In certain aspects, the calcium indicator dye is further defined as a ratiometric dye.

In certain aspects, the test compound is selected from the group consisting of a small molecule, an inorganic compound, an organic compound, a biomolecule, a chemical, a protein, a peptide, or a nucleic acid.

In some aspects, the glutamate receptor agonist is further defined as an AMPA receptor agonist or a NMDA receptor agonist. In certain aspects, the AMPA receptor agonist is 5-fluorowilardine, domoic acid, quisqualic acid, or (2R, 6R)-hydroxynorketamine. In some aspects, the NMDA receptor agonist is aminocyclopropanecarboxylic acid, D-cycloserine, cis-2,3-Piperidinedicarboxylic acid, aspartic acid, glutamic acid, quinolinate, homocysteic acid, serine, alanine, nebostinel, or curcumin.

In some aspects, the cell has endogenous expression of glutamate receptor and α2δ-1, such as a neuron. In other aspects, the cell is engineered to express glutamate receptor and α2δ-1. In some aspects, the glutamate receptor is AMPA receptor or NMDA receptor. In certain aspects, AMPA receptor comprises the GluA1 subunit and the GluA2 subunit. In some aspects, measuring calcium signaling is further defined as quantifying calcium influx and/or intracellular calcium response. In particular aspects, measuring calcium signaling comprises using a fluorescent imaging plate reader (FLIPR).

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figures 1A, 1B, 1C, 1D, 1E, 1F:
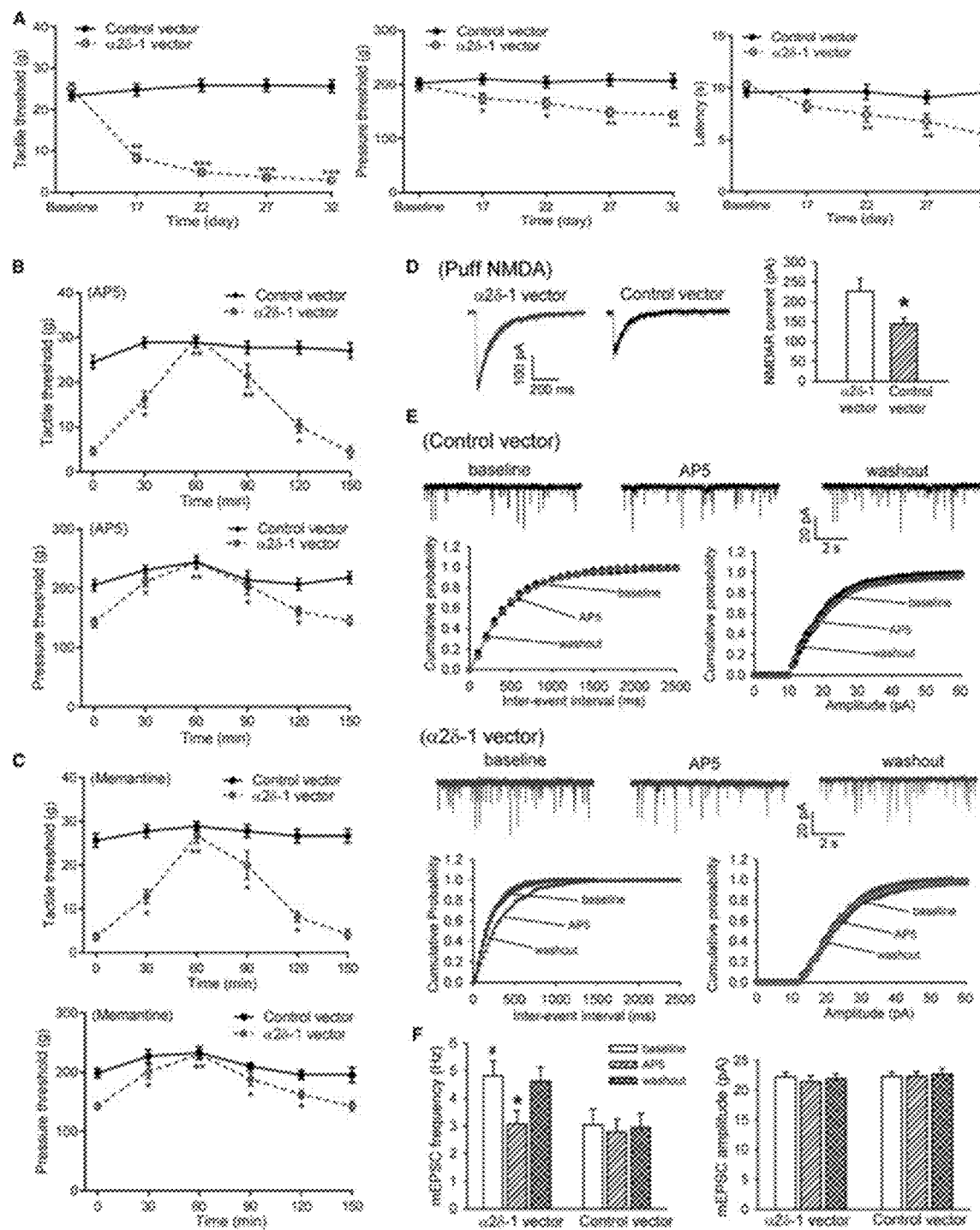
FIG. 1A-1F: α2δ-1 Overexpression Induces Pain Hypersensitivity and Increases Pre- and Postsynaptic NMDAR Activity of Spinal Dorsal Horn Neurons. (A) Time course of changes in the tactile and pressure withdrawal thresholds and heat withdrawal latency after a single intrathecal injection of the Cacna2d1 vector or control vector (n=7 rats in each group). Data are expressed as means±SEM. *$p<0.05$; $p<0.01$; *$p<0.001$ (versus respective baseline), one-way ANOVA followed by Dunnett's post hoc test. (B and C) Effects of a single intrathecal injection of 5 mg AP5 (B) or intraperitoneal injection of 10 mg/kg memantine (C) on the tactile and pressure withdrawal thresholds in rats treated with the Cacna2d1 vector or control vector (n=8 rats in each group). Data are expressed as means±SEM. *$p<0.05$; **$p<0.01$ (versus baseline before drug injection, time 0), one-way ANOVA followed by Dunnett's post hoc test. (D) Original traces and mean changes of NMDAR currents elicited by puff application of 100 mM NMDA to spinal dorsal horn neurons in rats 5 weeks after treatment with the Cacna2d1 vector or control vector (n=12 neurons in each group). Data are expressed as means±SEM. *$p<0.05$ (versus control vector-treated rats), two-tailed Student's t test. (E and F) Representative traces and cumulative plots (E) and mean changes (F) of miniature excitatory postsynaptic currents (mEPSCs) of spinal dorsal horn neurons before (baseline), with (AP5), and after (washout) bath application of 50 mM AP5. Slice recordings were performed using rat spinal cords 5 weeks after treatment with the control vector (n=10 neurons) or Cacna2d1 vector (n=11 neurons). Data are expressed as means±SEM. *$p<0.05$ (versus baseline). #$p<0.05$, compared with the baseline value in the control vector-treated group, one-way ANOVA followed by Tukey's post hoc test.

FIGS. 23A-23D: Gabapentin, α2δ-1Tat peptide, or α2δ-1 genetic deletion reduces MCAO-induced calpain activity in brain tissues. (A and B) Original gel images (A) and quantification (B) of spectrin BD levels in the cerebral cortex, hippocampus (Hippo), and striatum from sham control mice, MCAO mice treated with vehicle (Veh) or gabapentin (GBP), and Cacna2d1 knockout (KO, α2δ-1$_{-/-}$) MCAO mice (n=8 mice per group). (C and D) Original blotting images (C, two pairs of samples) and quantification (D) of spectrin BD levels in the cerebral cortex, hippocampus, and striatum from MCAO mice treated with α2δ-1Tat peptide or control peptide (n=8 mice per group). Data are shown as means±SEM. *p<0.05 compared with the sham group. #p<0.05 compared with MCAO+vehicle group or control peptide group in the same brain region (repeated measures ANOVA for panel B; paired Student's t-test for panel D).

FIGS. 24A-24D: Gabapentin, α2δ-1Tat peptide, or α2δ-1 ablation suppresses MCAO-induced apoptotic signaling in brain tissues. (A and B) Representative blotting images (A) and quantification (B) of cleaved caspase-3 protein levels in the cerebral cortex, hippocampus (Hippo), and striatum from WT sham control mice, WT MCAO mice treated with vehicle (Veh) or gabapentin (GBP), and Cacna2d1 knockout (KO, α2δ-1$_{-/-}$) MCAO mice (n=8 mice per group). (C and D) Original gel images (C, two pairs of samples) and quantification (D) of cleaved caspase-3 protein levels in the cerebral cortex, hippocampus, and striatum from MCAO mice treated with α2δ-1Tat peptide or control peptide (n=8 mice per group). Data are shown as means±SEM. *p<0.05 compared with the sham group. #p<0.05 compared with MCAO+vehicle group or control peptide group in the same brain region (repeated measures ANOVA for panel B; paired Student's t-test for panel D).

FIGS. 25A-25E: α2δ-1 physically interacts with NMDARs in the hypothalamus, and Ang II increases the synaptic expression level of α2δ-1-NMDAR complexes in the hypothalamus. (A) Co-immunoprecipitation analysis shows the protein-protein interaction between α2δ-1 and GluN1 in the membrane extracts of the hypothalamic tissues from rats (for each sample, tissues were pooled from 3 rats) and humans (2 separate subjects). Proteins were immunoprecipitated first with an anti-GluN1 or IgG. Western immunoblotting was performed by using an anti-α2δ-1 antibody. B and C, Representative images (B) and quantification data (C) show the effect of Ang II (2 μmol/L) on the protein level of GluN1 and α2δ-1 in the hypothalamic synaptosomes (n=6 independent experiments, samples pooled from 2 rats in each group). Data are presented as means±SEM. *P<0.05, **P<0.01 compared with the vehicle group. D and E, Representative images (D) and quantification data (E) show the protein levels of GluN1 and α2δ-1 in hypothalamic synaptosomes treated with Ang II (2 μmol/L) plus α2δ-1Tat peptide (1 μmol/L) or Ang II plus control peptide (n=7 independent experiments, each tissue sample was pooled from 2 rats). The protein levels of GluN1 and α2δ-1 were normalized to PSD-95 on the same gel (an internal control). The PSD-95 level was calculated by considering the relative density of PSD-95 protein in the control peptide group as 1. Data are presented as means±SEM. *P<0.05, ***P<0.001 compared with the control peptide plus Ang II group.

FIGS. 26A-26H: Ang II increases pre- and postsynaptic NMDAR activity via AT1 receptors in spinally projecting PVN neurons. (A) Identification of a retrogradely labeled spinally projecting PVN neuron. (a) A FluoSphere-labeled PVN neuron in the slice viewed with fluorescence illumination. (b) Photomicrograph of the same neuron shown in (a) with an attached recording electrode in the slice viewed with differential interference contrast optics. (B and C) Original traces and mean changes show NMDAR currents elicited by the puff application of 100 μmol/L NMDA to labeled PVN neurons in brain slices pre-incubated with vehicle (n=8 neurons), Ang II (2 μmol/L, n=11 neurons), or losartan (Los, 2 μmol/L) plus Ang II (n=8 neurons). (D-F) Representative current traces (left) and cumulative plots (right) of the mEPSCs of three separate labeled PVN neurons before (baseline), with (AP5), and after (washout) bath application of 50 μmol/L AP5 in brain slices pretreated with vehicle, Ang II, or losartan plus Ang II. (G and H) Mean changes show the frequency and amplitude of mEPSCs and the AP5 effect in labeled PVN neurons pretreated with vehicle (n=8 neurons), 2 μmol/L Ang II (n=8 neurons), or Ang II plus 2 μmol/L losartan (Los, n=7 neurons). Data are presented as means±SEM. **P<0.01 compared with the baseline value of the vehicle group. #P<0.05, ##P<0.01 compared with the baseline of the Ang II group.

FIGS. 27A-27G: Pregabalin blocks the potentiating effect of Ang II on pre- and postsynaptic NMDAR activity in spinally projecting PVN neurons. (A and B) Original recording traces and mean changes of NMDAR currents elicited by the puff application of 100 μmol/L NMDA to labeled PVN neurons in brain slices treated with vehicle plus 2 μmol/L Ang II (n=10 neurons) or 20 μmol/L pregabalin plus Ang II (n=7 neurons). Labeled neurons without Ang II treatment were used as the control (n=8 neurons). (C-E) Representative traces and cumulative plots show the mEPSCs of labeled PVN neurons before (baseline), with (AP5), and after (washout) bath application of 50 μmol/L AP5 in brain slices treated with vehicle plus Ang II or pregabalin plus Ang II. (F and G) Mean changes show the frequency and amplitude of mEPSCs in labeled PVN neurons treated with vehicle plus 2 μmol/L Ang II (n=9 neurons) or 20 μmol/L pregabalin plus Ang II (n=9 neurons). Labeled neurons without Ang II treatment were used as the control (n=7 neurons). Data are presented as means±SEM. *P<0.05 compared with the baseline of the vehicle group. #P<0.05, ##P<0.01 compared with the baseline of the Ang II group.

FIGS. 28A-28F: α2δ-1Tat peptide abrogates the potentiating effect of Ang II on pre- and postsynaptic NMDAR activity in spinally projecting PVN neurons. (A and B) Original recording traces and mean changes of NMDAR currents elicited by the puff application of 100 μmol/L NMDA to labeled PVN neurons in brain slices treated with 1 μmol/L control peptide plus 2 μmol/L Ang II (n=13 neurons) or 1 μmol/L α2δ-1Tat peptide plus 2 μmol/L Ang II (n=9 neurons). (C and D) Representative traces and cumulative plots show mEPSCs of labeled PVN neurons before (baseline), with (AP5), and after (washout) bath application of 50 μmol/L AP5 in brain slices treated with control peptide plus Ang II or α2δ-1Tat peptide plus Ang II. (E and F) Mean changes show the frequency and amplitude of mEPSCs in labeled PVN neurons treated with control peptide plus Ang II (n=9 neurons) or α2δ-1Tat peptide plus Ang II (n=8 neurons). Data are presented as means±SEM. *P<0.05, **P<0.01 compared with the baseline of the control peptide plus Ang II group.

FIGS. 29A-29H: α2δ-1 ablation abolishes the potentiating effect of Ang II on pre- and postsynaptic NMDAR activity in spinally projecting PVN neurons of mice. A and B. Original traces (A) and mean changes (B) show NMDAR currents elicited by puff application of 100 μmol/L NMDA to labeled PVN neurons in brain slices treated with vehicle or 2 μmol/L Ang II in wild-type (WT, vehicle: n=11 neurons; Ang II: n=9 neurons) and Cacna2d1 knockout (KO, vehicle: n=14 neurons; Ang II: n=10 neurons) mice. (C-F) Representative traces and cumulative plots of mEPSCs in labeled PVN neurons of WT and Cacna2d1 KO mice before (baseline), with (AP5), and after (washout) bath application of 50 μmol/L AP5 in brain slices treated with vehicle or 2 μmol/L Ang II. (G and H) Mean changes show the effect of AP5 on the frequency and amplitude of mEPSCs in the labeled PVN neurons of brain slices from WT mice (n=8 neurons per group) and Cacna2d1 KO mice (n=9 neurons per group) treated with vehicle or 2 μmol/L Ang II. Data are presented as means±SEM. ***P<0.001 compared with the baseline value of WT mice treated with vehicle. ##P<0.01, ###P<0.001 compared with the baseline value of WT mice treated with Ang II.

FIGS. 30A-30J: α2δ-1Tat peptide blocks sympathoexcitatory responses to the microinjection of Ang II into the PVN. (A and B) Representative recording traces show the effect of bilateral microinjection of Ang II on ABP, RSNA, and HR in anesthetized rats before and after microinjection of the control peptide (A) or α2δ-1Tat peptide (B) into the PVN. C-H, Summary data show changes in mean ABP, RSNA, and HR in response to microinjection of Ang II before and after microinjection of the control peptide (C-E, n=10 rats) or α2δ-1Tat peptide (F-H, n=10 rats) into the PVN. Data are presented as means±SEM. P<0.01, *P<0.001, compared with the baseline value. In I and J, A representative image (I) and schematic drawing (J) show the microinjection sites (solid circle, rats treated with control peptide; open circle, rats treated with α2δ-1Tat peptide) in the PVN tissue sections. 3V, third ventricle; AH, anterior hypothalamus; Fx, fornix; VMH, ventromedial hypothalamus.

FIGS. 31A-31J: Paclitaxel increases α2δ-1 expression levels and synaptic trafficking of α2δ-1-bound NMDARs in the spinal cord. (A-C) Original gel images (A and B, 2 pairs of samples) and quantification (C) of the α2δ-1 protein level in the DRG and dorsal spinal cord tissues of paclitaxel-treated (P) and vehicle-treated (V) rats (n=9 rats per group). (D-F) Quantification of the mRNA level of α2δ-1, α2δ-2, and α2δ-3 in the DRG and dorsal spinal cord tissues of paclitaxel-treated (P) and vehicle-treated (V) rats (n=6 rats per group). (G,H) co-IP analysis showing the interaction between α2δ-1 and GluN1 in the membrane extracts of dorsal spinal cord tissues from rats treated with paclitaxel (P) or vehicle (V) (n=6 rats per group). Proteins were immunoprecipitated initially with a mouse anti-GluN1 or anti-IgG antibody. Immunoblotting was performed by using rabbit anti-α2δ-1 and anti-GluN1 antibodies. IgG and input (tissue lysates only, without immunoprecipitation) were used as negative and positive controls, respectively. (I, J) Representative gel images (I, 3 pairs of samples) and quantification (J) of the protein levels of α2δ-1, GluN1, and PSD-95 (a synaptic marker) in synaptosomes isolated from dorsal spinal cord tissues of paclitaxel-treated (P) and vehicle-treated (V) rats (n=8 rats per group). GAPDH and PSD-95 were used as internal controls for normalizing the protein level on the same gel. Values in C-F, H, and J are normalized to expression levels in vehicle-treated rats. Data are expressed as means±SEM. *P<0.05 compared with the vehicle-treated group.

FIGS. 32A-32D: Inhibiting α2δ-1 with pregabalin reverses paclitaxel-induced tonic activation of presynaptic NMDARs in the spinal cord. (A,B) Representative recording traces and cumulative plots (A) and box-and-whisker plots (B) show the effect of bath application of 50 μM AP5 on the frequency and amplitude of mEPSCs of lamina II neurons from paclitaxel-treated rats. Neurons were treated with 20 μM pregabalin (+pregabalin, n=10 neurons) or untreated (-pregabalin, n=12 neurons). (C, D) Original recording traces and cumulative plots (C) and box-and-whisker plots (D) show the effect of bath application of AP5 on the frequency and amplitude of mEPSCs of lamina II neurons from vehicle-treated rats. Neurons were treated with 20 μM pregabalin (+pregabalin, n=10 neurons) or untreated (-pregabalin, n=12 neurons). Data are expressed as means±SEM. *P<0.05 compared with the respective baseline control. #P<0.05 compared with the baseline level in the group without pregabalin treatment.

FIGS. 33A-33F: Inhibiting α2δ-1 with pregabalin normalizes paclitaxel-induced activation of presynaptic NMDARs at primary afferent terminals. (A, B). Original recording traces (A) and box-and-whisker plots (B) show the effect of bath application of 50 μM AP5 on evoked monosynaptic EPSCs of lamina II neurons from paclitaxel-treated rats. Neurons were treated with 20 μM pregabalin (+pregabalin, n=8 neurons) or untreated (-pregabalin, n=12 neurons). (C,D). Representative recording traces (C) and box-and-whisker plots (D) shows the effect of bath application of 50 μM AP5 on evoked monosynaptic EPSCs of lamina II neurons from vehicle-treated rats. Neurons treated with 20 μM pregabalin (+pregabalin, n=9 neurons) or untreated (-pregabalin, n=8 neurons). In B and D (right panels), values are normalized to their respective baselines. (E, F). Original recording traces (E) and box-and-whisker plots (F) shows the effect of bath application of AP5 on the paired-pulse ratio (PPR) of lamina II neurons treated with pregabalin (+pregabalin) and of untreated neurons (-pregabalin) from vehicle-treated (n=9 neurons with pregabalin; n=8 neurons without pregabalin) and paclitaxel-treated rats (n=8 neurons with pregabalin; n=9 neurons without pregabalin). Data are expressed as means±SEM. *P<0.05 compared with the respective baseline control. #P<0.05 compared with the baseline level in the group without pregabalin treatment.

FIGS. 34A-34D: Interrupting the α2δ-1-NMDAR interaction using α2δ-1Tat peptide reverses paclitaxel-induced tonic activation of presynaptic NMDARs in the spinal cord. (A, B). Representative recording traces and cumulative plots (A) and box-and-whisker plots (B) show the effect of bath application of 50 μM AP5 on the frequency and amplitude of mEPSCs of lamina II neurons from paclitaxel-treated rats, Neurons were treated with 1 μM α2δ-1Tat peptide (n=10 neurons) or 1 μM control peptide (n=11 neurons). (C, D) Original recording traces and cumulative plots (C) and box-and-whisker plots (D) show the effect of bath application of AP5 on the frequency and amplitude of mEPSCs of lamina II neurons from vehicle-treated rats. Neurons were treated with 1 μM α2δ-1Tat peptide (n=11 neurons) or 1 μM control peptide (n=12 neurons). Data are expressed as means±SEM. *P<0.05 compared with the respective baseline control. #P<0.05 compared with the baseline level in the group treated with control peptide.

FIGS. 35A-35F: Interrupting the α2δ-1-NMDAR interaction using α2δ-1Tat peptide abrogates paclitaxel-induced activation of presynaptic NMDARs at primary afferent terminals. (A, B). Original recording traces (A) and box-and-whisker plots (B) show the effect of bath application of 50 μM AP5 on evoked monosynaptic EPSCs of lamina II neurons from paclitaxel-treated rats. Neurons were treated with 1 μM α2δ-1Tat peptide (n=9 neurons) or 1 μM control peptide (n=12 neurons). (C,D). Representative recording traces (C) and box-and-whisker plots (D) show the effect of bath application of 50 μM AP5 on evoked monosynaptic EPSCs of lamina II neurons from vehicle-treated rats. Neurons were treated with 1 μM α2δ-1Tat peptide (n=10 neurons) or 1 μM control peptide (n=9 neurons). In B and D (right panels), values are normalized to their respective baselines. (E,F). Original recording traces (E) and box-and-whisker plots (F) shows the effect of bath application of 50 μM AP5 on the paired-pulse ratio (PPR) of lamina II neurons treated with α2δ-1Tat peptide or control peptide from vehicle-treated (n=10 neurons with α2δ-1Tat peptide; n=9 neurons with control peptide) and paclitaxel-treated rats (n=9 neurons with α2δ-1Tat peptide; n=9 neurons with control peptide). Data are expressed as means±SEM. *P<0.05 compared with the respective baseline control. #P<0.05 compared with the baseline level in the group treated with control peptide.

Figures 36A, 36B, 36C:
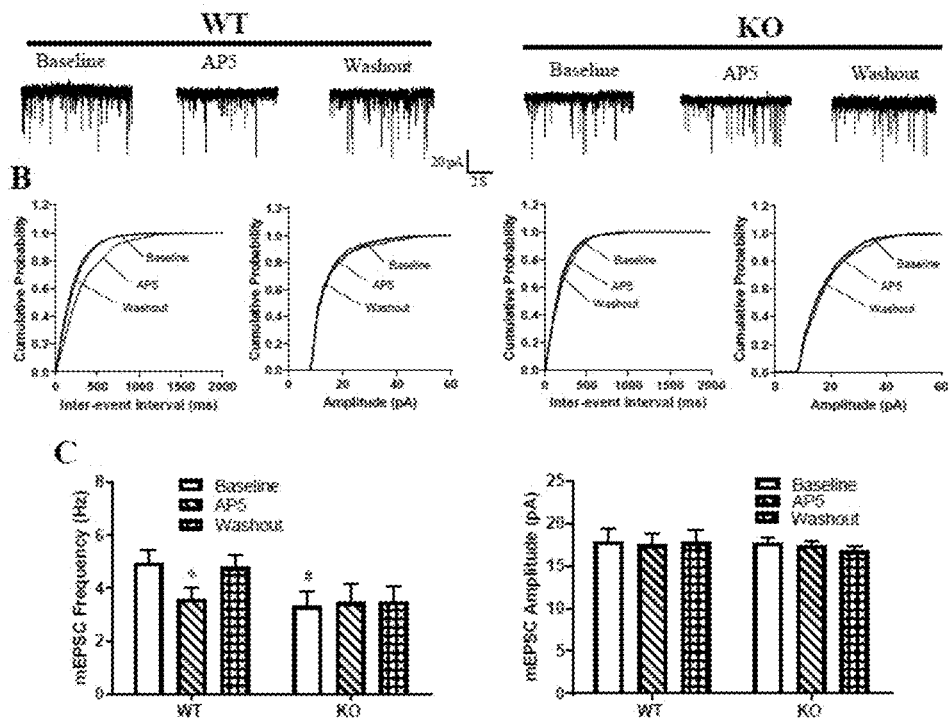

FIGS. 36A-36C: Ablation of α2δ-1 prevents paclitaxel-induced tonic activation of presynaptic NMDARs in the spinal cord in mice. (A-C). Representative recording traces (A), cumulative plots (B), and box-and-whisker plots (C) show the effect of bath application of 50 μM AP5 on the frequency and amplitude of mEPSCs of lamina II neurons from wild-type (WT, n=11 neurons) and α2δ-1 knockout (KO, n=16 neurons) mice treated with paclitaxel. Data are expressed as means±SEM. *P<0.05 compared with the respective baseline control. #P<0.05 compared with the baseline level in WT mice.

FIGS. 37A-37D: Ablation of α2δ-1 abolishes paclitaxel-induced activation of presynaptic NMDARs at primary afferent terminals in mice. (A,B). Original recording traces (A) and box-and-whisker plots (B) shows the effect of bath application of 50 μM AP5 on evoked monosynaptic EPSCs of lamina II neurons from wild-type (WT, n=13 neurons) and α2δ-1 knockout (KO, n=11 neurons) mice treated with paclitaxel. In B (right panel), values are normalized to the respective baselines. (C,D). Original recording traces (C) and box-and-whisker plots (D) shows the effect of bath application of AP5 on the paired-pulse ratio (PPR) of lamina II neurons from WT (n=13 neurons) and α2δ-1 KO (n=10 neurons) mice treated with paclitaxel. Data are expressed as means±SEM. *P<0.05 compared with the respective baseline control. #P<0.05 compared with the baseline level in WT mice.

FIGS. 38A-38F: α2δ-1 at the spinal cord level is involved in paclitaxel-induced pain hypersensitivity. (A-C). Time course of the effect of intrathecal injection with vehicle, 5 μg pregabalin, 1 μg α2δ-1Tat peptide, or 1 μg control peptide on the paw withdrawal thresholds measured with von Frey filaments (A), a pressure stimulus (B), and a heat stimulus (C) in paclitaxel-treated rats (n=8 rats per group). Data are expressed as means±SEM. *P<0.05, compared with the control (time 0) before intrathecal injection. BL, baseline before paclitaxel treatment. Vehicle or agent injections are indicated by the arrows. (D-F). Time course of changes in the paw withdrawal thresholds tested with von Frey filaments (D), a heat stimulus (E), and a cold stimulus (F) in wild-type (WT) and α2δ-1 knockout (KO) mice treated with paclitaxel (n=8 mice per group). Data are expressed as means±SEM. *P<0.05, compared with respective baseline (BL) value before paclitaxel treatment. The 4 paclitaxel injections are indicated by the arrows. #P<0.05 compared with the corresponding value at the same time point in WT mice.

FIGS. 39A-39D: Chronic morphine treatment increases α2δ-1 association with NMDARs at spinal cord synapses. (A and B) Original blots and quantification of α2δ-1 protein levels in the DRG (A) and dorsal spinal cord (B) from vehicle- and morphine-treated rats (n=6 rats in each group). C, Co-IP analysis shows GluN1 coprecipitated with α2δ-1 in the membrane extracts of dorsal spinal cord tissues of rats treated with vehicle (V) or morphine (M) for 8 days (n=6 rats in each group). The amount of α2δ-1 proteins was normalized to GluN1 in the same sample, and the mean value of α2δ-1 levels in vehicle-treated rats was considered to be 1. (D) Representative gel images and quantification of GluN1 and α2δ-1 protein levels in dorsal spinal cord synaptosomes from vehicle- and morphine-treated rats (n=6 rats in each group). Data are shown as means±S.E. *, P<0.05 vs. the vehicle group.

FIGS. 40A-40D: α2δ-1 mediates chronic morphine-induced potentiation of presynaptic NMDAR activity in the spinal dorsal horn. (A) Representative recording traces and cumulative plots show the baseline and the effect of bath application of 50 μM AP5 on the frequency and amplitude of mEPSCs of a lamina II neuron from a morphine-treated rat. (B) summary data show the baseline and the effect of 50 μM AP5 on the mean frequency and amplitude of mEPSCs in morphine-treated (n=11 neurons) rats. (C) Original recording traces and cumulative plots show the lack of effect of 50 μM AP5 on the frequency or amplitude of mEPSCs of a lamina II neuron pretreated with 100 μM gabapentin from a spinal cord slice of a morphine-treated rat. (D) group data show the effect of 50 μM AP5 on the mean frequency and amplitude of mEPSCs (n=10 neurons) in spinal cord slices pretreated with 100 μM gabapentin in morphine-treated rats. Data are shown as means±S.E. *, P<0.05 vs. the baseline. #, P<0.05 vs. the baseline in morphine+vehicle group.

FIGS. 41A-41F: α2δ-1 is involved in chronic morphine-induced potentiation of NMDAR activity at primary afferent terminals in the spinal dorsal horn. (A and B) Original recording traces and summary data show the effect of 50 μM AP5 on evoked monosynaptic EPSCs (A) and paired-pulse ratio (PPR, B) of a lamina II neuron from a morphine-treated rat. C, Summary data show the effect of 50 μM AP5 on the amplitude (n=10 neurons) and PPR (n=10 neurons) of evoked monosynaptic EPSCs of lamina II neurons in morphine-treated rats. (D and E) Representative traces show the lack of the effect of 50 μM AP5 on the amplitude of monosynaptically evoked EPSCs (D) and PPR (E) of a lamina II neuron in spinal cord slices pretreated with 100 μM gabapentin in a morphine-treated rat. (F) Group data show the lack of the effect of 50 μM AP5 on the amplitude (n=11 neurons) and PPR (n=11 neurons) of monosynaptic EPSCs of lamina II neurons pretreated with 100 μM gabapentin in spinal cord slices from morphine-treated rats. Data are shown as means±S.E. *, P<0.05 vs. the baseline. #, P<0.05 vs. the baseline in morphine+vehicle group.

FIGS. 42A-42D: α2δ-1 is essential for the chronic morphine-induced activation of presynaptic NMDARs in the spinal dorsal horn. (A) Representative recording trace and cumulative plots show the effect of AP5 on the baseline frequency and amplitude of mEPSCs of the lamina II neuron from a morphine-treated WT mouse. (B) Summary data show the effect of 50 μM AP5 on the mean frequency and amplitude of mEPSCs (n=11 neurons) in spinal cord slices of morphine-treated WT mice. (C) Original recording traces and cumulative plots show the lack of effect of 50 μM AP5 on the frequency or amplitude of mEPSCs of a lamina II neuron from a spinal cord slice of a morphine-treated α2δ-1 KO mouse. (D) Mean changes show the lack of effect of AP5 on the frequency and amplitude of mEPSCs (n=10 neurons) in spinal cord slices obtained from morphine-treated α2δ-1 KO mice. Data are shown as means±S.E. *, $P<0.05$ vs. the baseline. #, $P<0.05$ vs. the baseline in the WT group.

FIGS. 43A-43F: α2δ-1 is required for the chronic morphine-induced increase in NMDAR activity at primary afferent terminals. (A and B) Representative current traces show the effect of 50 μM AP5 on the amplitude of monosynaptic EPSCs (A) and the PPR (B) of lamina II neurons from the spinal cord slice in a morphine-treated WT mouse. (C) Summary data show the effect of 50 μM AP5 on the amplitude (n=11 neurons) and PPR (n=11 neurons) of monosynaptic EPSCs of lamina II neurons from spinal cord slices of morphine-treated WT mice. (C and D) Original current traces show the lack of effect of 50 μM AP5 on the amplitude of evoked monosynaptic EPSCs (C) and the PPR (D) of a lamina II neuron of a morphine-treated α2δ-1 KO mouse. (E-F) Group data show the lack of effect of 50 μM AP5 on the amplitude (n=11 neurons) and the PPR (n=11 neurons) of monosynaptic EPSCs of lamina II neurons from spinal cord slices of morphine-treated α2δ-1 KO mice. Data are shown as means±S.E. *, $P<0.05$ vs. the baseline. #, $P<0.05$ vs. the baseline in the WT group.

FIGS. 44A-44D: α2δ-1-bound NMDARs mediate the chronic morphine-induced increase in presynaptic NMDAR activity in the spinal cord. (A) Representative recording traces and cumulative plots show the baseline and the effect of bath application of 50 μM AP5 on the frequency and amplitude of mEPSCs of a lamina II neuron pretreated with control peptide (1 μM) from a spinal cord slice of a morphine-treated rat. (B) Summary data show the effect of 50 μM AP5 on the mean frequency and amplitude of mEPSCs (n=10 neurons) in spinal cord slices pretreated with control peptide in morphine-treated rats. (C) Original recording traces and cumulative plots show the lack of effect of 50 μM AP5 on the frequency or amplitude of mEPSCs of a lamina II neuron pretreated with α2δ-1Tat peptide (1 μM) from a spinal cord slice of a morphine-treated rat. (D) Mean changes show the lack of effect of AP5 on the frequency and amplitude of mEPSCs (n=11 neurons) in spinal cord slices pretreated with α2δ-1Tat peptide from morphine-treated rats. Data are shown as means±S.E. *, $P<0.05$ vs. the baseline. #, $P<0.05$ vs. the baseline in morphine+control peptide group.

FIGS. 45A-45F: α2δ-1-bound NMDARs are critically involved in chronic morphine-induced activation of NMDARs at primary afferent terminals. (A and B) Representative current traces show the effect of 50 μM AP5 on the amplitude of monosynaptic EPSCs (A) and the PPR (B) of lamina II neurons from the spinal cord slice pretreated with control peptide (1 μM) in a morphine-treated rat. (C) Summary data show the effect of 50 μM AP5 on the amplitude (n=11 neurons) and PPR (n=11 neurons) of monosynaptic EPSCs of lamina II neurons from spinal cord slices pretreated with control peptide in morphine-treated rats. (C and D) Original current traces show the lack of effect of 50 μM AP5 on the amplitude of evoked monosynaptic EPSCs (C) and the PPR (D) of a lamina II neuron from spinal cord slices pretreated with α2δ-1Tat peptide (1 μM) in a morphine-treated rat. (E-F) Group data show the lack of effect of 50 μM AP5 on the amplitude (n=11 neurons) and PPR (n=11 neurons) of monosynaptic EPSCs of lamina II neurons from spinal cord slices pretreated with α2δ-1Tat peptide in morphine-treated rats. Data are shown as means±S.E. *, $P<0.05$ vs. the baseline. #, $P<0.05$ vs. the baseline in morphine+control peptide group.

FIGS. 46A-46F: α2δ-1 at the spinal cord level mediates chronic morphine-induced hyperalgesia and analgesic tolerance. (A and B) Time course of changes in the baseline mechanical (A) and thermal (B) withdrawal thresholds and the analgesic effect of morphine in rats treated with systemic morphine plus vehicle (n=8 rats) or gabapentin (100 mg/kg, n=8 rats). (C and D) Time course of changes in the baseline mechanical (C) and thermal (D) withdrawal thresholds and the analgesic effect of morphine in rats treated with systemic morphine plus control peptide (1 μg) or α2δ-1Tat peptide (1 μg) (n=10 rats in each group). (E and F) Time course of changes in the baseline mechanical (E) and thermal (F) withdrawal thresholds and the analgesic effect of morphine in WT and α2δ-1 KO mice (n=8 mice per group). The baseline withdrawal threshold was measured before each morphine injection, and the analgesic effect of morphine was tested 30 min after morphine injection. *, $P<0.05$ vs. values at day 1. #, $P<0.05$ vs. values in the corresponding control group (vehicle, control peptide, and WT) at the same time point.

FIGS. 47A-47F: α2δ-1 interacts with NMDARs in the hypothalamus and increases the synaptic expression of α2δ-1-bound NMDARs in SHRs. (A) Representative blot images and mean changes show the α2δ-1 protein level in the PVN in adult WKY rats and SHRs (n=7 rats per group). (B) Original ABP traces and summary data show the effect of CGx or sham surgery on the mean ABP in SHRs (n=6 rats in each group). (C) Original blot images and summary data show the α2δ-1 levels (normalized to GAPDH) in the PVN in SHRs subjected to CGx or sham surgery (n=6 rats in each group). (D) Representative blot images and mean changes show the α2δ-1 protein level in the PVN in young WKY rats and SHRs (n=6 rats per group). (E) Representative blot images and co-immunoprecipitation analysis show the interaction between α2δ-1 and GluN1 in total protein extracts of hypothalamic tissues from WKY rats and SHRs (n=6 independent experiments per group, each tissue sample was pooled from two rats). Proteins were immunoprecipitated first with an anti-GluN1 antibody or IgG and then immunoblotted using an anti-α2δ-1 antibody. (F) Original blot images and quantification data show the protein levels of α2δ-1 and GluN1 (normalized to PSD-95, a synaptic protein) in hypothalamic synaptosomes in WKY rats and SHRs (n=6 independent experiments per group, each tissue sample was pooled from two rats). *$P<0.05$, $P<0.01$, *$P<0.001$ compared to the sham group. ###$P<0.001$ compared to the sham group.

FIGS. 48A-48F: α2δ-1 is required for increased postsynaptic NMDAR activity of RVLM-projecting PVN neurons in SHRs. (A) Representative images show the microinjection site in the RVLM in bright-field (Aa), fluorescence (Ab) and overlay images (Ac) from the same tissue section. Scale bar=1 mm. (B) Representative current traces of evoked AMPAR-EPSCs (at −60 mV) and NMDAR-EPSCs (at +40 mV) recorded in a labelled PVN neuron treated with vehicle or 100 μmol L-1 gabapentin in slices obtained from a WKY rat and an SHR. (C, D) Summary of evoked AMPAR-EPSC and NMDAR-EPSC data (C) and the ratio of NMDAR- EPSCs to AMPAR-EPSCs (D) in labelled PVN neurons pretreated with vehicle or gabapentin in slices from WKY rats (n=9 neurons in each group) or SHRs (n=8 neurons in each group). (E, F) Original current traces (E) and summary data (F) show the effect of 100 µmol L-1 gabapentin on puff NMDA (100 µmol L-1) elicited currents of labelled PVN neurons recorded from WKY rats (n=11 neurons in each group) and SHRs (vehicle, n=12 neurons; gabapentin, n=11 neurons). ***P<0.001 compared to the WKY+vehicle group. ###P<0.001 compared to the SHR+vehicle group.

FIGS. 49A-49D: α2δ-1-bound NMDARs are essential for enhanced postsynaptic NMDAR activity of PVN presympathetic neurons in SHRs. (A) Representative current traces of evoked AMPAR-EPSCs (at −60 mV) and NMDAR-EPSCs (at +40 mV) recorded in labelled PVN neurons treated with control peptide or α2δ-1Tat peptide (1 µmol L-1) in slices from a WKY rat and an SHR. (B, C) Summary of evoked AMPAR-EPSC and NMDAR-EPSC data (B) and the ratio of NMDAR-EPSCs to AMPAR-EPSCs (C) in labelled PVN neurons pretreated with control peptide or α2δ-1Tat peptide in slices from WKY rats (n=10 neurons in each group) or SHRs (n=9 neurons in each group). (D, E) Original current traces (D) and mean data (E) show the effect of 1 µmol L-1 control peptide or 1 µmol L-1 α2δ-1Tat peptide on puff NMDA (100 µmol L-1) elicited currents of labelled PVN neurons recorded from WKY rats (n=8 neurons in each group) and SHRs (n=11 neurons in each group). ***P<0.001 compared to the WKY+control peptide group. ###P<0.001 compared to the SHR+control peptide group.

FIGS. 50A-50F: α2δ-1 mediates increased presynaptic NMDAR activity of RVLM-projecting PVN neurons in SHRs. (A-D) Original traces and cumulative probability plots show the effect of bath application of 50 µmol L-1 AP5 on the frequency and amplitude of mEPSCs of labelled PVN neurons pretreated with vehicle or 100 µmol L-1 gabapentin in slices from WKY rats and SHRs. (E, F) Summary data show the effects of gabapentin and AP5 on the frequency (E) and amplitude (F) of mEPSCs in labelled PVN neurons from WKY rats (vehicle, n=10 neurons; gabapentin, n=12 neurons) and SHRs (n=11 neurons in each group). **P<0.01 compared to baseline in the WKY+vehicle group. #P<0.05 compared to baseline in the SHR+vehicle group.

FIGS. 51A-51F: α2δ-1-bound NMDARs are essential for tonic activation of presynaptic NMDAR of PVN presympathetic neurons in SHRs. (A-D) Original traces and cumulative probability plots show the effect of bath application of 50 µmol L AP5 on mEPSCs of labelled PVN neurons pretreated with 1 µmol L-1 control peptide or 1 µmol L-1 α2δ-1Tat peptide in slices from WKY rats and SHRs. (E, F) Group data show the effects of α2δ-1Tat peptide and AP5 on the frequency (E) and amplitude (F) of mEPSCs in labelled PVN neurons from WKY rats (control peptide, n=12 neurons; α2δ-1Tat peptide, n=11 neurons) and SHRs (control peptide, n=9 neurons; α2δ-1Tat peptide, n=10 neurons). **P<0.01 compared to baseline in the WKY+control peptide group. #P<0.05 compared to baseline in the SHR+control peptide group.

FIGS. 52A-52E: α2δ-1-bound NMDARs in the PVN maintain heightened sympathetic outflow in SHRs. (A, B) Original recording traces show the effects of bilateral microinjection of control peptide (A) or α2δ-1Tat peptide (B) followed by AP5 microinjection into the PVN on ABP, RSNA and HR in SHRs. (C) Summary data show changes in mean ABP, integrated RSNA (int. RSNA) and HR in response to microinjection of AP5 after microinjection of control peptide or α2δ-1Tat peptide into the PVN in SHRs (n=9 rats in each group). (D, E) Representative tissue section images (D) and schematic drawing (E) show the microinjection sites for control peptide plus AP5 (solid circle) and α2δ-1Tat peptide plus AP5 (open circle) in the PVN in SHRs. ***P<0.001 compared to the baseline control. 3V, third ventricle; AH, anterior hypothalamus; Fx, fornix; VMH, ventromedial hypothalamus. Scale bars=1 mm.

Figure 53:
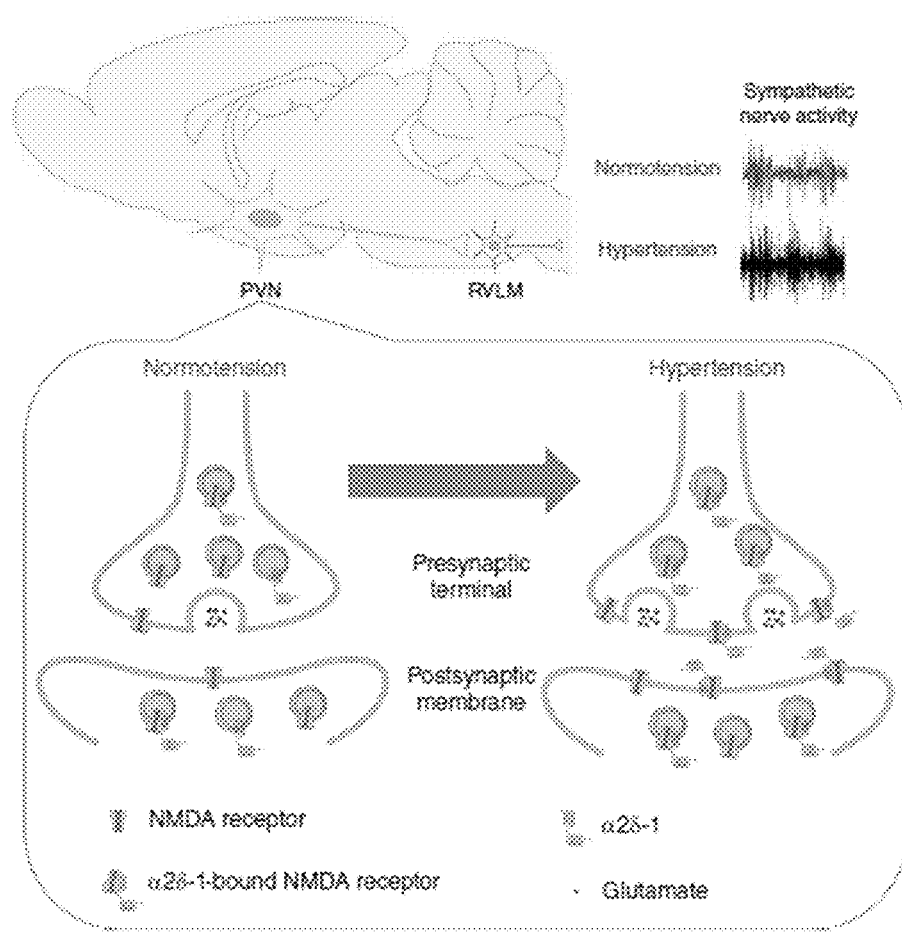

FIG. 53: Schematic representation shows the proposed role of α2δ-1 in the regulation of synaptic NMDARs of PVN presympathetic neurons and sympathetic outflow in SHRs. In normotensive condition, most NMDARs are not associated with α2δ-1 in the PVN. In hypertensive condition, α2δ-1 is upregulated and physically interacts with NMDARs to promote synaptic trafficking of α2δ-1-bound NMDARs, which leads to increased pre- and postsynaptic NMDAR activity of RVLM-projecting PVN neurons. The increased synaptic NMDAR activity in the PVN contributes to elevated sympathetic vasomotor activity in SHRs.

DESCRIPTION OF ILLUSTRATIVE EMBODIMENTS

The NMDA-type glutamate receptor (NMDAR) plays an essential role in learning, memory, synaptic plasticity and neuropathic pain (Nicoll and Malemka, 1995; Bashir et al., 1991; Chen et al., 2014; Zhou et al., 2012). Nerve injury potentiates NMDAR activity, at both pre- and postsynaptic sites, in the spinal dorsal horn (Li et al., 2016). The present studies provide evidence that α2δ-1 forms a heteromeric complex with NMDARs to potentiate their synaptic trafficking and that targeting the C-terminal domain of α2δ-1 reverses the synaptic NMDAR activity associated with neuropathic pain. This information redefines the function and role of α2δ-1 in neuropathic pain and the therapeutic effects of gabapentinoids.

In particular, the present studies show that α2δ-1 overexpression potentiates presynaptic and postsynaptic NMDAR activity of spinal dorsal horn neurons to cause pain hypersensitivity. Conversely, α2δ-1 knockdown or ablation normalizes synaptic NMDAR activity increased by nerve injury. α2δ-1 forms a heteromeric complex with NMDAR subunits in rodent and human spinal cords through its C-terminal transmembrane domain and promotes surface trafficking and synaptic targeting of NMDARs. Remarkably, gabapentin or an α2δ-1 C-terminus-interfering peptide blocks synaptic trafficking of α2δ-1-bound NMDARs and restores NMDAR activity increased by nerve injury. Further, it was shown that an α2δ-1 C-terminus domain mimetic peptide can disrupt interaction of α2δ-1 to AMPA-type glutamate receptor. Thus, α2δ-1 is a glutamate receptor-interacting protein that increases synaptic delivery of functional glutamate receptors in neuropathic pain. Accordingly, the present disclosure provides α2δ-1 C-terminal domain mimetics, such as peptides, and methods for their use in treating neuropathic pain, such as chemotherapy-induced neuropathic pain, hypertension, ischemic stroke, opioid-induce analgesic tolerance, and epilepsy. The disclosure further provides vectors encoding the present peptide, such as viral vectors, particularly lentiviral vectors. The α2δ-1 C-terminal domain may be inhibited by gene editing, such as CRISPR-mediated knockdown, or by RNA interference, such as shRNA.

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

"Treating" or treatment of a disease or condition refers to executing a protocol, which may include administering one or more drugs to a patient, in an effort to alleviate signs or symptoms of the disease. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient. "Treating pain" includes a decrease in pain and does not require complete alleviation of pain signs or symptoms, and does not require a cure. In various embodiments, reducing pain includes even a marginal decrease in pain. By way of example, the administration of one or more effective dosages of $\alpha 2\delta$-1 C-terminal domain mimetics may be used to prevent, treat or relieve the symptoms of neuropathic pain.

The term "pain" includes nociception and the sensation of pain, both of which can be assessed objectively and subjectively, using pain scores and other methods well-known in the art. In various embodiments, pain may include allodynia (e.g., increased response to a normally non-noxious stimulus) or hyperalgesia (e.g., increased response to a normally noxious or unpleasant stimulus), which can in turn be thermal or mechanical (tactile) in nature. In some embodiments, pain is characterized by thermal sensitivity, mechanical sensitivity and/or resting pain. In other embodiments, pain comprises mechanically-induced pain or resting pain. In still other embodiments, the pain comprises resting pain. The pain can be primary or secondary pain, as is well-known in the art. Exemplary types of pain reducible, preventable or treatable by the methods and compositions disclosed herein include, without limitation, chemotherapy-induced pain, post-operative pain, and neuropathic pain of the arm, neck, back, lower back, or leg.

"Neuropathic pain" refers to any form of pain associated with a neuropathic disease or condition caused by injury or primary irritation of a nerve, including degenerative, toxic, metabolic, ischaemic and mechanical forms of injury. Neuropathic conditions include all forms of neuritis and polyneuritis. "Peripheral neuropathic pain" refers to pain caused by damage to peripheral neurons, and is typically characterized as "burning," "shooting," "stabbing," or "electric-shock-like." It may occur without external stimulation or, very commonly, it may be manifested as allodynia (an experience of pain from normally non-painful stimuli, such as from light touching) or hyperalgesia (an exaggerated sense of pain from a normally painful stimulation).

The term "hyperalgesia" or "hyperalgesic sensation" as used herein refers to an extreme sensitivity to pain, which in one form is caused by damage to nociceptors in the body's soft tissues. Hyperalgesia can be experienced in focal, discrete areas, or as a more diffuse, body-wide form.

"Subject" and "patient" refer to either a human or non-human, such as primates, mammals, and vertebrates. In particular embodiments, the subject is a human.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 μg/kg/body weight to about 1000 mg/kg/body weight (this such range includes intervening doses) or more per administration, and any range derivable therein. In non-limiting examples of a derivable range from the numbers listed herein, a range of about 5 μg/kg/body weight to about 100 mg/kg/body weight, about 5 μg/kg/body weight to about 500 mg/kg/body weight, etc., can be administered. The practitioner responsible for administration will, in any event, determine the concentration of active ingredient(s) in a composition and appropriate dose(s) for the individual subject. In some embodiments, the dosage of antigen-specific T cell infusion may comprise about 100 million to about 30 billion cells, such as 10, 15, or 20 billion cells.

A polynucleotide or polynucleotide region (or a polypeptide or polypeptide region) has a certain percentage (for example, 80%, 85%, 90%, or 95%) of "sequence identity" or "homology" to another sequence means that, when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR.

In the present disclosure, the term "α2δ-1 C-terminal domain mimetic" refers to an agent which competes with α2δ-1 for binding with a glutamate receptor, including NMDA receptor and AMPA receptor. In one exemplary embodiment, the α2δ-1 C-terminal domain mimetic is a peptide.

By "expression construct" or "expression cassette" is meant a nucleic acid molecule that is capable of directing transcription. An expression construct includes, at a minimum, one or more transcriptional control elements (such as promoters, enhancers or a structure functionally equivalent thereof) that direct gene expression in one or more desired cell types, tissues or organs. Additional elements, such as a transcription termination signal, may also be included.

A "vector" or "construct" (sometimes referred to as a gene delivery system or gene transfer "vehicle") refers to a macromolecule or complex of molecules comprising a polynucleotide to be delivered to a host cell, either in vitro or in vivo.

A "plasmid," a common type of a vector, is an extrachromosomal DNA molecule separate from the chromosomal DNA that is capable of replicating independently of the chromosomal DNA. In certain cases, it is circular and double-stranded.

II. α2δ-1 C-TERMINAL DOMAIN MIMETICS

Certain embodiments of the disclosure concern α2δ-1 C-terminal domain mimetics that block binding of α2δ-1 to glutamate receptors NMDAR and AMPAR. These include peptides or expression vectors encoding the peptides disclosed herein as well as that structurally similar compounds (i.e., small molecules) that may be formulated to mimic the key portions of peptide.

A. α2δ-1 C-terminal Domain Mimetic Peptide

The present disclosure provides compositions of various α2δ-1 C-terminal domain mimetic peptides as well as methods of their use. In particular embodiments, the peptide has at least 90, 91, 92, 93, 94, 95, 96, 97, 98, 99, or 100% sequence identity with the sequence VSGLNPSLWSIFGLQFILLWLVSGSRHYLW (SEQ ID NO:1) or the sequence YGRKKRRQRRRVSGLNPSLWSIFGLQFILLWLVSGSRHYLW (SEQ ID NO:4).

In general, the peptides will be 50 residues or less. The overall length may be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 residues. Ranges of peptide length of 10-50 residues, 15-50 residues, 20-25 residues 21-25, residues, 20-30 residues, 30-40 residues, and 35-45 residues, and 25-35 residues are contemplated. The present disclosure may utilize L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary). The peptides may be linear or cyclic peptides.

One form of an "all-D" peptide is a retro-inverso peptide. Retro-inverso modification of naturally occurring polypeptides involves the synthetic assemblage of amino acids with u-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

The present disclosure contemplates fusing or conjugating a cell-penetrating domain (also called a cell delivery domain, or cell transduction domain). Such domains are well known in the art and are generally characterized as short amphipathic or cationic peptides and peptide derivatives, often containing multiple lysine and arginine resides (Fischer, 2007). Of particular interest are the TAT sequence from HIV1 (YGRKKRRQRRR; SEQ ID NO: 2), and poly-D-Arg and poly-D-Lys sequences (e.g., dextrorotary residues, eight residues in length). Other cell delivery domains are shown in the table below.

TABLE 1

| CPP/CTD PEPTIDES | SEQ ID NO |
|---|---|
| QAATATRGRSAASRPTERPRAPARSASRPRRPVE | 5 |
| RQIKIWFQNRRMKWKK | 6 |
| RRMKWKK | 7 |
| RRWRRWWRRWWRRWRR | 8 |
| RGGRLSYSRRRFSTSTGR | 9 |
| YGRKKRRQRRR | 10 |
| RKKRRQRRR | 11 |
| YARAAARQARA | 12 |
| RRRRRRRR | 13 |
| KKKKKKKK | 14 |
| GWTLNSAGYLLGKINLKALAALAKXIL | 15 |
| LLILLRRRIRKQANAHSK | 16 |
| SRRHHCRSKAKRSRHH | 17 |
| NRARRNRRRVR | 18 |

TABLE 1-continued

| CPP/CTD PEPTIDES | SEQ ID NO |
|---|---|
| RQLRIAGRRLRGRSR | 19 |
| KLIKGRTPIKFGK | 20 |
| RRIPNRRPRR | 21 |
| KLALKLALKALKAALKLA | 22 |
| KLAKLAKKLAKLAK | 23 |
| GALFLGFLGAAGSTNGAWSQPKKKRKV | 24 |
| KETWWETWWTEWSQPKKKRKV | 25 |
| GALFLGWLGAAGSTMGAKKKRKV | 26 |
| MGLGLHLLVLAAALQGAKSKRKV | 27 |
| AAVALLPAVLLALLAPAAANYKKPKL | 28 |
| MANLGYWLLALFVTMWTDVGLCKKRPKP | 29 |
| LGTYTQDFNKFHTFPQTAIGVGAP | 30 |
| DPKGDPKGVTVTVTVTVTGKGDPXPD | 31 |
| PPPPPPPPPPPPPP | 32 |
| VRLPPPVRLPPPVRLPPP | 33 |
| PRPLPPPRPG | 34 |
| SVRRRPRPPYLPRPRPPPFFPPRLPPRIPP | 35 |
| TRSSRAGLQFPVGRVHRLLRK | 36 |
| GIGKFLHSAKKFGKAFVGEIMNS | 37 |
| KWKLFKKIEKVGQNIRDGIIKAGPAVAVVGQATQIAK | 38 |
| ALWMTLLKKVLKAAAKAALNAVLVGANA | 39 |
| GIGAVLKVLTTGLPALISWIKRKRQQ | 40 |
| INLKALAALAKKIL | 41 |
| GFFALIPKIISSPLPKTLLSAVGSALGGSGGQE | 42 |
| LAKWALKQGFAKLKS | 43 |
| SMAQDIISTIGDLVKWIIQTVNXFTKK | 44 |
| LLGDFFRKSKEKIGKEFKRIVQRIKQRIKDFLANLVPRIES | 45 |
| LKKLLKKLLKKLLKKLLKKL | 46 |
| KLKLKLKLKLKLKLKL | 47 |
| PAWRKAFRWAWRMLKKAA | 48 |

Peptides may be modified for in vivo use by the addition, at the amino- and/or carboxyl-terminal ends, of a blocking agent to facilitate survival of the peptide in vivo are contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino and/or carboxyl terminal residues. In addition, nanoparticles could be used for the packaging and delivery of the peptide.

B. Synthesis

It will be advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine. In addition, vectors that can deliver plasmids can be used to produce the desired peptide, such as in vivo.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the twenty standard amino acids can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

C. Linkers

Linkers or cross-linking agents may be used to fuse peptides to other proteinaceous sequences. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

D. Mimetics

In addition to the peptides disclosed herein, the present disclosure also contemplates that structurally similar compounds may be formulated to mimic the key portions of peptide or polypeptides of the present disclosure. Such compounds, which may be termed peptidomimetics, may be used in the same manner as the peptides of the present disclosure and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

By "molecular modeling" is meant quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods. Computer programs that use X-ray crystallography data are particularly useful for designing such compounds. Programs such as RasMol, for example, can be used to generate three dimensional models. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures. The methods can involve the additional step of outputting to an output device a model of the 3-D structure of the compound. In addition, the 3-D data of candidate compounds can be compared to a computer database of, for example, 3-D structures.

Compounds of the present disclosure also may be interactively designed from structural information of the compounds described herein using other structure-based design/modeling techniques (see, e.g., Jackson, 1997; Jones et al., 1996). Candidate compounds can then be tested in standard assays familiar to those skilled in the art. Exemplary assays are described herein.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with the present disclosure (e.g., Cohen et al., 1990; Navia et al., 1992), the disclosures of which are incorporated herein by reference in their entirety). All these methods produce data that are amenable to computer analysis. Other spectroscopic methods that can also be useful in the method of the invention, but that do not currently provide atomic level structural detail about biomolecules, include circular dichroism and fluorescence and ultraviolet/visible light absorbance spectroscopy. One method of analysis is x-ray crystallography.

E. Stabilized Peptides

A particular modification is in the context of peptides as therapeutics is the so-called "Stapled Peptide" technology of Aileron Therapeutics. The general approach for "stapling" a peptide is that two key residues within the peptide are modified by attachment of linkers through the amino acid side chains. Once synthesized, the linkers are connected through a catalyst, thereby creating a bridge that physically constrains the peptide into its native α-helical shape. In addition to helping retain the native structure needed to interact with a target molecule, this conformation also provides stability against peptidases as well as promotes cell-permeating properties.

More particularly, the term "peptide stapling" may encompasses the joining of two double bond-containing sidechains, two triple bond-containing sidechains, or one double bond-containing and one triple bond-containing side chain, which may be present in a polypeptide chain, using any number of reaction conditions and/or catalysts to facilitate such a reaction, to provide a singly "stapled" polypeptide. In a specific embodiment, the introduction of a staple entails a modification of standard peptide synthesis, with α-methy, α-alkenyl amino acids being introduced at two positions along the peptide chain, separated by either three or six intervening residues (i+4 or i+7). These spacings place the stapling amino acids on the same face of the α-helix, straddling either one (i+4) or two (i+7) helical turns. The fully elongated, resin-bound peptide can be exposed to a ruthenium catalyst that promotes cross-linking of the alkenyl chains through olefin metathesis, thereby forming an all-hydrocarbon macrocyclic cross-link. U.S. Pat. Nos. 7,192,713 and 7,183,059, and U.S. Patent Publications 2005/02506890 and 2006/0008848, describing this technology, are hereby incorporated by reference. See also Schafmeister et al., *Journal of the American Chemical Society*, 122(24): p. 5891-5892 (2000); Walensky et al., *Science* 305:1466-1470 (2004). Additionally, the term "peptide stitching" refers to multiple and tandem "stapling" events in a single peptide chain to provide a "stitched" (multiply stapled) polypeptide, each of which is incorporated herein by reference. See WO 2008/121767 for a specific example of stitched peptide technology.

F. Peptide Delivery

A nucleic acid encoding a peptide of the present disclosure may be made by any technique known to one of ordinary skill in the art. Non-limiting examples of a synthetic nucleic acid, particularly a synthetic oligonucleotide, include a nucleic acid made by in vitro chemical synthesis using phosphotriester, phosphite or phosphoramidite chemistry and solid phase techniques such as described in EP 266,032, or via deoxynucleoside H-phosphonate intermediates as described by Froehler et al., 1986, and U.S. Pat. No. 5,705,629. A non-limiting example of enzymatically produced nucleic acid includes one produced by enzymes in amplification reactions such as PCR™ (see for example, U.S. Pat. Nos. 4,683,202 and 4,682,195), or the synthesis of oligonucleotides described in U.S. Pat. No. 5,645,897. A non-limiting example of a biologically produced nucleic acid includes recombinant nucleic acid production in living cells, such as recombinant DNA vector production in bacteria (see for example, Sambrook et al. 1989).

The nucleic acid(s), regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). The overall length may vary considerably between nucleic acid constructs. Thus, a nucleic acid segment of almost any length may be employed, with the total length preferably being limited by the ease of preparation or use in the intended recombinant nucleic acid protocol.

1. Nucleic Acid Delivery by Expression Vector

Vectors provided herein are designed, primarily, to express an α2δ-1 C-terminal domain mimetic under the control of regulated eukaryotic promoters (i.e., constitutive, inducible, repressable, tissue-specific). Also, the vectors may contain a selectable marker if, for no other reason, to facilitate their manipulation in vitro.

One of skill in the art would be well-equipped to construct a vector through standard recombinant techniques (see, for example, Sambrook et al., 2001 and Ausubel et al., 1996, both incorporated herein by reference). Vectors include but are not limited to, plasmids, cosmids, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus vectors, herpes virus vectors, vaccinia virus vectors, Harvey murine sarcoma virus vectors, murine mammary tumor virus vectors, Rous sarcoma virus vectors, parvovirus vectors, polio virus vectors, vesicular stomatitis virus vectors, maraba virus vectors and group B adenovirus enadenotucirev vectors.

a. Viral Vectors

Viral vectors encoding a α2δ-1 C-terminal domain mimetic may be provided in certain aspects of the present disclosure. In generating recombinant viral vectors, non-essential genes are typically replaced with a gene or coding sequence for a heterologous (or non-native) protein. A viral vector is a kind of expression construct that utilizes viral sequences to introduce nucleic acid and possibly proteins into a cell. The ability of certain viruses to infect cells or enter cells via receptor-mediated endocytosis, and to integrate into host cell genomes and express viral genes stably and efficiently have made them attractive candidates for the transfer of foreign nucleic acids into cells (e.g., mammalian cells). Non-limiting examples of virus vectors that may be used to deliver a nucleic acid of certain aspects of the present invention are described below.

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136).

Recombinant lentiviral vectors are capable of infecting non-dividing cells and can be used for both in vivo and ex vivo gene transfer and expression of nucleic acid sequences. For example, recombinant lentivirus capable of infecting a non-dividing cell—wherein a suitable host cell is transfected with two or more vectors carrying the packaging functions, namely gag, pol and env, as well as rev and tat—is described in U.S. Pat. No. 5,994,136, incorporated herein by reference.

(i) Adenoviral Vector

One method for delivery of α2δ-1 C-terminal domain mimetic involves the use of an adenovirus expression vector. Although adenovirus vectors are known to have a low capacity for integration into genomic DNA, this feature is counterbalanced by the high efficiency of gene transfer afforded by these vectors. Adenovirus expression vectors include constructs containing adenovirus sequences sufficient to (a) support packaging of the construct and (b) to ultimately express a recombinant gene construct that has been cloned therein.

Adenovirus growth and manipulation is known to those of skill in the art, and exhibits broad host range in vitro and in vivo. This group of viruses can be obtained in high titers, e.g., 109-1011 plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them particular mRNA's for translation.

A recombinant adenovirus provided herein can be generated from homologous recombination between a shuttle vector and provirus vector. Due to the possible recombination between two proviral vectors, wild-type adenovirus may be generated from this process. Therefore, a single clone of virus is isolated from an individual plaque and its genomic structure is examined.

The adenovirus vector may be replication competent, replication defective, or conditionally defective, the nature of the adenovirus vector is not believed to be crucial to the successful practice of the invention. The adenovirus may be of any of the 42 different known serotypes or subgroups A-F. Adenovirus type 5 of subgroup C is the particular starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector. However, other serotypes of adenovirus may be similarly utilized.

Nucleic acids can be introduced to adenoviral vectors as a position from which a coding sequence has been removed. For example, a replication defective adenoviral vector can have the E1-coding sequences removed. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Generation and propagation of replication deficient adenovirus vectors can be performed with helper cell lines. One unique helper cell line, designated 293, was transformed from human embryonic kidney cells by Ad5 DNA fragments and constitutively expresses E1 proteins (Graham et al., 1977). Since the E3 region is dispensable from the adenovirus genome (Jones and Shenk, 1978), adenovirus vectors, with the help of 293 cells, carry foreign DNA in either the E1, the E3, or both regions (Graham and Prevec, 1991).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, a particular helper cell line is 293.

Methods for producing recombinant adenovirus are known in the art, such as U.S. Pat. No. 6,740,320, incorporated herein by reference. Also, Racher et al. (1995) have disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) are employed as follows. A cell inoculum, resuspended in 5 ml of medium, is added to the carrier (50 ml) in a 250 ml Erlenmeyer flask and left stationary, with occasional agitation, for 1 to 4 hours. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 hours.

(ii) Retroviral Vector

Additionally, the α2δ-1 C-terminal domain mimetic may be encoded by a retroviral vector. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, packaging cell lines are available that should greatly decrease the likelihood of recombination (Markowitz et al., 1988; Hersdorffer et al., 1990).

(iii) Adeno-associated Viral Vector

Adeno-associated virus (AAV) is an attractive vector system for use in the present disclosure as it has a high frequency of integration and it can infect nondividing cells, thus making it useful for delivery of genes into mammalian cells (Muzyczka, 1992). AAV has a broad host range for infectivity (Tratschin, et al., 1984; Laughlin, et al., 1986; Lebkowski, et al., 1988; McLaughlin, et al., 1988), which means it is applicable for use with the present invention. Details concerning the generation and use of rAAV vectors are described in U.S. Pat. Nos. 5,139,941 and 4,797,368.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild-type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild-type AAV coding sequences without the terminal repeats, for example pIM45 (McCarty et al., 1991). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994; Clark et al., 1995). Cell lines carrying the rAAV DNA as an integrated provirus can also be used (Flotte et al., 1995).

2. Other Viral Vectors

Other viral vectors may be employed as constructs in the present disclosure. Vectors derived from viruses such as vaccinia virus (Ridgeway, 1988; Baichwal and Sugden, 1986; Coupar et al., 1988) and herpesviruses may be employed. They offer several attractive features for various mammalian cells (Friedmann, 1989; Ridgeway, 1988; Baichwal and Sugden, 1986; Coupar et al., 1988; Horwich et al., 1990).

A molecularly cloned strain of Venezuelan equine encephalitis (VEE) virus has been genetically refined as a replication competent vaccine vector for the expression of heterologous viral proteins (Davis et al., 1996). Studies have demonstrated that VEE infection stimulates potent CTL responses and has been suggested that VEE may be an extremely useful vector for immunizations (Caley et al., 1997).

In further embodiments, the nucleic acid encoding chimeric CD154 is housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

For example, targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

3. Regulatory Elements

Expression cassettes included in vectors useful in the present disclosure in particular contain (in a 5'-to-3' direction) a eukaryotic transcriptional promoter operably linked to a protein-coding sequence, splice signals including intervening sequences, and a transcriptional termination/polyadenylation sequence. The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation. A promoter used in the context of the present invention includes constitutive, inducible, and tissue-specific promoters.

a. Promoter/Enhancers

The expression constructs provided herein comprise a promoter to drive expression of the α2δ-1 C-terminal domain mimetic. A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally, any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e.g., beta actin promoter (Ng, 1989; Quitsche et al., 1989), GADPH promoter (Alexander et al., 1988, Ercolani et al., 1988), metallothionein promoter (Karin et al., 1989; Richards et al., 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007). In certain embodiments, the promoter is CMV IE, dectin-1, dectin-2, human CD11c, F4/80, SM22, RSV, SV40, Ad MLP, beta-actin, MHC class I or MHC class II promoter, however any other promoter that is useful to drive expression of the therapeutic gene is applicable to the practice of the present invention.

In certain aspects, methods of the disclosure also concern enhancer sequences, i.e., nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter.

b. Initiation Signals and Linked Expression

A specific initiation signal also may be used in the expression constructs provided in the present disclosure for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

Additionally, certain 2A sequence elements could be used to create linked- or co-expression of genes in the constructs provided in the present disclosure. For example, cleavage sequences could be used to co-express genes by linking open reading frames to form a single cistron. An exemplary cleavage sequence is the F2A (Foot-and-mouth disease virus 2A) or a "2A-like" sequence (e.g., *Thosea asigna* virus 2A; T2A) (Minskaia and Ryan, 2013).

c. Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively a replication origin of other extra-chromosomally replicating virus as described above or an autonomously replicating sequence (ARS) can be employed.

4. Selection and Screenable Markers

In some embodiments, cells containing a construct of the present disclosure may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art.

5. Other Methods of Nucleic Acid Delivery

In addition to viral delivery of the nucleic acids encoding α2δ-1 C-terminal domain mimetic, the following are additional methods of recombinant gene delivery to a given host cell and are thus considered in the present disclosure. Thus, other forms of gene therapy may be combined with the therapeutic viral compositions including gene editing methods such as meganucleases, zinc finger nucleases (ZFNs), transcription activator-like effector-based nucleases (TALEN), and the CRISPR-Cas system.

Introduction of a nucleic acid, such as DNA or RNA, may use any suitable methods for nucleic acid delivery for transformation of a cell, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538, 877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563, 055, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

a. Electroporation

In certain particular embodiments of the present disclosure, the gene construct is introduced into target hyperproliferative cells via electroporation. Electroporation involves the exposure of cells (or tissues) and DNA (or a DNA complex) to a high-voltage electric discharge.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

It is contemplated that electroporation conditions for hyperproliferative cells from different sources may be optimized. One may particularly wish to optimize such parameters as the voltage, the capacitance, the time and the electroporation media composition. The execution of other routine adjustments will be known to those of skill in the art. See e.g., Hoffman, 1999; Heller et al., 1996.

b. Lipid-Mediated Transformation

In a further embodiment, the α2δ-1 C-terminal domain mimetic may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL).

Lipid-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of lipid-mediated delivery and expression of foreign DNA in cultured chick embryo, HeLa and hepatoma cells.

Lipid based non-viral formulations provide an alternative to adenoviral gene therapies. Although many cell culture studies have documented lipid based non-viral gene transfer, systemic gene delivery via lipid based formulations has been limited. A major limitation of non-viral lipid based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in lipid vehicle stability in the presence and absence of serum proteins. The interaction between lipid vehicles and serum proteins has a dramatic impact on the stability characteristics of lipid vehicles (Yang and Huang, 1997). Cationic lipids attract and bind negatively charged serum proteins. Lipid vehicles associated with serum proteins are either dissolved or taken up by macrophages leading to their removal from circulation. Current in vivo lipid delivery methods use subcutaneous, intradermal, intratumoral, or intracranial injection to avoid the toxicity and stability problems associated with cationic lipids in the circulation. The interaction of lipid vehicles and plasma proteins is responsible for the disparity between the efficiency of in vitro (Felgner et al., 1987) and in vivo gene transfer (Zhu el al., 1993; Philip et al., 1993; Solodin et al., 1995; Liu et al., 1995; Thierry et al., 1995; Tsukamoto et al., 1995; Aksentijevich et al., 1996).

Advances in lipid formulations have improved the efficiency of gene transfer in vivo (Templeton et al. 1997; WO 98/07408). A novel lipid formulation composed of an equimolar ratio of 1,2-bis(oleoyloxy)-3-(trimethyl ammonio) propane (DOTAP) and cholesterol significantly enhances systemic in vivo gene transfer, approximately 150 fold. The DOTAP:cholesterol lipid formulation forms unique structure termed a "sandwich liposome". This formulation is reported to "sandwich" DNA between an invaginated bilayer or 'vase' structure. Beneficial characteristics of these lipid structures include a positive p, colloidal stabilization by cholesterol, two dimensional DNA packing and increased serum stability. Patent Application Nos. 60/135,818 and 60/133,116 discuss formulations that may be used with the present invention.

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Lipid encapsulation has resulted in a lower toxicity and a longer serum half-life for such compounds (Gabizon et al., 1990). Numerous disease treatments are using lipid based gene transfer strategies to enhance conventional or establish novel therapies, in particular therapies for treating hyperproliferative diseases.

c. CRISPR-Cas System

In some embodiments, the α2δ-1 C-terminal domain is inhibited using one or more DNA-binding nucleic acids, such as via an RNA-guided endonuclease (RGEN). For example, the inhibition can be carried out using clustered regularly interspaced short palindromic repeats (CRISPR) and CRISPR-associated (Cas) proteins. In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus.

The CRISPR/Cas nuclease or CRISPR/Cas nuclease system can include a non-coding RNA molecule (guide) RNA, which sequence-specifically binds to DNA, and a Cas protein (e.g., Cas9), with nuclease functionality (e.g., two nuclease domains). One or more elements of a CRISPR system can derive from a type I, type II, or type III CRISPR system, e.g., derived from a particular organism comprising an endogenous CRISPR system, such as *Streptococcus pyogenes*.

In some aspects, a Cas nuclease and gRNA (including a fusion of crRNA specific for the target sequence and fixed tracrRNA) are introduced into the cell. In general, target sites at the 5' end of the gRNA target the Cas nuclease to the target site, e.g., the gene, using complementary base pairing. The target site may be selected based on its location immediately 5' of a protospacer adjacent motif (PAM) sequence, such as typically NGG, or NAG. In this respect, the gRNA is targeted to the desired sequence by modifying the first 20, 19, 18, 17, 16, 15, 14, 14, 12, 11, or 10 nucleotides of the guide RNA to correspond to the target DNA sequence. In general, a CRISPR system is characterized by elements that promote the formation of a CRISPR complex at the site of a target sequence. Typically, "target sequence" generally refers to a sequence to which a guide sequence is designed to have complementarity, where hybridization between the target sequence and a guide sequence promotes the formation of a CRISPR complex. Full complementarity is not necessarily required, provided there is sufficient complementarity to cause hybridization and promote formation of a CRISPR complex.

The CRISPR system can induce double stranded breaks (DSBs) at the target site, followed by disruptions as discussed herein. In other embodiments, Cas9 variants, deemed "nickases," are used to nick a single strand at the target site. Paired nickases can be used, e.g., to improve specificity, each directed by a pair of different gRNAs targeting sequences such that upon introduction of the nicks simultaneously, a 5' overhang is introduced. In other embodiments, catalytically inactive Cas9 is fused to a heterologous effector domain such as a transcriptional repressor or activator, to affect gene expression.

The target sequence may comprise any polynucleotide, such as DNA or RNA polynucleotides. The target sequence may be located in the nucleus or cytoplasm of the cell, such as within an organelle of the cell. Generally, a sequence or template that may be used for recombination into the targeted locus comprising the target sequences is referred to as an "editing template" or "editing polynucleotide" or "editing sequence". In some aspects, an exogenous template polynucleotide may be referred to as an editing template. In some aspects, the recombination is homologous recombination.

Typically, in the context of an endogenous CRISPR system, formation of the CRISPR complex (comprising the guide sequence hybridized to the target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. The tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of the CRISPR complex, such as by hybridization along at least a portion of the tracr sequence to all or a portion of a tracr mate sequence that is operably linked to the guide sequence. The tracr sequence has sufficient complementarity to a tracr mate sequence to hybridize and participate in formation of the CRISPR complex, such as at least 50%, 60%, 70%, 80%, 90%, 95% or 99% of sequence complementarity along the length of the tracr mate sequence when optimally aligned.

One or more vectors driving expression of one or more elements of the CRISPR system can be introduced into the cell such that expression of the elements of the CRISPR system direct formation of the CRISPR complex at one or more target sites. Components can also be delivered to cells as proteins and/or RNA. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. The vector may comprise one or more insertion sites, such as a restriction endonuclease recognition sequence (also referred to as a "cloning site"). In some embodiments, one or more insertion sites are located upstream and/or downstream of one or more sequence elements of one or more vectors. When multiple different guide sequences are used, a single expression construct may be used to target CRISPR activity to multiple different, corresponding target sequences within a cell.

A vector may comprise a regulatory element operably linked to an enzyme-coding sequence encoding the CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of S. pyogenes Cas9 protein may be found in the SwissProt database under accession number Q99ZW2.

The CRISPR enzyme can be Cas9 (e.g., from S. pyogenes or S. pneumonia). The CRISPR enzyme can direct cleavage of one or both strands at the location of a target sequence, such as within the target sequence and/or within the complement of the target sequence. The vector can encode a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from S. pyogenes converts Cas9 from a nuclease that cleaves both strands to a nickase (cleaves a single strand). In some embodiments, a Cas9 nickase may be used in combination with guide sequence(s), e.g., two guide sequences, which target respectively sense and antisense strands of the DNA target. This combination allows both strands to be nicked and used to induce NHEJ or HDR.

In some embodiments, an enzyme coding sequence encoding the CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

In general, a guide sequence is any polynucleotide sequence having sufficient complementarity with a target polynucleotide sequence to hybridize with the target sequence and direct sequence-specific binding of the CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more.

Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), Clustal W, Clustal X, BLAT, Novoalign (Novocraft Technologies, ELAND (Illumina, San Diego, Calif.), SOAP (available at soap.genomics.org.cn), and Maq (available at maq.sourceforge.net).

The CRISPR enzyme may be part of a fusion protein comprising one or more heterologous protein domains. A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4A DNA binding domain fusions, and herpes simplex virus (HSV) BP16 protein fusions. Additional domains that may form part of a fusion protein comprising a CRISPR enzyme are described in US 20110059502, incorporated herein by reference.

G. Compounds Targeting α2δ-1 and Glutamate Receptor Interaction

Most AMPA receptors contain GluA2 and thus can be calcium-impermeable. However, in the presence of α2δ-1, the surface of AMPA receptor becomes calcium permeable.

This can be due to α2δ-1 preventing heteromer (e.g., GluA1-GluA2) formation in the cell. Thus, in further embodiments, the present disclosure provides a high-throughput assay to screen for compounds that can target the α2δ-1 receptor interaction site with glutamate receptors, including NMDA and AMPA receptors. The compounds identified by the method can mimic the key portions of the α2δ-1 C-terminal domain mimetic peptides provided herein. The test compound may be selected from the group consisting of a small molecule, an inorganic compound, an organic compound, a biomolecule, a chemical, a protein, a peptide, or a nucleic acid. The cell may have any tissue origin, such as neuronal tissue, brain tissue, liver tissue, kidney tissue, cardiac tissue, pancreatic tissue, stomach tissue, lymphatic tissue, retinal tissue, intestinal tissue, or reproductive organ tissues. In particular aspects, the cell is a neuron, such as a primary neuron.

Calcium indicator dyes are substances which show a change in a fluorescent characteristic upon binding calcium, e.g., greatly increased intensity of fluorescence and/or a change in fluorescent spectra (i.e., a change in emission or excitation maxima). Fluo-3, fura-2, and indo-1 are commonly used calcium indicator dyes that were designed as structural analogs of the highly selective calcium chelators ethylene glycol-bis(β-aminoethyl ether) N,N,N',N'-tetraacetic acid (EGTA) and 1,2-bis(2-aminophenoxy) ethane-N,N,N',N'-tetraacetic acid (BAPTA). The use of calcium indicator dyes entails loading cells with the dye, a process which can be accomplished by exposing cells to the membrane-permeable acetoxymethyl esters of the dyes. Once inside the plasma membrane of the cells, intracellular esterases cleave the esters, exposing negative charges in the free dyes. This prevents the free dyes from crossing the plasma membrane and thus leaves the free dyes trapped in the cells. Measurements of fluorescence from the dyes are then made, the cells are treated in such a way that the internal calcium concentration is changed (e.g., by exposing cells to an activator or inhibitor of a voltage-gated ion channel), and fluorescence measurements are again taken. Exemplary calcium dyes include Quin-2, Fura-2, Bis-Fura-2, Fura-4F, Fura-5F, Fura-6F, FFP18, Fura-Red, Mag-Fura-2, Indo-1, Fluo-3, Fluo-4, Mag-Fluo-4, Fluo-5F, Fluo-5N, Fluo-4FF, Fluo-8, Fluo-8H, Fluo-8L, Rhod-2, X-Rhod-1, Rhod-FF, X-Rhod-FF, Rhod-5N, Calcium-Green-1, Calcium-Green-2, Calcium-Green-5N, BAPTA-1, BAPTA-2, BAPTA-6F, BAPTA-5N, calcium crimson, calcium ruby, calcium orange. In particular embodiments, the calcium indicator dye is selected from the group consisting of: fluo-3, fura-2, fluo-4, fluo-5, calcium green-1, Oregon green, 488 BAPTA, SNARF-1, and indo-1.

In one embodiment, a high-throughput assay is provided that comprises contacting cells with a calcium indicator dye (or ratiometric dye) and a glutamate receptor agonist to stimulate calcium influx. The cells may contain both glutamate receptors and α2δ-1, such as cultured primary cells which endogenously express glutamate receptors, such as AMPA receptor, and α2δ-1. In other aspects, the cells may be engineered to heterologously express (e.g., via transfection) glutamate receptors (e.g., AMPA receptors subunits GluA1 and GluA2) and α2δ-1. The glutamate receptor agonist, such as AMPA agonist, may be used to stimulated calcium influx by acting on calcium-permeable AMPA receptors due to the presence of α2δ-1 in the presence of a test compound. The calcium influx and/or intracellular calcium response is then quantified, such as by using a Fluorescent Imaging Plate Reader (FLIPR). Thus, any test compounds that can reduce calcium influx or intracellular calcium response by glutamate receptors agonists are identified as agents for inhibiting α2δ-1 activity, particularly the functional interaction between α2δ-1 and glutamate receptor subunits, such as AMPA receptor subunits or NMDA receptor. As α2δ-1 interacts with NMDA via the same C-terminal domain, the identified compounds can also have an effect on α2δ-1-NMDA receptor complexes (i.e., inhibiting the activity if α2δ-1-bound NMDA receptors). In some aspects, the positive control cell is treated with a α2δ-1 C-terminal domain mimetic peptide provided herein.

Fluorescence from the indicator dyes can be measured with a luminometer or a fluorescence imager. One preferred detection instrument is the Fluorometric Imaging Plate Reader (FLIPR) (Molecular Devices, Sunnyvale, Calif.). The FLIPR is well suited to high throughput screening using the methods of the present invention as it incorporates integrated liquid handling capable of simultaneously pipetting to 96 or 384 wells of a microtiter plate and rapid kinetic detection using an argon laser coupled to a charge-coupled device imaging camera. The FLIPR assay may be performed by methods known in the art, such as described in Vetter, Calcium Signaling, Advances in Experimental Medicine and Biology, 2012.

The screening assay does not have to be comprised of only two time points (before and after) of administration of the test compound. Multiple "doses" of a test compound can be administered to an aliquot of cells over time, which are sequentially imaged for changes in calcium ion storage and flux; or a compound can be added to separate individual aliquots of cells over a period of time and separate images obtained for each aliquot so that any changes in calcium imaging can be followed over that period of time.

After treatment with the test compound, the cell may have a decrease in intracellular calcium or calcium influx by about 10% as compared to a control cell, such as at least 15, 20, 25, 30, 35, 40, 45, 50, 60, 70, 80, 90, 95, 96, 97, 98, 99, or 100% decrease as compared to the control cell.

III. METHODS OF USE

A. Treatment of Pain

Embodiments of the present disclosure provide methods for the treatment of pain comprising the administration of the α2δ-1 C-terminal domain mimetics described herein, such as a peptide of sequence VSGLNPSLWSIFGLQFILL-WLVSGSRHYLW (SEQ ID NO:1) or the sequence YGRKKRRQRRRVSGLNPSLWSIFGLQFILL-WLVSGSRHYLW (SEQ ID NO:4). Pain treatable by methods of the present disclosure (e.g., itching, allodynia, hyperalgesia, paresthesia, and discomfort, as well as combinations of these) is not restricted to any particular cause, disease, or disorder. Examples of treatable pain include, without limitation, neuropathic pain; pain associated with inflammation, including that from arthritis, hemorrhoids, or plantar fasciitis as examples; pain associated with trauma, injury, surgery, infection (e.g., bacterial, viral, fungal, protozoan, helminthic, parasitic), neoplasia, hyperplasia, radiation, irritation, or burns; pain associated with locally or systemically contacted toxins; pain associated with insect, spider, or animal bites or stings; and pain associated with allergic or other sensitivity reactions, pruritus, and painful conditions with unknown causes, such as fibromyalgia.

Furthermore, peripheral neuropathic pain treatable by this invention is not restricted to any particular cause, disease, or disorder. Examples of treatable peripheral neuropathic pain include, without limitation, painful diabetic neuropathy;

infection-related neuropathic pain, including HIV-related neuropathic pain, herpes zoster related neuropathic pain, and herpes simplex related neuropathic pain; postherpetic neuralgia; facial neuralgia, including trigeminal neuralgia; cancer-associated neuralgia, including neuralgia caused by neuronal tumors, tumor infiltration of neurons, tumors pressing on neurons, chemotherapy, surgery, and radiation treatment; pain associated with trauma, including that caused by surgery; pain associated with root avulsions, nerve entrapment, carpal tunnel syndrome, or ischemic nerve injury; painful traumatic mononeuropathy or polyneuropathy; distal sensory polyneuropathy; complex regional pain syndrome; and neuropathy caused by systemic or locally contacted toxins.

In some aspects, the pain is nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived. Moderate to severe acute nociceptive pain is a prominent feature of pain from central nervous system trauma, strains/sprains, burns, myocardial infarction and acute pancreatitis, post-operative pain (pain following any type of surgical procedure), posttraumatic pain, renal colic, cancer pain and back pain. Cancer pain may be chronic pain such as tumor related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament.

In particular embodiments, the pain is neuropathic pain which is currently defined as pain initiated or caused by a primary lesion or dysfunction in the nervous system. Nerve damage can be caused by trauma and disease and thus the term 'neuropathic pain' encompasses many disorders with diverse etiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, 5141-5147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

B. Treatment of Epilepsy

Further embodiments of the present disclosure provide methods for the treatment of epilepsy comprising the administration of the α2δ-1 C-terminal domain mimetics described herein, such as a peptide of sequence VSGLNPSLWSIFGLQFILLWLVSGSRHYLW (SEQ ID NO:1) or the sequence YGRKKRRQRRRVSGLNPSLWSIFGLQFILLWLVSGSRHYLW (SEQ ID NO:4). The α2δ-1 C-terminal domain mimetic is administered in an amount sufficient to prevent, retard or ameliorate epileptic seizures. Typically, administration to the central nervous system, and especially, localized delivery by intraventricular or intraparenchymal administration to the brain, are preferred as the quickest and most direct means. Local infusion by injection, by means of a catheter or a reservoir implant are preferred. However, any other means which effectively delivers therapeutic amounts of the α2δ-1 C-terminal domain mimetic to the affected site in the brain can be alternatively employed, for example, intravenous, intramuscular, subcutaneous, etc., as properly formulated.

In some embodiments, an effective amount of an α2δ-1 C-terminal domain mimetic is an amount that is effective to reduce the incidence of an epileptic seizure in an individual by at least about 10%, at least about 15%, at least about 20%, at least about 25%, at least about 30%, at least about 40%, at least about 50%, or more than 50%, compared to the incidence of epileptic seizure in the individual in the absence of treatment with the agent.

C. Pharmaceutical Compositions

Where clinical applications are contemplated, it will be necessary to prepare pharmaceutical compositions in a form appropriate for the intended application. In some embodiments, such formulation with the compounds of the present disclosure is contemplated. Generally, this will entail preparing compositions that are essentially free of pyrogens, as well as other impurities that could be harmful to humans or animals.

The pharmaceutical dosage units of the present disclosure may be formulated for various forms of administration, including, for example, sublingual, mucosal, parenteral, intravenous, intramuscular, buccal, lingual, intra-lingual, nasal, intra-sinus, intraocular, topical, oral, vaginal, urethral, subcutaneous, peritoneal, intra-arterial, and by inhalation and/or transdermal administration and combinations thereof. Consistent with the various forms of administration, the pharmaceutical dosage unit can generally be formulated, for example, as a tablet, capsule, injection, and/or patch.

Sublingual tablets are designed to dissolve very rapidly. Examples of such formulations include ergotamine tartrate, isosorbide dinitrate, isoproterenol HCl. The necessary ingredients for the pharmaceutical dosage unit may be processed in accordance with known methods, using or incorporating familiar coatings and additives as required. By way of example only, in addition to the pharmaceutically active components, a dosage unit may contain effective amounts of binders, fillers, disintegrants, sustained-release agents, diluents, anti-adherents, glidants, flow aids, plasticizers and lubricants, which are well known in the field of pharmaceutical processing. For instance, the formulation of these tablets may contain, in addition to the active agent, a limited number of soluble excipients, including a binder such as povidone or hydroxypropyl methylcellulose (HPMC), diluents such as lactose, mannitol, starch or cellulose, a disintegrant such as pregelatinized or modified starch, lubricants such as magnesium stearate, stearic acid or hydrogenated vegetable oil, a sweetener such as saccharin or sucrose and suitable flavoring and coloring agents. The process of making sublingual tablets generally involves moistening the blended powder components with an alcohol-water solvent system containing approximately 60% alcohol and 40% water and pressing this mixture into tablets.

The pharmaceutical dosage unit may be presented in a single dose or as divided doses administered at appropriate intervals, for example, as two, three, four or more sub-doses per day. In one embodiment, the pharmaceutical dosage unit may be formulated such that a single sublingual tablet is administered twice daily.

Alternatively, the pharmaceutical dosage unit may be formulated so that the active ingredient exhibits sustained-release characteristics upon administration to the patient. For example, the active ingredient may be delivered with an oral mucosal patch. Methods of making such patches are well known to one of skill in the art. In one embodiment, the oral mucosal patch is prepared by homogeneously mixing the active component with appropriate amounts of Carbopol 934, polyisobutylene, and polyisoprene using a two-roll mill and then compressing the mixture to the appropriate thickness. A membrane backing such as ethylcellulose is then applied to one side of the compressed material and circular disks, having an area of about 0.5 cm² and thickness of about 0.6 mm for example, may be punched from the material. The backing inhibits drug release from one side of the disk and reduces adhesion to opposing side tissues. The oral mucosal patches may be secured to mucosal buccal surfaces such as the gums, lips, and cheeks, and worn for extended periods. In one instance, the oral mucosal patches may be work for about 12 hours.

In another sustained release embodiment, the active ingredient may be delivered using a tablet-form dosage unit having a partially hydrophilic matrix which exhibits sustained release of the active component. In addition to the active ingredient, the tablet is comprised of, for example, ethylcellulose as a sustained-release agent and hydroxypropyl methylcellulose (HPMC) as a film former. Further, bulking agents such as microcrystalline cellulose and starch, a polyvinylpyrrolidone binder, silicon dioxide as an antiadherent, dibutyl sebacate as a plasticizer, and magnesium stearate as a lubricant may be included. Using conventional processes, the listed ingredients, other than ethylcellulose, HPMC and dibutyl sebacate, are combined and pressed into a tablet. The tablet is then coated with the ethylcellulose, HPMC and dibutyl sebacate prior to administration of the tablet. When this tablet encounters an aqueous environment, such as the mucosal buccal surfaces, portions of the tablet coating dissolve, leaving a non-continuous film of water-insoluble ethylcellulose surrounding the remaining tablet core. The rate of diffusion of the active ingredients from the tablet core into the aqueous environment is determined by the concentration of ethylcellulose, HPMC and dibutyl sebacate in the coating.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment of the present disclosure, the compound is given in a dosage lying in a range of from about 1 to about 1000 mg, such as for example about 1 to 500 mg, 5 to 500 mg, 5 to 250 mg or 10 to 200 mg. The patient may be administered a dosage whenever the patient experiences pain. Hence, the dosage may be administered 1, 2, 3, 4, 5, 6, 7, 8, 9 or 10 times during a 24 hour period. The physician will in any event determine the actual dosage, which will be most suitable for any particular patient and it may vary with the severity of disease, age, weight and response of the particular patient. The above dosages are, of course only exemplary of the average case and there may be instances where higher or lower doses are merited and such are within the scope of the invention.

Another way of expressing the dosage level in accordance with the present invention is as mg/kg bodyweight. Accordingly, for administration to human patients the dosage levels of the compounds in accordance with the present invention, or pharmaceutically acceptable salts, solvates, or prodrugs thereof, will be in a range from about 0.01 to about 15 mg/kg bodyweight, such as for example from about 0.01 to about 10 mg/kg bodyweight, about 0.05 to about 10 mg/kg bodyweight, 0.05 to 5 mg/kg bodyweight or 0.1 to 2.5 mg/kg bodyweight.

In yet another way of expressing the dosage is as unit dosages. Such unit dosages may be administered one or more time during the day and is typically administered whenever the patient feels the need to be treated. In some embodiments the unit dosage of the compounds in accordance with the present invention will be in a range of from about 0.01 to about 0.2 mg/kg bodyweight, such as for example from about 0.01 to 0.10 mg/kg bodyweight, about 0.02 to 0.08 mg/kg bodyweight, about 0.03 to 0.07 mg/kg bodyweight or 0.04 to 0.06 mg/kg bodyweight. In another embodiment the dosage is 0.05 mg/kg bodyweight. The compounds for use in accordance with the present invention may be administered alone, or as part of a combination therapy. If a combination of active agents is administered, then it may be administered simultaneously, separately or sequentially. Depending on the disease and the state of the disease to be treated, it may be relevant to include one or more additional active compound in the medicament.

In various embodiments, the pharmaceutical compositions may have a drug loading, such that the active component comprises about 0.5-90 weight percent of the pharmaceutical composition, 1-50 weight percent of the pharmaceutical composition, 1-25 weight percent of the pharmaceutical composition, or 1-10 weight percent of the pharmaceutical composition. In various embodiments, the amount of active component is present in the pharmaceutical composition in a range from about 0.1% to about 40% by weight (including 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, and ranges between any two of these points, for instance, 0.5-5%, 5-10% and 10-20%, etc.).

In various embodiments, the pharmaceutical composition may comprise 0.1 µg, 0.2 µg, 0.3 µg, 0.4 µg, 0.5 µg, 0.6 µg, 0.7 µg, 0.8 µg, 0.9 µg, 1 µg, 10 µg, 20 µg, 30 µg, 40 µg, 50 µg, 60 µg, 70 µg, 80 µg, 90 µg, 0.1 mg, 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 30 mg, 35 mg, or 40 mg, 45 mg, or 50 mg of the active component.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration three times a day, twice a day, every day, every two days, every three days, every four days, every five days, every six days, a weekly basis, a monthly basis or any set number of days or weeks there-between. Alternatively, the methods of the invention can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

D. Combination Therapy

Treating pain and avoiding tolerance to pain killers are major issues in clinical medicine. One goal of current research is to find ways to improve the efficacy of pain relief, as well as prevent the development of tolerance or addiction, and reduce side effects. One way is by combining such traditional therapies with the therapies of the present invention. In the context of the present disclosure, it is contemplated that an α2δ-1 C-terminal domain mimetic could be used similarly in conjunction with one or more standard pain intervention treatments or epilepsy treatments.

The therapies could be provided in a combined amount effective to reduce pain in a subject, to reduce side effects associated with one or the other agent alone, or to avoid patient tolerance or addiction. This process may involve contacting the patient with the agents/therapies at the same time. This may be achieved by contacting the patient with a single composition or pharmacological formulation that includes both agents, or by administering two distinct compositions or formulations, at the same time, wherein one composition includes the α2δ-1 C-terminal domain mimetic and the other includes the standard pain intervention agent.

Alternatively, the treatment according to the present invention may precede or follow the other treatment by intervals ranging from minutes to weeks. In embodiments where the standard treatment and the α2δ-1 C-terminal domain mimetic are administered separately, one would generally ensure that a significant period of time did not expire between the times of each delivery, such that the therapies would still be able to exert an advantageously combined effect on the cell. In such instances, it is contemplated that one would administer both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

Non-limiting examples of other combination therapy include combination of one or more compounds of the invention with another anti-inflammatory agent, a chemotherapeutic agent, radiation therapy, an antidepressant, an antipsychotic agent, an anticonvulsant, a mood stabilizer, an anti-infective agent, an antihypertensive agent, a cholesterol-lowering agent or other modulator of blood lipids, an agent for promoting weight loss, an antithrombotic agent, an agent for treating or preventing cardiovascular events such as myocardial infarction or stroke, an antidiabetic agent, an agent for reducing transplant rejection or graft-versus-host disease, an anti-arthritic agent, an analgesic agent, an anti-asthmatic agent or other treatment for respiratory diseases, or an agent for treatment or prevention of skin disorders. Compounds of the invention may be combined with agents designed to improve a patient's immune response to cancer, including (but not limited to) cancer vaccines. See Lu et al. (2011), which is incorporated herein by reference.

Combination therapies for treating epileptic seizures could include anticonvulsants including barbiturates (e.g., phenobarbital, methylphenobarbital, and barbexaclone), benzodiazepines (e.g., clobazam, clonazepam, clorazepate, diazepam, midazolam, or lorazepam), bromide (e.g., potassium bromide), carbamate (e.g., felbamate), or carboxamide (e.g., carbamazepine, oxcarbezapine, and eslicarbezepne acetate).

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Inhibition of α2δ-1-Mediated Pain

Figures 8A, 8B:
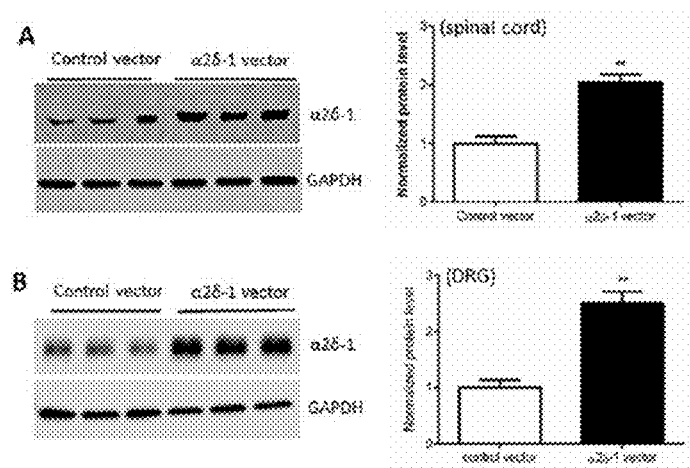
FIGS. 8A-8B: Effect of expressing Cacna2d1 on α2δ-1 expression levels in the spinal cord and DRG tissues in naive rats. (A,B) Original gel images and mean changes in the protein level of α2δ-1 (~140 kDa) in the dorsal spinal cord (A) and DRG (B) tissues of naive rats 5 weeks after intrathecal injection of the wild-type Cacna2d1 vector or control vector (n=6 rats in each group). GAPDH was used as an internal control. Data are means±s.e.m. **P<0.01 (versus control vector-treated rats). Two-tailed Student's t-test.

Cacna2d1 Overexpression Causes NMDAR-Mediated Pain Hypersensitivity: To study the relationship between α2δ-1 and NMDARs, it was first determined whether Cacna2d1 overexpression at the spinal cord level increased NMDAR activity in spinal dorsal horn neurons. Intrathecal injection of lentiviral vectors was used, which effectively induce transgene expression in both spinal cord and DRG neurons (Li et al., 2016). Transfection with lentiviral vectors expressing GFP-Cacna2d1 significantly increased α2δ-1 protein levels in the DRG and dorsal spinal cord in rats (FIGS. 8A and 8B). Cacna2d1 overexpression caused long-lasting tactile allodynia and mechanical and thermal hyperalgesia, whereas injection of lentiviral vectors expressing GFP alone had no effect (FIG. 1A). The pain hypersensitivity induced by Cacna2d1 overexpression was readily reversed by intrathecal injection of (2R)-amino-5-phosphonopentanoate (AP5), a specific NMDAR antagonist, or systemic injection of memantine, a clinically used NMDAR antagonist (FIGS. 1B and 1C).

Figures 2A, 2B, 2C, 2D, 2E, 2F:
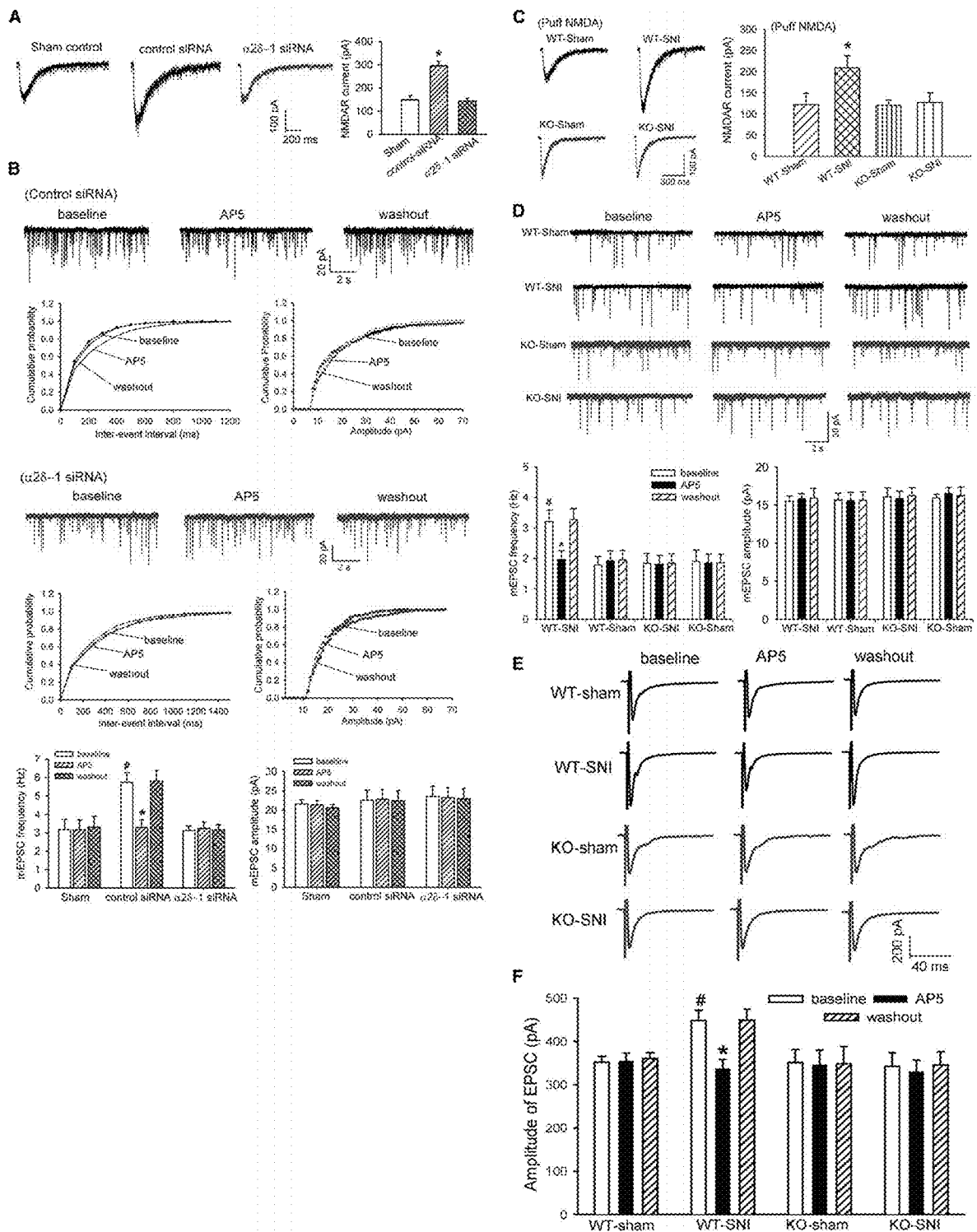
FIGS. 2A-2F: α2δ-1 Contributes to Increased Pre- and Postsynaptic NMDAR Activity of Spinal Dorsal Horn Neurons after Nerve Injury. (A) Representative recording traces and mean changes of NMDAR currents elicited by puff application of 100 mM NMDA to spinal dorsal horn neurons of sham control rats (n=11 neurons) and SNL rats injected with control siRNA (n=12 neurons) or Cacna2d1-specific siRNA (n=12 neurons). Data are expressed as means±SEM. *$p<0.05$ (versus sham group), one-way ANOVA followed by Tukey's post hoc test. (B) Original traces, cumulative plots, and mean changes in the baseline frequency and amplitude of mEPSCs and the AP5 effect in spinal dorsal horn neurons recorded from sham control rats (n=14 neurons) and SNL rats receiving control siRNA (n=13 neurons) or Cacna2d1-specific siRNA (n=12 neurons) before (baseline), with (AP5), and after (washout) bath application of 50 mM AP5. Data are expressed as means±SEM. *$p<0.05$ (versus baseline); #$p<0.05$ (versus baseline in sham group), one-way ANOVA followed by Tukey's post hoc test. (C) Original current traces and mean changes in NMDAR currents elicited by puff application of 100 mM NMDA to spinal dorsal horn neurons in wild-type (WT; n=12 neurons in each group) and Cacna2d1 KO (n=11 neurons in each group) mice 3 weeks after spared nerve injury (SNI) or sham surgery. Data are expressed as means±SEM. *$p<0.05$ (versus WT sham group), one-way ANOVA followed by Tukey's post hoc test. (D) Representative traces and mean changes in baseline values and the AP5 effect on the frequency and amplitude of mEPSCs of spinal dorsal horn neurons in wild-type (WT; n=11 neurons in each group) and Cacna2d1 KO (n=12 neurons in each group) mice subjected to spared nerve injury (SNI) or sham surgery. Data are expressed as means±SEM. *p<0.05 (versus baseline); #p<0.05 (versus baseline in the WT sham group), one-way ANOVA followed by Tukey's post hoc test. (E and F) Representative traces (E) and mean changes (F) in baseline values and the AP5 effect on the amplitude of EPSCs of spinal dorsal horn neurons monosynaptically evoked by dorsal root stimulation in wild-type (WT) and Cacna2d1 KO mice subjected to spared nerve injury (SNI; n=11 neurons in each group) or sham surgery (n=12 neurons in each group). Data are expressed as means±SEM. *p<0.05 (versus baseline); #p<0.05 (versus baseline in the WT sham group); one-way ANOVA followed by Tukey's post hoc test.
Figures 9A, 9B, 9C, 9D:
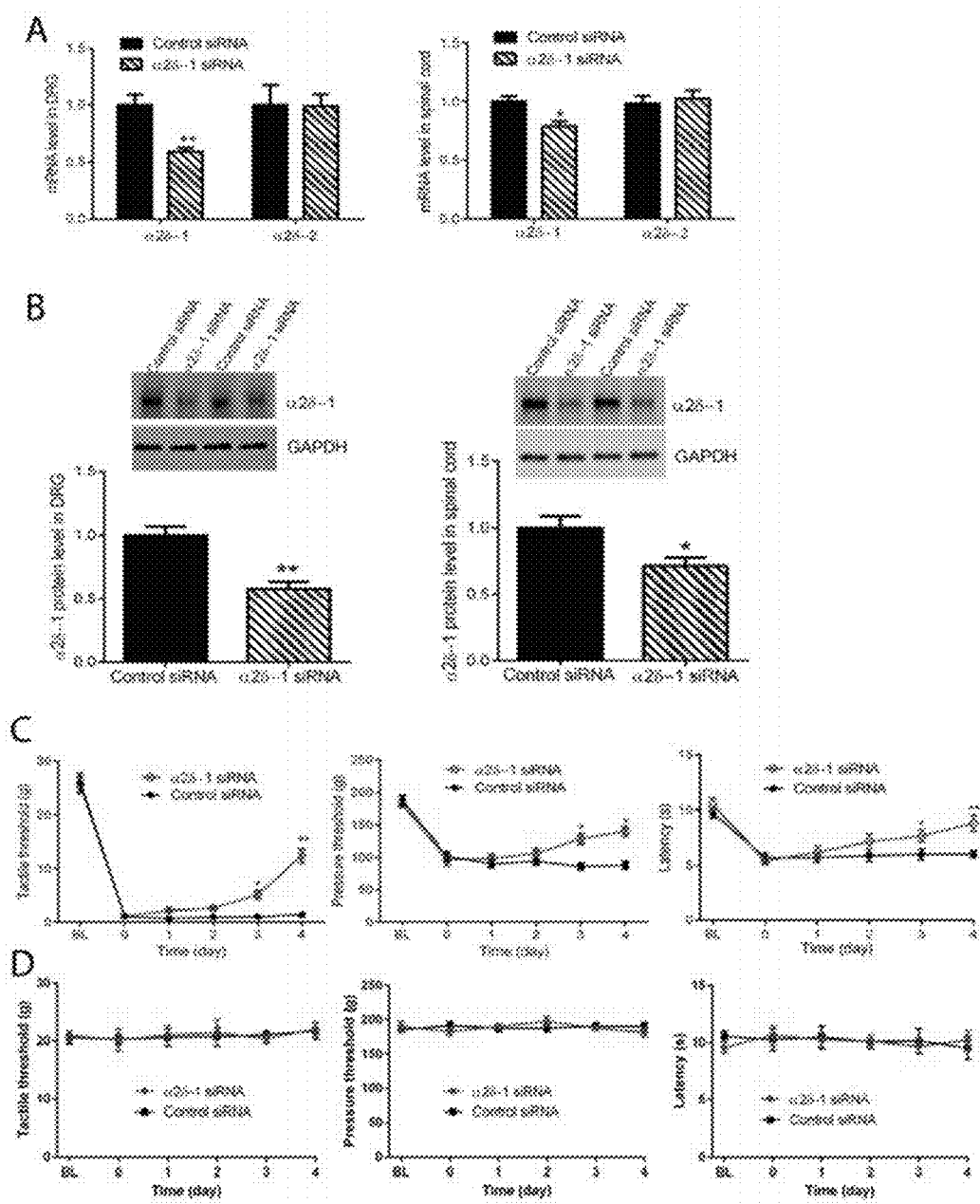
FIGS. 9A-9D: Intrathecal injection of Cacna2d1-specific siRNA reduces the α2δ-1 expression level in the spinal cord and DRG and pain hypersensitivity induced by nerve injury. (A) Differential effects of Cacna2d1-specific siRNA (4 Fg/day for 4 days) on the mRNA level of α2δ-1 and α2δ-2 in the DRG and dorsal spinal cord (n=6 rats in each group). Data are presented as means±s.e.m. *P<0.05, **P<0.01 (versus control siRNA-treated rats). Two-tailed Student's t-test. (B) Western blot analysis and quantification of the α2δ-1 protein level in the DRG and dorsal spinal cord (n=6 rats in each group). GAPDH was used as an internal control. Data are means±s.e.m. *P<0.05, **P<0.01 (versus control siRNA-treated rats). Two-tailed Student's t-test. (C) Effects of intrathecal treatment with control siRNA or Cacna2d1-specific siRNA (4 Fg/day for 4 days) on the tactile, pressure and heat withdrawal thresholds of SNL rats (n=8 rats in each group). Data are means±s.e.m. *P<0.05, **P<0.01 (versus baseline, BL). One-way ANOVA analysis followed by Dunnett's post hoc test. (D) No significant effects were observed for intrathecal treatment with control siRNA or Cacna2d1-specific siRNA (4 Fg/day for 4 days) on the tactile, pressure and heat withdrawal thresholds of naive control rats (n=8 rats in each group).

The first sensory synapse formed by central terminals of primary afferent neurons and spinal dorsal horn neurons is critically involved in nociceptive transmission and regulation. Electrophysiological recordings in spinal cord slices showed that Cacna2d1 overexpression significantly increased postsynaptic NMDAR currents elicited by puff application of NMDA to the recorded neuron (FIG. 1D). Cacna2d1 overexpression also significantly potentiated presynaptic NMDAR activity, as reflected by the increase in the AP5-sensitive frequency of miniature excitatory postsynaptic currents (mEPSCs) of dorsal horn neurons (Chen et al., 2014a; Li et al., 2016) (FIGS. 1E and 1F). The increase in the mEPSC frequency induced by Cacna2d1 overexpression was normalized by AP5 application within 5 min; therefore, the excitatory synaptic transmission potentiated by α2δ-1 is fully maintained by NMDARs. These data indicate that increased α2δ-1 expression at the spinal cord level augments pre- and postsynaptic NMDAR activity and leads to NMDAR-mediated pain hypersensitivity.

α2δ-1 Is Essential for Increased Pre- and Postsynaptic NMDAR Activity in Neuropathic Pain: Intrathecally injected small interfering RNA (siRNA) (Laumet et al., 2015) was used to assess the contribution of α2δ-1 to the increased spinal NMDAR activity in rats that have undergone spinal nerve ligation (SNL), a commonly used animal model of neuropathic pain. Intrathecal injection of Cacna2d1-specific siRNA reduced the expression level of α2δ-1, but not α2δ-2, in the DRG and dorsal spinal cord and reduced pain hypersensitivity in SNL rats (FIG. 9A-C). Treatment with Cacna2d1-specific siRNA had no effect on the withdrawal thresholds in naive control rats (FIG. 9D). Remarkably, treatment with Cacna2d1-specific siRNA completely normalized SNL-induced increases in puff NMDA currents and the baseline frequency of the mEPSCs of dorsal horn neurons (FIGS. 2A and 2B).

Figures 3A, 3B, 3C, 3D, 3E, 3F, 3G, 3H, 3I:
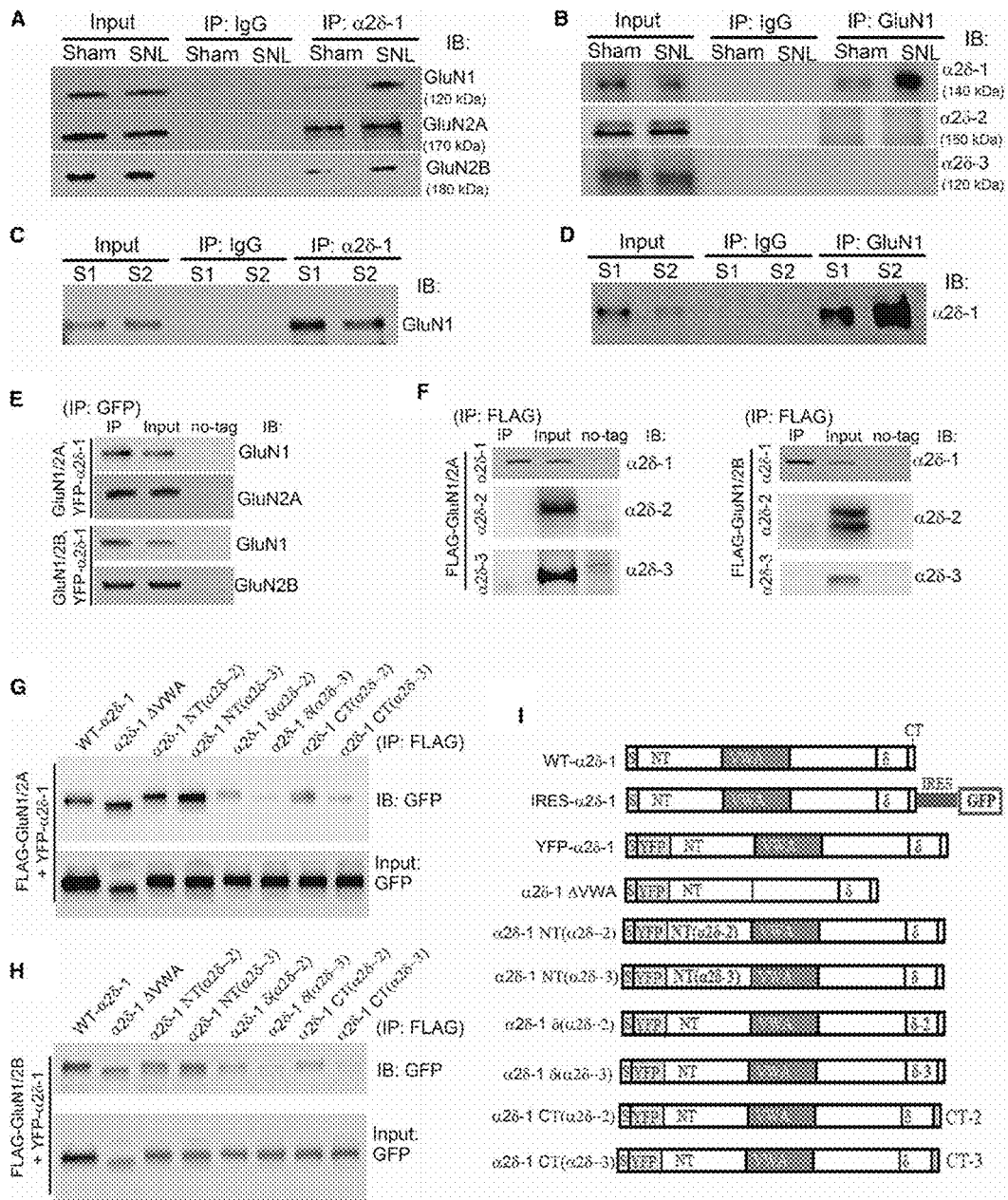
FIGS. 3A-3I: α2δ-1 Physically Interacts with NMDARs In Vivo and In Vitro. (A and B) Reciprocal coimmunoprecipitation analysis shows the protein-protein interaction between α2δ-1 and NMDAR subunits in the membrane extracts of dorsal spinal cord tissues of rats from the sham control and SNL groups 3 weeks after surgery. (A) Proteins were immunoprecipitated first with a rabbit anti-α2δ-1 or anti-IgG antibody. Western immunoblotting (IB) was performed by using mouse anti-GluN1, anti-GluN2A, or anti-GluN2B antibodies. (B) Proteins were immunoprecipitated initially with a mouse anti-GluN1 or anti-IgG antibody. IB was performed by using a rabbit anti-α2δ-1, anti-α2δ-2, or anti-α2δ-3 antibody. IgG and input (tissue lysates only, without immunoprecipitation) were used as negative and positive controls, respectively. Similar data were obtained from 4 independent experiments. (C and D) Reciprocal coimmunoprecipitation analysis shows the α2δ-1 and GluN1 interaction in the membrane extracts of two human lumbar spinal cord tissue samples (labeled as S1 and S2). (C) Proteins were immunoprecipitated first with a rabbit anti-α2δ-1 or anti-IgG antibody. Western immunoblotting (IB) was performed by using a mouse anti-GluN1 antibody. (D) Proteins were immunoprecipitated initially with a mouse anti-GluN1 or anti-IgG antibody. IB was performed by using a rabbit anti-α2δ-1 antibody. Similar data were obtained from spinal cord tissues of each of the 4 human donors. (E and F) Coimmunoprecipitation analysis shows that α2δ-1 heterodimerized with NMDAR subunits in membrane extracts of HEK293 cells. HEK293 cells were cotransfected as indicated on the left side of the gel images. (E) GluN1/GluN2A/YFP-α2δ-1 (top images) or GluN1/GluN2B/YFP-α2δ-1 (bottom images). (F) FLAG-GluN1/GluN2A (left) or FLAG-GluN1/GluN2B (right) with a2d-1, a2d-2, or a2d-3. IRES-α2δ-1 (no-tag) was used as a negative control for YFP-α2δ-1 in (E), and untagged GluN1 (no-tag) was used as a negative control for FLAG-GluN1 in (F). Proteins were immunoprecipitated first with anti-GFP (E) or anti-FLAG antibody (F) using membrane fractions of HEK293 cells. IB was performed by using the antibodies indicated on the right side of the gel images. Data were from 5 independent experiments. (G and H) α2δ-1 interacts with NMDARs predominantly through its C-terminal domain. Coimmunoprecipitation analysis of FLAG-GluN1/GluN2A (G) and FLAG-GluN1/GluN2B (H) interactions with various YFP-tagged α2δ-1 constructs, indicated above the gel images, coexpressed in HEK293 cells. Coimmuno-precipitation and IB were performed using the antibodies indicated on the right side of the gel images. Data were from 5 independent experiments. (I) Schematic representation of α2δ-1 constructs and chimeras used for coexpression with NMDAR subunits in HEK293 cells. S, signal peptide; NT, putative N terminus; VWA, von Willebrand factor type-A domain; d, d peptide; CT, C-terminal domain. All α2δ-1 constructs and chimeras used for coimmunoprecipitation experiments were tagged with yellow fluorescent protein (YFP).

To confirm that α2δ-1 plays a role in the increased NMDAR activity observed in neuropathic pain, Cacna2d1 knockout (KO; Cacna2d1$_{-/-}$) mice were used, which show reduced pain hypersensitivity after nerve injury (Patel et al., 2013). Peripheral nerve injury markedly increased the amplitude of puff NMDA currents and the NMDAR-mediated frequency of mEPSCs of spinal dorsal horn neurons in wild-type (Cacna2d1$_{+/+}$) mice. Also, nerve injury significantly increased the amplitude of monosynaptic EPSCs evoked by dorsal root stimulation in spinal dorsal horn neurons in Cacna2d1$_{+/+}$ mice, which was readily normalized after bath application of AP5 (FIG. 2C-2F). These data suggest that nerve injury causes tonic activation of presynaptic NMDARs expressed at primary afferent terminals, as shown previously (Li et al., 2016). These increases in pre- and postsynaptic NMDAR activity were abrogated in Cacna2d1$_{-/-}$ mice (FIG. 2C-2F). Collectively, these findings strongly indicate that α2δ-1 is essential for the nerve injury-induced increase in synaptic NMDAR activity at the spinal cord level.

α2δ-1 Physically Interacts with NMDARs In Vitro and In Vivo: The functional link between α2δ-1 and NMDAR activity in neuropathic pain prompted us to examine whether α2δ-1 and NMDARs physically interact. To determine the interaction between α2δ-1 and NMDARs in vivo, coimmunoprecipitation (co-IP) analyses were conducted using membrane extracts of dorsal spinal cords obtained from SNL and sham control rats. An anti-α2δ-1 antibody coprecipitated the NMDAR subunits GluN1, GluN2A, and GluN2B in spinal membrane fractions (FIG. 3A). The α2δ-1-GluN1 protein complex in the dorsal spinal cord was much higher (97.3±8.3%) in SNL rats than in sham controls. Similarly, reciprocal coimmunoprecipitation showed that α2δ-1 was precipitated by an anti-GluN1 antibody but not by an irrelevant rabbit anti-immunoglobulin G (anti-IgG) antibody (FIG. 3B). SNL caused a large increase in the GluN1-α2δ-1 complex in the spinal cord (by 116.0±10.3%). Although α2δ-2 and α2δ-3 proteins were also present in rat spinal cords, they did not coimmunoprecipitate with GluN1 (FIG. 3B). In addition, using membrane extracts from spinal cord tissues of human donors, it was demonstrated that anti-α2δ-1, but not anti-IgG, antibody coimmunoprecipitated with GluN1 and vice versa (FIGS. 3C and 3D).

Figure 10:
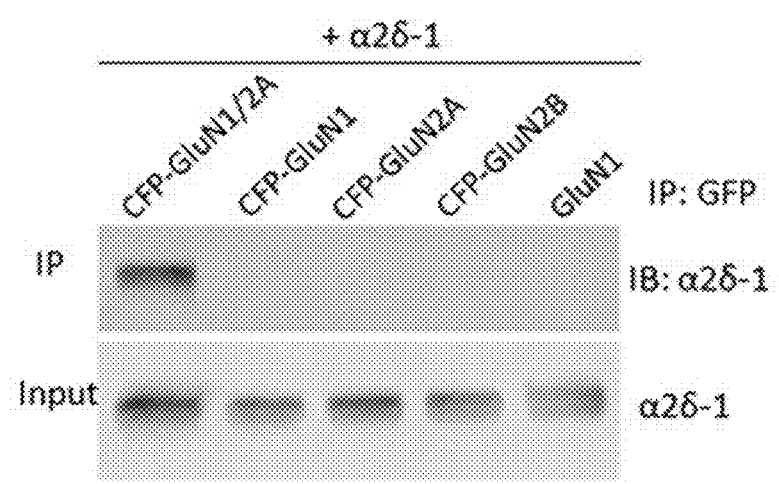
FIG. 10: Co-IP analysis using membrane extracts of HEK293 cells show that α2δ-1 does not interact with GluN1, GluN2A or GluN2B when these subunits are expressed individually with α2δ-1. HEK293 cells were cotransfected with α2δ-1 and individual CFP-tagged NMDAR subunit constructs as indicated above the gel images. Co-IP was performed using an anti-GFP antibody, which cross-reacts with CFP. Immunoblotting (IB) was performed using an anti-α2δ-1 antibody. Data were from three independent experiments.

Coimmunoprecipitation was performed using membrane extracts of HEK293 cells expressing yellow fluorescent protein (YFP)-tagged α2δ-1 together with either GluN1 plus GluN2A or GluN1 plus GluN2B. GluN1, GluN2A, and GluN2B, when coexpressed with YFP-a2d-1, were all precipitated by an anti-GFP antibody (FIG. 3E). Conversely, precipitation with an anti-FLAG antibody identified a protein band corresponding to α2δ-1 in cells coexpressing either FLAG-GluN1 and GluN2A or FLAG-GluN1 and GluN2B (FIG. 3F). This physical interaction is specific to α2δ-1, because neither α2δ-3 nor α2δ-3 coprecipitated (FIG. 3F). However, α2δ-1 did not precipitate GluN1, GluN2A, or GluN2B on the membrane surface when these NMDAR subunits were expressed individually with α2δ-1 in HEK293 cells (FIG. 10). These results demonstrate that α2δ-1 and NMDAR subunits form a heteromeric complex on the plasma membrane and that physical interactions between α2δ-1 and NMDARs occur both in vitro and in vivo.

α2δ-1 Interacts with NMDARs Primarily via Its C-Terminal Domain: It was next attempted to identify the molecular determinants of the α2δ-1-NMDAR interaction. The large a2 protein is entirely extracellular, whereas the d part has a C-terminal domain that anchors α2δ-1 to the membrane (Davies et al., 2007; Dolphin, 2013). Although the C terminus of α2δ-1 is predicted to be a transmembrane region, its structure has not been resolved by cryo-electron microscopy (Wu et al., 2016). Furthermore, one study suggests that α2δ-1 is a GPI-anchored protein (Davies et al., 2007). However, a subsequent study has disputed the presence of any glycophosphatidylinositol (GPI) motifs in α2δ-1 (Robinson et al., 2011). The highly conserved von Willebrand factor type-A (VWA) domain in α2δ-1 is required for its interaction with VACCs or thrombospondin (Eroglu et al., 2009; Hoppa et al., 2012), and the region just upstream of the VWA domain on the N terminus in a2 is required for gabapentin binding (Field et al., 2006; Wang et al., 1999). The VWA domain was deleted and the truncated α2δ-1 (α2δ-1 DVWA) was expressed with FLAG-GluN1 and GluN2A or with FLAG-GluN1 and GluN2B in HEK293 cells. Surprisingly, deleting the VWA domain did not affect coprecipitation of α2δ-1 and GluN1 in membrane extracts (FIGS. 3G and 3H). Because α2δ-2 and α2δ-3 do not interact with NMDARs, chimeras were created by swapping the N terminus of α2δ-1 with that of a2d-2 or a2d-3 (termed a2d-1NT(α2δ-2) and a2d-1NT(α2δ-3), respectively) (FIG. 3I). YFP-a2d-1NT(a2d-2) or YFP-a2d-1NT(α2δ-3) was coexpressed with FLAG-GluN1/GluN2A or FLAG-GluN1/GluN2B in HEK293 cells. Coimmunoprecipitation analysis showed that the anti-FLAG antibody still precipitated a2d-1NT(α2δ-2) or a2d-1NT(a2d-3) similarly to wild-type α2δ-1 (FIGS. 3G and 3H).

Having found that neither the VWA domain nor the N terminus of α2δ-1 is essential for the interaction of α2δ-1 with NMDARs, it was investigated whether the d sequence and C terminus domain are required for a2d-1-NMDAR interaction. Chimeras by replacing the d sequence or C terminus of α2δ-1 with those of a2d-2 and a2d-3 (a2d-1d (a2d-2) and a2d-1d(a2d-3) or a2d-1CT(a2d-2) and a2d-1CT (a2d-3), respectively) (FIG. 3I). These chimeras were expressed individually with GluN1/GluN2A or GluN1/GluN2B in HEK293 cells. Coimmunoprecipitation using cell-membrane extracts showed that substituting the d sequence or C terminus of α2δ-1 with that of a2d-2 markedly reduced coprecipitation of α2δ-1 and NMDARs, whereas replacing the d sequence or C terminus of α2δ-1 with that of a2d-3 nearly abolished a2d-1-NMDAR coupling (FIGS. 3G and 3H). These findings demonstrate that α2δ-1 interaction with NMDARs predominantly requires the C-terminal, but not VWA, domain of a2d-1.

Figures 4A, 4B, 4C, 4D, 4E:
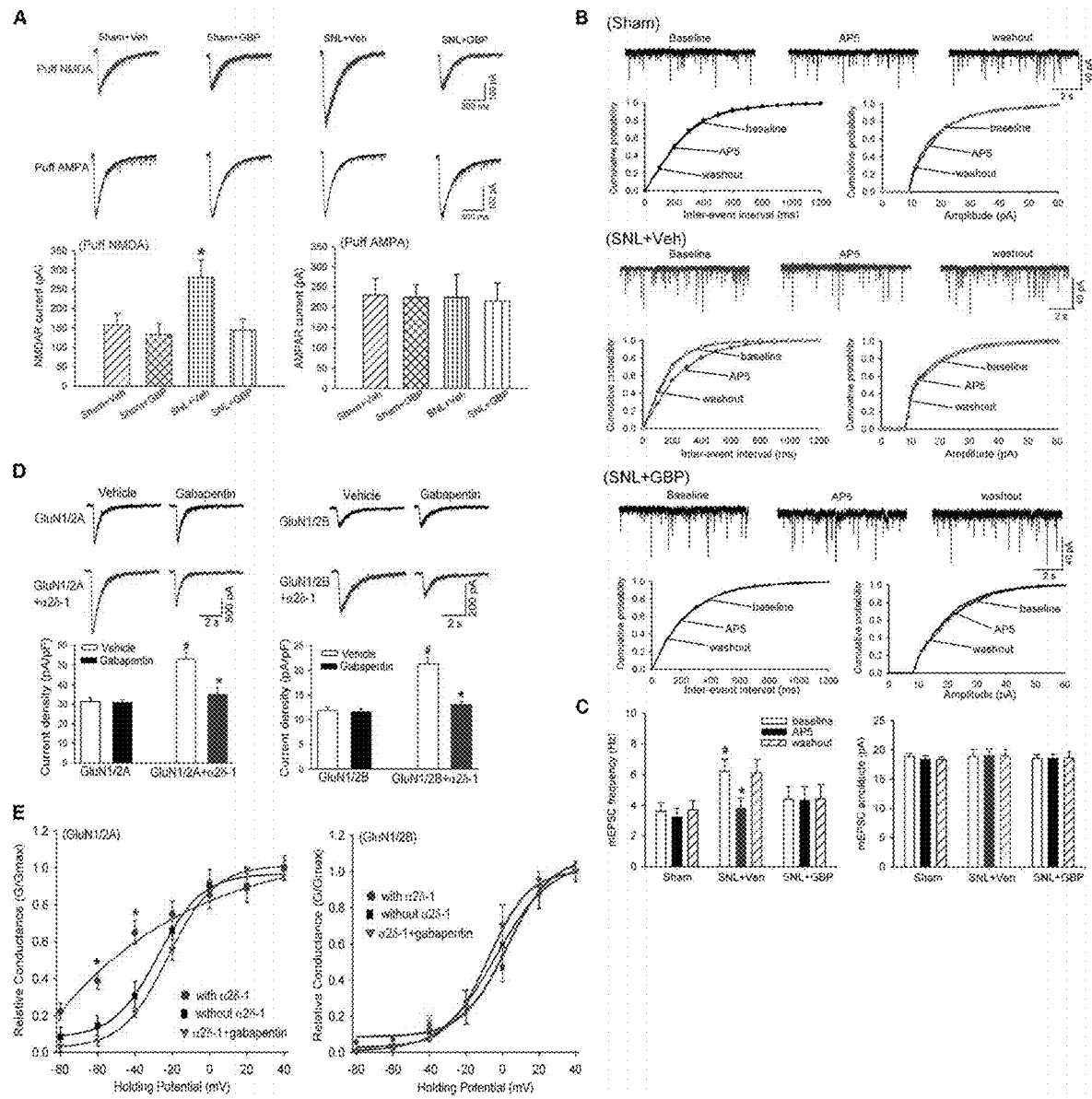
FIGS. 4A-4E: Gabapentin Restores NMDAR Activity Increased by Nerve Injury or α2δ-1 Coexpression In Vivo and In Vitro. (A) Original traces and mean effects of gabapentin (GBP; 100 mM for 30 min) on currents elicited by puff application of 100 mM NMDA or AMPA to spinal dorsal horn neurons in rats that had undergone sham surgery (n=12 neurons in the vehicle group; n=13 neurons in the gabapentin group) or SNL (n=11 neurons in the vehicle group; n=12 neurons in gabapentin group) 3 weeks after surgery. Data are expressed as means±SEM. *p<0.05 (versus sham rats treated with vehicle), one-way ANOVA followed by Tukey's post hoc test. (B and C) Representative traces and cumulative probabilities (B) and mean changes (C) of baseline values and the AP5 effect on the frequency and amplitude of mEPSCs of spinal dorsal neurons recorded from rats subjected to sham surgery (n=10 neurons) or SNL (n=12 neurons in the vehicle group; n=11 neurons in the gabapentin group). Data are expressed as means±SEM. *p<0.05 (versus respective baseline); #p<0.05, compared with the baseline in sham group, one-way ANOVA followed by Tukey's post hoc test. (D-E) Original traces and mean changes show the effect of α2δ-1 coexpression and gabapentin treatment (100 mM for 30 min) on whole-cell NMDAR currents in HEK293 cells expressing GluN1/GluN2A (n=10 cells in each group) or GluN1/GluN2B (n=12 cells in each group). Current responses were elicited by application of 300 mM NMDA plus 10 mM glycine. Data are expressed as means±SEM. *p<0.05 (versus respective vehicle control); #p <0.05, compared with the current reconstituted with GluN1/GluN2A or GluN1/GluN2B alone, one-way ANOVA followed by Tukey's post hoc test.
Figures 11A, 11B:
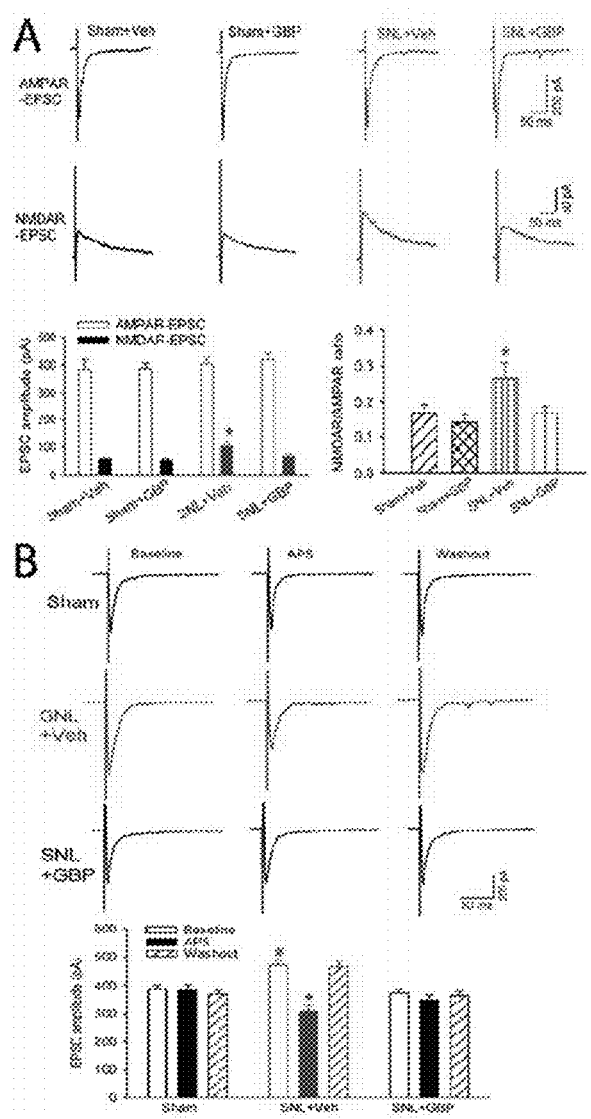
FIGS. 11A-11B: Gabapentin treatment normalizes nerve injury-induced increases in synaptic NMDAR activity of spinal dorsal horn neurons. (A) Representative recordings and mean changes of the amplitude of evoked NMDAR-EPSCs, AMPAR-EPSCs and ratio of NMDAR-EPSCs to AMPAR-EPSCs of spinal dorsal horn neurons in sham (n=10 neurons in the vehicle group, n=11 neurons in the gabapentin [GBP] group) and SNL (n=10 neurons in vehicle group, n=12 neurons in the gabapentin group) rat spinal cord slices treated with vehicle or 100 FM gabapentin for 30 min. Data are means±s.e.m. *P<0.05 (versus corresponding value in the sham+vehicle group). One-way ANOVA analysis followed by Tukey's post hoc test. (B) Original traces and mean data show the AP5 effect on the amplitude of EPSCs of spinal dorsal horn neurons monosynaptically evoked by dorsal root stimulation in sham (n=12 neurons) and SNL (n=12 neurons in the vehicle group, n=11 neurons in the gabapentin group) rat spinal cord slices treated with vehicle or gabapentin. Data are means±s.e.m. *P<0.05 (versus respective baseline). #P<0.05 (versus baseline in the sham group). One-way ANOVA analysis followed by Tukey's post hoc test.

Gabapentin Selectively Targets a2d-1-Bound NMDARs and Their Surface Expression: Gabapentin binds to α2δ-1 (and to a2d-2 at a lower affinity) (Fuller-Bicer et al., 2009; Gee et al., 1996; Marais et al., 2001; Wang et al., 1999). Because α2δ-1 directly interacts with NMDARs, it was investigated whether gabapentin might block the increase in dorsal horn neuron NMDAR activity that results from nerve injury. Gabapentin treatment (100 mM for 30 min) normalized the amplitude of puff NMDA currents and the NMDAR-mediated mEPSC frequency that had been potentiated by SNL (FIG. 4A-4C). Also, gabapentin reversed SNL-induced increases in the amplitude of NMDAR-mediated EPSCs and the ratio of NMDAR EPSCs to a-amino-3-hydroxy-5-methyl-4-isoxazole-propionic acid receptor (AMPAR) EPSCs monosynaptically evoked by dorsal root stimulation (Chen et al., 2014a; Li et al., 2016) (FIG. 11).

Figures 12A, 12B, 12C, 12D, 12E:
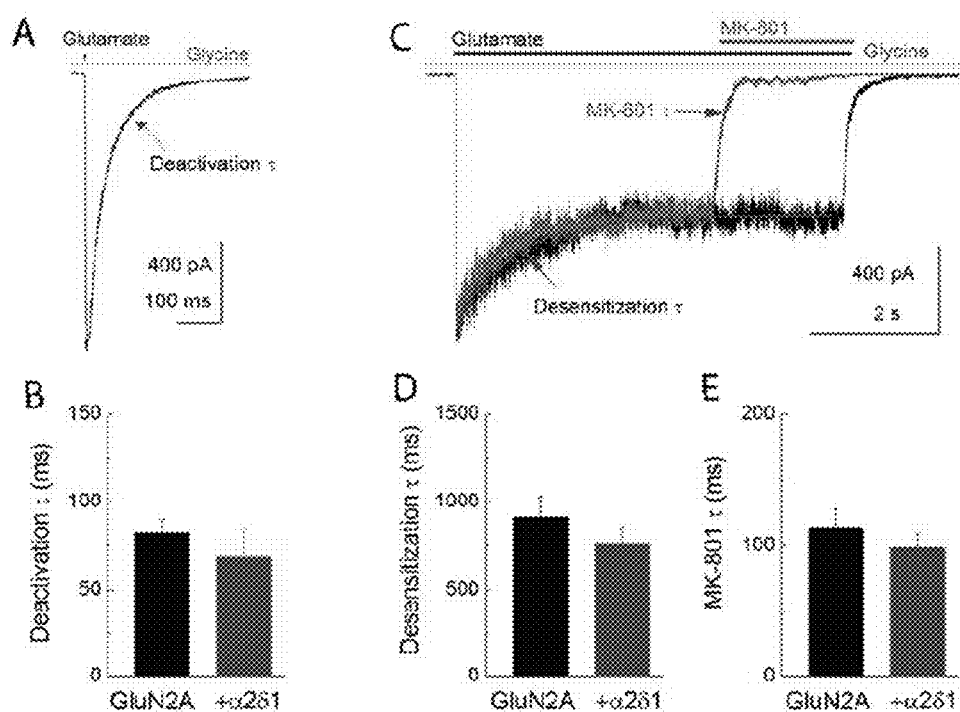
FIGS. 12A-12E: Biophysical properties of NMDARs are not altered by α2δ-1 coexpression. (A) Response from an outside-out patch transfected with GluN1/GluN2A alone (black) or GluN1/GluN2A plus α2δ-1 (red) to a 1-ms 1-mM glutamate jump (deactivation) in the continual presence of 100 FM glycine. (B) Summary of deactivation time constants from all patches transfected with either GluN1/GluN2A alone (black, n=13 cells) or GluN1/GluN2A plus α2δ-1 (red, n=12). (C) Responses from the same patch as panel a to either a 6-s 1 mM glutamate jump (desensitization) or 4 s of glutamate followed by 2 s of glutamate plus MK-801 (300 nM, green trace) in the continual presence of 100 FM glycine. (D) Summary of weighted desensitization from all patches transfected with either GluN1/GluN2A alone (black, n=14) or GluN1/GluN2A plus α2δ-1 (n=10). (E) Summary of MK-801 time constants from all patches transfected with either GluN1/GluN2A alone (black, n=12) or GluN1/GluN2A plus α2δ-1 (n=10). Data are means±s.e.m. (B, D and E, two-tailed Student's t-test).
Figure 13:
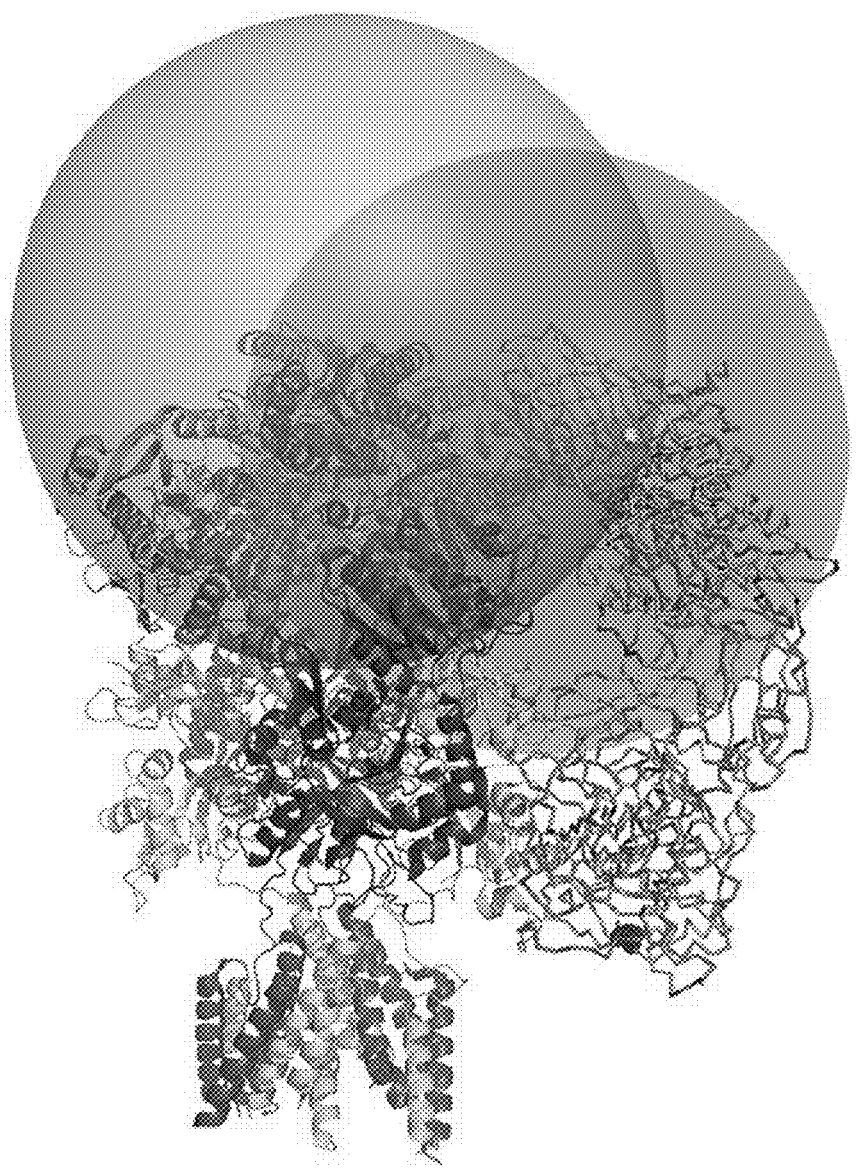
FIG. 13: LRET nanopositioning system-based model of α2δ-1-NMDAR interaction. The LRET-determined distances to the acceptor fluorophore [59 C for site 30 on GluN2A and 57 C for site 20 on GluN1] were used to generate the spheres: blue for GluN2A and green for GluN1. The extracellular domains of the α2δ-1 and NMDAR structures were moved to place the YFP fluorophore tagged to α2δ-1 at the plane of intersection of the LRET radii spheres with the additional constraint of having Cys1071 of the extracellular domain of α2δ-1 near the membrane. There is currently no structural information for the transmembrane C-terminus (residues beyond 1071) of α2δ-1.

It was then determined whether α2δ-1 and gabapentin affect NMDAR currents reconstituted in a heterologous expression system. In HEK293 cells expressing GluN1/GluN2A or GluN1/GluN2B diheteromers, cotransfection with α2δ-1 markedly increased the NMDAR current density (FIG. 4D) but had no effect on the deactivation, desensitization, or apparent open probability of NMDARs (FIG. 12). Remarkably, gabapentin (100 mM for 30 min) completely reversed the α2δ-1 co-expression-induced increase in the NMDAR current density but had no effect on NMDAR currents in cells expressing GluN1/GluN2A or GluN1/GluN2B alone (FIG. 4D). α2δ-1 co-expression also reduced the voltage-dependent Mg2+ block of NMDARs reconstituted with GluN1/GluN2A at −40 and −60 mV, and gabapentin treatment reversed this effect (FIG. 4E). However, α2δ-1 coexpression did not alter the voltage-dependent Mg2+ block of NMDARs containing GluN1/GluN2B. These data indicate that the interaction of α2δ-1 and NMDARs is a prerequisite for the effect of gabapentin on NMDAR activity.

Luminescence resonance energy transfer (LRET) was used (Sirrieh et al., 2013) to assess α2δ-1-NMDAR interaction on the plasma membrane and the gabapentin effect in live HEK293 cells cotransfected with GluN1, terbium-labeled GluN2A, and YFP-α2δ-1. LRET between terbium-labeled GluN2A and YFP-α2δ-1 yielded a single-exponential decay, with a corresponding distance of 59.2±0.4 A° between YFP on the N terminus of α2δ-1 and terbium on the N terminus of GluN2A. Gabapentin treatment completely abrogated the LRET signal in cells transfected with wild-type α2δ-1 (FIG. 5A; Table 2). When the wild-type α2δ-1 was replaced with the R217A mutant, which diminishes the therapeutic effect of gabapentinoids (Field et al., 2006; Lotar-ski et al., 2014), gabapentin failed to alter the LRET signal (FIG. 5A; Table 2). Similar LRET findings were obtained for terbium-labeled GluN1 and YFP-α2δ-1 (FIG. 5B; Table 2). The LRET nanopositioning system-based model illustrates a close interaction between α2δ-1 and GluN1/GluN2A proteins (FIG. S6). These results demonstrate that α2δ-1 is in the proximity of NMDARs and that gabapentin diminishes the expression of a2d-1-bound NMDARs on the plasma membrane.

Figures 5A, 5B, 5C, 5D, 5E:
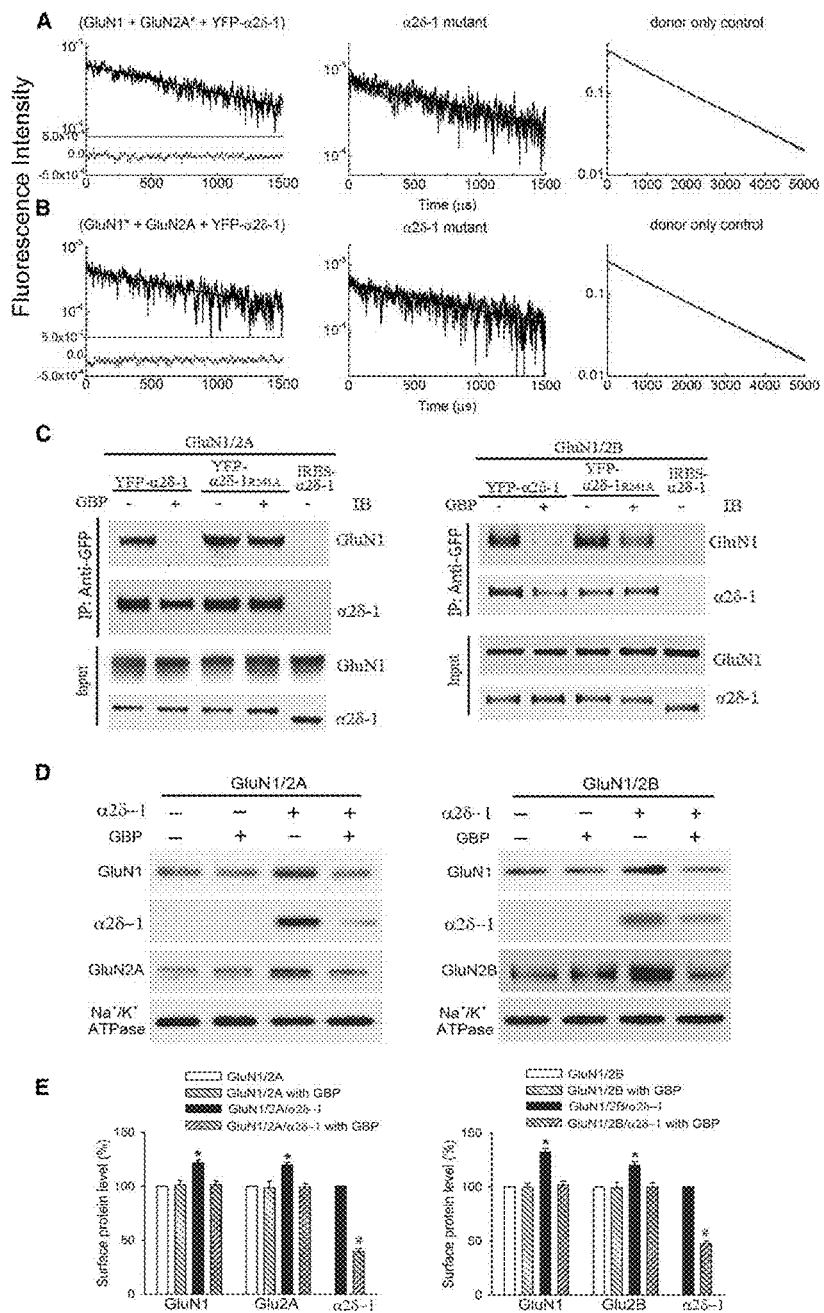
FIGS. 5A-5E: Gabapentin Diminishes Membrane Surface Expression of a2d-1-Bound NMDARs. (A) Luminescence resonance energy transfer (LRET) between terbium-labeled GluN2A (GluN2A*), GluN1, and YFP-a2d-1. Black curve: without gabapentin; red curve: with gabapentin. Left: LRET lifetime signals show that gabapentin resulted in loss of the LRET signal between terbium labeled-GluN2A* and YFP-α2δ-1 on the membrane. Middle: gabapentin had no effect on the LRET signal when YFP-α2δ-1 was replaced with its R217A mutant. Right: donor-only curves of terbium-labeled GluN2A* and unlabeled a2d-1. Data were from 4 or 5 independent experiments. (B) LRET between terbium-labeled GluN1 (GluN1*), GluN2A, and YFP-a2d-1. Black curves without gabapentin; red curve: with gabapentin. Left: LRET lifetime signals show that gabapentin diminished the interaction between terbium labeled-GluN1* and YFP-α2δ-1 on the membrane. Middle: gabapentin had no effect on the LRET signal when YFP-α2δ-1 was replaced with its R217A mutant. Right: donor-only curves of terbium-labeled GluN1* and unlabeled a2d-1. Data were from 4 or 5 independent experiments. (C) Coimmunoprecipitation and immunoblotting (IB) analysis shows that gabapentin (GBP; 100 mM for 30 min) diminished the expression of a2d-1-bound NMDARs in the membrane extract of HEK293 cells. Left: the GluN1/GluN2A heterodimer was cotransfected with YFP-a2d-1, a YFP-α2δ-1 mutant (R217A, also called R241A), or IRES-α2δ-1 (no tag) in HEK293 cells. Right: the GluN1/GluN2B heterodimer was cotransfected with YFP-a2d-1, a YFP-α2δ-1 mutant (R217A, also called R241A), or IRES-α2δ-1 (no tag) in HEK293 cells. Data were from four independent experiments. (D and E) Membrane surface protein analysis (D) and mean levels (E) show that gabapentin treatment reversed the α2δ-1 coexpression-induced increase in NMDAR surface expression. Immunoblotting was performed using antibodies against GluN1, GluN2A, GluN2B, and α2δ-1 for the membrane surface proteins isolated with biotinylation. HEK293 cells were cotransfected and treated with gabapentin or vehicle as indicated above the gel images. Na+/K+-ATPase, a known membrane protein marker, was used as an internal control. Data are expressed as means±SEM (n=5 independent experiments). *p<0.05 (versus GluN1/GluN2A or GluN1/GluN2B alone), one-way ANOVA followed by Tukey's post hoc test; #p<0.05 (versus GluN1/GluN2A/α2δ-1 or GluN1/GluN2B/α2δ-1 without gabapentin), two-tailed Student's t test.

To determine the gabapentin effect on a2d-1-bound NMDARs on the plasma membrane, HEK293 cells were transfected with YFP-α2δ-1 and GluN1/GluN2A or GluN1/GluN2B. Coimmunoprecipitation with membrane extracts revealed that gabapentin abolished the GluN1 band precipitated with anti-GFP antibody (FIG. 5C). When the YFP-R217A mutant was cotransfected, the anti-GFP antibody still effectively precipitated the GluN1 protein, but gabapentin failed to produce an effect (FIG. 5C). Biotinylation was used to label and isolate the membrane surface proteins of HEK293 cells (Li et al., 2014) expressing GluN1/GluN2A or GluN1/GluN2B heterodimers with or without α2δ-1. Coexpression with α2δ-1 markedly increased the amount of GluN1, GluN2A, and GluN2B proteins on the membrane surface (FIGS. 5D and 5E). Gabapentin (100 mM for 60 min) normalized the surface protein levels of GluN1, GluN2A, and GluN2B that had been increased by α2δ-1 coexpression (FIGS. 5D and 5E), indicating that gabapentin diminishes α2δ-1-bound NMDARs on the membrane surface. These convergent data support the notion that gabapentin inhibits surface trafficking of a2d-1-bound NMDARs.

Figures 14A, 14B, 14C, 14D:
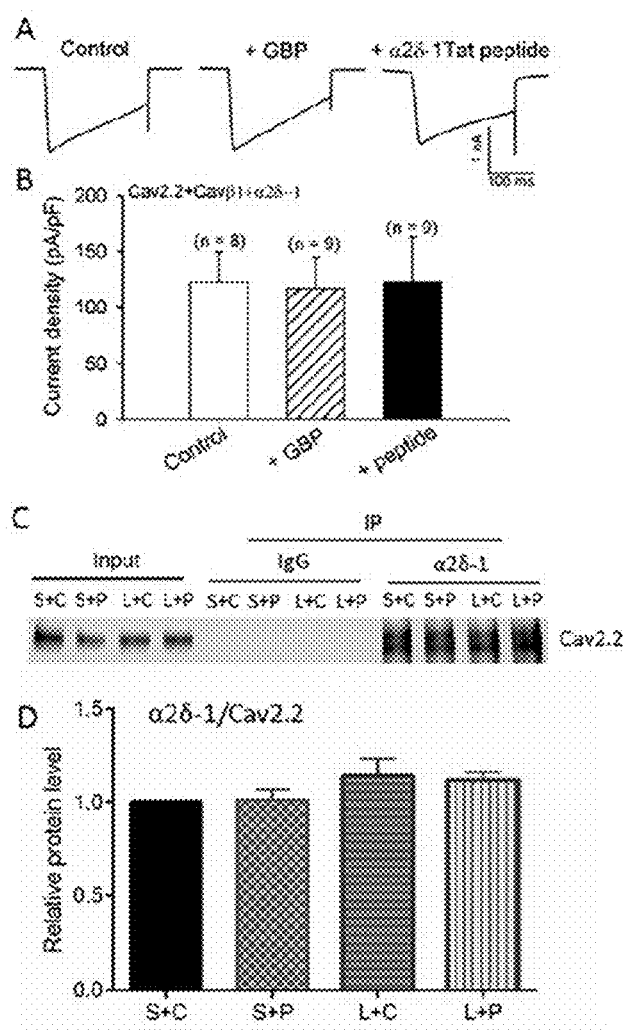
FIGS. 14A-14D: Treatment with gabapentin or α2δ-1Tat peptide does not affect VACC currents or the α2δ-1-Cav2.2 interaction. (A) Original current traces show the IBa of N-type Ca2+ channels reconstituted in HEK293 cells treated with vehicle, gabapentin (GBP, 100 FM) or α2δ-1Tat peptide (1 FM) for 60 min. Whole-cell IBa was elicited by a depolarizing pulse to 0 mV for 200 ms from a holding potential of −90 mV. (B) Mean data show no effect of GBP or α2δ-1Tat peptide on N-type Ca2+ channel currents in HEK293 cells. Data are means±s.e.m. The numbers of cells recorded in each group are indicated in parentheses (cells from 4 separate experiments). (C,D) Original gel images (C) and quantification data (D) show the lack of an effect of α2δ-1Tat peptide on the interaction between α2δ-1 and Cav2.2 in the spinal cord of SNL and sham rats (n=6 rats in each group). The dorsal spinal cord at the L5 and L6 level was removed 60 min after intrathecal injection of α2δ-1Tat peptide (1 μg) or control peptide (1 μg). Membrane proteins were immunoprecipitated first with a rabbit anti-α2δ-1 or anti-IgG antibody. Western immunoblotting was performed by using an anti-Cav2.2 antibody. S, sham; L, SNL; C, control peptide; P, α2δ-1Tat peptide. Data are means±s.e.m.
Figure 15:
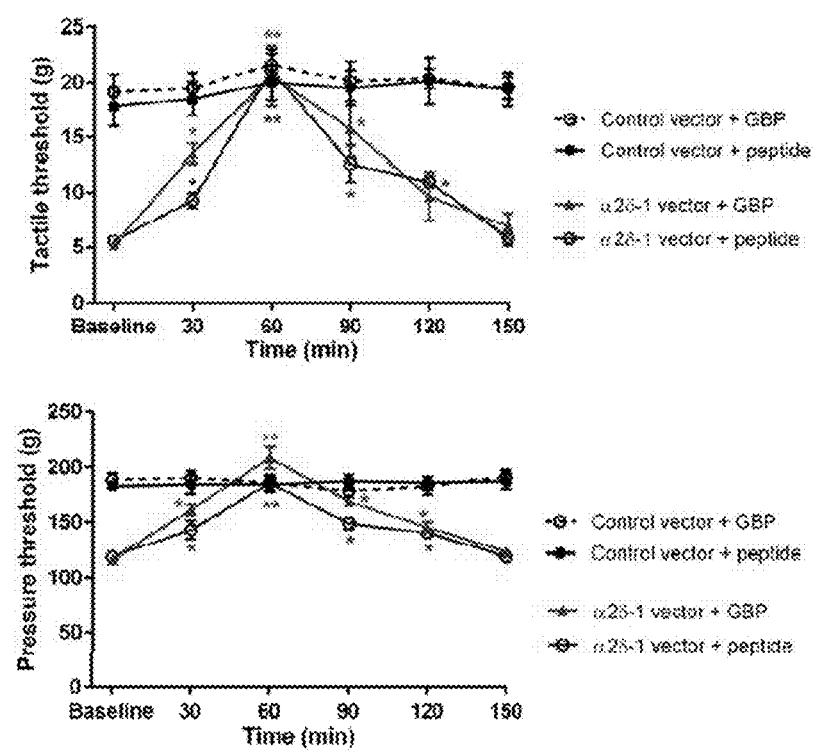
FIG. 15: Treatment with gabapentin or α2δ-1Tat peptide attenuates pain hypersensitivity induced by overexpression of Cacna2d1 in rats. Effects of a single intrathecal injection of α2δ-1Tat peptide (1 μg) or gabapentin (GBP, 30 μg) on the tactile (top) and pressure (bottom) withdrawal thresholds in rats treated with the Cacna2d1 vector or control vector (n=7 rats in each group). Data are means±s.e.m. *P<0.05, **P<0.01 (versus baseline before drug injection). One-way ANOVA analysis followed by Dunnett's post hoc test.
Figures 16A, 16B:
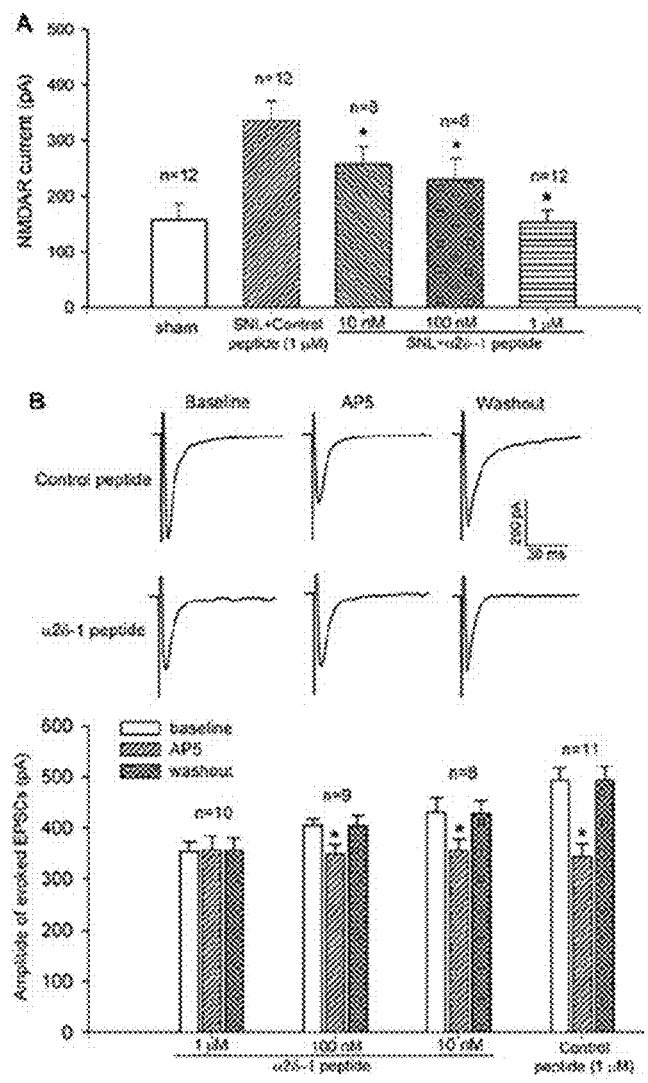
FIGS. 16A-16B: Disruption of α2δ-1-NMDAR association attenuates nerve injury-induced increases in NMDAR activity of spinal dorsal horn neurons. (A) Mean effects of α2δ-1Tat peptide (0.01, 0.1 and 1 μM) or scrambled control peptide (1 μM) on currents elicited by puff application of 100 FM NMDA to spinal dorsal horn neurons of SNL rats. Data are means±s.e.m. *P<0.05 (versus control peptide group). One-way ANOVA analysis followed by Dunnett's post hoc test. (B) Representative recordings and mean data show the AP5 effect on the amplitude of EPSCs of spinal dorsal horn neurons monosynaptically evoked by dorsal root stimulation in SNL rat spinal cord slices treated with 0.01, 0.1 and 1 μM α2δ-1Tat peptide or control peptide. Data are means±s.e.m. *P<0.05 (versus respective baseline). The numbers of cells recorded in each group are indicated in parentheses. One-way ANOVA analysis followed by Dunnett's post hoc test.

The C Terminus of α2δ-1 Is Crucial for Increased Synaptic NMDAR Activity in Neuropathic Pain: Because the C terminus of α2δ-1 is essential for its interaction with NMDARs, a 30-amino-acid peptide (VSGL-NPSLWSIFGLQFILLWLVSGSRHYLW; SEQ ID NO:1) was designed mimicking the C-terminal domain of α2δ-1 to determine whether it could uncouple the α2δ-1-NMDAR interaction. Because α2δ-1 primarily promotes forward trafficking of intracellular α2δ-1-bound NMDARs (FIGS. 5D and 5E), the C terminus-mimicking peptide was fused to the cell-penetrating peptide Tat (YGRKKRRQRRR; SEQ ID NO:2) (Schwarze et al., 1999), generating α2δ-1 Tat to target intracellular a2d-1-NMDAR complexes. Gabapentin or α2δ-1 Tat peptide had no significant effect on VACC currents in HEK293 cells cotransfected with Cav2.2, Cavb1, and α2δ-1 (FIG. 14A-B). Also, intrathecal administration of α2δ-1 Tat peptide had no effect on the interaction between α2δ-1 and Cav2.2 proteins in the spinal cord tissue (FIG. 14C-14D).

Figures 6A, 6B, 6C, 6D:
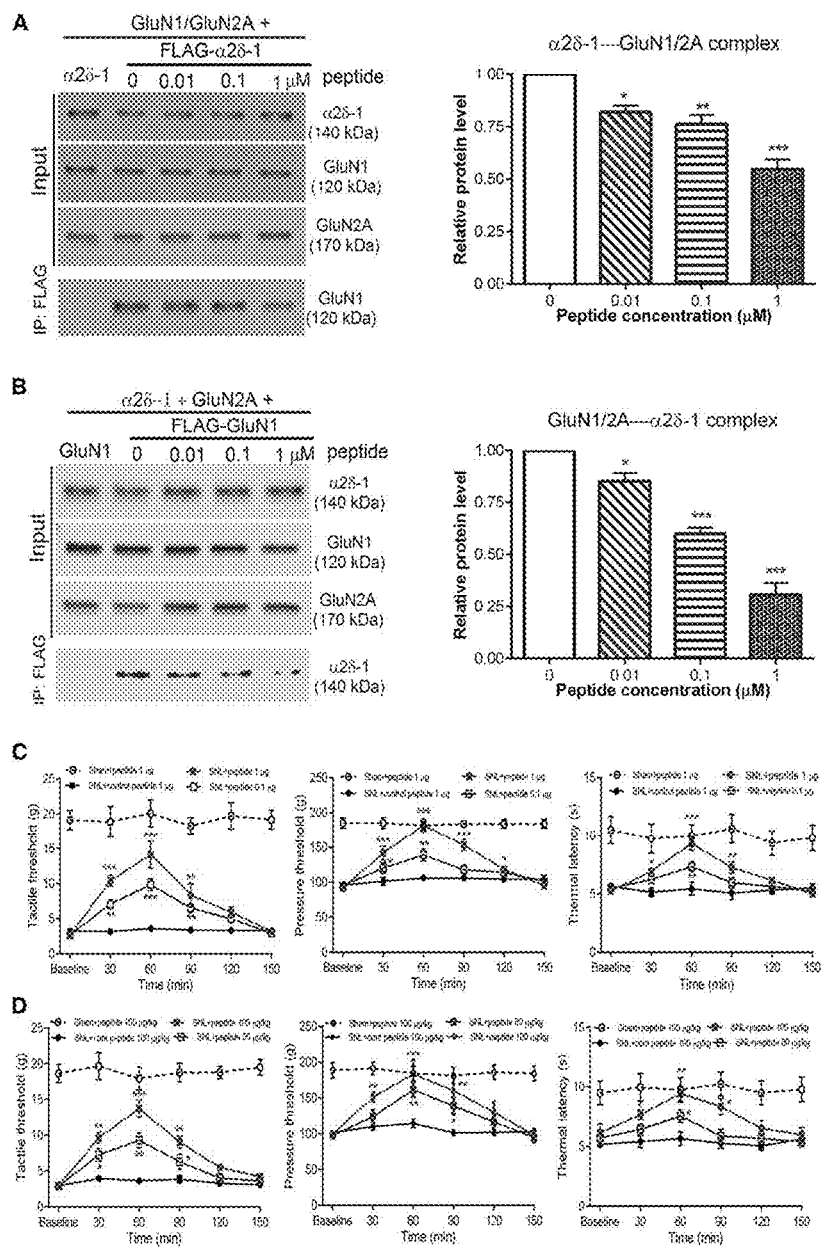
FIGS. 6A-6D: Uncoupling a2d-1-NMDAR Interaction via the C Terminus of α2δ-1 Reduces Neuropathic Pain. (A and B) Original gel images and quantification data show the effect of a2d-1Tat peptide on the a2d-1-GluN1 interaction. (A) HEK293 cells were cotransfected with GluN1, GluN2A, and α2δ-1 or FLAG-a2d-1. (B) HEK293 cells were cotransfected with a2d-1, GluN2A, and GluN1 or FLAG-GluN1. Forty-eight hours after transfection, the transfected cells were incubated with 0.01, 0.1, or 1 mM a2d-1Tat peptide for 30 min. The cell membranes were then isolated and used for coimmunoprecipitation using anti-FLAG antibody. Western blotting was conducted using (A) an anti-GluN1 antibody or (B) an anti-α2δ-1 antibody (n=6 replicates). Data are expressed as means±SEM. *p<0.05; p<0.01; *p<0.001 (versus control group), one-way ANOVA followed by Dunnett's post hoc test. (C and D) Effects of a single intrathecal injection (C) or intraperitoneal injection (D) of a2d-1Tat peptide on the tactile, pressure, and heat withdrawal thresholds in sham and SNL rats (n=8 rats in each group). Data are expressed as means±SEM. *p<0.05; p<0.01; *p<0.001 (versus baseline before drug injection), one-way ANOVA followed by Dunnett's post hoc test.
Figures 7A, 7B, 7C, 7D, 7E:
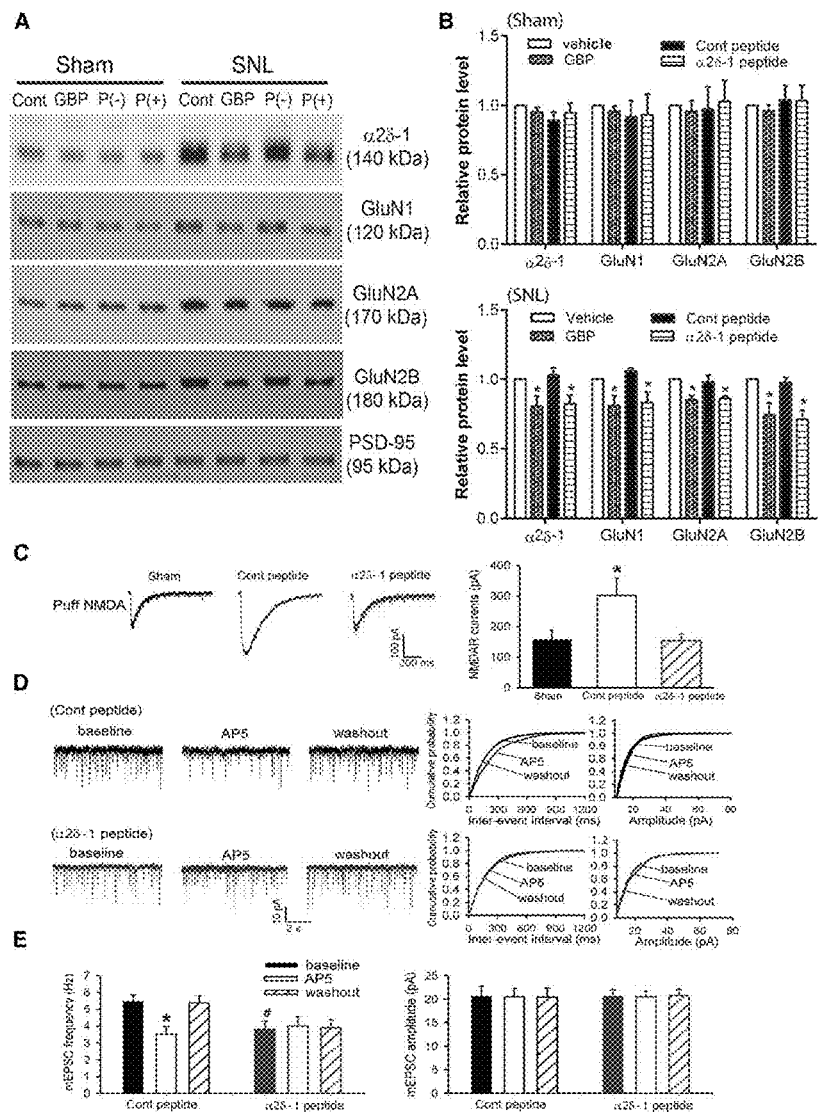
FIGS. 7A-7E: α2δ-1 Bound NMDARs Are Critically Involved In Nerve-Injury-Induced Synaptic Targeting and Activity of NMDARs (A and B) Representative gel images (A) and quantification data (B) show the protein levels of α2δ-1 and NMDAR subunits in spinal cord synaptosomes of sham and SNL rats (n=6 samples from 6 rats in each group). The spinal cord slices were incubated with control vehicle (Cont), 100 mM gabapentin (GBP), 1 mM α2δ-1 Tat peptide (P+), or 1 mM scrambled control peptide (P−) for 30 min. PSD-95, a known postsynaptic protein, was used as an internal control. Data are expressed as means±SEM. *p<0.05 (versus vehicle control), one-way ANOVA followed by Dunnett's post hoc test. (C) Original traces and mean effects of the a2d-1Tat peptide or scrambled control peptide (1 mM for 30 min) on currents elicited by puff application of 100 mM NMDA to spinal dorsal horn neurons in SNL (n=12 neurons in each group) rats 3 weeks after surgery. Data are expressed as means±SEM. *p<0.05 (versus sham rats), one-way ANOVA followed by Tukey's post hoc test. (D and E) Representative traces and cumulative probabilities (D), and mean changes (E) of baseline values and the AP5 effect on the frequency and amplitude of mEPSCs of spinal dorsal neurons recorded from SNL rats (n=12 neurons in the control peptide group; n=11 neurons in the a2d-1Tat peptide group). Data are expressed as means±SEM. *p<0.05 (versus respective baseline value); #p<0.05 (versus baseline in the control peptide group), one-way ANOVA followed by Tukey's post hoc test.
Figure 17:
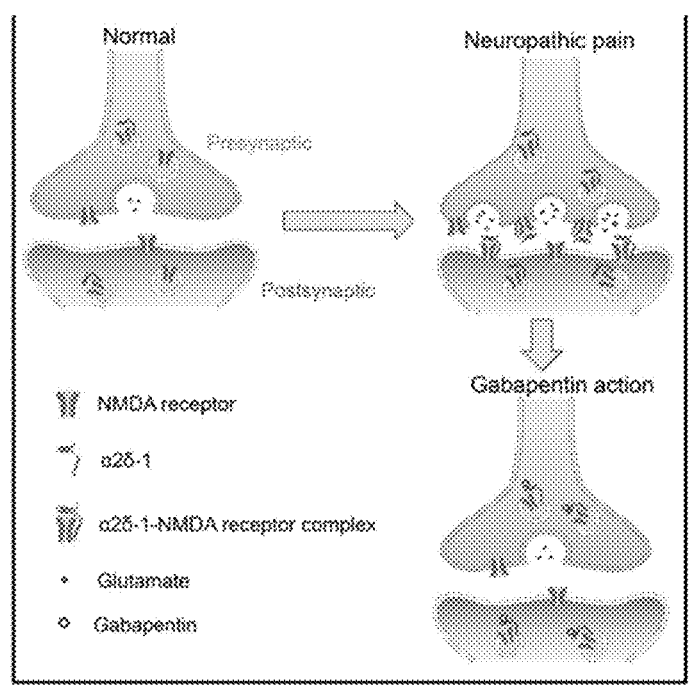
FIG. 17: Schematic of a2d1 mechanism.
Figure 18:
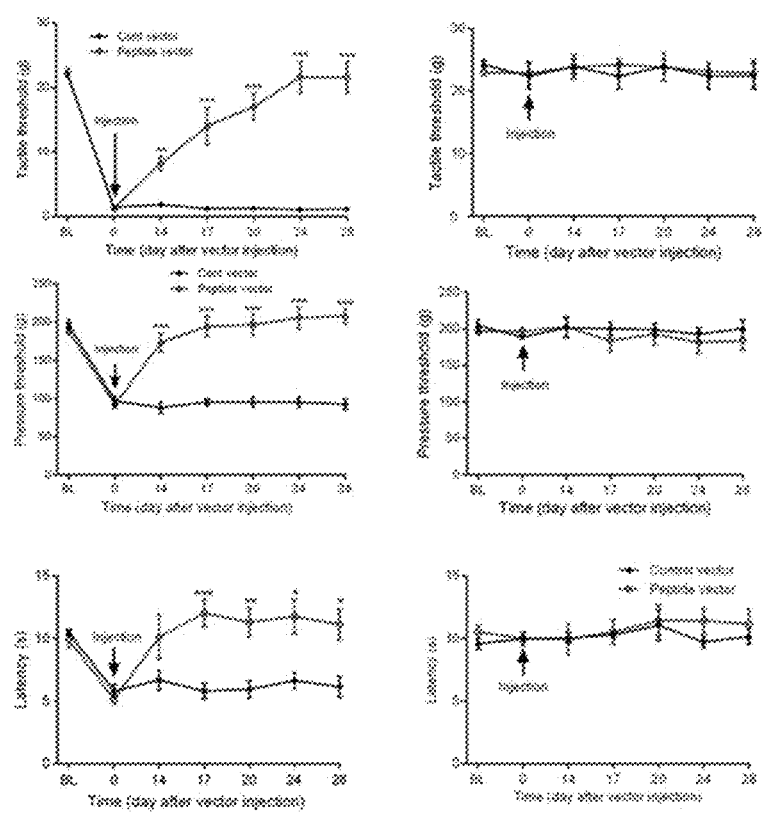
FIG. 18: Time course data showing the effect of a single intrathecal injection of lentiviral vector-mediated α2δ-1 C-terminus peptide on chronic neuropathic pain rats subjected to the left spinal nerve ligation (the right side shows the lack of effect on the normal/right side).

Application of the a2d-1Tat peptide (1 mM for 60 min) disrupted the direct interaction between α2δ-1 and GluN1 in a concentration-dependent manner (FIGS. 6A and 6B). Intrathecal or systemic injection of the a2d-1Tat peptide, but not a Tat-fused scrambled control peptide (FGL-GWQPWSLSFYLVWSGL ILSVLHLIRSN; SEQ ID NO:3), produced a large reduction in the pain hyper-sensitivity of SNL rats (FIGS. 6C and 6D). Also, intrathecal injection of a2d-1Tat peptide (1 mg) or gabapentin (30 mg) similarly reversed pain hypersensitivity caused by Cacna2d1 overexpression in rats but had no effect on the withdrawal thresholds in rats treated with the control vector (FIG. 17). The α2δ-1 Tat peptide had no effect on nerve injury-induced pain hypersensitivity in Cacna2d1 KO mice or on withdrawal thresholds in sham control rats. These data indicate that uncoupling the a2d-1-NMDAR interaction via the C terminus of α2δ-1 alleviates neuropathic pain.

α2δ-1 Promotes, whereas Gabapentin Inhibits, Synaptic Trafficking of NMDARs in Neuropathic Pain: In addition, it was determined whether gabapentin affects nerve injury-induced synaptic targeting of α2δ-1 and NMDARs in vivo. Spinal cord slices from sham and SNL rats were treated with gabapentin or vehicle for 30 min, and then synaptosomes were isolated from the tissue slices. Immunoblotting showed that SNL increased the protein levels of α2δ-1 and GluN1 in spinal cord synaptosomes by about 124% and 25%, respectively. Gabapentin reversed the increased protein levels of GluN1, GluN2A, GluN2B, and α2δ-1 in the spinal synaptosomes of SNL, but not sham, rats (FIGS. 7A and 7B). These results indicate that gabapentin inhibits synaptic targeting and trafficking of α2δ-1-bound NMDARs. Similarly, treatment with the α2δ-1 Tat peptide largely normalized the increased protein levels of GluN1, GluN2A, GluN2B, and α2δ-1 in the spinal cord synaptosomes of SNL, but not sham, rats (FIGS. 7A and 7B). However, the scrambled control peptide had no such effects in SNL or sham control rats. As expected, treatment with the a2d-1Tat peptide (1 mM for 60 min), but not the control peptide (1 mM for 60 min), normalized the increased pre- and postsynaptic NMDAR activity of spinal dorsal horn neurons in SNL rats (FIGS. 7C-7E and 18). These findings support the concept that increased synaptic expression of α2δ-1-bound NMDARs is essential for the increased synaptic NMDAR activity observed in neuropathic pain.

The findings reveal that α2δ-1 is a powerful regulator of NMDARs and that it contributes to neuropathic pain by potentiating the synaptic expression and targeting of NMDARs. This study provides an eloquent example showing that an auxiliary subunit of VACCs is, in fact, a critical interacting protein regulating the ionotropic glutamate receptor. An interesting analogy is g2 (stargazin), which was, like α2δ-1, initially identified as a VACC subunit but is now recognized as an auxiliary subunit of the AMPA subtype of glutamate receptors (Chen et al., 2000; Tomita et al., 2005). Although the coimmunoprecipitation assay showed that there is an association of NMDARs with α2δ-1 under the control condition, the level of α2δ-1-bound NMDAR complexes at the synaptic site is likely to be very low. Accordingly, presynaptic NMDARs are not tonically active in control animals but become activated under neuropathic pain conditions (Li et al., 2016; Xie et al., 2016). Because nerve injury induces a profound increase in α2δ-1 protein levels in the DRG and spinal cord, α2δ-1 can form more protein complexes with NMDARs and promote their trafficking to the synaptic sites. This identification of α2δ-1 as an NMDAR-interacting protein provides new insight into the molecular composition, heterogeneity, and function of native NMDARs, as well as synaptic plasticity under pathophysiological conditions.

TABLE 2

Lifetimes of terbium-labeled (*, donor) NMDAR subunits and YFP-tagged (acceptor) α2δ-1 constructs transfected in HEK293 cells.

|  | Donor only lifetime (μs) | Donor-acceptor lifetime (μs) | Distance (Å) |
|---|---|---|---|
| GluN1* + GluN2A + YFP-α2δ-1 |  |  |  |
| No gabapentin | 1,776 ± 1 | 1,312 ± 24 | 57.1 ± 0.5 |
| With gabapentin | 1,779 ± 1 | no LRET | >95 # |
| GluN1* + GluN2A + YFP-α2δ-1 mutant |  |  |  |
| No gabapentin | 1,776 ± 1 | 1,319 ± 52 | 57.3 ± 1.1 |
| With gabapentin | 1,779 ± 1 | 1,344 ± 38 | 57.9 ± 0.9 |
| GluN1 + GluN2A* + YFP-α2δ-1 |  |  |  |
| No gabapentin | 1,755 ± 1 | 1,378 ± 15 | 59.2 ± 0.4 |
| With gabapentin | 1,770 ± 1 | no LRET | >95 # |
| GluN1 + GluN2A* + YFP-α2δ-1 mutant |  |  |  |
| No gabapentin | 1,755 ± 1 | 1,307 ± 21 | 57.1 ± 0.5 |
| With gabapentin | 1,770 ± 1 | 1,409 ± 16 | 60.4 ± 0.7 |

N = 4-5 independent experiments in each condition.
$P < 0.05$, compared with the group without gabapentin (Mann-Whitney test).

Example 2—Materials and Methods

Animal models of neuropathic pain: All surgical preparations and experimental protocols were approved by the Animal Care and Use Committee of the University of Texas MD Anderson Cancer Center and conformed to the National Institutes of Health guidelines for the ethical use of animals. Male Sprague-Dawley rats (8-10 weeks of age) were purchased from Harlan Laboratories (Indianapolis, Ind.). L5 and L6 spinal nerve ligation (SNL) were used as an experimental model of neuropathic pain (Cole et al., 2005). In brief, anesthesia was induced with 2-3% isoflurane, isolated the left L5-L6 spinal nerves and ligated them tightly with 6-0 silk sutures. The rats in the sham control group underwent the same surgical procedures except for the nerve ligation.

Intrathecal catheters were implanted in some SNL group rats during isoflurane-induced anesthesia 2-3 weeks after SNL surgery. Briefly, the anesthetized animal was placed on a stereotaxic frame, and a small incision was made at the back of its neck. Then, a small puncture was made in the atlanto-occipital membrane of the cisterna magna, and a PE-10 catheter (~8 cm) was inserted with the caudal tip reaching the lumbar enlargement of the spinal cord (Luo et al., 2001; Patel et al., 2013). The rostral end of the catheter was exteriorized and closed the wound with sutures. The animals were allowed to recover for at least 4 days before the intrathecal injections were performed. Animals displaying signs of motor or neurological dysfunction were immediately killed with an intraperitoneal injection of phenobarbital (200 mg/kg) or by inhalation of $CO_2$.

The doses of memantine (Tocris Bioscience, Ellisville, Mo.) and (2R)-amino-5-phosphonopentanoate (AP5) (Abcam, Cambridge, Mass.) were selected based on previous studies (Patel et al., 2013; Li et al., 2004). α2δ-1-specific siRNA (CAAGCAACGAAGUUGUCUA; SEQ ID NO:49) or universal negative-control siRNA (#SIC001, Sigma-Aldrich, St. Louis, Mo.) was mixed with i-Fect (Neuromics, Edina, Minn.) to a final concentration of 400 mg/L for the intrathecal injections. α2δ-1-specific siRNA or negative control siRNA (4 µg/day for 4 days) was administered intrathecally in the SNL rats 3 weeks after surgery (Dolphin et al., 2012).

Conventional α2δ-1 KO mice (C57BL/6 genetic background) were generated as described previously (Muller et al., 2010). Two breeding pairs of α2δ-1$^{+/-}$ mice were purchased from Medical Research Council (Harwell Didcot, Oxfordshire, UK), and α2δ-1$^{-/-}$ mice and α2δ-1$^{+/+}$ (wild-type) littermates were obtained by breeding the heterozygous mice. The spared nerve injury (SNI) procedure (Gee et al., 1996) was performed on both male and female mice (10-11 weeks of age). Under a surgical microscope, the left common peroneal and tibial nerves were ligated and sectioned, leaving the sural nerve intact. The sham procedure consisted of the same surgery without nerve ligation and sectioning.

Behavioral assessments of nociception: To detect tactile allodynia, von Frey filaments were applied to the animals' left hindpaws (ipsilateral to the nerve injury). The rats or mice were placed individually in suspended chambers on a mesh floor. After an acclimation period of 30 min, a series of calibrated von Frey filaments were applied (Stoelting, Wood Dale, Ill.) perpendicularly to the plantar surface of the hindpaw with sufficient force to bend the filament for 6 s. Brisk withdrawal or paw flinching was considered a positive response. After a response, the filament of the next lower force was applied. In the absence of a response, the filament of the next greater force was applied. Using the up-down method, the tactile stimulus that produced a 50% likelihood of a withdrawal response was calculated (Fuller-Bicer et al., 2009).

To quantify the mechanical nociceptive threshold in the rats and mice (Patel et al., 2013; Dolphin et al., 2012), the paw pressure tests were conducted on the hindpaw with an analgesiometer (Ugo Basile, Varese, Italy). The device was activated by pressing a foot pedal, which triggered a motor that applied a constantly increasing force on a linear scale. When the animal displayed pain by either withdrawing its paw or vocalizing, the pedal was immediately released, and the animal's nociceptive threshold was read on the scale (Patel et al., 2013; Marais et al., 2001). The investigators conducting the behavioral experiments were blinded to the treatment.

Lentiviral vector constructs and preparation: The full-length coding sequence of rat α2δ-1 tagged with enhanced green fluorescent protein (GFP) at the N-terminus or GFP alone was cloned into the lentiviral vector pLenti6/V5-DEST with a cytomegalovirus promoter (Invitrogen, Carlsbad, Calif.). The viral vector was produced using the ViraPower system (Invitrogen) according to the manufacturer's instructions. Briefly, vectors were transfected into HEK293FT cells using Lipofectamine 3000 (#L3000015, Invitrogen). The virus-containing supernatant was collected 72 h after transfection and filtered through Millex-HV 0.45-µm filters (Millipore, Bedford, Mass.). The viruses were purified and concentrated about 1,000-fold by centrifugation at 90,000×g. The viral titer, measured by infecting HEK293FT cells with 10× gradient-diluted virus, was about $10^8$ infectious units/mL. Viral vectors (2×$10^6$ viral particles in 20 µl) expressing GFP-α2δ-1 (α2δ-1 vector) or GFP only (control vector) were slowly injected into the rats through an intrathecal catheter, and the catheter was then removed. After vector injection, all rats were placed in a restricted biohazardous housing area for 2 weeks before undergoing behavioral tests. The transduction efficiency of the lentiviral vector in dorsal root ganglion (DRG) and dorsal horn neurons after intrathecal injection has been previously demonstrated (Rowbotham et al., 1998).

Electrophysiological recordings in spinal cord slices: Anesthesia was induced in rats or mice with isoflurane and removed the lumbar spinal cords via laminectomy. The spinal cords at the L5-L6 level were placed in ice-cold sucrose artificial cerebrospinal fluid containing (in mM) 234 sucrose, 3.6 KCl, 1.2 MgCl$_2$, 2.5 CaCl$_2$), 1.2 NaH$_2$PO$_4$, 12.0 glucose and 25.0 NaHCO$_3$, presaturated with 95% O$_2$ and 5% CO$_2$. The spinal cord tissue was glued onto the stage of a vibratome, and transverse slices (400 µm) of spinal cords were cut in ice-cold sucrose artificial cerebrospinal fluid and then preincubated in Krebs solution oxygenated with 95% O$_2$ and 5% CO$_2$ at 34° C. for at least 1 h before being transferred to the recording chamber. The Krebs solution contained (in mM) 117.0 NaCl, 3.6 KCl, 1.2 MgCl$_2$, 2.5 CaCl$_2$, 1.2 NaH$_2$PO$_4$, 11.0 glucose and 25.0 NaHCO$_3$. The spinal cord slices were placed in a glass bottom chamber and continuously perfused with Krebs solution at 5.0 ml/min at 34° C. maintained by an inline solution heater and a temperature controller.

A glass pipette (5-10 MΩ) was filled with internal solution containing (in mM) 135.0 potassium gluconate, 5.0 TEA, 2.0 MgCl$_2$, 0.5 CaCl$_2$, 5.0 HEPES, 5.0 EGTA, 5.0 Mg-ATP, 0.5 Na-GTP and 10 lidocaine (lignocaine) N-ethyl bromide (adjusted to pH 7.2-7.4 with 1 M KOH; 290-300 mOsmol/L). The lamina II outer neurons were identified for recording because they receive nociceptive input from primary afferents and show increased synaptic N-methyl-D-aspartate receptor (NMDAR) activity after nerve injury (Rowbotham et al., 1998). It becomes impossible to visualize neurons in other laminas in adult (>10-week-old) rodent spinal cords because of heavy laminar myelination. It has been shown that most neurons in lamina II are glutamate-releasing excitatory interneurons (Schumacher et al., 1998). Also, α2δ-1 is expressed in neurons and nerve terminals in the spinal lamina II (Hoppa et al., 2012). Postsynaptic NMDAR currents were elicited by puff application of 100 µM NMDA to the recorded neuron using a positive pressure system (4 p.s.i., 15 ms; Toohey Company, Fairfield, N.J.) (Anhut et al., 1994). The tip of the puff pipette was placed 150 µm away from the recorded neuron. The recordings were performed in the extracellular solution containing 10 µM glycine and 1 µM tetrodotoxin at a holding potential of −60 mV and using the pipette internal solution containing (in mM) 110.0 Cs$_2$SO$_4$, 2.0 MgCl$_2$, 0.1 CaCl$_2$, 1.1 EGTA, 10.0 HEPES, 2.0 Mg-ATP and 0.3 Na$_2$GTP (pH was adjusted to 7.25 with 1.0 M CsOH; 280-300 mOsmol/L).

In some experiments, the attached dorsal root was electrically stimulated with a stimulating electrode (0.5 ms, 0.6 mA and 0.1 Hz) to evoke monosynaptic excitatory postsynaptic currents (EPSCs). The α-amino-3-hydroxy-5-methyl-4-isoxazolepropionic acid receptor (AMPAR)-mediated EPSCs were recorded at a holding potential of −60 mV in the presence of 10 µM bicuculline and 1 µM strychnine, whereas NMDAR-mediated EPSCs were recorded at +40 mV in the presence of 10 µM 6-cyano-7-nitroquinoxaline-2,3-dione, 10 µM bicuculline, and 1 µM strychnine. Miniature EPSCs (mEPSCs) were recorded at a holding potential of −60 mV in the presence of 1 µM strychnine, 10 µM bicuculline and 1 µM tetrodotoxin, and presynaptic NMDAR-mediated glutamate release was tested by bath application of 50 µM AP5 (Anhut et al., 1994). The input resistance was monitored, and the recording was abandoned if the input resistance changed more than 15%. All signals were recorded using an amplifier (MultiClamp700B; Axon Instruments Inc., Union City, Calif.), filtered at 1-2 kHz, digitized at 10 kHz, and stored for off-line analysis. Final spinal cord slice recordings were performed 3-4 weeks after the nerve injury or sham surgery. In all electrophysiological experiments, 3-5 animals were used for each recording protocol, and only 1 neuron was recorded in each spinal cord slice.

Western immunoblotting analysis of α2δ-1: Western blotting was used to quantify the α2δ-1 expression level in the DRG and dorsal spinal cord. Spinal cord and DRG tissues at the L5 and L6 levels were removed, dissected, and homogenized in 300 µl radioimmunoprecipitation assay buffer containing 50 mM Tris-HCl (pH 7.4), 1% Nonidet P-40, 0.25% sodium-deoxycholate, 150 mM NaCl, 1 mM EDTA, 1 mM $Na_3VO_4$, and 1 mM NaF in the presence of a proteinase inhibitor cocktail (Sigma-Aldrich). Samples were then put on ice for 30 min with shaking. Lysates were centrifuged at 13,000×g for 30 min at 4° C. The supernatant was carefully collected, and the protein concentration was measured using a DC Protein Assay Kit (Bio-Rad, Hercules, Calif.). Thirty µg of total proteins from each sample was loaded and separated by 4-15% Tris-HCl sodium dodecyl sulfate-polyacrylamide gel electrophoresis (SDS-PAGE) (Bio-Rad). The resolved proteins were transferred to an Immobilon-P membrane (Millipore). The membrane was treated with 5% nonfat dry milk in Tris-buffered saline (TBS) at 25° C. for 1 h and then incubated in TBS supplemented with 0.1% Triton X-100, 1% bovine serum albumin and rabbit anti-α2δ-1 (#C5105, 1:1,000, Sigma-Aldrich) overnight at 4° C. The membrane was washed 3 times and then incubated with horseradish peroxidase-conjugated anti-rabbit IgG (1:5,000; Jackson ImmunoResearch, West Grove, Pa.) for 1 h at room temperature. The specific protein band detected by using the α2δ-1 antibody was confirmed by assays of protein knockdown using the α2δ-1-specific siRNA in vivo. The protein bands were detected with ECL kit (Thermo Fisher Scientific, Waltham, Mass.), and protein band intensity was visualized and quantified using the Odyssey Fc Imager (LI-COR Biosciences, Lincoln, Nebr.).

Coimmunoprecipitation using spinal cord tissue membrane extracts: The dorsal quadrants of rat spinal cords at the L5 and L6 levels or the frozen lumbar spinal cord tissues from four human donors (2 males and 2 females, age ranged 18-42 years, post-mortem interval of 17-29 h; supplied by University of Maryland Brain and Tissue Bank) were dissected and homogenized in ice-cold hypotonic buffer (20 mM Tris [pH 7.4], 1 mM $CaCl_2$, 1 mM $MgCl_2$, and protease inhibitors) for membrane preparation. The nuclei and unbroken cells were removed by centrifugation at 300×g for 5 min. The supernatant was centrifuged for 20 min at 21,000× g. The pellets were re-suspended and solubilized in immunoprecipitation buffer (50 mM Tris [pH7.4], 250 mM NaCl, 10% glycerol, 0.5% NP-40, 20 mM NaF, 1 mM $Na_3VO_4$, 10 mM N-ethylmaleimide, 1 mM phenylmethylsulfonyl fluoride, 2 mM benzamide, and protease inhibitors), and the soluble fraction was incubated at 4° C. overnight with Protein A/G beads (#16-266, Millipore) prebound to mouse anti-GluN1 antibody or rabbit anti-α2δ-1 antibody. Protein A/G beads prebound to mouse IgG or rabbit IgG were used as controls. Samples were washed 5 times with immunoprecipitation buffer and then immunoblotted. The following antibodies were selected for immunoblotting on the basis of previously published studies uper 17-21: rabbit anti-α2δ-1 (#C5105, 1:1,000, Sigma-Aldrich; #ACC-015, Alomone Labs, Jerusalem, Israel), rabbit anti-α2δ-2 (#ACC-102, 1:500, Alomone Labs), rabbit anti-α2δ-3 (#ACC-103, 1:500, Alomone Labs), mouse anti-GluN1 (#75-272, 1:1, 000, NeuroMab, Davis, Calif.), mouse anti-GluN2A (#75-288, 1:1,000, NeuroMab), and mouse anti-GluN2B (#75-097, 1:1,000, NeuroMab).

Spinal cord synaptosome preparation: The spinal cord slices were pooled from 2 rats and were homogenized using glass-Teflon homogenizer in 10 volumes of ice-cold HEPES-buffered sucrose (0.32 M sucrose, 1 mM EGTA, and 4 mM HEPES at pH 7.4) containing the protease inhibitor cocktail (Sigma-Aldrich). The homogenate was centrifuged at 1,000×g for 10 min at 4° C. to remove the nuclei and large debris. The supernatant was centrifuged at 10,000×g for 15 min to obtain the crude synaptosomal fraction. The synaptosomal pellet was lysed via hypo-osmotic shock in 9 volumes of ice-cold HEPES-buffer with the protease inhibitor cocktail for 30 min. The lysate was centrifuged at 25,000×g for 20 min at 4° C. to obtain the synaptosomal membrane fraction, which was then dissolved in sodium dodecyl sulfate sample buffer at a final concentration of 0.25 µg/µl for immunoblotting. Gabapentin was obtained from Tocris Bioscience. The α2δ-1Tat peptide and scrambled control peptide were synthesized by Bio Basic Inc. (Marham, Ontario, Canada) and validated by using liquid chromatography and mass spectrometry.

Quantitative PCR analysis: Total RNA was extracted from the DRG and spinal cord tissues at the L5 and L6 levels using TRIzol-chloroform and then treated with DNase I (Invitrogen). cDNA was prepared by using the SuperScript III First-Strand Synthesis Kit and then treated with RNase H (Invitrogen). A quantitative PCR was performed using the iQ5 Real-Time PCR Detection System (Bio-Rad, Hercules, Calif.) and SYBR Green (Bioline, Taunton, Mass.). The thermal cycling conditions were: 1 cycle at 95° C. for 1 min; 40 cycles at 95° C. for 15 s and 60° C. for 15 s. The following primers were used: rat α2δ-1 forward, CGAGCATGATGAGACACCTG (SEQ ID NO:50); rat α2δ-1 reverse, TTGATGGCACATAGGCTGAG (SEQ ID NO:51); rat α2δ-2 forward, GCCTCTGCCTACAGCTTCC (SEQ ID NO:52); rat α2δ-2 reverse, CAGGTTCCGATTGTCCTTGT (SEQ ID NO:53); rat Gapdh forward, TGCCACTCAGAAGACTGTGG (SEQ ID NO:54); rat Gapdh reverse, TTCAGCTCTGGGATGACCTT (SEQ ID NO:55); mouse α2δ-1 forward, ACGCCAACTGGTTGAAATTG (SEQ ID NO:56); mouse α2δ-1 reverse, CTTGCAAAATCTTCCCTCCA (SEQ ID NO:57); mouse Gapdh forward, GGGTGTGAACCACGAGAAAT (SEQ ID NO:58); and mouse Gapdh reverse, CCTTCCACAATGCCAAAGTT (SEQ ID NO:59). Relative mRNA levels were calculated using the $2^{-\Delta\Delta CT}$ method and normalized to the Gapdh level in the same sample.

DNA constructs: The rat cDNAs of the NMDAR subunits GluN1-1a, GluN2A, and GluN2B and α2δ-1 were all expressed in the expression vector pcDNA 3.1. The α2δ-2 and α2δ-3 constructs were obtained from Addgene (Cambridge, Mass.). To generate N-terminal tagged fusion constructs (FLAG-GluN1, CFP-GluN1 and YFP-α2δ-1), the coding sequences of the tags FLAG, cyan fluorescent protein (CFP) and yellow fluorescent protein (YFP) were inserted after the predicted signal peptide cleavage site of GluN1 and α2δ-1 by using recombinant PCR techniques. The NMDAR currents reconstituted with these constructs were similar to those of wild-type GluN1 and α2δ-1 in HEK293 cells. The α2δ-1 coding sequence was inserted between the Nhe I and EcoR I sites of the pIRES-AcGFP1 vector, which was used for electrophysiological recording. The mutant $\alpha_2\delta\text{-}1_{R217A}$ was generated by mutating the gabapentin binding site on $\alpha 2\delta\text{-}1$ (the R217A mutant was also termed R241A when amino acid numbering included the N-terminal signal sequence of $\alpha 2\delta\text{-}1$). The von Willebrand factor type A (VWA) domain of $\alpha 2\delta\text{-}1$ (residues 239-417) was deleted to generate $a2\delta\text{-}1_{\Delta VWA}$.

The chimeras of $\alpha 2\delta\text{-}1$ (which swapped the N-terminus or 6 peptide of $\alpha 2\delta\text{-}1$ for that of $\alpha 2\delta\text{-}2$ or $\alpha 2\delta\text{-}3$) were generated based on multiple sequence alignment using the ClustalW2 program. $\alpha 2\delta\text{-}1_{NT(\alpha 2\delta\text{-}2)}$ and $\alpha 2\delta\text{-}1_{NT(\alpha 2\delta\text{-}3)}$ were generated by replacing the $\alpha 2\delta\text{-}1$ N-terminus (residues 25-237) with the N-terminal domain of $\alpha 2\delta\text{-}2$ (residues 65-278) and $\alpha 2\delta\text{-}3$ (residues 34-240), respectively. The 6 peptide of $\alpha 2\delta\text{-}1$ (residues 945-1091) was replaced with the $\delta$ part of $\alpha 2\delta\text{-}2$ (residues 1001-1157) or $\alpha 2\delta\text{-}3$ (residues 951-1085) to generate $\alpha 2\delta\text{-}1_{\delta(\alpha 2\delta\text{-}2)}$ and $\alpha 2\delta\text{-}1_{\delta(\alpha 2\delta\text{-}3)}$, respectively. $\alpha 2\delta\text{-}1_{CT(\alpha 2\delta\text{-}2)}$ and $\alpha 2\delta\text{-}1_{CT(\alpha 2\delta\text{-}3)}$ were generated by replacing the C-terminus of $\alpha 2\delta\text{-}1$ (residues 1059-1091) with the C-terminus of $\alpha 2\delta\text{-}2$ (residues 1111-1157) and $\alpha 2\delta\text{-}3$ (residues 1061-1085), respectively. The amino acid numbering includes the N-terminal signal sequence of $\alpha 2\delta\text{-}1$. The constructs were made using the QuickChange Site-Directed Mutagenesis Kit (#200521, Agilent Technologies, Santa Clara, Calif.) or In-Fusion HD Cloning Plus (#638916, Clontech Laboratories, Inc., Mountain View, Calif.). All cDNA clones and mutated constructs were confirmed by DNA sequencing.

Cell culture and transfection: HEK293 cells (American Type Culture Collection, Manassas, Va.) were maintained in Dulbecco's modified Eagle medium (DMEM) (#10-017-CV, Corning, Manassas, Va.) supplemented with 10% fetal bovine serum (#F4135, Sigma-Aldrich) and penicillin/streptomycin (#30-002-CI, Corning). Cells were passaged after they reached a confluence of 80-90%, approximately every 2 days. HEK293 cells were transfected using PolyJet reagents (#SL100688, SignaGen Laboratories, Gaithersburg, Md.) at a GluN1/GluN2/$\alpha 2\delta\text{-}1$ ratio of 1:3:1 (the DNA:PolyJet ratio was 1:3). For induction of NMDAR expression, cells were maintained in glutamine-free DMEM (#15-017-CV, Corning) supplemented with 20 mM $MgCl_2$, 0.1 mM AP5 (Abcam) and 3 mM kynurenic acid (Sigma-Aldrich).

Whole-cell recording of NMDAR currents in HEK293 cells: Whole-cell recording was performed using a fire-polished pipette (3-5 M$\Omega$) pulled from borosilicate glass and filled with an intracellular solution containing (in mM) 135 CsF, 2 $MgCl_2$, 0.5 $CaCl_2$, 5 EGTA, 2 Mg-ATP and 10 HEPES (pH, 7.25; 285 mOsmol/L). The extracellular solution contained (in mM) 160 NaCl, 2.5 KCl, 0.2 $CaCl_2$, 10 HEPES, and 10 glucose (pH, 7.35; 300-310 mOsmol/L). Whole-cell currents were recorded with an EPC-10 amplifier (HEKA Instruments, Lambrecht, Germany) at a holding potential of −60 mV. Signals were filtered at 1 kHz, digitized at 10 kHz and acquired using the Pulse program (HEKA Instruments). After the whole-cell configuration was established, the cell membrane capacitance and series resistance were electronically compensated for. Glycine (10 µM) and NMDA (300 µM) were used to elicit NMDAR currents. For voltage-dependent $Mg^{2+}$ block experiments, the conductance-voltage relation of NMDARs was assessed when 2 mM $MgCl_2$ was added to the extracellular solution. The sensitivity of NMDARs to $Mg^{2+}$ was estimated by fitting current-voltage relationships to a Boltzmann function (Zhou et al., 2012). All HEK293 cell recording experiments were performed at 25° C.

Outside-out patch recording of NMDAR currents in HEK293 cells: Outside-out patches were excised from transfected HEK293 cells with thick-walled borosilicate glass pipettes of 2-5 M$\Omega$ resistance coated with bees wax, fire polished and filled with a solution containing (in mM) 135 CsF, 33 CsOH, 11 EGTA, 10 HEPES, 2 $MgCl_2$ and 1 $CaCl_2$. The external solution was composed of (in mM) 150 NaCl, 10 HEPES, 10 tricine, 1 $CaCl_2$ and 100 µM added glycine (pH 7.4 with NaOH). All recordings were performed at 25° C. and a holding potential of −80 mV (Axopatch 200B, Molecular Devices, Sunnyvale, Calif.). Data were acquired at 40 kHz using pCLAMP 10 software and filtered at 10 kHz. Series resistance was compensated for ~95% where the absolute amplitude exceeded 100 pA. Solution exchange was performed using a piezoelectric system (#LSS-3000, Burleigh Instruments) and in-house triple-barrel glass application pipettes as described previously (Li et al., 2016). Solution exchange times as measured from open tip potentials were between 100 and 300 µs (10-90% rise time). For MK-801 experiments, patches were first equilibrated in the control solution from the first barrel, then jumped to the second barrel perfusing glutamate (1 mM) and finally jumped to the third barrel perfusing glutamate plus MK-801 (300 nM). Mean responses from each patch were fit with either double-exponential (deactivation) or single-exponential (desensitization and MK-801 inhibition) equations (Laumet et al., 2015; Chen et al., 2014). For deactivation experiments, the weighted time constant was reported.

Coimmunoprecipitation using HEK293 cell membrane extracts: HEK293 cells were transfected with FLAG-GluN1-1a, GluN2A/GluN2B, YFP-$\alpha 2\delta\text{-}1$, $\alpha 2\delta\text{-}1$ mutants, $\alpha 2\delta\text{-}2$ or $\alpha 2\delta\text{-}3$ when cells were grown to 80-90% confluence in 75-$cm^2$ culture flasks. HEK293 cells expressing NMDARs and $\alpha 2\delta\text{-}1$ were suspended and washed in phosphate-buffered saline (PBS) twice, and incubated at 25° C. for 20 min with a rabbit anti-FLAG antibody (#F7425, Sigma-Aldrich) to immunoprecipitate FLAG-tagged GluN1. A mouse anti-GFP antibody (#75-132, NeuroMab, Davis, Calif.), which cross-reacts with YFP, was used to immunoprecipitate YFP-tagged wild-type $\alpha 2\delta\text{-}1$ or $\alpha 2\delta\text{-}1$ mutants. Cells were then washed 3 times in PBS and lysed in Pierce IP Lysis Buffer (#87787, Thermo Fisher Scientific) with a cocktail of protease and phosphatase inhibitors (#78440, Thermo Fisher Scientific). The lysates were incubated on ice for 30 min and then centrifuged at 13,000×g for 10 min at 4° C. The supernatant was transferred to a tube with Dynabeads (#147187300, Thermo Fisher Scientific) and incubated with rotation at 25° C. for 20 min. The Dynabeads-antibody-antigen complex was washed 3 times using 200 µl IP Lysis Buffer for each wash. The IP Lysis Buffer with 100 µg/ml immunogen peptides of FLAG (#F3290, Sigma-Aldrich) was added to elute the coimmunoprecipitation complex. The eluted proteins were subjected to Western blot analysis with the following antibodies: rabbit anti-GluN1 (#G8913, Sigma-Aldrich), rabbit anti-$\alpha 2\delta\text{-}1$ (#C5105, Sigma-Aldrich), rabbit anti-GFP (#G1544, Sigma-Aldrich), rabbit anti-GluN2A (#1500-NR2A, PhosphoSolutions, Aurora, Colo.), and mouse anti-GluN2B (#5580S, Cell Signaling, Danvers, Mass.).

Isolation and analysis of HEK293 cell membrane surface proteins: HEK293 cells were transfected with GluN1-1a, GluN2A/GluN2B and/or $\alpha 2\delta\text{-}1$ after they had grown to 80-90% confluence in 75-$cm^2$ culture flasks. Cell surface biotinylation was performed using the Pierce Cell Surface Protein Isolation Kit (#89881, Thermo Fisher Scientific) according to the manufacturer's instructions. Briefly, cells were incubated with Sulfo-NHS—SS-biotin, which covalently binds to primary amino groups of extracellular proteins at 4° C. with constant rotation for 30 min. Excess biotin was quenched with quenching solution (Chaplan et al., 1997). The cells were washed, harvested by gentle scraping and lysed using the provided lysis buffer in the cocktail of protease and phosphatase inhibitors (#78440, Thermo Fisher Scientific) for 30 min at 4° C. The lysates were then centrifuged for 2 min at 10,000×g at 4° C., and the clear supernatants were added to NeutrAvidin agarose and incubated for 60 min at 25° C. with end-over-end mixing. The unbound (unbiotinylated) proteins, representing the intracellular fraction, were separated from the captured surface proteins by centrifugation of the column. Finally, the captured surface proteins were eluted from the biotin-NeutrAvidin agarose by incubation with dithiothreitol in SDS-PAGE sample buffer and subjected to Western blot analysis with antibodies against GluN1, GluN2A, GluN2B and α2δ-1. $Na^+/K^+$ ATPase (#ab7671, Abcam), a specific plasma membrane marker, was used as a loading control. Protein bands were quantified using Image Studio software (version 3.1, LI-COR Biosciences).

Luminescence resonance energy transfer (LRET) measurements: For constructs used for LRET measurements, the extracellular non-disulfide-bonded cysteines were mutated to serines so that they were not labeled with the maleimide reactive fluorophore. For the GluN1 subunit, Cys22 and Cys459 were mutated; for the GluN2A subunit, Cys231, Cys399 and Cys461 were mutated. For measurement of LRET between GluN1 and α2δ-1, Cys22 was not mutated and was used as the site for attachment of the thiol-reactive fluorophore. Additionally, for quantitative analysis of the background, a thrombin recognition sequence (amino acids LVPRGS) was inserted immediately at the C-terminal to the cysteine (Kim and Chung, 1992). For measurement of LRET between GluN2A and α2δ-1, a cysteine followed by the thrombin recognition sequence was inserted after Lys29 (Cys30). The thrombin cleavage site allows subtraction of the background signal from free cysteines of α2δ-1 and other proteins on the surface of HEK293 cells (Kim and Chung, 1992), thus providing the specific measurement of the LRET signal between the NMDAR and α2δ-1.

Cysteines at the GluN1 and GluN2A sites labeled with thiol-reactive terbium chelate served as donor fluorophore sites, and YFP fused to α2δ-1 served as the acceptor fluorophore. HEK293 cells transfected with GluN1, GluN2A and YFP-α2δ-1 were harvested and labeled with 200 nM terbium chelate (Invitrogen) for 1 h at 25° C. After labeling, cells were washed twice in extracellular buffer composed of (in mM) 150 NaCl, 2.8 KCl, 1 $CaCl_2$, and 5 HEPES (pH 7.3). The washed and labeled cells were then re-suspended in extracellular buffer and probed in a cuvette-based LRET analysis. The sample was excited at 337 nm, and emission was detected at 527 nm in a QuantaMaster QM3-SS system with Fluorescan software (Photon Technology International, Edison, N.J.). The temperature was maintained at 20° C. using a Peltier TE temperature controller. Data were analyzed with Origin 8.6 software (OriginLab Corp., Northampton, Mass.). Each sample was scanned 3 times for each ligated condition, and each scan was recorded as an average of 99 sweeps. To determine the gabapentin effect, cells were maintained in 100 μM gabapentin (Tocris Bioscience) for 30 min before terbium labeling. The distance between the donor and acceptor was calculated using the Förster equation (Kim and Chung, 1992).

Data analysis: Data are presented as means±s.e.m. No statistical methods were used to predetermine sample sizes for biochemical studies, but the sample sizes were similar to those generally employed in the field. All the data were randomly collected, and their distribution was determined using the Kolmogorov-Smirnov normality test. For proper exclusion of data points, the criteria were established before data collection. Animals in which motor function was impaired after intrathecal cannulation or treatment were excluded. In electrophysiological recording experiments, cell capacitance, input resistance, series resistance, resting membrane potential, and baseline holding current were monitored; cells were excluded if the recording indicated a rundown condition. The PulseFit software program (HEKA Instruments) was used to analyze the whole-cell current data obtained from transfected HEK293 cells. The amplitude of evoked EPSCs and NMDAR currents recorded from spinal dorsal horn neurons was analyzed with Clampfit 9.2 software (Axon Instruments). The amplitude and frequency of mEPSCs were analyzed off-line with a peak detection program (MiniAnalysis; Synaptosoft Inc., Decatur, Ga.). The cumulative probability of the amplitude and interevent interval was compared by the Kolmogorov-Smirnov test, which estimates the probability that two cumulative distributions are similar. The two-tailed Student t test was used to compare two groups and one-way or two-way analysis of variance (ANOVA, followed by Dunnett's and Tukey's post hoc tests) to compare more than two groups. The appropriate nonparametric analysis (i.e., the Mann-Whitney or Kruskal-Wallis test) was used when electrophysiological and behavioral data were not normally distributed. Statistical analyses were performed using Prism 6 software (GraphPad Software Inc., La Jolla, Calif.). The level of significance was set at $P<0.05$.

Figures 19A, 19B:
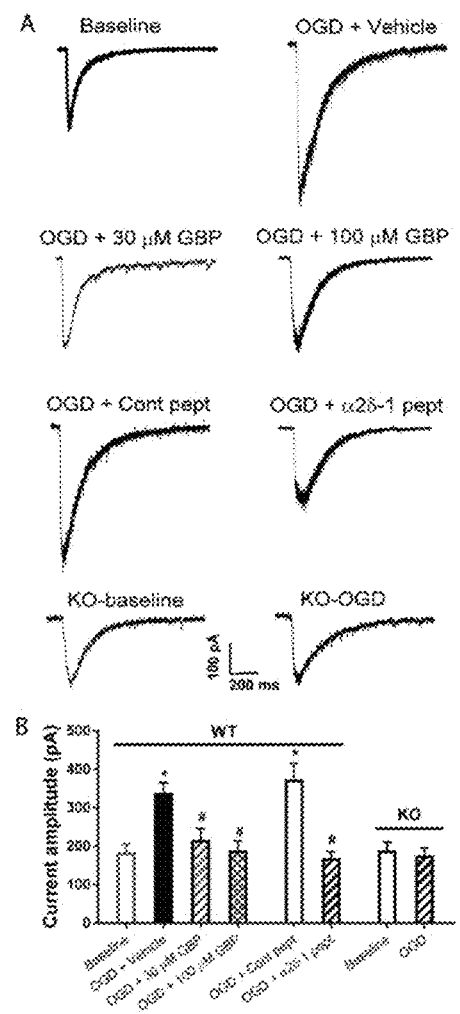
FIGS. 19A-19B: α2δ-1 and its interaction with NMDARs are essential for OGD-induced potentiation of NMDAR activity in hippocampal CA1 neurons. (A and B) Representative recording traces (A) and quantification (B) of puff NMDA-elicited NMDAR currents show the effects of gabapentin (GBP, 30 μM for 60 min, n=10 neurons; 100 μM for 60 min, n=12 neurons), vehicle (n=11 neurons), α2δ-1Tat peptide (1 μM for 60 min, n=10 neurons), control peptide (cont peptide; 1 μM for 60 min, n=10 neurons), and Cacna2d1 KO (n=12 neurons for baseline and OGD groups) on NMDAR activity in hippocampal CA1 neurons subjected to 5 min of oxygen-glucose deprivation (OGD). Data are shown as means±SEM. *p<0.05 compared with the baseline amplitude of NMDAR currents before OGD induction. #p<0.05 compared with the OGD+vehicle or OGD+control peptide group (repeated measures ANOVA for the gabapentin effect; paired Student's t-test for the α2δ-1Tat effect).

Example 3—Focal Cerebral Ischemia and Reperfusion Induce Brain Injury Through 2-1-Bound NMDA Receptors α2δ-1 and its interaction with NMDARs are essential for the OGD-induced increase in neuronal NMDAR activity: Although increased NMDAR activity has been implicated in neuronal injury during cerebral ischemia, the underlying mechanisms remain unclear. It was thus determined the potential role of α2δ-1 in ischemia-induced NMDAR hyperactivity in the brain. Because MCAO causes severe neuronal damage, it is difficult to record neuronal NMDAR activity in and around the ischemic region. Hippocampal brain slices were subjected to oxygen-glucose deprivation (OGD) to simulate cerebral ischemia. OGD can increase NMDAR activity in hippocampal CA1 pyramidal neurons, which are highly susceptible to ischemic injury. OGD induction for 5 min induced a large increase in the amplitude of inward NMDAR currents in WT mice (FIGS. 19A and 19B). Gabapentin binds primarily to α2δ-1 and is a clinically used α2δ-1 inhibitory ligand. Treatment with gabapentin (30 μM or 100 μM for 60 min) had no effect on the basal puff NMDAR currents of hippocampal CA1 pyramidal neurons before OGD. Strikingly, the OGD-induced increase in the puff NMDAR currents was abolished in the presence of 30 μM or 100 μM gabapentin (FIGS. 19A and 19B).

α2δ-1 interacts with NMDARs predominantly through its C-terminal domain, and a 30-amino acid peptide (VSGLNPSLWSIFGLQFILLWLVSGSRHYLW; SEQ ID NO:1) mimicking the C-terminal domain of α2δ-1 fused with Tat protein (YGRKKRRQRRR; SEQ ID NO:2, α2δ-1Tat peptide) can interrupt the α2δ-1-NMDAR interaction in vivo. Treatment with α2δ-1Tat peptide (1 μM for 60 min) had no effect on the basal puff NMDAR currents of hippocampal CA1 pyramidal neurons from WT mice. However, OGD failed to increase NMDAR currents in neurons treated with α2δ-1Tat peptide (FIGS. 19A and 19B). Similar treatment with a control peptide, which was a Tat-fused scrambled peptide (FGLGWQPWSLSFYLVWSGLILSVLHLIRSN; SEQ ID NO:3), did not alter the OGD-induced increase in the NMDAR currents (FIGS. 19A and 19B).

In addition, Cacna2d1 KO mice were used to validate the critical role of α2δ-1 in OGD-induced NMDAR hyperactivity of hippocampal CA1 pyramidal neurons. Cacna2d1 KO mice do not show any evident neurological abnormalities although they exhibit reduced pain and reduced spinal NMDAR activity potentiated by nerve injury. The basal NMDAR currents of hippocampal CA1 neurons were similar in WT and Cacna2d1 KO mice before OGD induction. In contrast to OGD in the WT mice, OGD failed to affect puff NMDAR currents in CA1 pyramidal neurons in Cacna2d1 KO mice (FIGS. 19A and 19B). Collectively, these data indicate that α2δ-1, by interacting with NMDARs, is essential for ischemia-induced neuronal NMDAR hyperactivity in the brain.

Figures 20A, 20B, 20C, 20D:
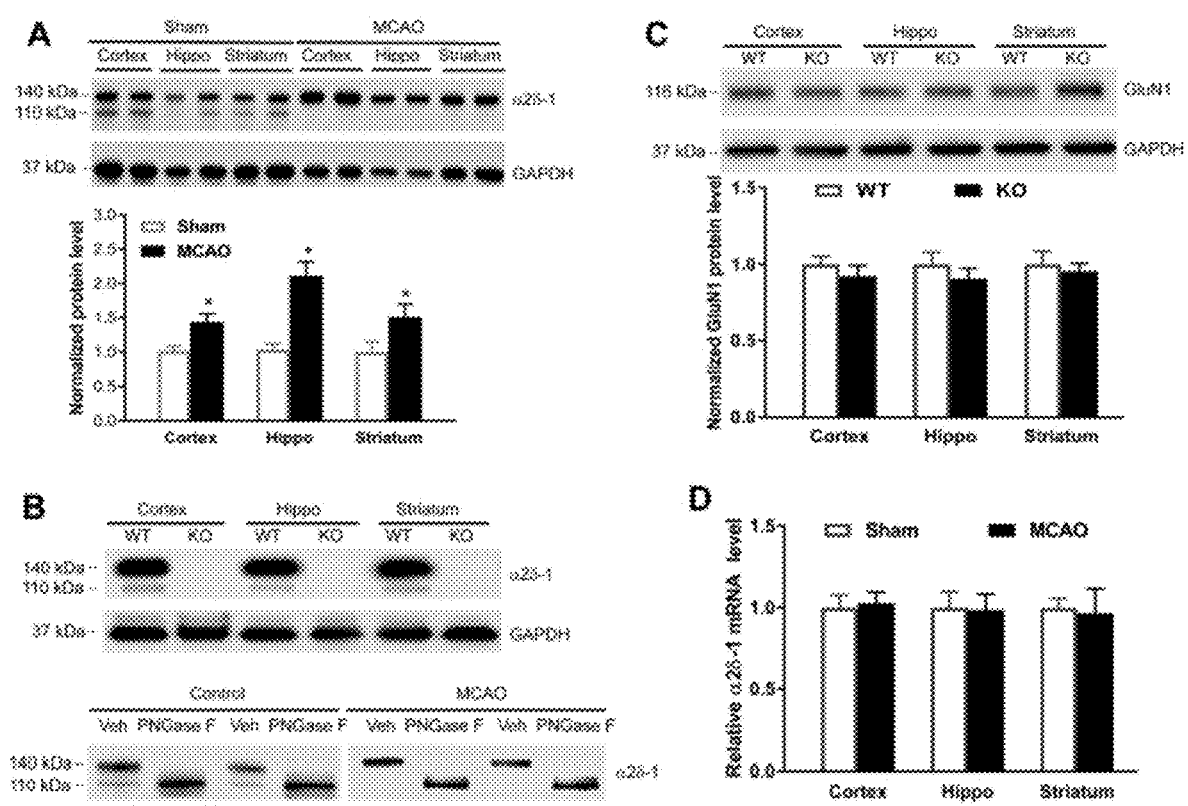
FIGS. 20A-20D: Focal cerebral ischemia increases the protein level and glycosylation of α2δ-1. (A) Representative gel images show α2δ-1 protein levels in different regions of brain tissues from sham control mice and mice subjected to 90 min of MCAO followed by 24 h of reperfusion. (B) Quantification of α2δ-1 protein levels in the cerebral cortex, hippocampus (Hippo), and striatum in mice with MCAO and sham control mice (n=8 mice per group). (C) Representative gel images of α2δ-1 protein bands in different regions of brain tissues from wild-type (WT) and Cacna2d1 knockout (KO) mice. (D) α2δ-1 protein bands detected in 2 sets of cortical tissue lysates treated with PNGase F or vehicle (Veh).
Figures 21A, 21B, 21C, 21D:
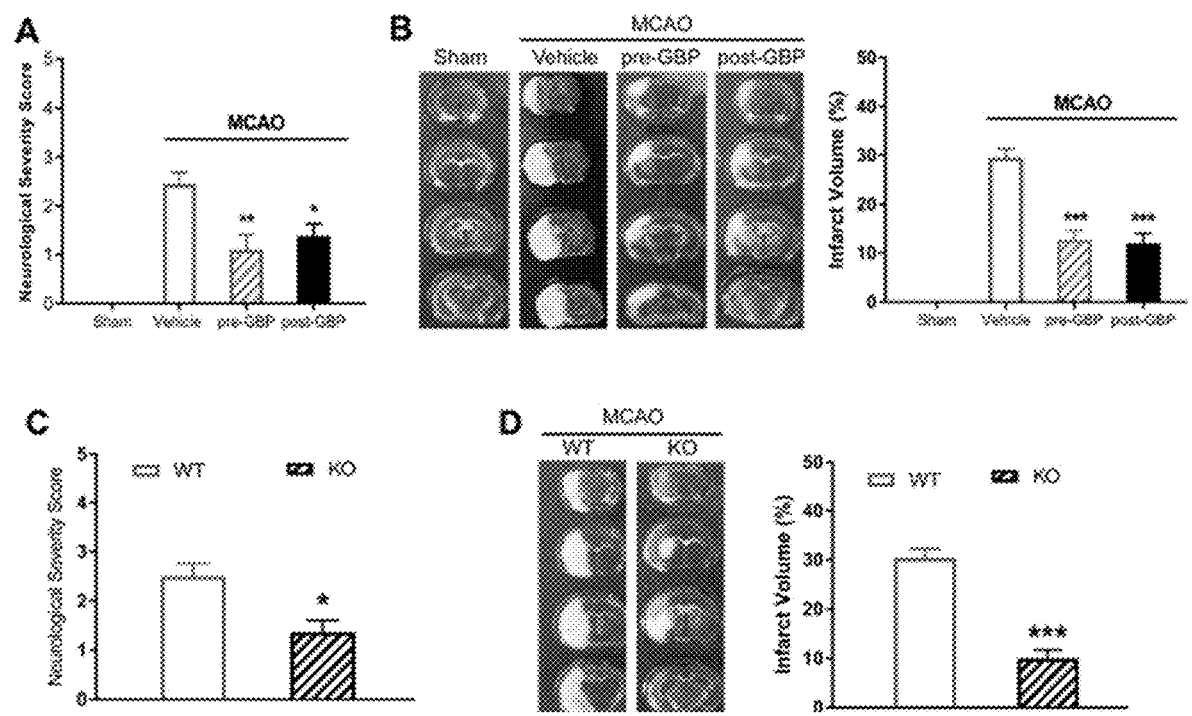
FIGS. 21A-21D: α2δ-1 critically contributes to brain injury and neurological deficit caused by MCAO. (A) Neurological deficit scores in sham control mice (n=8 mice) and MCAO mice treated with vehicle (n=9 mice), gabapentin before MCAO (pre-GBP, n=10 mice), or gabapentin after MCAO (post-GBP, n=8 mice). (B) Representative triphenyltetrazolium chloride (TTC) staining and quantification of brain infarct volume in sham control mice (n=8 mice) and MCAO mice treated with vehicle (n=9 mice), gabapentin before MCAO (n=10 mice), or gabapentin after MCAO (n=8 mice). (C) Neurological deficit scores in Cacna2d1 knockout (KO) mice and wild-type (WT) mice subjected to 90 min of MCAO followed by 24 h reperfusion (n=8 mice per group). (D) Representative TTC staining and quantification of brain infarct volume in Cacna2d1 KO and WT mice (n=8 mice per group). Data are shown as means±SEM. *p<0.05, p<0.01, *p<0.001 each compared with the vehicle MCAO or WT control group (Kruskal-Wallis test for panel A; repeated measures ANOVA for panel B; Mann-Whitney test for panel C; paired Student's t-test for panel D).
Figures 22A, 22B, 22C, 22D:
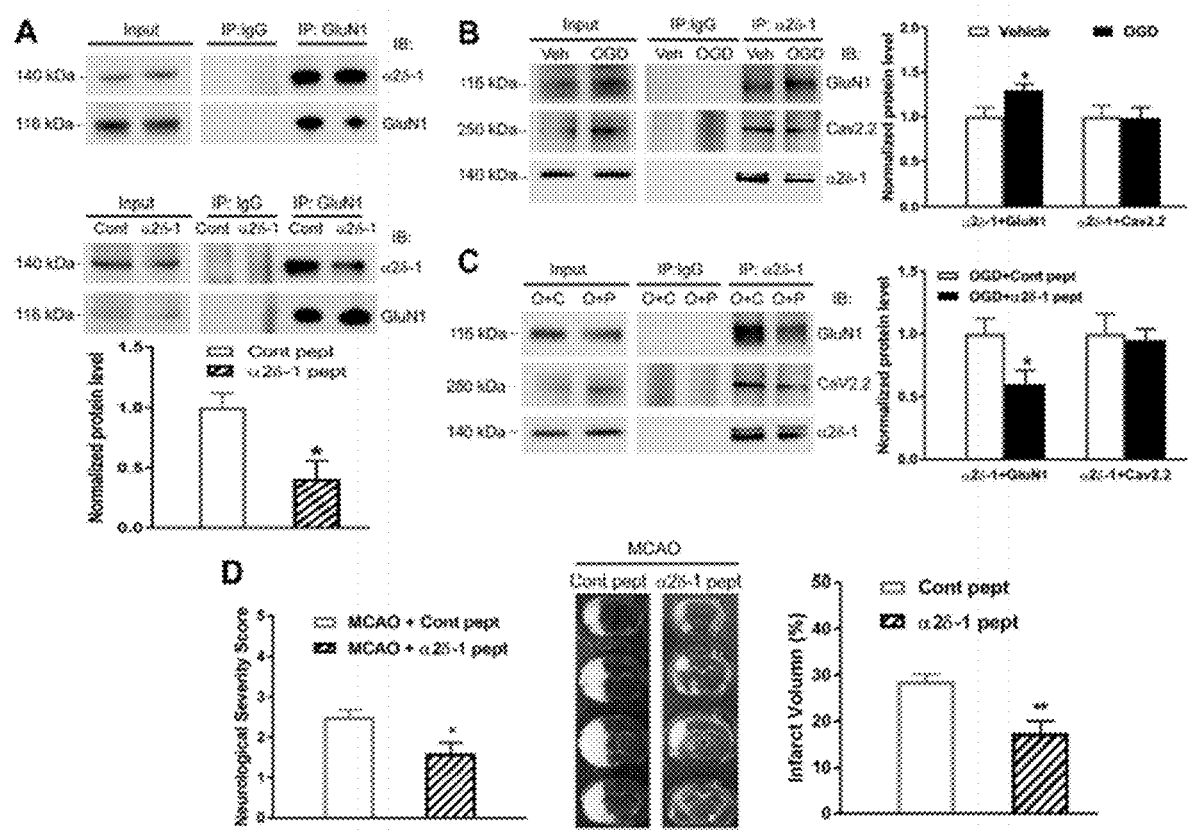
FIGS. 22A-22D: α2δ-1-bound NMDARs contribute to brain injury and neurological deficit caused by MCAO in the brain. (A) Upper: Original gel images of coimmunoprecipitation (co-IP) analysis show the interaction between α2δ-1 and GluN1 in two samples from mouse brain tissues; Lower: Effect of α2δ-1Tat peptide (1 μM for 60 min) on the α2δ-1-GluN1 protein complex in mouse brain tissues (n=6 mice per group). (B) Representative gel images and quantification of co-IP analysis show the effect of OGD on the α2δ-1-GluN1 or α2δ-1-Cav2.2 association in mouse brain tissues (n=6 mice per group). IgG and input were used as negative and positive controls, respectively. (C) Original gel images and quantification of co-IP analysis show the effect of α2δ-1Tat peptide (P) and control peptide (C; both 1 μM for 30 min) on the α2δ-1-GluN1 or α2δ-1-Cav2.2 association in mouse brain slices subjected to OGD (O, n=6 mice per group). (D) Neurological severity scores (left) and representative TTC staining and quantification (right) of brain infarct volume in MCAO mice treated with α2δ-1Tat peptide or control peptide (both 200 μg/kg, i.p.) at 15 min before MCAO and immediately before reperfusion (n=8 mice per group). Data are shown as means±SEM. *p<0.05, **p<0.01 compared with the control peptide- or vehicle-treated group (paired Student's t-test for panels B-D and F; Mann-Whitney test for panel E).

Focal cerebral ischemia/reperfusion increases α2δ-1 protein glycosylation in the brain: To determine whether focal cerebral ischemia/reperfusion affects α2δ-1 protein levels in brain tissues, 90 min of middle cerebral artery occlusion (MCAO) was induced followed by 24 h of reperfusion in mice to produce stable infarct volume and neurological impairment. Immunoblotting of the forebrain tissues detected two α2δ-1 protein bands at 140 kDa and 110 kDa in sham control mice but a single 140 kDa band in MCAO mice (FIG. 20A). The α2δ-1 protein level at 140 kDa in the cerebral cortex, hippocampus, and striatum was significantly higher in the MCAO group than in the sham control group (FIG. 20A). Immunoblotting of brain tissues using Cacna2d1 KO mice confirmed that both 110 kDa and 140 kDa protein bands in control mice were α2δ-1 proteins (FIG. 20B). Because α2δ-1 is a highly glycosylated protein, it was determined whether the MCAO-induced α2δ-1 protein band shift results from increased glycosylation. Cortical tissue samples were treated from sham and MCAO mice with 500 units of PNGase F for 60 min. In tissues treated with PNGase F, only a single 110 kDa protein brand was detected in both sham and MCAO mice (FIG. 20B). The GluN1 protein level in brain tissues was similar in WT and Cacna2d1 KO mice (FIG. 20C). The α2δ-1 mRNA level did not differ significantly between sham control and MCAO groups (FIG. 20D). These data suggest that cerebral ischemia/reperfusion increases α2δ-1 glycosylation in brain tissues.

α2δ-1 Contributes to MCAO-induced neurological deficits and brain infarct: Gabapentin was used to determine the contribution of α2δ-1 to brain injury and neurological deficits caused by 90 min of MCAO followed by 24 h of reperfusion in WT mice. Gabapentin was administered intraperitoneally (i.p.) either before or after initiating MCAO in separate groups of mice (pretreatment and posttreatment groups). For pretreatment, a single dose of gabapentin (100 mg/kg, i.p.) was injected 15 min before MCAO. For posttreatment, two doses of gabapentin (100 mg/kg, i.p.) were injected: one at 30 min after MCAO and another at 6 h after reperfusion. Saline at the same volume as the gabapentin was administered i.p. in a vehicle group that also received MCAO. Both pretreatment and posttreatment with gabapentin significantly improved neurological deficit scores compared with vehicle treated MCAO mice (FIG. 21A). Furthermore, the MCAO-induced brain infarct volume was much smaller in both groups of mice treated with gabapentin than in mice treated with vehicle (FIG. 21B). These data suggest that α2δ-1 contributes significantly to ischemia/reperfusion-induced brain damage and neurological deficits.

α2δ-1 Ablation attenuates MCAO-induced neurological deficits and brain injury: To validate the important role of α2δ-1 in MCAO-induced brain damage, 90 min of MCAO was induced followed by 24 h of reperfusion in Cacna2d1 KO mice. The MCAO-induced neurological deficit score (1.36±0.81 vs. 2.50±0.76, p=0.0064) and brain infarct volume (11.54±3.07% vs. 30.41±5.08%, p<0.0001) were much lower in Cacna2d1 KO mice than in WT mice (FIGS. 21C and D). These findings provide unequivocal evidence for the critical role of α2δ-1 in ischemia/reperfusion induced brain injury and neurological impairment.

α2δ-1-bound NMDARs contribute to MCAO-induced neurological deficits and brain infarct: Because the α2δ-1 and NMDAR interaction has been shown only in the spinal cord, coimmunoprecipitation (co-IP) was used to determine whether α2δ-1 physically interacts with GluN1, an obligatory subunit of NMDARs, in mouse brain tissues. Co-IP analysis showed that the α2δ-1 protein was precipitated by an anti-GluN1 antibody, but not by an irrelevant IgG, in the mouse brain tissues (FIG. 22A). To determine whether the α2δ-1Tat peptide reduces the α2δ-1-NMDAR interaction in the mouse tissue, additional co-IP assays were conducted using mouse brain slices treated with α2δ-1Tat peptide or a Tat-fused control peptide (1 µM for 60 min). Treatment with α2δ-1Tat peptide caused a large reduction in the α2δ-1-GluN1 protein complex in the brain tissues (FIG. 22A). Furthermore, co-IP analysis showed that OGD increased the α2δ-1-GluN1 protein complex level but had no effect on the α2δ-1-Cav2.2 association in membrane extracts from brain tissues (FIG. 22B). Treatment with α2δ-1Tat peptide substantially reduced the α2δ-1-GluN1 interaction but had no effect on the α2δ-1-Cav2.2 association in brain tissues subjected to OGD (FIG. 22C).

Figures 23A, 23B, 23C, 23D:
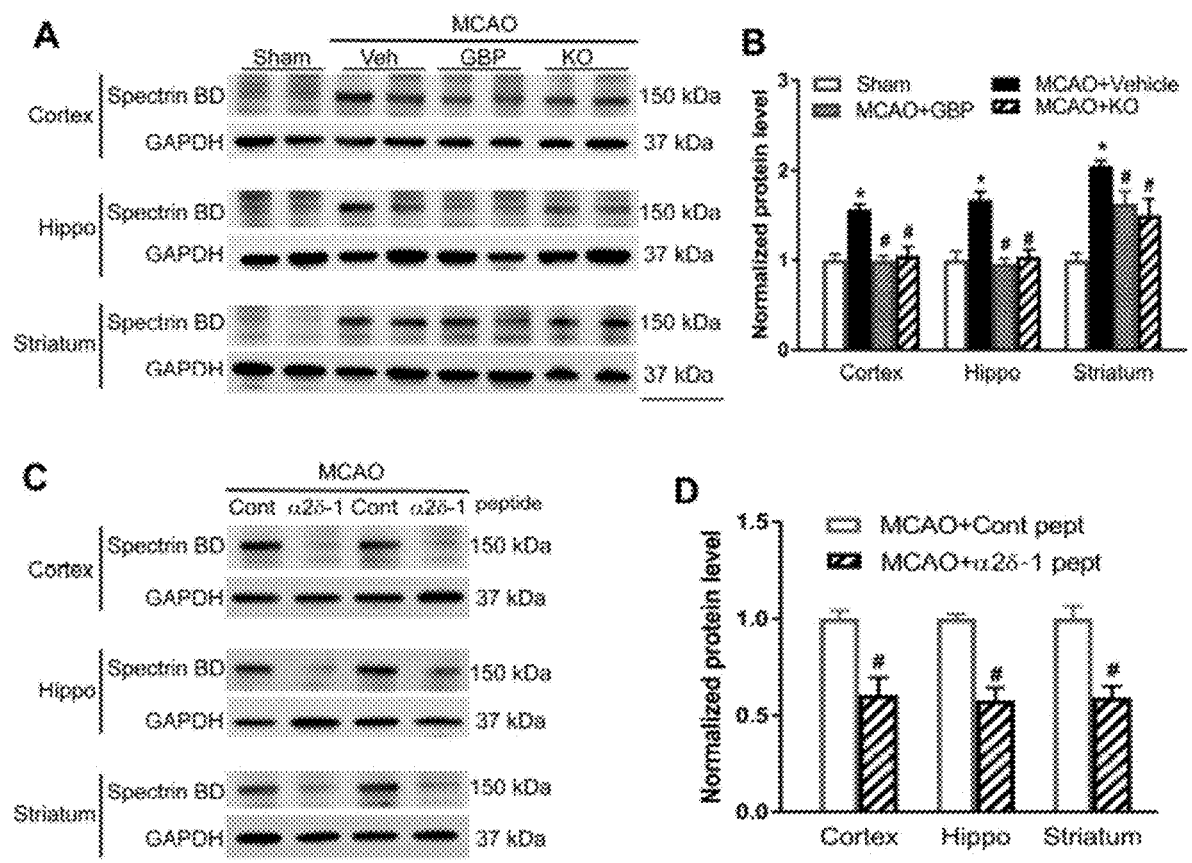
Figures 24A, 24B, 24C, 24D:
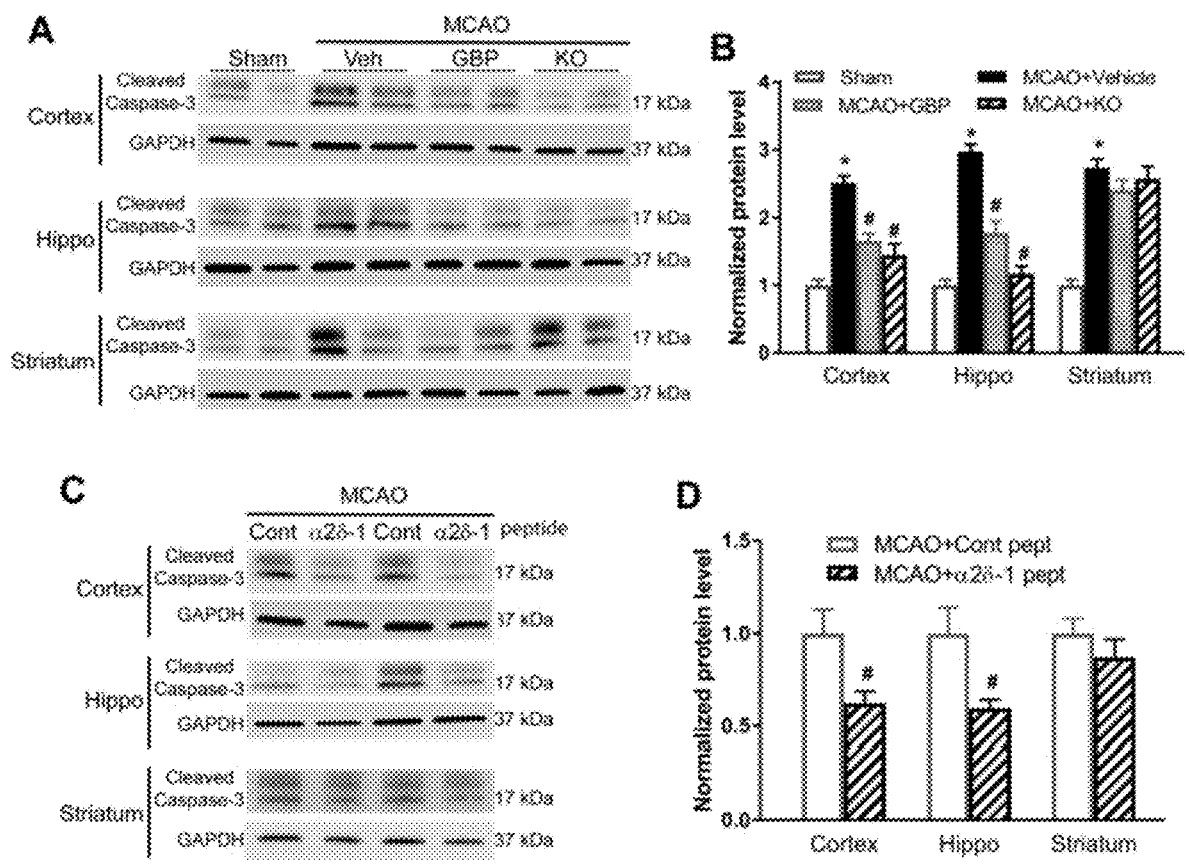

It was then determined whether the α2δ-1-NMDAR interaction is involved in brain injury and neurological deficits caused by MCAO. In this protocol, MCAO-subjected mice with two injections of α2δ-1Tat peptide or control peptide (both 200 µg/kg, i.p.): one at 15 min before MCAO and another immediately before reperfusion. Systemic treatment with α2δ-1Tat peptide significantly reduced the neurological deficit score increased by MCAO compared with that in control peptide-treated mice (FIG. 22D). Furthermore, the brain infarct volume was much less in mice treated with α2δ-1Tat peptide than in mice treated with the control peptide (FIG. 22D). These results indicate that α2δ-1-bound NMDARs play a major role in ischemia/reperfusion-induced brain injury and associated neurological deficits.

α2δ-1 and α2δ-1-bound NMDARs contribute to MCAO-induced calpain activation in brain tissues: Cerebral ischemia increases calpain activity, and calpain inhibition is neuroprotective against ischemia-induced brain injury. Spectrin is highly sensitive to proteolysis by calpain, and the stable αIIspectrin breakdown product (spectrin BD, 150 kDa) is commonly used as a biochemical assay for calpain activation. Immunoblotting analysis showed that compared with the sham control group, 90 min of MCAO followed by 24 h of reperfusion caused a large increase in the spectrin BD level in the cerebral cortex, hippocampus, and striatum in WT mice subjected to MCAO (FIGS. 23A and B). Systemic administration of gabapentin in WT mice subjected to MCAO (posttreatment protocol) and Cacna2d1 KO mice subjected to MCAO significantly reduced the spectrin BD level in all three regions compared with that in vehicle-treated WT mice subjected to MCAO (FIGS. 23A and B).

Also, compared with the MCAO group treated with control peptide, α2δ-1Tat peptide treatment (two injections of 200 µg/kg, i.p.: one at 15 min before MCAO and another immediately before reperfusion) significantly reduced the spectrin BD level in the cortex, hippocampus, and striatum in WT mice (FIGS. 23C and D). Together, these data suggest that α2δ-1, through its interaction with NMDARs, mediates ischemia/reperfusion-induced calpain activation in brain tissues.

In summary, this study provides evidence that α2δ-1-bound NMDARs play a major role in brain damage caused by ischemia/reperfusion. This information advances the understanding of the molecular mechanism of neuronal NMDAR hyperactivity during ischemic stroke. α2δ-1-bound NMDARs are a promising target for the development of novel neuroprotective therapies that could have greater therapeutic windows than general NMDAR antagonists.

Example 4—Materials and Methods

Animal model. All procedures and protocols were approved by the Institutional Animal Care and Use Committee of The University of Texas MD Anderson Cancer Center. Adult male wild-type (WT) and conventional Cacna2d1 knockout (KO) mice (25-30 g, 8-10 weeks of age) were used in the study. MCAO was used in mice as an ischemic stroke model. The neurological deficits of mice subjected to MCAO were evaluated using a modified Longa test on a scale of 0-5. The brain coronal sections were stained using 1% 2,3,5-triphenyltetrazolium chloride (TTC), and the stained sections were captured as digital images and quantified for infarct volume.

Brain slice preparation and recording. The tissues containing the hippocampus were sliced sagittally (300 µm thick) using a vibratome. Oxygen-glucose deprivation (OGD) was induced by perfusing brain slices with aCSF saturated with 95% $N_2$/5% $CO_2$ and by replacing the 11 mM glucose in aCSF with 11 mM sucrose. NMDAR currents of pyramidal neurons in the hippocampal CA1 region were recorded by puff application of 100 µM NMDA directly to the recorded neuron at a holding potential of −60 mV.

Example 5—Angiotensin II-Induced Sympathetic Output and NMDAR Activation in the Hypothalamus α2δ-1 physically interacts with NMDARs in the hypothalamus of rats and humans: To determine whether α2δ-1 and NMDARs interact in the hypothalamus, coimmunoprecipitation (co-IP) analyses were conducted using membrane extracts of the rat hypothalamus. Using specific antibodies, α2δ-1 was coprecipitated with GluN1, an obligatory subunit of NMDARs (FIG. 25A), whereas the irrelevant IgG did not pull down α2δ-1 in the hypothalamic tissue.

Figures 25A, 25B, 25C, 25D, 25E:
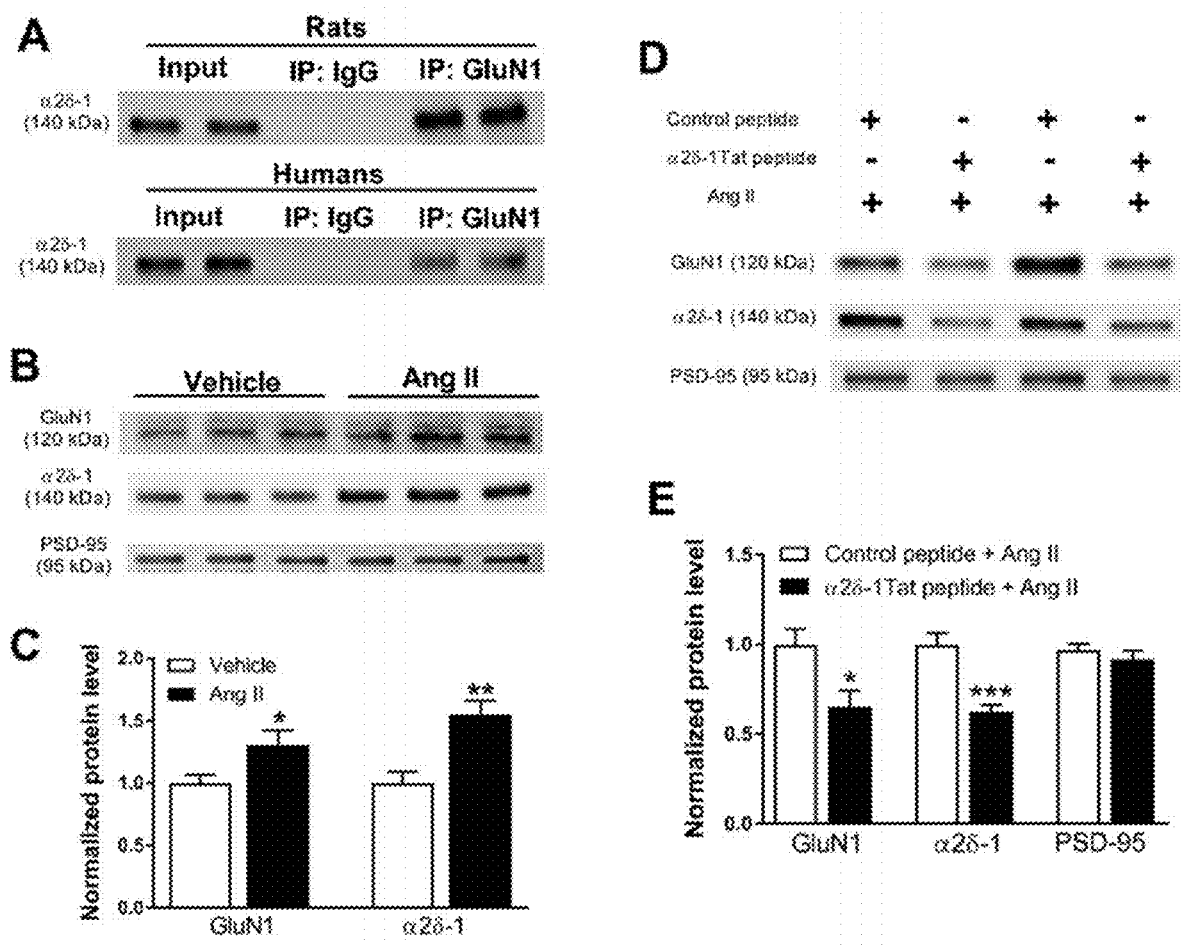

In addition, the anti-GluN1 antibody, but not IgG, coimmunoprecipitated with α2δ-1 in membrane extracts from human hypothalamic tissues (n=4 subjects; FIG. 25A). These results indicate that α2δ-1 physically interacts with NMDARs in the hypothalamus in both rats and humans Ang II increases the prevalence of α2δ-1-NMDAR complexes in the hypothalamus: The synaptic NMDARs are highly dynamic and depend on trafficking from their intracellular pool (Tovar and Westbrook, 2002; Chen et al., 2018). It was thus determined whether Ang II increases synaptic targeting of α2δ-1-NMDAR complexes in the PVN. Hypothalamic slices were sectioned 1.08 to 2.12 mm caudal to the bregma and treated with Ang II (2 µmol/L) or vehicle for 60 min. Synaptosomes were then isolated from the tissue slices. Immunoblotting showed that Ang II significantly increased the protein levels of GluN1 (P=0.043, t(10)=2.237; n=12 rats/group) and α2δ-1 (P=0.004, t(10)=3.724, n=12 rats/group) in hypothalamic synaptosomes (FIG. 1B,C).

It was next determined whether the α2δ-1-NMDAR interaction is involved in Ang II-induced increases in the protein levels of GluN1 and α2δ-1 at the synaptic sites. Hypothalamic slices were incubated with Ang II for 60 min in the presence of control peptide or α2δ-1Tat peptide. It was shown that the C-terminus of α2δ-1 is essential for its interaction with NMDARs and that a 30-amino-acid peptide (VSGLNPSLWSIFGLQFILLWLVSGSRHYLW; SEQ ID NO:1) mimicking the C-terminal domain of α2δ-1 fused with Tat protein (YGRKKRRQRRR; SEQ ID NO:2) can uncouple the α2δ-1-NMDAR interaction (Chen et al., 2018). The effect of Ang II on the protein levels of GluN1 (P=0.014, t(12)=2.862; n=14 rats/group) and α2δ-1 (P=0.0003, t(12)=4.956; n=14 rats/group) was significantly attenuated in hypothalamic synaptosomes treated with α2δ-1Tat peptide (1 µmol/L for 30 min), compared with those treated with a Tat-fused scrambled control peptide (FGLGWQPWSLSFYLVWSGLILSVLHLIRSN; SEQ ID NO:3) (FIG. 25D,E). These data suggest that Ang II increases the synaptic targeting/trafficking of α2δ-1-bound NMDARs in the hypothalamus.

Figures 26A, 26B, 26C, 26D, 26E, 26F, 26G, 26H:
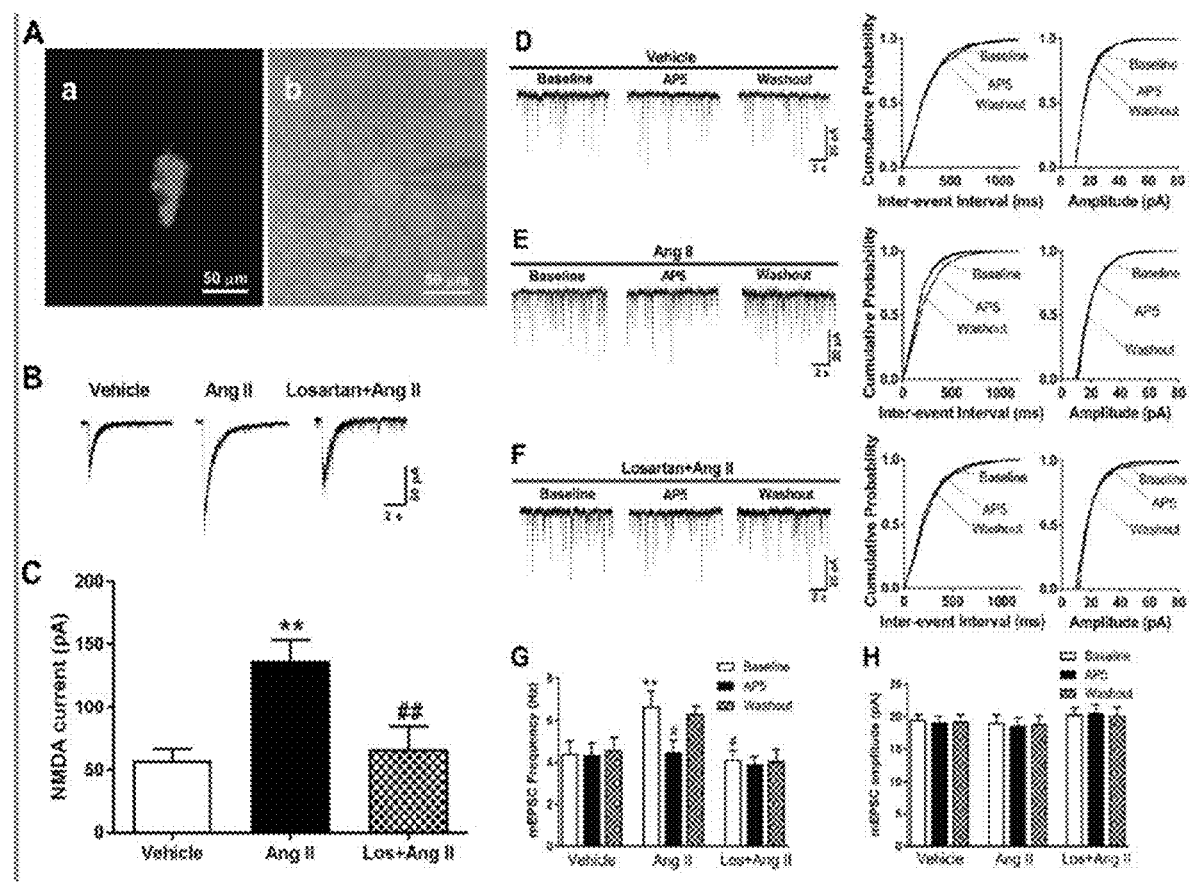

Ang II increases pre- and postsynaptic NMDAR activity via AT1 receptors in spinally projecting PVN neurons: Systemic administration of Ang II in mice is associated with an increased amplitude of NMDA-elicited currents in PVN neurons (Wang et al., 2013). To determine whether Ang II affects the postsynaptic NMDAR activity in spinally projecting PVN neurons, the NMDAR current elicited by puff NMDA application were recorded directly to labeled PVN neurons. Incubation of brain slices with Ang II (2 µmol/L for 30-60 min) markedly increased the amplitude of puff NMDA currents (n=11 neurons, P=0.002, F(2,24)=8.020; FIG. 26A-C). This effect of Ang II on puff NMDAR currents was abolished by co-incubation with an angiotensin AT1 receptor antagonist, losartan (2 µmol/L, 30 min; n=8 neurons, FIG. 26B,C).

Figures 27A, 27B, 27C, 27D, 27E, 27F, 27G:
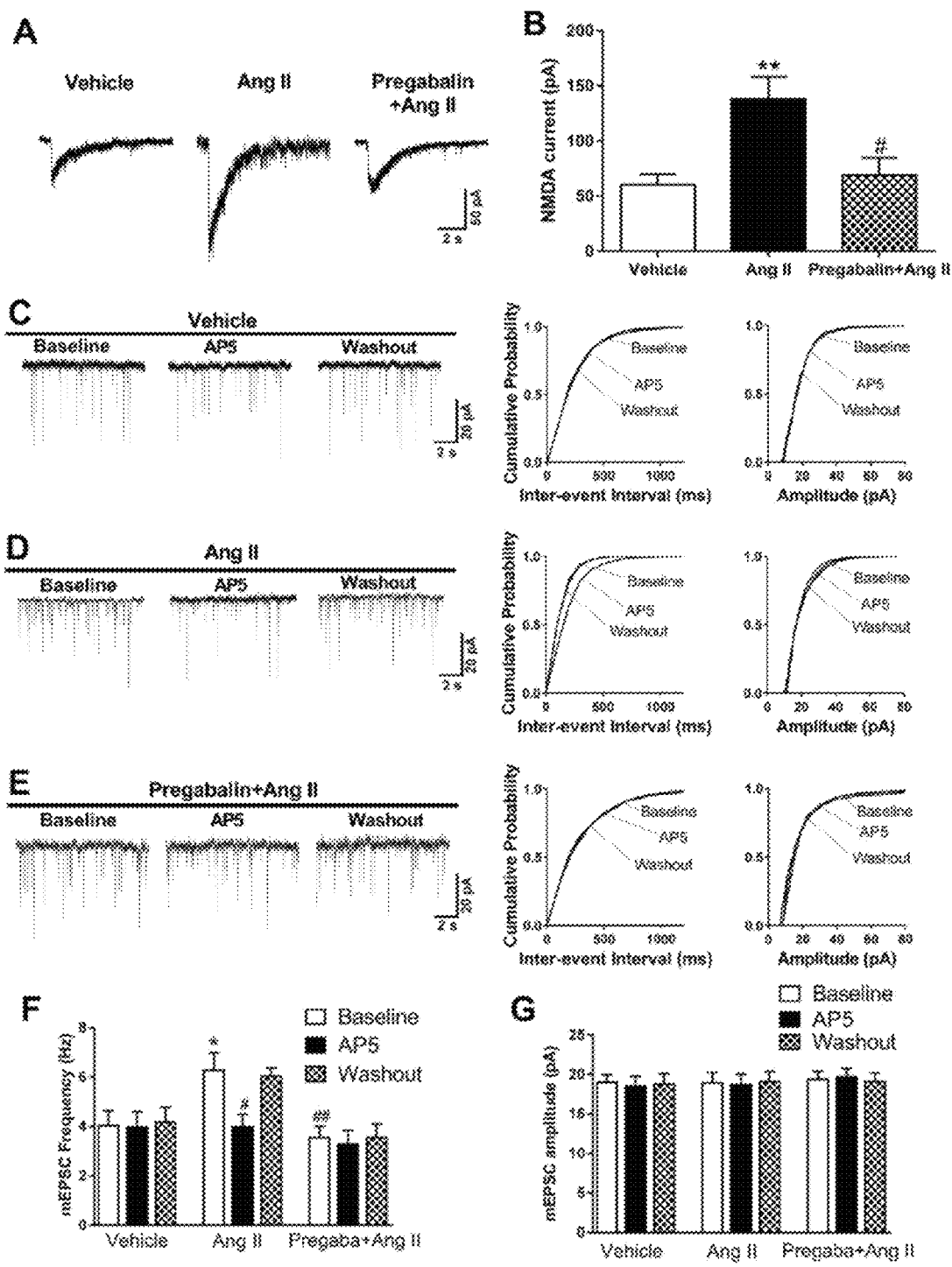

To specifically determine whether Ang II affects the presynaptic NMDAR activity of labeled PVN neurons, the effect of Ang II on mEPSCs was examined, which reflects spontaneous quantal release of glutamate from presynaptic terminals (Ye et al., 2011; Qiao et al., 2017). Incubation of brain slices with Ang II (2 µmol/L for 30-60 min) significantly increased the baseline frequency, but not the amplitude, of the mEPSCs of the retrogradely labeled PVN neurons that project to the spinal cord (n=8 neurons, P=0.004, F(8,60)=3.295; FIG. 26D-H). Bath application of the NMDAR antagonist AP5 (50 µmol/L) rapidly reversed the Ang II-induced increase in mEPSC frequency, indicating that presynaptic NMDARs mediate the Ang II-induced increase in synaptic glutamate. In contrast, AP5 application had no effect on the frequency of the mEPSCs of labeled PVN neurons in vehicle-treated slices (n=8 neurons in each group; FIG. 26D-H). The effect of Ang II on mEPSCs was completely blocked by pretreatment with 2 µmol/L losartan (Li et al., 2003) (n=7 neurons; FIG. 26D-H). These data suggest that Ang II increases pre- and postsynaptic NMDAR activity in PVN presympathetic neurons via AT1 receptors.

α2δ-1 activity is required for Ang II's effect on pre- and postsynaptic NMDAR activity in PVN presympathetic neurons: α2δ-1 is a highly glycosylated protein involved in protein trafficking. Both gabapentin and pregabalin bind predominantly to α2δ-1 (Gee et al., 1996; Wang et al., 1999;

Marais et al., 2001; Fuller-Bicer et al., 2009) and act as an inhibitory α2δ-1 ligand. In contrast to the potentiating effect of Ang II on the amplitude of NMDAR currents elicited by puff application of NMDA in labeled PVN neurons treated with vehicle (n=10 neurons), Ang II had no significant effect on puff NMDA currents in brain slices pretreated with pregabalin (n=7 neurons; FIG. 27A,B).

Although it stimulated the mEPSC frequency in vehicle-treated slices (n=9 neurons), Ang II failed to increase the frequency of mEPSCs of labeled PVN neurons in brain slices treated with pregabalin (20 μmol/L for 30-60 min, n=9 neurons; FIG. 27E,F). Furthermore, bath application of AP5 (50 μmol/L) readily normalized the frequency of mEPSCs increased by Ang II plus vehicle but had no effect on the mEPSC frequency in brain slices treated with Ang II plus pregabalin (FIG. 27C-F). These data suggest that $\alpha_2\delta$-1 mediates the Ang II-induced increases in pre- and postsynaptic NMDAR activity in PVN presympathetic neurons.

Disrupting the α2δ-1-NMDAR interaction abolishes Ang II's effect on pre- and postsynaptic NMDAR activity in PVN presympathetic neurons: The α2δ-1Tat peptide was used to determine whether $\alpha_2\delta$-1-bound NMDARs are required for the Ang II effect on synaptic NMDAR activity of spinally projecting PVN neurons. In brain slices pretreated with α2δ-1Tat peptide (1 μmol/L, 30 min), Ang II (2 μmol/L) had no effect on the amplitude of puff NMDA currents of labeled PVN neurons (n=9 neurons). In contrast, Ang II significantly increased the amplitude of puff NMDA currents in the presence of the control peptide (1 μmol/L, 30 min; n=13 neurons, FIG. 28A,B).

Figures 28A, 28B, 28C, 28D, 28E, 28F:
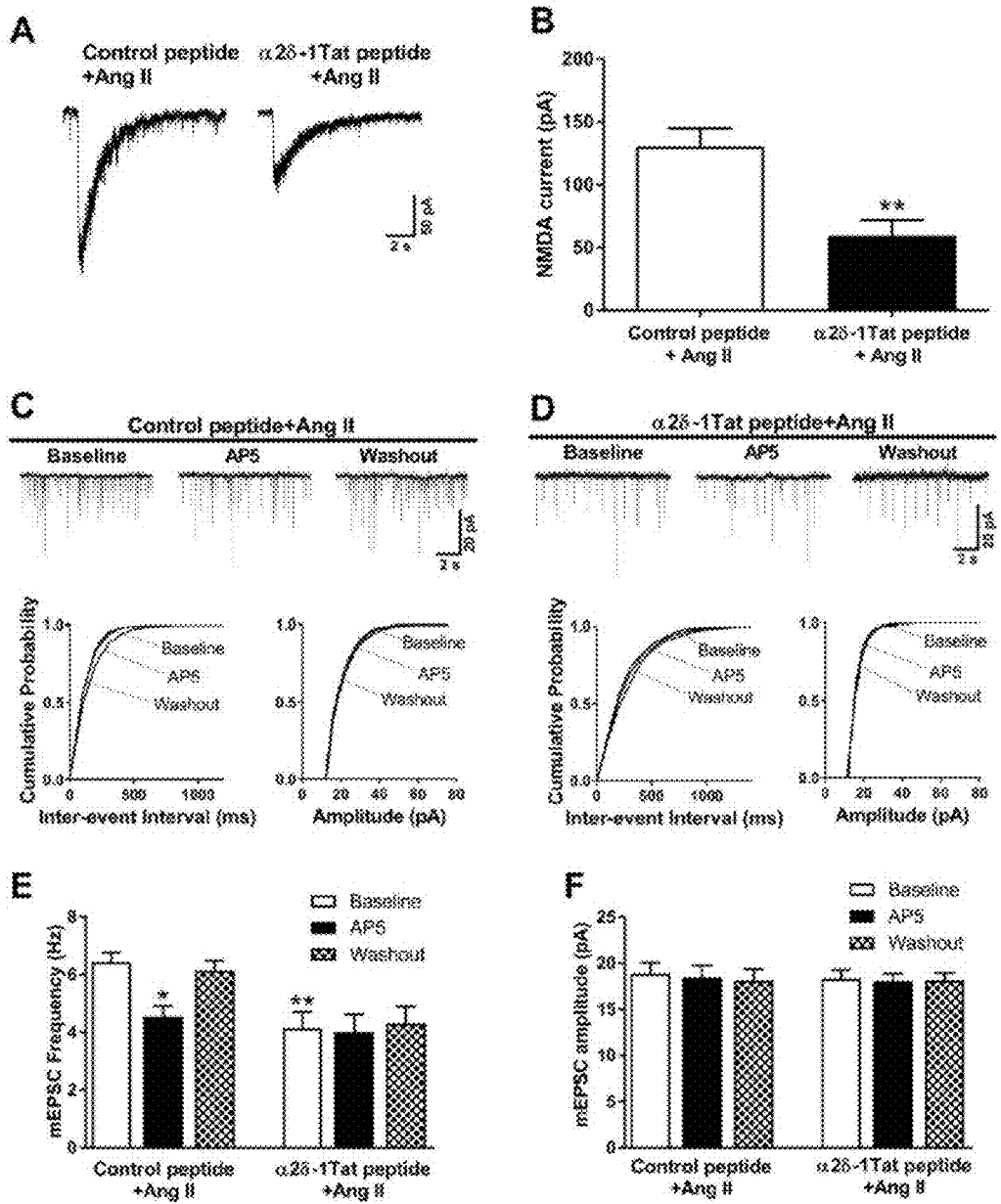
Figures 29A, 29B, 29C, 29D, 29E, 29F, 29G, 29H:
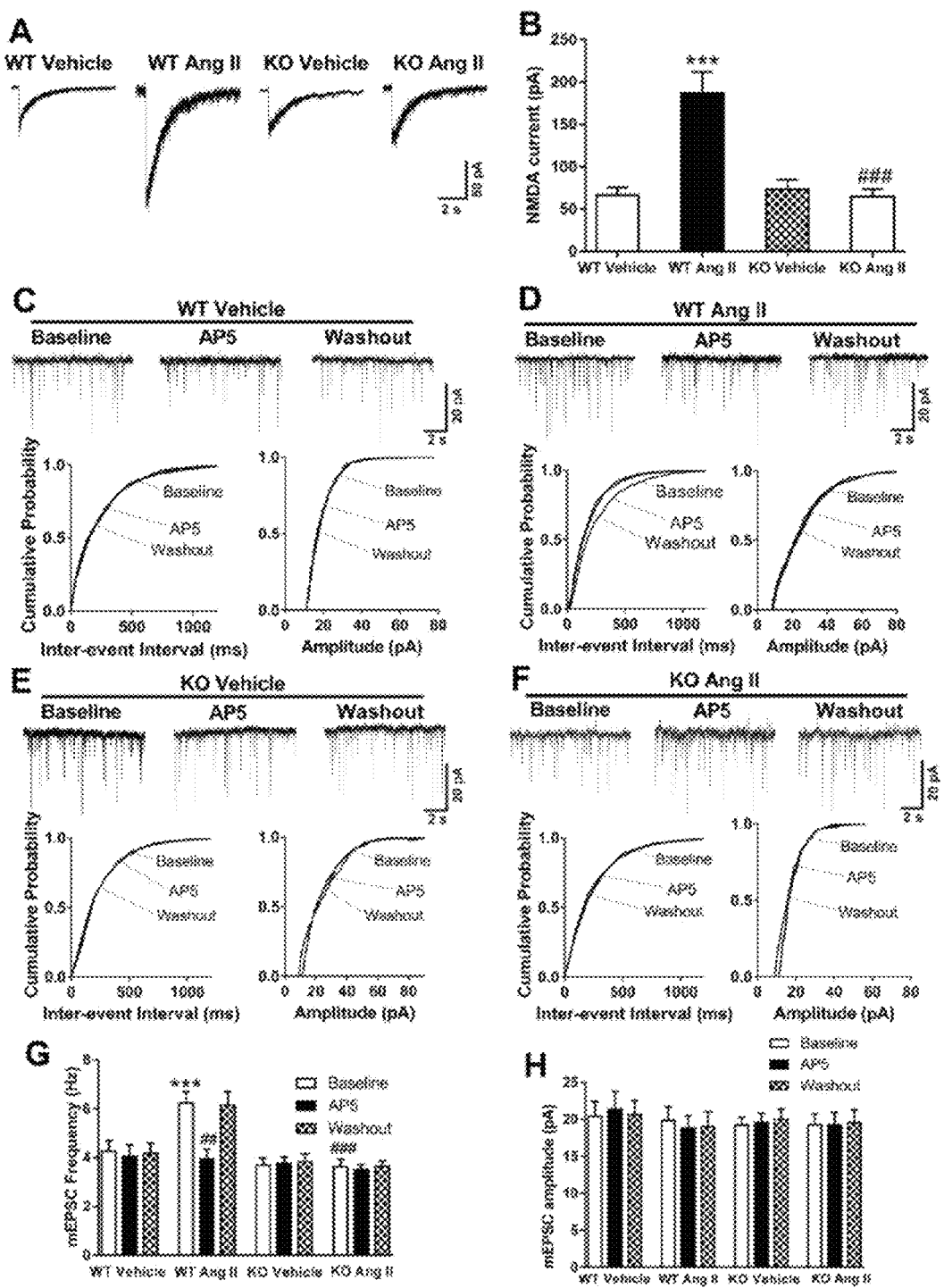
Figures 30A, 30B, 30C, 30D, 30E, 30F, 30G, 30H, 30I, 30J:
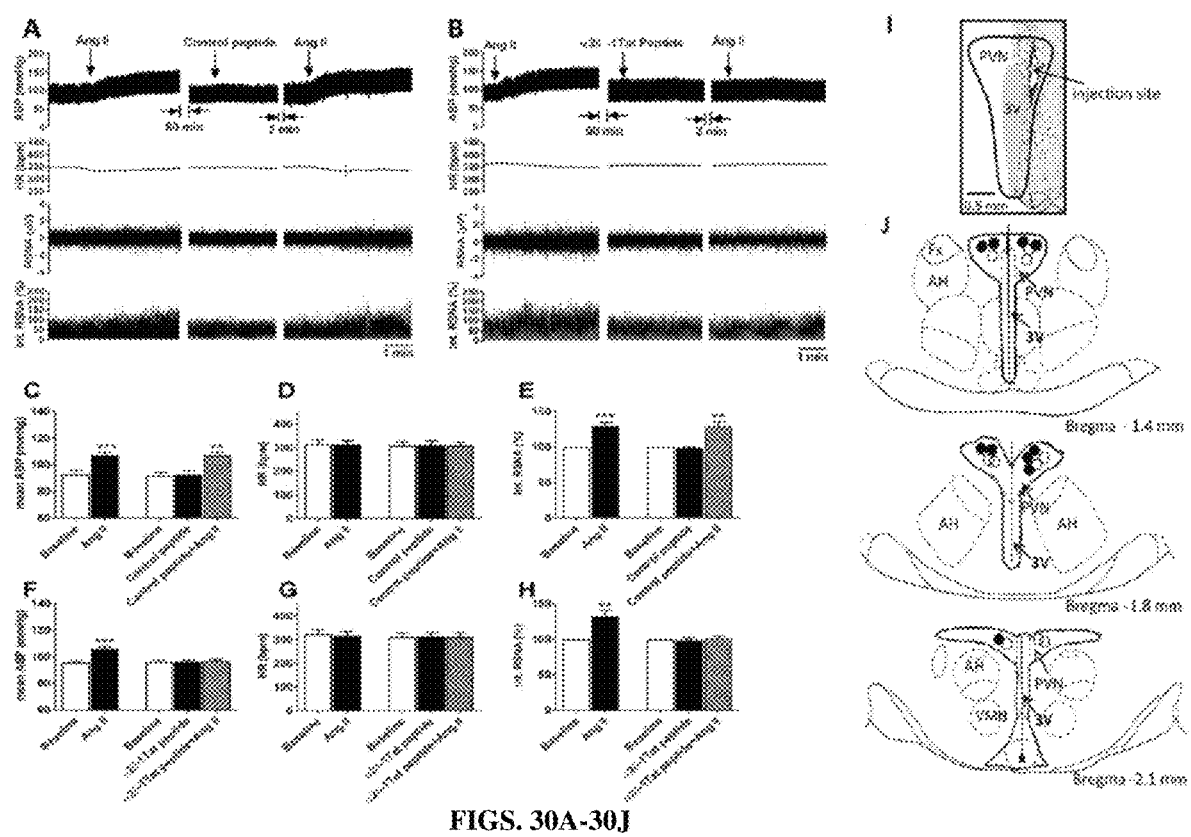

In brain slices incubated with the α2δ-1Tat peptide, Ang II failed to increase the frequency of mEPSCs in all labeled PVN neurons (n=8 neurons, FIG. 28D,E). However, a Tat-fused scrambled control peptide did not affect the stimulating effect of Ang II on the mEPSC frequency in separate labeled PVN neurons (n=9 neurons, FIG. 28C,E). Bath application of AP5 (50 μmol/L) normalized the increased frequency of mEPSCs in brain slices treated with Ang II plus the control peptide but had no effect on the mEPSC frequency in brain slices treated with Ang II plus α2δ-1Tat peptide (FIG. 28C-F). These findings indicate that α2δ-1-bound NMDARs are essential for Ang II-induced increases in the pre- and postsynaptic NMDAR activity of PVN presympathetic neurons.

α2δ-1 is required for Ang II's effect on pre- and postsynaptic NMDAR activities in PVN presympathetic neurons: Because pharmacological agents may produce off-target effects, Cacna2d1 knockout (Cacna2d1$^{-/-}$) mice were used to validate the critical role of α2δ-1 in the Ang II-induced increase in synaptic NMDAR activity. In wild-type (Cacna2d1$^{+/+}$) mice, Ang II treatment markedly increased the amplitude of puff NMDA-elicited currents (n=8 neurons per group; FIG. 29A,B) and the NMDAR-mediated frequency of mEPSCs (n=8 neurons per group; FIG. 29C-H) in spinally projecting PVN neurons. In contrast, in Cacna2d1$^{-/-}$ mice, Ang II treatment had no effect on the amplitude of puff NMDA-elicited currents (n=10 neurons per group) or the frequency of mEPSCs (n=9 neurons per group) in labeled PVN neurons. These data provide unequivocal evidence showing that α2δ-1 is essential for Ang II-induced increases in the synaptic NMDAR activity of PVN presympathetic neurons.

α2δ-1-bound NMDARs are critically involved in the sympathoexcitatory responses to Ang II in the PVN: In addition, it was determined whether α2δ-1-bound NMDARs in the PVN play a role in sympathoexcitatory responses to Ang II in vivo. Because pregabalin and gabapentin bind to both α2δ-1 and α2δ-2 (Gee et al., 1996; Gong et al., 2001; Marais et al., 2001; Li et al., 2011), the α2δ-1Tat peptide was used, which selectively targets and disrupts the α2δ-1-NMDAR association (Chen et al., 2018). The sympathoexcitatory responses elicited by microinjection of Ang II in the PVN were examined in the presence of α2δ-1Tat peptide or the control peptide. As reported previously (Khanmoradi and Nasimi, 2016), microinjection of Ang II (200 μmol/L, 50 nl) into the PVN in anesthetized rats significantly increased the RSNA and mean ABP, and such effects were not altered by prior microinjection of the control peptide (n=10 rats; FIG. 30A-H). In contrast, when α2δ-1Tat peptide (100 μmol/L, 50 nl) was microinjected into the PVN, subsequent microinjection of Ang II into the PVN failed to significantly increase ABP and RSNA (n=10 rats; FIG. 30A, C-E). These data suggest that α2δ-1-bound NMDARs are required for the sympathoexcitatory responses to Ang II in the PVN.

In the present study, it was found that α2δ-1 physically interacts with NMDARs in the hypothalamus in both rats and humans. It was also found that Ang II increases the protein levels of α2δ-1 and NMDARs in the hypothalamic synaptosomes and that blocking the α2δ-1-NMDAR interaction with α2δ-1Tat peptide abolishes this effect of Ang II. These findings suggest that Ang II increases the synaptic trafficking of α2δ-1-bound NMDARs in the hypothalamus. It was shown that the α2δ-1-NMDAR interaction is increased after nerve injury when there is an excess supply of α2δ-1 in the spinal cord (Chen et al., 2018). Here it was shown that this interaction can occur quickly in the hypothalamus following brief Ang II treatment. Thus, α2δ-1 plays an important role in Ang II signaling and in the regulation of NMDARs in the brain.

Example 6—Materials and Methods

Animals: 10- to 12-week-old male Sprague Dawley rats were used (Harlan Sprague Dawley, Indianapolis, Ind.) and both male and female mice (C57BL/6 genetic background) in the experiments. Two breeding pairs of Cacna2d1$_{+/-}$ mice were purchased from Medical Research Council (Harwell Didcot, Oxfordshire, UK), and Cacna2d1$_{-/-}$ (knockout) mice and Cacna2d1$_{+/+}$ (wild-type) littermates were obtained by breeding the heterozygous mice. Because no sex differences were found in the effect of Ang II on synaptic NMDAR activity, electrophysiological data from male and female mice were pooled. All surgical preparation and experimental protocols were approved by the Animal Care and Use Committee of The University of Texas MD Anderson Cancer Center and conformed to the National Institutes of Health guidelines for the ethical use of animals. All efforts were made to minimize both the suffering and number of animals used.

Retrograde labeling of spinally projecting PVN neurons: Rats or mice were anesthetized with 2-3% isoflurane, and their spinal cords at the T1-T4 level were exposed through dorsal laminectomy. A fluorescent microsphere suspension (FluoSpheres, 0.04 μm; Molecular Probes, Invitrogen, Eugene, Oreg.) was pressure ejected (Nanoject II Microinjectors, Drummond Scientific Company, Broomall, Pa.) bilaterally into the IML region of the spinal cord in six separate 50-nl injections using a glass micropipette (tip diameter, 20-30 μm). The tracer injection was monitored through a surgical microscope (Li et al., 2002, 2003). The wound was closed with sutures after injection. Animals were returned to their cages for 4-7 days, which was sufficient time to permit the tracer to be retrogradely transported to the PVN. The animals were inspected daily for motor activity, signs of infection, and food and water intake.

Brain slice preparation: Four to seven days after fluorescent tracer injection, the animals were anesthetized with isoflurane and rapidly decapitated. The brain was quickly removed and placed in ice-cold artificial CSF (aCSF) saturated with 95% $O_2$ and 5% $CO_2$. A tissue block containing the hypothalamus was cut from the brain and glued onto the stage of a vibratome (Leica VT1000 S, Leica Biosystems Inc. Buffalo Grove, Ill.) as described previously (Li et al., 2003; Ye et al., 2011). Coronal slices (thickness, 300 μm) containing the PVN were cut from the tissue block in the ice-cold aCSF. The slices were pre-incubated in aCSF, which was continuously gassed with 95% $O_2$ and 5% $CO_2$ at 34° C. for at least 1 h before being used for recording. The perfusion solution contained (in mmol/L) 126 NaCl, 3 KCl, 1.5 $MgCl_2$, 2.4 $CaCl_2$), 1.2 $NaH_2PO_4$, 11 glucose, and 26 $NaHCO_3$ (300-310 mOsmol/L). The brain slices were placed in a glass-bottom chamber and continuously perfused with aCSF at 3.0 ml/min at 34° C. maintained by an inline solution heater and temperature controller.

Electrophysiological recordings: The fluorescence-labeled neurons located in the medial one-third of the PVN area between the third ventricle and the fornix were selected for recording (Li et al., 2002, 2003). The labeled PVN neurons were briefly identified with the aid of epifluorescence illumination, and whole-cell recordings from labeled PVN neurons were performed under differential interference contrast optics on an upright microscope (BX50 WI; Olympus Optical, Tokyo, Japan). Recordings of postsynaptic currents began 5 min after the whole-cell access was established and the current reached a steady state.

The miniature excitatory postsynaptic currents (mEPSCs) were recorded in the presence of 1 μmol/L tetrodotoxin (TTX) and 20 μmol/L bicuculline at a holding potential of −60 mV (Li et al., 2003; Ye et al., 2011). The recording glass pipette (5-10 MΩ) was filled with internal solution containing (in mmol/L) 135.0 potassium gluconate, 5.0 tetraethylammonium, 2.0 $MgCl_2$, 0.5 $CaCl_2$, 5.0 4-(2-hydroxyethyl)-1-piperazineethanesulfonic acid (HEPES), 5.0 ethylene glycol tetraacetic acid (EGTA), 5.0 Mg-ATP, 0.5 Na-GTP, and 10 lidocaine N-ethyl bromide (adjusted to pH 7.2-7.4 with 1 M KOH; 290-300 mOsmol/L). Signals were processed with an Axopatch 700B amplifier (Axon Instruments, Foster City, Calif.). A liquid junction potential of 15 mV (for the potassium gluconate pipette solution) was corrected during off-line analysis. Signals were filtered at 1-2 kHz, digitized at 10 kHz using Digidata 1440A (Axon Instruments), and saved to the computer.

Postsynaptic NMDAR currents were elicited by puff application of 100 μmol/L NMDA to the recorded neuron using a positive pressure system (4 p.s.i., 50 ms; Toohey Company, Fairfield, N.J.). The tip of the puff pipette was placed 150 μm from the recorded neuron. The recordings were performed in the $Mg^{2+}$-free extracellular solution containing 10 μmol/L glycine and 1 μmol/L TTX at a holding potential of −60 mV (Li et al., 2008; Ye et al., 2011). The pipette internal solution contained (in mmol/L) 110.0 $Cs_2SO_4$, 2.0 $MgCl_2$, 0.1 $CaCl_2$, 1.1 EGTA, 10.0 HEPES, 2.0 Mg-ATP, 0.3 $Na_2GTP$, and 10 lidocaine N-ethyl bromide (pH was adjusted to 7.25 with 1.0 M CsOH; 280-300 mOsmol/L). The puff NMDAR currents were fairly stable during the recordings. The NMDAR current data presented in the manuscript were the average of 3 consecutive currents elicited by repeated puff NMDA. The neuron was discarded if the current was not stable.

Ang II, losartan, and NMDA were obtained from Sigma (St. Louis, Mo.). The α2δ-1Tat peptide and scrambled control peptide were synthesized by Bio Basic Inc. (Markham, Ontario, Canada) and validated by liquid chromatography and mass spectrometry. Pregabalin was obtained from Tocris Bioscience (Bristol, UK). TTX and DL-2-amino-5-phosphonopentanoic acid (AP5) were purchased from Hello Bio Inc. (Princeton, N.J.). All drugs were prepared immediately before the experiments and applied to the slice chamber. The brain slices were first pretreated with Ang II, losartan, α2δ-1Tat peptide, or control peptide in the slice incubation chamber before recording. For electrophysiological recording, the treatment agents were immediately removed and the brain slice transferred to a separate recording chamber.

Coimmunoprecipitation using hypothalamic tissues: Rat hypothalamic slices containing the PVN were sectioned 1.08-2.12 mm caudal to the bregma. For each sample used for coimmunoprecipitation assay, pooled hypothalamic tissues from 3 rats were used. The frozen hypothalamic tissues were also obtained from four human donors (2 males and 2 females, age ranged 18-36 years; University of Maryland Brain and Tissue Bank). The tissues were dissected and homogenized in ice-cold hypotonic buffer (20 mmol/L Tris [pH 7.4], 1 mmol/L $CaCl_2$, 1 mmol/L $MgCl_2$, and the protease inhibitor cocktail) for membrane preparation. The nuclei and unbroken cells were removed by centrifugation at 2,000×g for 10 min. The supernatant was centrifuged for 30 min at 21,000×g. The pellets were re-suspended and solubilized in immunoprecipitation buffer (50 mmol/L Tris [pH, 7.4], 250 mmol/L NaCl, 0.5% NP-40, and a protease inhibitor cocktail), and the soluble fraction was incubated at 4° C. overnight with Protein G beads (#16-266, EMD Millipore, Darmstadt, Germany) prebound to mouse anti-GluN1 antibody (#75-272, 1:1,000, NeuroMab, Davis, Calif., RRID: AB_11000180). Protein G beads prebound to mouse immunoglobulin G (IgG) were used as controls. Samples were washed 3 times with immunoprecipitation buffer and then immunoblotted with rabbit anti-α2δ-1 antibody (#ACC-015, 1:500, Alomone Labs, Jerusalem, Israel, RRID: AB_2039785).

Protein level analysis in hypothalamic synaptosomes: The hypothalamic tissues containing the PVN (pooled from 2 rats per sample) were homogenized using 10 volumes of ice-cold HEPES-buffered sucrose (0.32 mol/L sucrose, 1 mmol/L EGTA, and 4 mmol/L HEPES at pH 7.4) containing the protease inhibitor cocktail (Sigma-Aldrich). The homogenate was centrifuged at 2,000×g for 10 min at 4° C. to remove the nuclei and large debris. The supernatant was centrifuged at 20,000×g for 30 min to obtain the crude synaptosomal fraction. The synaptosomal pellet was lysed via hypo-osmotic shock in 9 volumes of ice-cold HEPES-buffer with the protease inhibitor cocktail for 30 min. The lysate was centrifuged at 25,000×g for 45 min at 4° C. to obtain the synaptosomal membrane fraction (Chen et al., 2018), which was then dissolved in sodium dodecyl sulfate sample buffer at a final concentration of 0.25 μg/μl for immunoblotting.

Western blotting was used to quantify GluN1 and α2δ-1 protein levels in the hypothalamic synaptosome. Fifteen micrograms of total proteins from each sample was loaded and separated by 4-15% Tris-HCl sodium dodecyl sulfate-polyacrylamide gel electrophoresis (#456-1086, Bio-Rad, Hercules, Calif.). The resolved proteins were transferred to a polyvinylidene difluoride membrane (Millipore). The membrane was treated with 5% nonfat dry milk in Tris-buffered saline (TBS) at 25° C. for 1 h and then incubated in TBS supplemented with 0.1% Triton X-100, 1% bovine serum albumin, and rabbit anti-GluN1 (#G8913, 1:100; Sigma, RRID: AB_259978), rabbit anti-α2δ-1 (#ACC-015, 1:500, Alomone, Jerusalem, Israel, RRID: AB_2039785), and mouse anti-PSD-95 (#75-348, 1:1,000, NeuroMab, Davis, Calif., RRID: AB_2315909) antibodies overnight at 4° C. The membrane was washed 3 times and then incubated with horseradish peroxidase-conjugated anti-rabbit IgG (1:5,000; Jackson ImmunoResearch, West Grove, Pa.) for 1 h at room temperature. The protein bands were detected with an enhanced chemiluminescence kit (Thermo Fisher Scientific, Waltham, Mass.), and protein band intensity was visualized and quantified using an Odyssey Fc Imager (LI-COR Biosciences, Lincoln, Nebr.). The protein levels of GluN1 and α2δ-1 were normalized by the PSD-95 protein band on the same gel.

PVN microinjection and recording of renal sympathetic nerve activity: Rats were anesthetized with a mixture of α-chloralose (60 mg/kg, i.p.) and urethane (800 mg/kg, i.p.). A retroperitoneal incision was made, and a branch of the left renal postganglionic sympathetic nerve was isolated under a surgical microscope. The renal sympathetic nerve was cut distally to ensure that afferent nerve activity was not recorded. The renal sympathetic nerve activity (RSNA), arterial blood pressure (ABP), and heart rate (HR) were recorded using a 1401-PLUS analog-to-digital converter and Spike2 system (Cambridge Electronic Design, Cambridge, UK). A microinjection pipette (tip diameter, 20-30 μm) was advanced into the PVN according to the following stereotactic coordinates: 1.6-2.0 mm caudal to the bregma, 0.5 mm lateral to the midline, and 7.0-7.5 mm ventral to the dura. The microinjection was done using a calibrated microinjection system (Nanoject II; Drummond Scientific) and monitored using a surgical microscope as described previously (Li and Pan, 2006, 2007; Qiao et al., 2017). Ang II (200 μmol/L, 50 nl) was microinjected into the PVN to observe the change in RSNA and ABP in the absence or presence of α2δ-1Tat peptide (100 μmol/L, 50 nl) or control peptide (100 μmol/L, 50 nl). The microinjections were separated by 10- to 15-min intervals to allow recovery of the response. To determine the location of the injection site and diffusion of the drugs in the PVN, 5% rhodamine-labeled fluorescent microspheres (0.04 μm; Molecular Probes) were included in the injection solution (Li and Pan, 2006, 2007; Qiao et al., 2017).

Study design and data analysis: Data are presented as means±standard errors of the mean (SEM). No statistical methods were used to predetermine sample sizes for biochemical studies, but the sample sizes were similar to those generally employed in the field. Data collection was randomized, and data distribution was determined using the Kolmogorov-Smirnov normality test. Rats were excluded from analysis if the microinjection site was outside the PVN. In electrophysiological recording experiments, cell capacitance, input resistance, series resistance, and baseline holding current were monitored; cells were excluded if the recording indicated a rundown condition. Only one neuron in each brain slice was recorded, and at least three animals were used for each recording protocol. The amplitude and frequency of mEPSCs were analyzed off-line with a peak detection program (MiniAnalysis; Synaptosoft Inc., Decatur, Ga.). The cumulative probability of the amplitude and inter-event interval was compared using the Kolmogorov-Smirnov test, which estimates the probability that two cumulative distributions are similar. The peak amplitude of puff NMDA-induced currents was determined and analyzed using pClamp and Clampfit 10.2 (Molecular Devices, Sunnyvale, Calif.). The mean ABP, RSNA, and HR were analyzed using Spike2 software. The mean ABP was derived from the pulsatile ABP and calculated as the diastolic pressure plus one-third of the pulse pressure. RSNA was rectified and integrated offline after subtracting the background noise, which was recorded after the proximal end of renal nerve was crushed at the end of each experiment. The integrated RSNA value was calculated and derived from raw RSNA with an integrating time of 1.0 s using Spike2 software. Control values were obtained by averaging the signal over a 60-s period immediately before PVN microinjection. Response values after each intervention were averaged over 30 s when the maximal responses occurred. A two-tailed Student t-test was used to compare two groups, and one-way analysis of variance (ANOVA), followed by Dunnett's and Tukey's post hoc tests, was used to compare more than two groups. Statistical analyses were performed using Prism 6 software (GraphPad Software Inc., La Jolla, Calif.). $P<0.05$ was considered statistically significant.

Example 7—Chemotherapy-Induced Neuropathic Pain

Figures 31A, 31B, 31C, 31D, 31E, 31F, 31G, 31H, 31I, 31J:
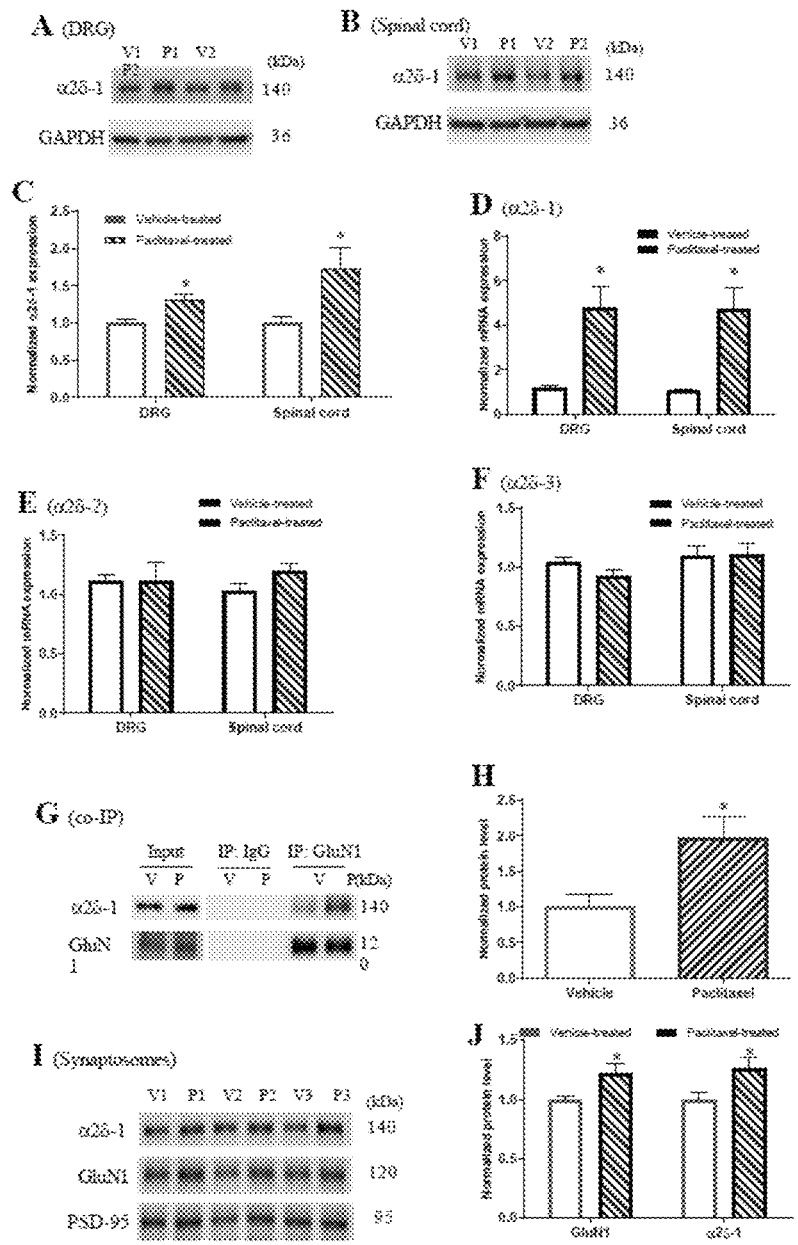

Paclitaxel treatment increases α2δ-1 protein and mRNA levels in the DRG and spinal cord: α2δ-1 is expressed in dorsal root ganglion (DRG) neurons and primary afferent nerve terminals in the superficial dorsal horn of the spinal cord. Peripheral nerve injury causes a large increase in the α2δ-1 expression level in the DRG and spinal cord (Luo et al., 2001; Newton et al., 2001). Western immunoblotting and real-time PCR were used to determine whether paclitaxel treatment affects the α2δ-1 expression level in the DRG and dorsal spinal cord tissues of rats. Immunoblotting detected a protein band corresponding to the molecular mass of α2δ-1 (~140 kDa). The α2δ-1 protein levels in the DRG and spinal cord tissues were much higher in paclitaxel-treated than in vehicle-treated rats (n=9 rats in each group; FIG. 31A-C). Real-time PCR analysis showed that the α2δ-1 mRNA levels in the DRG and dorsal spinal cord were substantially higher in paclitaxel-treated than in vehicle-treated rats (n=6 rats in each group; FIG. 1D). However, the mRNA level of α2δ-2 or α2δ-3 in the DRG and dorsal spinal cord was similar in paclitaxel-treated and vehicle-treated rats (n=6 rats in each group, FIGS. 1, E and 1F). These results indicate that paclitaxel treatment causes upregulation of α2δ-1 in the DRG and dorsal spinal cord.

Figures 32A, 32B, 32C, 32D:
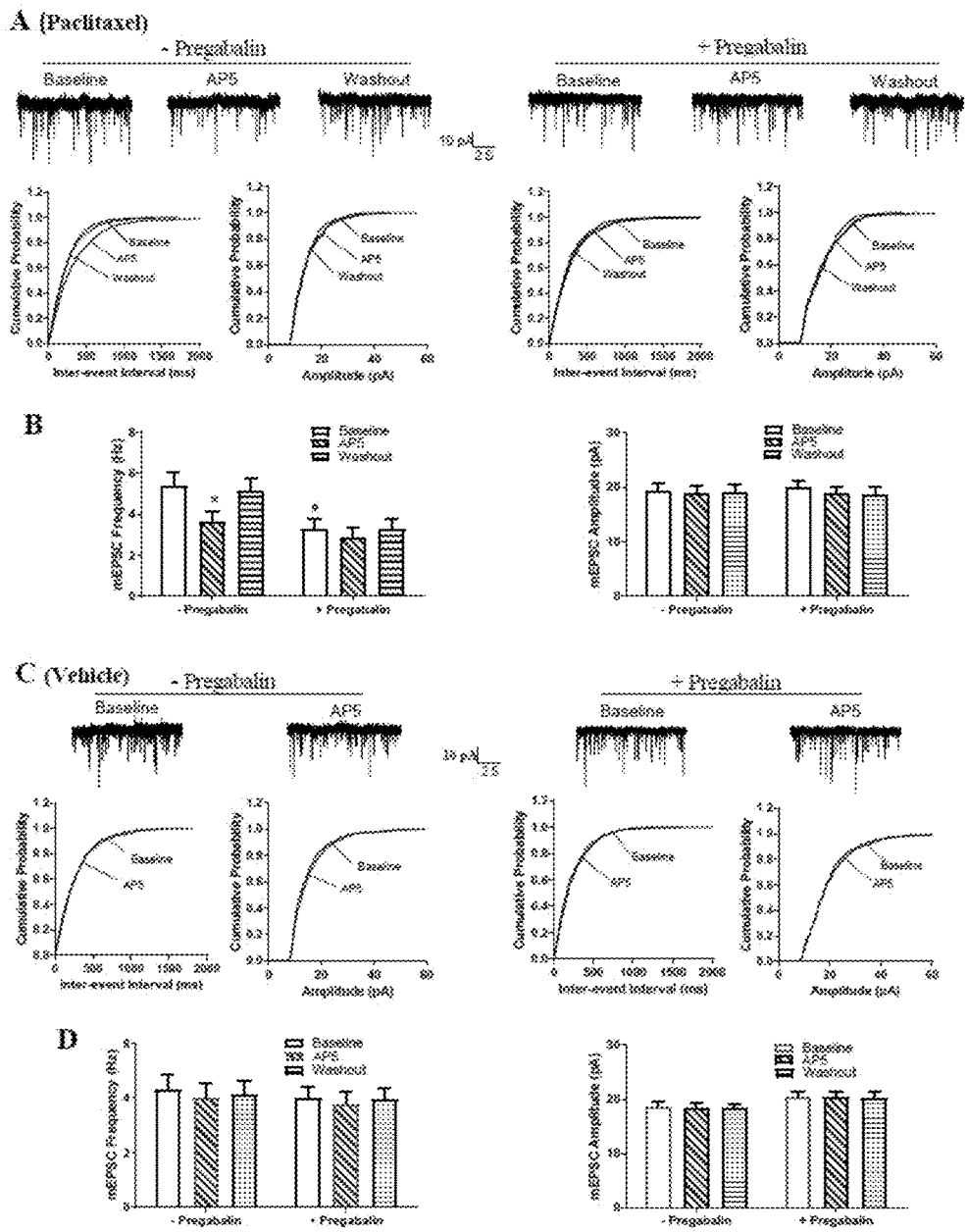

Paclitaxel treatment increases the interaction between α2δ-1 and NMDARs and the synaptic targeting of NMDARs in the spinal cord: Coimmunoprecipitation (co-IP) was performed to determine whether paclitaxel treatment affects the interaction of α2δ-1 and GluN1 (an obligatory subunit of NMDARs) in the dorsal spinal cord. Co-IP assays showed that a mouse anti-GluN1 antibody, but not an irrelevant mouse anti-immunoglobulin G (anti-IgG) antibody, coprecipitated with α2δ-1 in spinal cord membrane extracts (FIG. 31G). In addition, the expression level of the α2δ-1-GluN1 complex in the dorsal spinal cord was significantly higher in paclitaxel-treated than in vehicle-treated rats (P=0.0059, t=4.591; n=6 rats in each group; FIGS. 31G and H). To determine whether paclitaxel treatment increases synaptic trafficking of NMDARs α2δ-1 and GluN1 proteins were quantified in synaptosomes isolated from dorsal spinal cord tissues. Immunoblotting showed that both α2δ-1 and GluN1 protein levels in spinal synaptosomes were significantly higher in paclitaxel-treated than in vehicle-treated rats (n=8 rats in each group; FIGS. 31I and J). These data suggest that paclitaxel treatment promotes the α2δ-1-GluN1 interaction and the synaptic trafficking of α2δ-1-bound NMDARs at the spinal cord level.

α2δ-1 mediates paclitaxel-induced tonic activation of presynaptic NMDARs in the spinal dorsal horn: Chemotherapy-induced neuropathic pain is associated with tonic activation of presynaptic NMDARs, which promotes nociceptive glutamatergic input to spinal dorsal horn neurons (Xie et al., 2017; Xie et al., 2016). To determine the contribution of α2δ-1 to the increase in presynaptic NMDAR activity caused by paclitaxel treatment, the effect of pregabalin was examined, a clinically used α2δ-1 inhibitory ligand (Li et al., 2011; Patel et al., 2013), on glutamatergic miniature excitatory postsynaptic currents (mEPSCs), which represent spontaneous quantal glutamate release from presynaptic terminals of spinal dorsal horn neurons. The baseline frequency, but not the amplitude, of mEPSCs in lamina II neurons was significantly higher in paclitaxel-treated rats than in vehicle-treated rats (n=12 neurons in each group; FIG. 32). Bath application of the specific NMDAR antagonist 2-amino-5-phosphonopentanoate (AP5, 50 µM) rapidly reversed the increase in the frequency of mEPSCs in paclitaxel-treated rats but had no effect in vehicle-treated rats (FIG. 32), confirming that presynaptic NMDARs in the spinal dorsal horn are tonically activated by paclitaxel treatment (Xie et al., 2016). Treatment with pregabalin (20 µM for 30-60 min) completely normalized the baseline frequency of mEPSCs of lamina II neurons, which had been increased by paclitaxel treatment (n=10 neurons, FIG. 32, A,B). In these pregabalin-treated neurons from paclitaxel-treated rats, subsequent bath application of 50 µM AP5 no longer had any effect on the frequency of mEPSCs. In contrast, pregabalin had no effect on the baseline frequency of mEPSCs in lamina II neurons from vehicle-treated rats (n=10 neurons; FIG. 32C-D). These data suggest that α2δ-1 mediates paclitaxel-induced tonic activation of presynaptic NMDARs in the spinal cord.

α2δ-1 is critical for paclitaxel-induced activation of NMDARs at primary afferent terminals: NMDARs are expressed at primary afferent terminals in the superficial dorsal horn of the spinal cord (Liu et al., 1994), where they mediate chemotherapy-induced potentiation of glutamatergic input to the spinal dorsal horn (Xie et al., 2017; Xie et al., 2016). To determine the role of α2δ-1 in the increased activity of NMDARs at primary afferent terminals caused by paclitaxel treatment, EPSCs of lamina II neurons monosynaptically evoked from the dorsal root were recorded, which correspond to synaptic glutamate release elicited from primary afferent nerve terminals. The baseline amplitude of evoked monosynaptic EPSCs was significantly larger in paclitaxel-treated rats (n=12 neurons) than in vehicle-treated rats (n=8 neurons) (FIG. 33). Bath application of 50 µM AP5 rapidly reversed the increased amplitude of monosynaptic EPSCs of lamina II neurons from paclitaxel-treated rats but had no effect in vehicle-treated rats (FIG. 33).

Figures 33A, 33B, 33C, 33D, 33E, 33F:
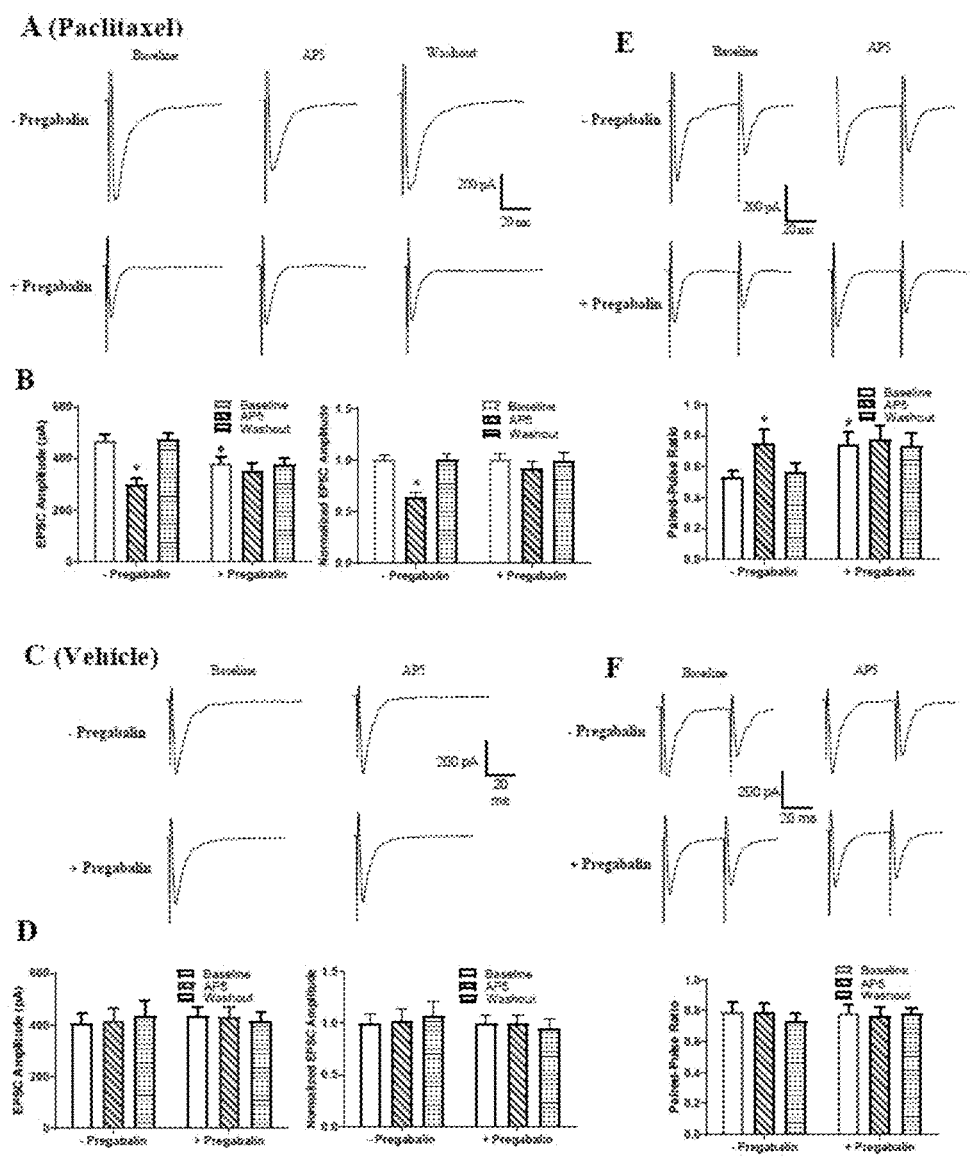
Figures 35A, 35B, 35C, 35D, 35E, 35F:
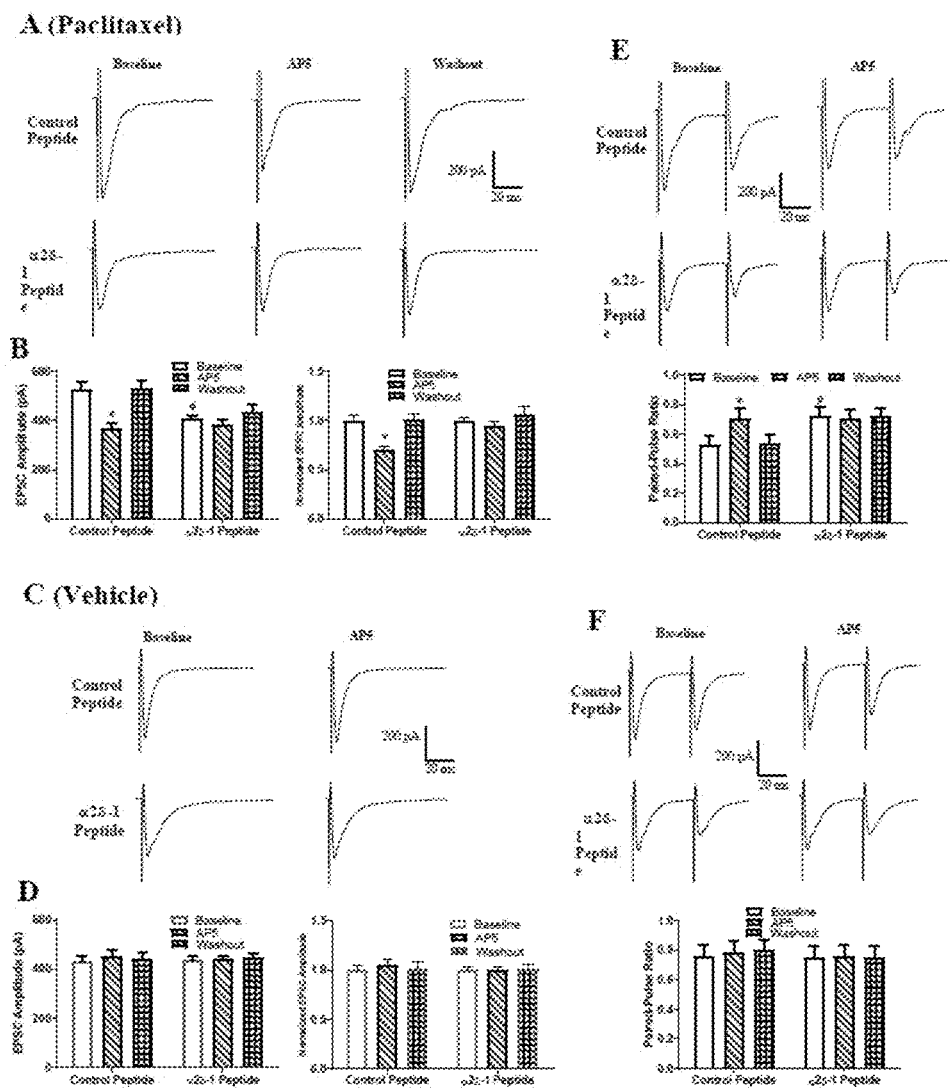

In spinal cord slices from paclitaxel-treated rats, treatment with 20 µM pregabalin for 30 to 60 min returned the amplitude of evoked monosynaptic EPSCs of lamina II neurons to the baseline level observed in vehicle-treated rats (n=8 neurons, FIG. 33A-B). However, pregabalin treatment had no effect on the amplitude of evoked monosynaptic EPSCs of lamina II neurons from vehicle-treated rats (n=9 neurons, FIG. 33C-D). In addition, the effect of pregabalin on the paired-pulse ratio (PPR) was determined, a commonly used measure of the probability of neurotransmitter release from the presynaptic neuron, of monosynaptically evoked EPSCs of spinal lamina II neurons. Paclitaxel treatment significantly reduced the PPR in lamina II neurons (n=9) compared with that in neurons (n=8) from vehicle-treated rats (FIG. 33, E,F).

Bath application of AP5 reversed the reduction in the PPR of lamina II neurons from paclitaxel-treated rats but had no effect on the PPR in neurons from vehicle-treated rats (FIG. 33E-F). Treatment with pregabalin completely normalized the PPR that had been reduced by paclitaxel treatment (n=8 neurons) but had no effect on the PPR in neurons from vehicle-treated rats (n=9 neurons) (FIG. 33E-F). These results suggest that α2δ-1 is critically involved in paclitaxel-induced activation of NMDARs at primary afferent terminals.

α2δ-1-bound NMDARs are essential for paclitaxel-induced tonic activation of presynaptic NMDARs in the spinal dorsal horn: It was next determined whether the α2δ-1-NMDAR interaction is involved in the paclitaxel-induced activation of presynaptic NMDARs in the spinal dorsal horn. The C-terminus of α2δ-1 is essential for its interaction with NMDARs, and a 30-amino-acid peptide (VSGLNPSLWSIFGLQFILLWLVSGSRHYLW; SEQ ID NO:1) mimicking the C-terminal domain of α2δ-1 fused with Tat protein (YGRKKRRQRRR; SEQ ID NO:2) effectively interrupts the α2δ-1-NMDAR interaction (Chen et al., 2018). Treatment with this α2δ-1Tat peptide (1 µM for 30-60 min) completely normalized the increased baseline frequency of mEPSCs in lamina II neurons from paclitaxel-treated rats (n=10 neurons) to the level seen in vehicle-treated rats (FIG. 34). Subsequent bath application of AP5 had no effect on the frequency of mEPSCs in α2δ-1Tat peptide-treated spinal cord slices from paclitaxel-treated rats.

However, in spinal cord slices from vehicle-treated rats, neither incubation with α2δ-1Tat peptide nor bath application of AP5 had any effect on the baseline frequency of mEPSCs in lamina II neurons (n=11 neurons; FIG. 34). In contrast, treatment with a Tat-fused scrambled control peptide (FGLGWQPWSLSFYLVWSGLILSVLHLIRSN; SEQ ID NO:3; 1 µM for 30-60 min) did not affect the mEPSC frequency of lamina II neurons from paclitaxel-treated rats (n=11 neurons) or vehicle-treated rats (n=12 neurons) (FIG. 34). These findings indicate that α2δ-1-bound NMDARs are responsible for the paclitaxel-induced tonic activation of presynaptic NMDARs in the spinal dorsal horn.

α2δ-1-bound NMDARs are crucial for paclitaxel-induced activation of NMDARs at primary afferent terminals: To determine whether α2δ-1-bound NMDARs contribute to the paclitaxel-induced increase in NMDAR activity at primary afferent terminals, the effect of α2δ-1Tat peptide on EPSCs was examined of lamina II neurons monosynaptically evoked from the dorsal root. In spinal cord slices from paclitaxel-treated rats (n=9 neurons), treatment with 1 µM α2δ-1Tat peptide for 30 to 60 min completely reversed the increased amplitude of evoked EPSCs to the level found in vehicle-treated rats (FIG. 35A-D). Subsequent bath application of AP5 had no effect on the amplitude of evoked EPSCs in neurons from paclitaxel-treated rats. Also, α2δ-1Tat peptide did not affect the amplitude of evoked EPSCs in neurons from vehicle-treated rats (n=10 neurons).

Figures 37A, 37B, 37C, 37D:
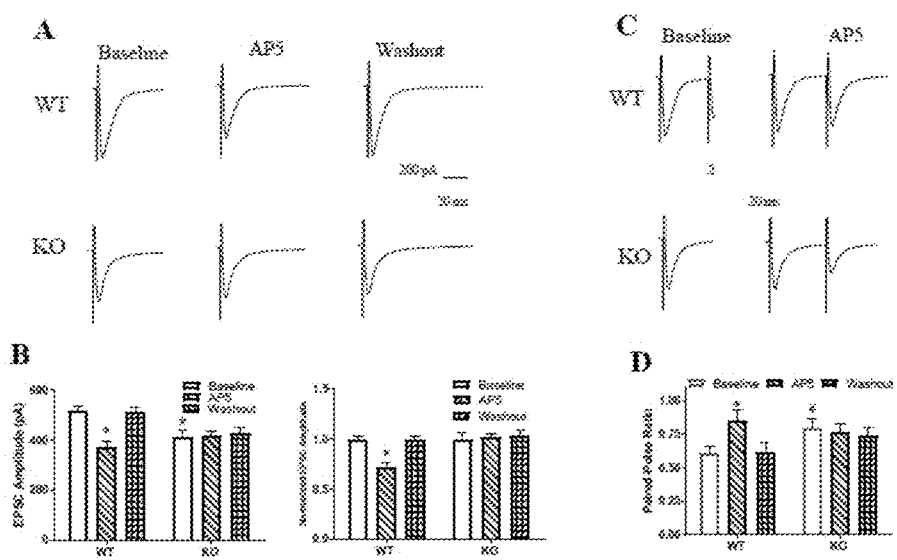

In contrast, treatment with Tat-fused control peptide (1 µM for 30-60 min) did not significantly alter the amplitude of evoked EPSCs of lamina II neurons from paclitaxel-treated rats (n=12 neurons) or vehicle-treated rats (n=9 neurons) (FIG. 35A-D). In control peptide-incubated neurons from paclitaxel-treated rats, bath application of AP5 returned the amplitude of evoked EPSCs to the level observed in vehicle-treated rats. In addition, treatment with α2δ-1Tat peptide, but not Tat-fused control peptide, fully reversed the reduction in the baseline PPR of evoked EPSCs in neurons from paclitaxel-treated rats (n=9 neurons in each group; FIG. 35E). Bath application of AP5 reversed the reduced PPR in control peptide-treated neurons from paclitaxel-treated rats but had no effect on the PPR in α2δ-1Tat peptide-treated neurons from paclitaxel-treated rats. In spinal cord slices from vehicle-treated rats, treatment with α2δ-1Tat peptide (n=10 neurons) or control peptide (n=9 neurons) had no effect on the baseline PPR of evoked EPSCs (FIG. 5F). These results indicate that α2δ-1-bound NMDARs are critically involved in paclitaxel-induced activation of NMDARs at primary afferent terminals in the spinal dorsal horn.

α2δ-1 ablation prevents paclitaxel-induced tonic activation of presynaptic NMDARs in the spinal dorsal horn: To further validate the critical role of α2δ-1 in paclitaxel-induced tonic activation of presynaptic NMDARs in the spinal dorsal horn, electrophysiological recordings were performed in spinal cord slices from wild-type (WT) and α2δ-1 knockout (KO) mice that had been treated with paclitaxel. The baseline frequency, but not the amplitude, of mEPSCs was significantly greater in lamina II neurons from WT mice (n=11 neurons) than in those from α2δ-1 KO mice (n=16 neurons). Also, bath application of AP5 normalized the paclitaxel-induced increase in the frequency of mEPSCs in WT mice but had no effect in α2δ-1 KO mice (FIG. 36A-C). The amplitude of monosynaptic EPSCs of spinal lamina II neurons evoked from the dorsal root in paclitaxel-treated WT mice (n=13 neurons) was significantly higher than that in paclitaxel-treated α2δ-1 KO mice (n=11 neurons). Bath application of AP5 normalized the increased baseline amplitude of evoked EPSCs in WT mice but had no effect in α2δ-1 KO mice (FIG. 37A-B). Furthermore, the PPR of evoked EPSCs was significantly lower in neurons from paclitaxel-treated WT mice (n=13 neurons) than in those from paclitaxel-treated α2δ-1 KO mice (n=10 neurons). Bath application of AP5 restored the baseline PPR that had been decreased by paclitaxel in WT mice but had no effect in paclitaxel-treated α2δ-1 KO mice (FIG. 37C-D). These data provide unequivocal evidence of the obligatory role of α2δ-1 in paclitaxel-induced tonic activation of presynaptic NMDARs in the spinal dorsal horn.

Figures 38A, 38B, 38C, 38D, 38E, 38F:
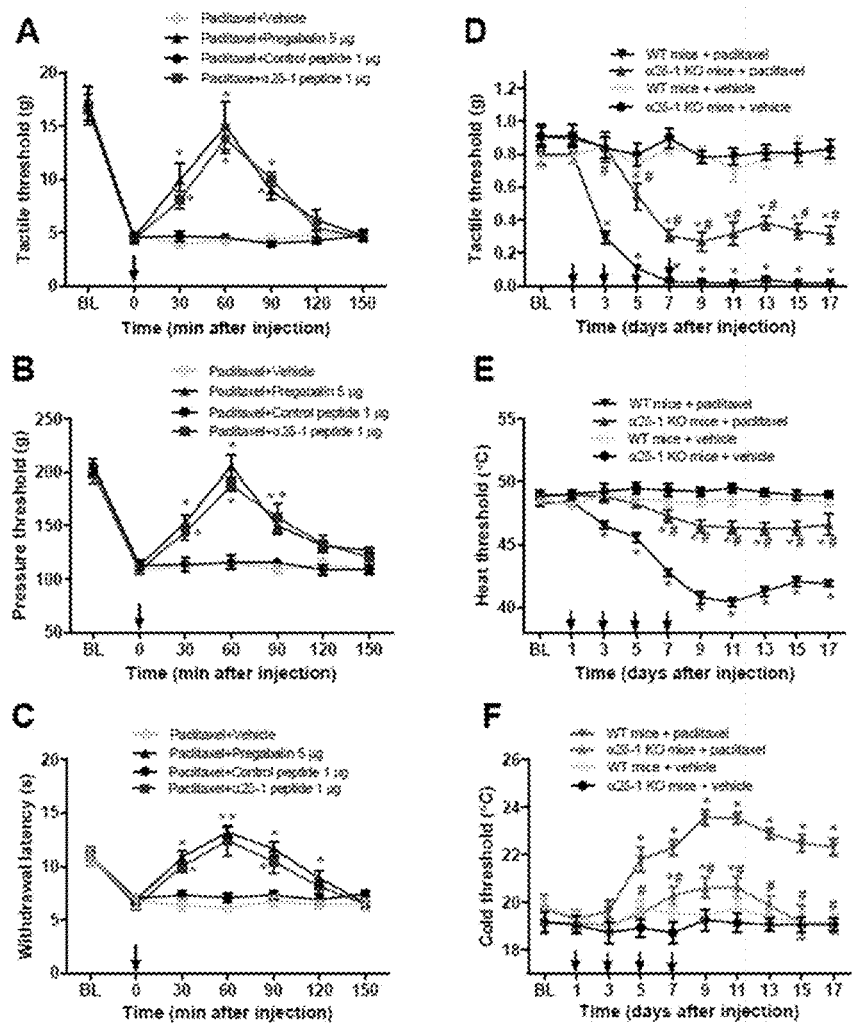
Figures 39A, 39B, 39C, 39D:
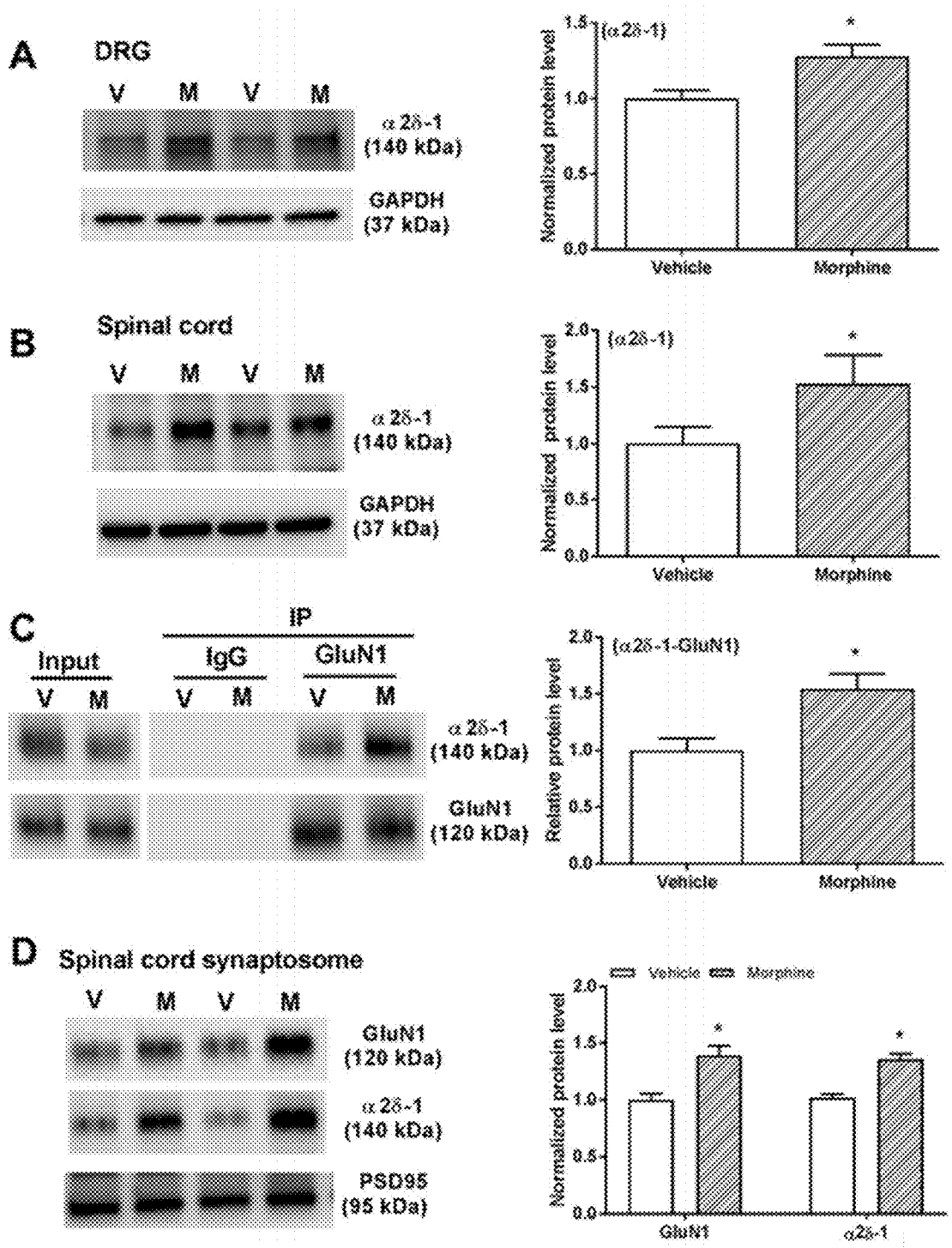

Inhibiting α2δ-1 or interrupting the α2δ-1-NMDAR interaction at the spinal cord level reverses paclitaxel-induced pain hypersensitivity: Blocking NMDARs at the spinal cord level can rapidly reverse pain hypersensitivity induced by chemotherapeutic agents (Xie et al., 2017; Xie et al., 2016). It was next determined specifically whether α2δ-1-bound NMDARs at the spinal cord level contribute to paclitaxel-induced neuropathic pain. Paclitaxel-treated rats had lower withdrawal thresholds in response to application of a tactile stimulus (von Frey filaments), a noxious pressure stimulus, and a noxious heat stimulus to the hindpaw than did vehicle-treated rats, indicating the presence of pain hypersensitivity. Intrathecal injection of 5 μg pregabalin readily reversed tactile allodynia and mechanical and thermal hyperalgesia in paclitaxel-treated rats (n=8 rats per group, FIG. 38A-C). Similarly, intrathecal injection of 1 μg α2δ-1Tat peptide, but not 1 μg control peptide, markedly attenuated the pain hypersensitivity induced by paclitaxel (n=8 rats per group; FIG. 38A-C). These data suggest that α2δ-1 and α2δ-1-bound NMDARs at the spinal cord level play a prominent role in paclitaxel-induced neuropathic pain.

α2δ-1 ablation attenuates the development of pain hypersensitivity caused by paclitaxel treatment: Next, α2δ-1 KO mice were used to confirm the contribution of α2δ-1 to the development of pain hypersensitivity after paclitaxel treatment. Systemic treatment with paclitaxel in WT mice induced tactile allodynia and heat and cold hyperalgesia, which began after the second paclitaxel injection and lasted for at least 10 days after the last injection (n=8 mice per group; FIG. 38D-F). The withdrawal thresholds in response to von Frey filaments and heat/cold stimuli at baseline (before paclitaxel treatment) did not differ significantly between WT and α2δ-1 KO mice. However, the degree of tactile allodynia and heat/cold hyperalgesia induced by paclitaxel was profoundly attenuated in α2δ-1 KO mice (n=8 mice per group; FIG. 38D-F). Treatment with vehicle had no effects on the tactile and thermal withdrawal thresholds in either WT or α2δ-1 KO mice (n=8 mice per group). These results provide substantial evidence that α2δ-1 contributes to the development of paclitaxel-induced neuropathic pain.

In summary, the study reveals that a switch from α2δ-1-free to α2δ-1-bound NMDARs serves as a key molecular mechanism by which presynaptic NMDARs are activated in chemotherapy-induced pain and that this switch also mediates the therapeutic effect of gabapentinoids. Chemotherapy induces dominance of α2δ-1-bound NMDARs at primary afferent terminals, causing long-lasting increases in glutamatergic nociceptive input to spinal dorsal horn neurons and thereby maintaining chronic pain. This new information not only extends the understanding of the fundamental molecular mechanism underlying chemotherapy-induced neuropathic pain but also provides a basis for the rational use of gabapentinoids. Targeting the α2δ-1-NMDAR interaction site may be a new strategy for specifically inhibiting abnormally increased NMDAR activity (without interfering with normal, α2δ-1-free NMDARs) to treat this painful condition and to minimize the adverse effects of gabapentinoids in cancer patients and survivors.

Example 8—Materials and Methods

Animals and paclitaxel treatment—Adult male Sprague-Dawley rats (weight: 220-250 g; Harlan, Indianapolis, Ind.) were used for most experiments. All animals were housed (2-3 rats per cage) on a standard 12:12 light-dark cycle with normal illumination. Generation of α2δ-1$_{-/-}$ (KO) mice has been described previously (Fuller-Bicer et al., 2009). Briefly, two breeding pairs of α2δ-1$_{+/-}$ mice (C57BL/6 genetic background) were purchased from Medical Research Council (Harwell Didcot, Oxfordshire, UK). α2δ-1$_{-/-}$ and α2δ-1$_{+/+}$ (WT) littermates were generated by breeding the α2δ-1$_{+/-}$ heterozygous mice. Both male and female adult mice were used for electrophysiological and behavioral experiments. Because no differences were observed in electrophysiological and behavioral data between male and female mice, these data were pooled. All surgical procedures and experimental protocols were approved by the Institutional Animal Care and Use Committee of The University of Texas MD Anderson Cancer Center and complied with the Guide for the Care and Use of Laboratory Animals of the National Institutes of Health.

To induce neuropathic pain, rats and mice were intraperitoneally injected with paclitaxel (2 mg/kg; TEVA Pharmaceuticals, North Wales, Pa.) every 2 days for a total of 4 injections (days 1, 3, 5 and 7; total dose, 8 mg/kg), as described previously (Polomano et al., 2001). Animals in the control group were intraperitoneally injected with the vehicle (Cremophor EL/ethanol, 1:1) on the same 4 days. The presence of tactile allodynia was confirmed 10 to 12 days after drug treatment. Intrathecal catheters were implanted in some paclitaxel-treated rats during isoflurane-induced anesthesia. Briefly, a small puncture was made in the atlanto-occipital membrane of the cisterna magna and inserted a PE-10 catheter with the caudal tip reaching the lumbar enlargement of the spinal cord (Chen et al., 2014a; Xie et al., 2016).

The animals were allowed to recover for at least 4 days before intrathecal injections. Rats displaying signs of motor or neurological dysfunction were immediately killed with an intraperitoneal injection of phenobarbital (200 mg/kg) or by $CO_2$ inhalation. All final biochemical and electrophysiological recordings were performed 14 to 20 days after the last paclitaxel or vehicle injection Quantitative PCR: Rats were deeply anesthetized with 5% isoflurane, and the DRG and dorsal half of spinal cord tissues at the L5 and L6 levels were removed. Total RNA was extracted from the DRG and spinal cord tissues using TRIsure (Cat. #BIO-38032, Bioline, Taunton, Mass.). After treatment with RNase-free DNase (Cat. #79254, QIAGEN, Hilden, Germany), 500 ng RNA was used for reverse transcription with a RevertAid RT Reverse Transcription Kit (Cat. #K1619, Thermo Fisher Scientific, Waltham, Mass.). One μL of 5-times diluted cDNA was added to a 10-μL reaction volume with SYBR Green Real-Time PCR Mix (Cat. #A25780, Thermo Fisher Scientific). Real-time PCR was performed using a QuantStudio 7 Flex Real-Time PCR System (Applied Biosystems, Waltham, Mass.). The thermal cycling conditions used were: 1 cycle at 95° C. for 10 min, 40 cycles at 95° C. for 15 s, and 60° C. for 60 s. The following primers were used: α2δ-1 forward, GGACCTAT-TCAGTGGATGGCTTG (SEQ ID NO:60); α2δ-1 reverse, CCATTGGTCTTCCCAGAACATCTAGA (SEQ ID NO:61); α2δ-2 forward, CGGCTGCTACAAAAGGA-GACACACT (SEQ ID NO:62); α2δ-2 reverse, CGGC-CACAGTCTGAGGTATCTTC (SEQ ID NO:63); α2δ-3 forward, GGCTCAGAAGATCAGACGACGTC (SEQ ID NO:64); α2δ-3 reverse, TTGAGAAGAGACTCG-AAACCAGG (SEQ ID NO:65); Gapdh forward, GACATGCCGCCTGGAGAAAC (SEQ ID NO:66); Gapdh reverse. AGCCCAGGATGCCCTTTAGT (SEQ ID NO:67). Relative mRNA levels were calculated using the $2_{-\Delta\Delta CT}$ method and normalized to the Gapdh level in the same sample.

Coimmunoprecipitation using spinal cord tissue membrane extracts: Tissues from the dorsal halves of the rat spinal cord at the L5 and L6 levels were collected under isoflurane anesthesia and homogenized in ice-cold hypotonic buffer (20 mM Tris [pH 7.4], 1 mM $CaCl_2$), 1 mM $MgCl_2$, and protease inhibitors) for extracting membrane proteins. The nuclei and unbroken cells were removed by centrifugation at 300×g for 5 min, and the supernatant was centrifuged for 20 min at 21,000×g. The pellets were resuspended and solubilized in immunoprecipitation buffer (50 mM Tris [pH7.4], 250 mM NaCl, 10% glycerol, 0.5% NP-40, 20 mM NaF, 1 mM $Na_3VO_4$, 10 mM N-ethylmaleimide, 1 mM phenylmethylsulfonyl fluoride, 2 mM benzamide, and protease inhibitors), and the soluble fraction was incubated at 4° C. overnight with Protein A/G beads (#16-2δ6, Millipore, Darmstadt, Germany) prebound to mouse anti-GluN1 antibody (#75-272, 1:1000, NeuroMab, Davis, Calif.). Protein A/G beads prebound to mouse IgG were uses as the control. All samples were washed 3 times with immunoprecipitation buffer and then immunoblotted with rabbit anti-α2δ-1 (#ACC-015, 1:500, Alomone Labs, Jerusalem, Israel) and rabbit anti-GluN1 antibodies (#G8913, 1:1,000, Sigma-Aldrich, St. Louis, Mo.). The amount of the α2δ-1-GluN1 protein complex was calculated by normalizing the amount of α2δ-1 to that of GluN1 on the same gel.

Spinal cord synaptosome preparation: The tissues from the dorsal half of the rat spinal cords were homogenized using a glass-Teflon homogenizer in 10 volumes of ice-cold HEPES-buffered sucrose (0.32 M sucrose, 1 mM EGTA, and 4 mM HEPES at pH 7.4) containing a protease inhibitor cocktail (Sigma-Aldrich). The homogenate was centrifuged at 1,000×g for 10 min at 4° C. to remove the sediment, including nuclei and large debris. Then the supernatant was centrifuged at 10,000×g for 15 min to obtain the crude synaptosomal fraction. The synaptosomal pellet was lysed in 9 volumes of ice-cold HEPES-buffer with the protease inhibitor cocktail for 30 min. The lysate was centrifuged at 25,000×g for 20 min at 4° C. to obtain the synaptosomal fraction. After the protein concentration was measured, 30 μg of proteins were used for Western immunoblotting. The amount of synaptic α2δ-1 and GluN1 proteins was normalized to that of PSD-95, a synaptic protein marker, on the same gel (see below).

Western immunoblotting: The rat DRG and dorsal spinal cord tissues at L5-L6 levels were homogenized in 300 μl radioimmunoprecipitation assay buffer containing 50 mM Tris-HCl (pH 7.4), 1% Nonidet P-40, 0.25% sodium-deoxycholate, 150 mM NaCl, 1 mM EDTA, 1 mM $Na_3VO_4$, and 1 mM NaF in the presence of a proteinase inhibitor cocktail (Sigma-Aldrich). The samples were homogenized with lysis buffer on ice for 30 min, and centrifuged at 13,000×g for 30 min at 4° C. The supernatant was collected, and its protein concentration was measured using a DC Protein Assay Kit (Bio-Rad, Hercules, Calif.). Thirty μg of protein was loaded and separated by 4-15% Tris-HCl sodium dodecyl sulfate-polyacrylamide gel electrophoresis (SDS-PAGE) (#456-1086, Bio-Rad, Hercules, Calif.). The resolved proteins were transferred to a polyvinylidene difluoride membrane. The membrane was treated with 5% nonfat dry milk in Tris-buffered saline (TBS) at 25° C. for 1 h and then incubated in TBS supplemented with 0.1% Triton X-100, 1% bovine serum albumin, and rabbit anti-α2δ-1 (#ACC-015, 1:500, Alomone Labs, Jerusalem, Israel), rabbit anti-GluN1 (#G8913, 1:1,000, Sigma-Aldrich), rabbit anti-GAPDH (#14C10, 1:5,000, Cell Signaling Technology, Danvers, Mass.), or mouse anti-PSD95 (#75-348, 1:1,000, NeuroMab, Davis, Calif.) antibodies overnight at 4° C. The membrane was washed 3 times and then incubated with horseradish peroxidase-conjugated anti-rabbit IgG (1:5,000; Jackson ImmunoResearch, West Grove, Pa.) for 1 h at 25° C. The protein bands were detected with an ECL kit (Thermo Fisher Scientific), and protein band intensity was visualized and quantified using an Odyssey Fc Imager (LI-COR Biosciences, Lincoln, Nebr.).

Electrophysiological recording in spinal cord slices: The rats and mice were anesthetized with isoflurane and rapidly removed the L3-L6 level of the lumbar spinal cord through laminectomy. The spinal cord tissues were immediately placed in ice-cold sucrose artificial cerebrospinal fluid (containing 234 mM sucrose, 3.6 mM KCl, 1.2 mM $NaH_2PO_4$, 12.2 mM glucose, 25.0 mM $NaHCO_3$, 1.2 mM $MgCl_2$, and 2.5 mM $CaCl_2$)) presaturated with 95% $O_2$ and 5% $CO_2$. Then the spinal cord tissue was placed onto the stage of a vibratome (Leica, Buffalo Grove, N.Y.) and sliced transversely into 400 μm sections, which were preincubated in Krebs solution (117.0 mM NaCl, 3.6 mM KCl, 1.2 mM $NaH_2PO_4$, 11.0 mM glucose, 25.0 mM $NaHCO_3$, 1.2 mM $MgCl_2$, and 2.5 mM $CaCl_2$)) oxygenated with 95% $O_2$ and 5% $CO_2$ at 34° C. for at least 1 h before being transferred to recording chamber.

The spinal cord slices were placed in a glass-bottomed recording chamber and continuously perfused with Krebs solution at 5.0 ml/min at 34° C., maintained by an inline solution heater and a temperature controller. The lamina II outer neurons were identified for recording because they are mostly glutamate-releasing excitatory neurons and they predominantly receive nociceptive input (Pan et al., 2002; Santos et al., 2007). Excitatory postsynaptic currents (EPSCs) were recorded using whole-cell voltage-clamp techniques. The impedance of the glass electrode was 4 to 7 MΩ when the pipette was filled with the internal solution containing 135 mM potassium gluconate, 5 mM KCl, 2.0 mM $MgCl_2$, 0.5 mM $CaCl_2$), 5.0 mM HEPES, 5.0 mM EGTA, 5.0 mM ATP-Mg, 0.5 mM Na-GTP, and 10 mM QX314 (280-300 mOsm, pH: 7.25).

To measure glutamate release from primary afferent nerves, EPSCs were evoked from the dorsal root using a bipolar tungsten electrode connected to a stimulator (0.5 ms, 0.6 mA, and 0.1 Hz). Monosynaptic EPSCs were recorded on the basis of the constant latency and absence of conduction failure of evoked EPSCs in response to a 20-Hz electrical stimulation, as described previously (Li et al., 2002; Zhou et al., 2010). The paired-pulse ratio (PPR) was evoked by a pair of stimuli given at 50-ms intervals; the PPR was defined as the ratio of the amplitude of the second synaptic response to the amplitude of the first synaptic response (Xie et al., 2016; Zhou et al., 2010). Miniature EPSCs (mEPSCs) were recorded at a holding potential of –60 mV in the presence of 2 µM strychnine, 10 µM bicuculline, and 1 µM tetrodotoxin. The input resistance was monitored, and the recording was abandoned if the input resistance changed by more than 15%. All signals were recorded using an amplifier (MultiClamp 700B; Axon Instruments Inc., Union City, Calif.), filtered at 1 to 2 kHz, and digitized at 10 kHz. All drugs were prepared in artificial cerebrospinal fluid before the recording and delivered via syringe pumps at their final concentrations. 2-Amino-5-phosphonopentanoic acid (AP5) and tetrodotoxin citrate were purchased from Hello Bio Inc. (Princeton, N.J.). Pregabalin was obtained from Tocris Bioscience (Bristol, UK). α2δ-1Tat peptide and scrambled control peptide were synthesized by Bio Basic Inc. (Marham, Ontario, Canada).

Behavioral assessment of nociception: To measure tactile allodynia, mice or rats were individually placed on a mesh floor within a suspended chamber. A series of calibrated von Frey filaments (Stoelting, Wood Dale, Ill.) were applied perpendicularly to the plantar surface of both hindpaws with sufficient force to bend the filament for 6 s. Brisk withdrawal of the paw or flinching was considered a positive response. When a response was observed, the filament of the next lower force was applied. In the absence of a response, the filament of the next greater force was applied. The "up-down" method was used (Chaplan et al., 1994) to calculate the tactile stimulus that produced a 50% likelihood of a withdrawal response.

To quantify the mechanical nociceptive threshold in rats, the paw pressure (Randall-Selitto) test was conducted on the left hindpaw using an analgesiometer (Ugo Basile, Varese, Italy). To activate the device, a foot pedal was pressed, which then applied a constantly increasing force on a linear scale. When the rat withdrew its paw or vocalized, the pedal was immediately released, and the withdrawal threshold was recorded (Chen et al., 2014a). The paw pressure test was not conducted in mice because it is difficult to determine the mouse's hindpaw withdrawal threshold using this analgesiometer.

To assess the thermal sensitivity of rats, the were placed individually on the glass surface of a thermal testing apparatus (IITC Life Sciences, Woodland Hills, Calif.). The rats were allowed to acclimate for 30 min before testing. The temperature of the glass surface was maintained at a constant 30° C. A mobile radiant heat source located under the glass was focused onto the hindpaw of each rat (Chen and Pan, 2006). The paw withdrawal latency was recorded with a timer, and the hindpaw was tested twice to obtain an average time. An incremental hot/cold plate analgesia meter (IITC Life Sciences) was used to determine the thermal sensitivity of mice. Mice were placed individually in the observation chamber on the plate, which had been preheated to 30° C. for 60 min. To measure heat sensitivity, the plate was heated at a rate of 6° C./min until the mice showed nocifensive behaviors such as paw shaking and jumping (Laumet et al., 2015). After the threshold temperature was recorded, the mice were immediately removed from the plate. The heat threshold measurement was repeated 30 min later, and the average of the 2 recorded temperatures was considered as the heat threshold. The cold threshold was measured by cooling the plate from 30° C. at a rate of 6° C./min until nocifensive behaviors were observed. The investigators performing the behavioral experiments were blinded to the treatment.

Experimental design and statistical analysis: For electrophysiological experiments, at least 3 animals were used for each recording protocol, and only 1 neuron was recorded from each spinal cord slice. The amplitude of evoked EPSCs was quantified by averaging 10 consecutive EPSCs measured using Clampfit 10.0 software (Axon Instruments). mEPSCs were analyzed off-line using the peak detection program (MiniAnalysis, Synaptosoft, Leonia, N.J.). Kolmogorov-Smirnov tests were used to compare the cumulative probability of the amplitude and inter-event interval of mEPSCs. The group data were presented in means±SEM. Two-tailed Student's t tests were used to compare 2 groups, and 1-way analysis of the variance (ANOVA) followed by Dunnett's or Tukey's post hoc test was used to determine the differences between more than 2 groups. Two-way ANOVA followed by Tukey's post hoc test was performed to compare the withdrawal thresholds in WT mice and KO mice. All statistical analyses were performed using Prism software (version 7, GraphPad Software Inc., La Jolla, Calif.). P values of less than 0.05 were considered to indicate statistically significant differences.

Example 9—Presynaptic α2δ-1-Bound NMDA Receptors Contribute to Opioid-induced Hyperalgesia and Analgesic Tolerance Chronic morphine treatment increases the prevalence of α2δ-1-NMDAR complexes in the DRG and spinal cord: To determine whether chronic administration of morphine alters the α2δ-1 expression level, α2δ-1 protein level was measured in the DRG and dorsal spinal cord tissues in morphine- and vehicle-treated rats. Morphine (5 mg/kg) or vehicle was injected intraperitoneally twice a day for 8 consecutive day. Immunoblotting analysis using total proteins showed that the α2δ-1 level in both the DRG and dorsal spinal cord was significantly higher in the morphine-treated than in vehicle-treated group (n=6 rats/group, FIG. 39A-B).

Figures 40A, 40B, 40C, 40D:
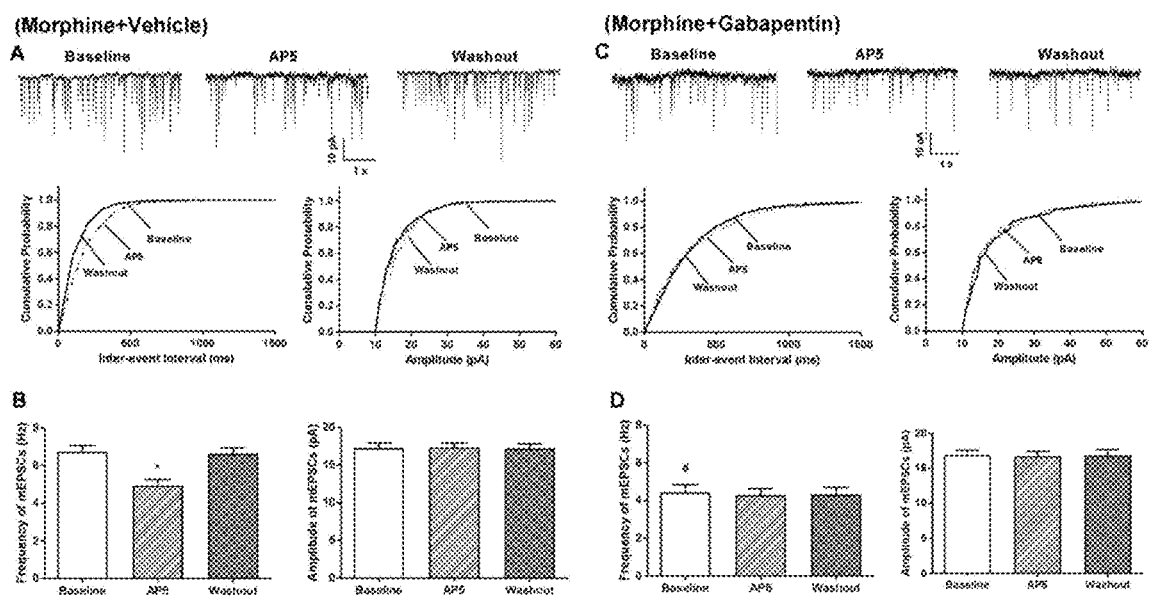
Figures 41A, 41B, 41C, 41D, 41E, 41F:
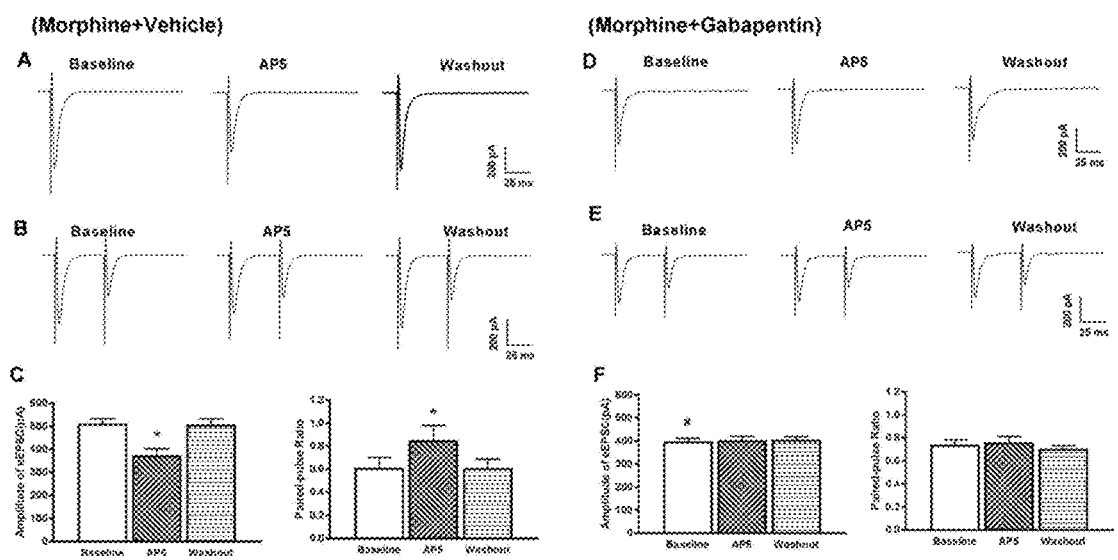

To determine whether chronic morphine treatment affects the physical interaction between α2δ-1 and NMDARs in vivo, coimmunoprecipitation (co-IP) analyses was conducted using membrane extracts of dorsal spinal cords obtained from vehicle- and morphine-treated rats. Using specific antibodies, GluN1, an obligatory subunit of NMDARs, was coprecipitated with the α2δ-1 in the dorsal spinal cord. The α2δ-1-GluN1 protein complex level in the dorsal spinal cord was much higher in morphine-treated rats than in vehicle-treated rats (n=6 rats/group, FIG. 39C).

α2δ-1 primarily increases synaptic NMDAR activity via promoting NMDAR trafficking (Chen et al., 2018). It was thus determined whether chronic morphine increases synaptic targeting of α2δ-1 and NMDARs. Immunoblotting analysis using synaptosomes isolated from the dorsal spinal cord showed that both GluN1 and α2δ-1 protein levels in the spinal cord synaptosomes were significantly higher in morphine-treated than in vehicle-treated rats (n=6 rats/group, FIG. 39D). These results indicate that chronic opioid treatment causes α2δ-1 upregulation and increases the α2δ-1-NMDAR interaction at spinal cord synapses.

α2δ-1 mediates chronic morphine-induced potentiation of presynaptic NMDAR activity in the spinal cord: Chronic morphine treatment increases presynaptic NMDAR, but diminishes postsynaptic NMDAR, activity in the spinal dorsal horn (Zhao et al., 2012). Gabapentin binds primarily to α2δ-1 (Gee et al., 1996; Marais et al., 2001) and is a clinically used α2δ-1 inhibitory ligand. Gabapentin was used to determine whether α2δ-1 contributes to the increased presynaptic NMDAR activity in the spinal cord induced by chronic morphine treatment. Glutamatergic mEPSCs were recorded, which reflect spontaneous quantal release of glutamate from presynaptic terminals (Zhao et al., 2012). In vehicle-incubated spinal cord slices from morphine-treated rats, bath application of 50 µM AP5, a specific NMDAR antagonist, largely normalized the frequency of mEPSCs in dorsal horn neurons recorded in morphine-treated rats (n=11 neurons, FIGS. 40A and B). These results suggest that chronic morphine increases the activity of presynaptic NMDARs in the spinal dorsal horn, which is similar to what was shown previously (Zhao et al., 2012). In spinal cord slices from morphine-treated rats, gabapentin pretreatment (100 µM for 60 min) substantially reduced the baseline frequency, but not the amplitude, of mEPSCs in dorsal horn neurons (n=10 neurons, FIGS. 40C and D). In these neurons, subsequent bath application of 50 µM AP5 had no effect on the frequency or amplitude of mEPSCs (FIGS. 40C and D).

Figures 42A, 42B, 42C, 42D:
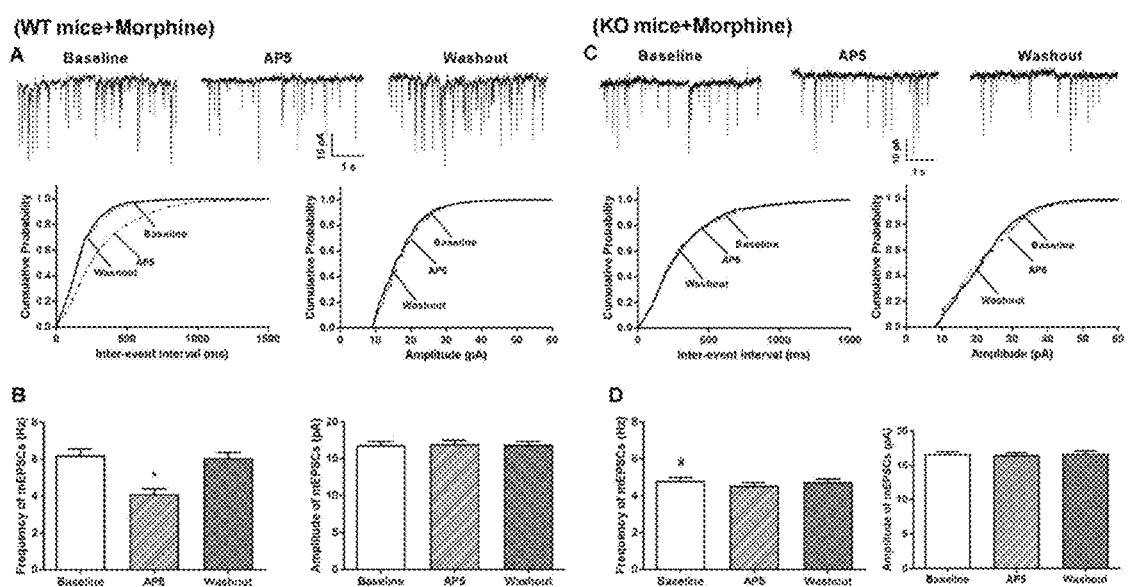
Figures 43A, 43B, 43C, 43D, 43E, 43F:
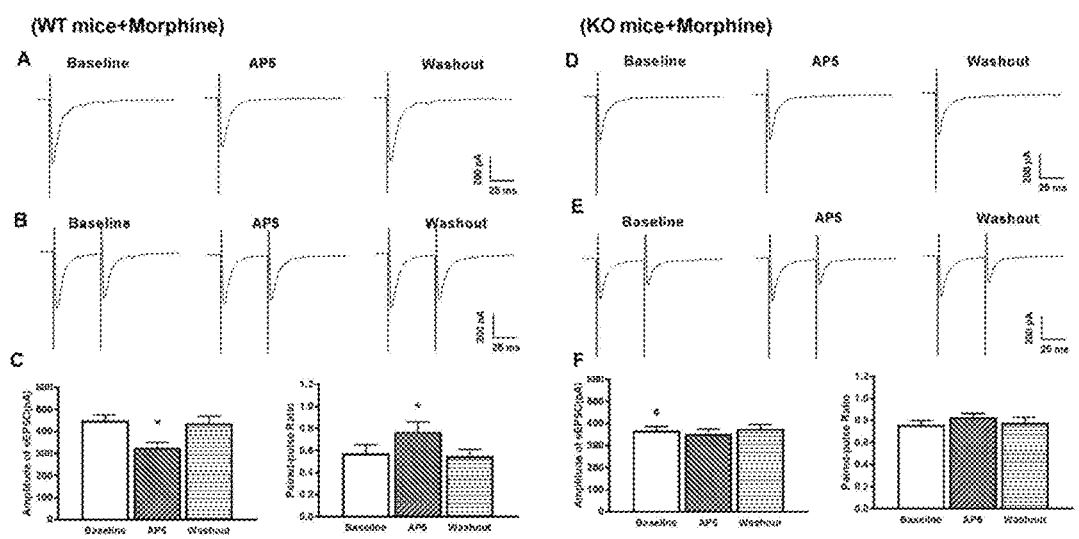
Figures 44A, 44B, 44C, 44D:
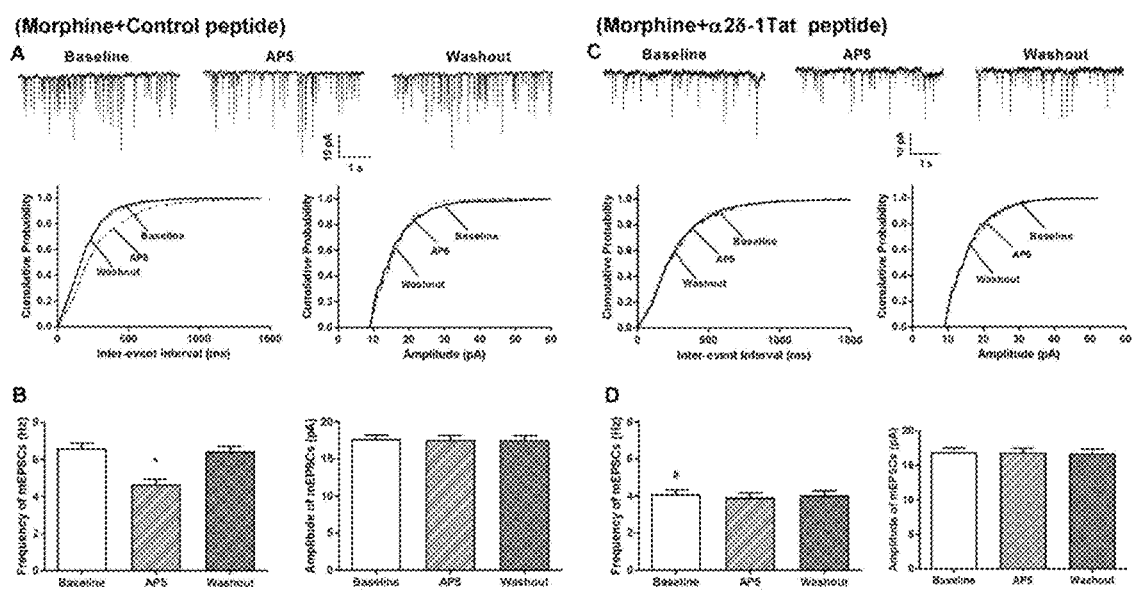
Figures 45A, 45B, 45C, 45D, 45E, 45F:
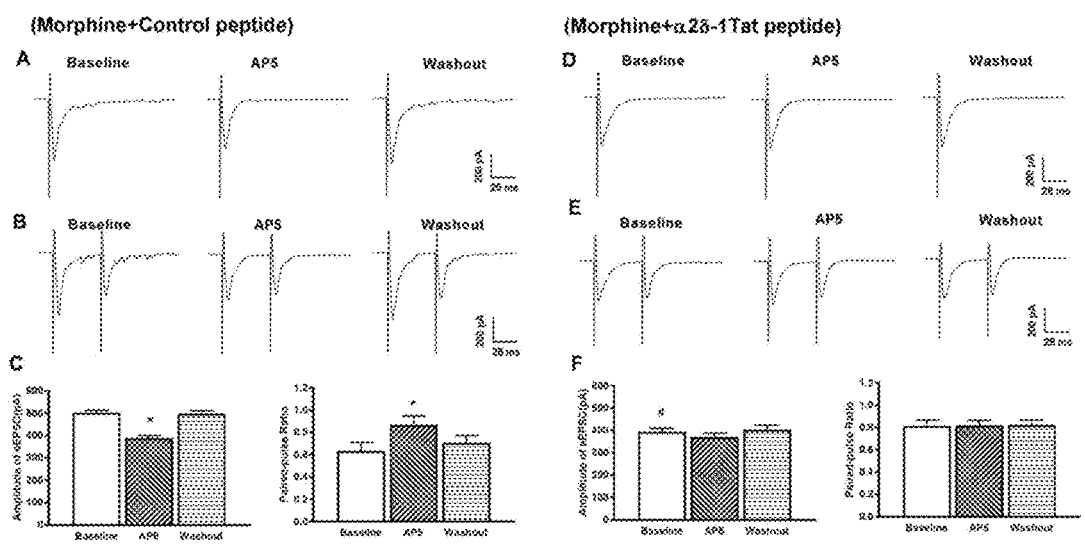
Figures 46A, 46B, 46C, 46D, 46E, 46F:
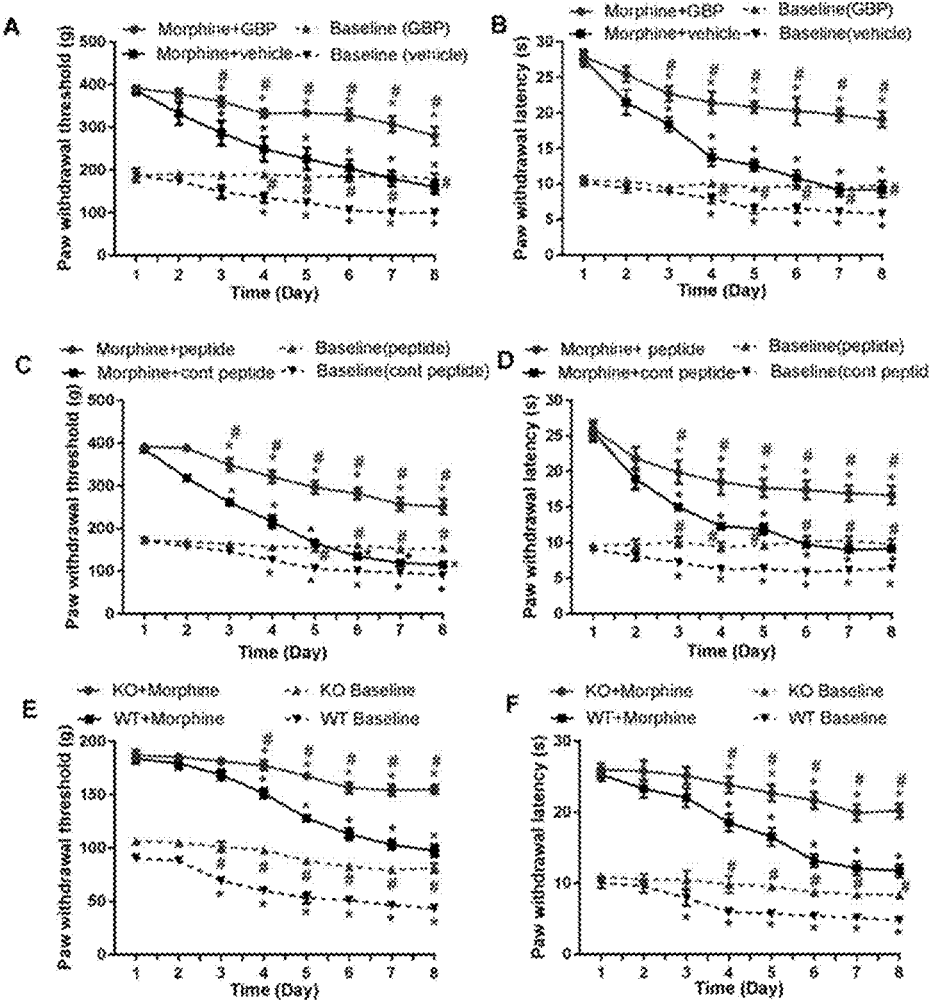

Furthermore, to determine the role of α2δ-1 in NMDAR-mediated synaptic glutamate release from central terminals of primary afferent nerves, the effect of gabapentin was examined on the amplitude of monosynaptic EPSCs evoked from the dorsal root. In vehicle-incubated spinal cord slices from morphine-treated rats, bath application of 50 µM AP5 significantly reduced the amplitude of monosynaptic EPSCs and increased the paired-pulse ratio (PPR) of monosynaptically evoked EPSCs of lamina II neurons (n=10 neurons, FIG. 41A-C). These data are consistent with the previous findings (Zhao et al., 2012). Gabapentin pretreatment (100 µM for 60 min) considerably reduced the amplitude of evoked EPSCs of lamina II neurons in spinal cord slices from morphine-treated rats. After gabapentin incubation, further bath application of AP5 had no significant effect on the amplitude or PPR of evoked EPSCs of dorsal horn neurons (n=10 neurons, FIG. 41D-F). These findings suggest that α2δ-1 plays a crucial role in the opioid-induced increase in presynaptic NMDAR activity in the spinal cord.

α2δ-1 is essential for chronic morphine-induced tonic activity of NMDARs at primary afferent terminals: To validate the critical role of α2δ-1 in the opioid-induced increase in presynaptic NMDAR activity, Cacna2d1 knockout (KO, Cacna2d1$^{-/-}$) mice were used. In wild-type (WT, Cacna2d1$^{+/+}$) mice, chronic intraperitoneal injection of morphine (10 mg/kg, twice a day for 8 day) significantly increased the NMDAR-mediated frequency of mEPSCs of spinal dorsal horn neurons, compared with that in Cacna2d1 KO mice (FIG. 42). Bath application of AP5 (50 µM) substantially reduced the baseline frequency of mEPSCs in dorsal horn neurons from morphine-treated WT mice (n=11 neurons, FIGS. 42A and B). In contrast, in dorsal horn neurons from morphine-treated Cacna2d1 KO mice, application of AP5 had no effect on the frequency or amplitude of mEPSCs (n=10 neurons, FIGS. 42C and D).

Furthermore, chronic morphine treatment markedly increased the amplitude of monosynaptic EPSCs evoked from the dorsal root in spinal cord slices in WT mice. In these neurons, bath application of 50 µM AP5 significantly reduced the amplitude of monosynaptic EPSCs and increased the PPR of evoked EPSCs (n=11 neurons, FIG. 43A-C). However, in dorsal horn neurons from morphine-treated Cacna2d1 KO mice, AP5 had no effect on the amplitude or the PPR of monosynaptic EPSCs (n=11 neurons, FIG. 43D-F). These data provide unequivocal evidence that α2δ-1 is essential for the opioid-induced increase in presynaptic NMDAR activity at the spinal cord level.

α2δ-1-bound NMDARs are required for the morphine-induced increase in presynaptic NMDAR activity in the spinal cord: The C terminus of α2δ-1 is required for its interaction with NMDARs, and a Tat (YGRKKRRQRRR; SEQ ID NO:2)-fused 30-amino-acid peptide (VSGL-NPSLWSIFGLQFILLWLVSGSRHYLW; SEQ ID NO:4) effectively disrupts the α2δ-1-NMDAR interaction in vivo (Chen et al., 2018). This α2δ-1Tat peptide was used to determine the role of α2δ-1-bound NMDARs the opioid-induced increase in presynaptic NMDAR activity. In dorsal horn neurons from morphine-treated rats, incubation with α2δ-1Tat peptide (1 µM for 60 min) significantly reduced the frequency, but not the amplitude, of mEPSCs, compared with that incubated with a Tat-fused scrambled control peptide (FGLGWQPWSLSFYLVWSGLILSVLHLIRSN; SEQ ID NO:3, 1 µM for 60 min). Furthermore, bath application of 50 µM AP5 significantly reduced the frequency of mEPSCs in control peptide-incubated dorsal horn neurons from morphine-treated rats (n=10 neurons, FIGS. 44A and B). In contrast, AP5 had no effect on the frequency of mEPSCs in α2δ-1Tat peptide-incubated dorsal horn neurons from morphine-treated rats (n=11 neurons, FIGS. 44C and D).

It was also examined whether α2δ-1Tat peptide affects the morphine-induced activation of NMDARs at primary afferent terminals. Tat-fused control peptide treatment did not affect the amplitude of monosynaptic EPSCs of dorsal horn neurons in morphine-treated rats. Bath application of 50 µM AP5 markedly reduced the amplitude and increased the PPR of monosynaptic EPSCs in these neurons (n=11 neurons, FIG. 45A-C). However, treatment with α2δ-1Tat peptide (1 µM for 60 min) normalized the increased amplitude of evoked EPSCs in dorsal horn neurons from morphine-treated rats. Further application of AP5 had no significant effect on the amplitude of evoked monosynaptic EPSCs (n=11 neurons, FIGS. 45D and F) or the PPR of evoked EPSCs (n=11 neurons, FIGS. 45E and F). These findings indicate that α2δ-1-bound NMDARs are indispensable for opioid-induced activation of presynaptic NMDARs in the spinal dorsal horn.

α2δ-1-bound NMDARs at the spinal cord level mediates opioid-induced hyperalgesia and tolerance: Having shown the importance of α2δ-1-bound NMDARs in the opioid-induced increase in presynaptic NMDAR activity, it was next determined whether α2δ-1 similarly contributes to opioid-induced hyperalgesia and tolerance. Rats were treated with intraperitoneal administration of morphine (5 mg/kg, twice a day) for 8 consecutive days (Chen et al., 2007; Zhao et al., 2012). The withdrawal thresholds were examined in response to the noxious pressure and heat stimuli 30 min before (baseline) and 30 min after morphine injection (5 mg/kg) each day. 100 mg/kg gabapentin (or vehicle) or intrathecally injected 1 µg α2δ-1Tat peptide or control peptide were intraperitoneally injected 20 min before each morphine treatment in separate groups of rats.

Daily morphine injection in vehicle- (n=8 rats) or control peptide-treated (n=10 rats) rats caused a gradual reduction in the baseline withdrawal thresholds, indicating the presence of mechanical and thermal hyperalgesia (FIG. 46A-D). These rats also showed a gradual decrease in the antinociceptive effect of morphine. By day 6, intraperitoneal injection of 5 mg/kg morphine failed to produce a significant effect on the withdrawal thresholds, indicating the development of analgesic tolerance (FIG. 46A-D). In contrast, co-treatment with gabapentin (n=8 rats) or α2δ-1Tat peptide (n=8 rats) completely blocked the reduction in baseline withdrawal thresholds induced by chronic morphine injections (FIG. 46A-D). Furthermore, co-treatment with gabapentin or α2δ-1Tat peptide substantially attenuated the reduction in the analgesic effect of morphine. Even at day 8, injection of 5 mg/kg morphine still significantly increased the nociceptive mechanical and thermal withdrawal thresholds (FIG. 46A-D).

In addition, Cacna2d1 KO mice were used to validate the role of α2δ-1 in opioid-induced hyperalgesia and tolerance. In WT mice, daily intraperitoneal injection of morphine (10 mg/kg, twice a day) for 8 consecutive days gradually reduced the baseline withdrawal thresholds in response to noxious pressure and heat stimuli and diminished the antinociceptive effect of morphine (n=8 mice, FIG. 46E-F). However, in Cacna2d1 KO mice, daily morphine injections did not significantly affect the baseline withdrawal threshold. Also, the anti-nociceptive effect of morphine was largely preserved at the end of 8-day morphine treatment in Cacna2d1 KO mice (n=8 mice, FIG. 46E-F). Together, these findings indicate that α2δ-1-bound NMDARs at the spinal cord level play a crucial role in the development of opioid-induced hyperalgesia and analgesic tolerance.

In the present study, chronic morphine treatments not only increased the α2δ-1 protein level but also potentiated the physical association between α2δ-1 and NMDARs in the spinal cord. It has been shown that protein kinase C play a major role in opioid-induced hyperalgesia and tolerance and presynaptic NMDAR hyperactivity in the spinal cord (Mao et al., 1994; Zhao et al., 2012). However, the potential link between α2δ-1-bound NMDARs and protein kinases in regulating NMDAR activity is still uncertain. Since increased protein phosphorylation can strengthen protein-protein binding complexes (Nishi et al., 2011), it is possible that protein kinase C may potentiate phosphorylation of α2δ-1 and/or NMDAR proteins to promote their physical interactions by changing their physicochemical conformation. It was also found that chronic morphine augmented the prevalence of α2δ-1-NMDAR complexes at spinal cord synapses. Hence, opioid-induced hyperalgesia and tolerance are associated with increased synaptic expression of α2δ-1-NMDARs at the spinal cord level.

In conclusion, the study provides new evidence that chronic opioid treatment causes upregulation of α2δ-1 and enhances the association between α2δ-1 and NMDARs in the spinal cord. These findings support the notion that α2δ-1-bound NMDARs are critically involved in opioid-induced tonic activation of presynaptic NMDARs in the spinal cord, which augments glutamatergic input to spinal dorsal horn neurons to cause hyperalgesia and analgesic tolerance. This information is important for understanding the mechanisms of opioid-induced synaptic plasticity and suggests new strategies for improving opioid analgesic efficacy by eliminating aberrant presynaptic NMDAR activation. Gabapentinoids and α2δ-1 C-terminus-interfering peptides do not affect physiological α2δ-1-free NMDARs and could avoid the adverse effects associated with the use of general NMDAR antagonists, such as ketamine. Thus, targeting α2δ-1-bound NMDARs is a more desirable approach than blocking total NMDARs with non-selective NMDAR antagonists.

Example 10—Materials and Methods

Animal model and intrathecal catheterization: All procedures and experimental protocols were approved by the Animal Care and Use Committee of the University of Texas MD Anderson Cancer Center and were performed in accordance with the Guide for the Care and Use of Laboratory Animals of the National Institutes of Health. Adult male Sprague-Dawley rats (280-320 g; Harlan, Ind.) were used in these experiments. Generation of conventional Cacna2d1 knockout mice (C57BL/6 genetic background) mice has been described previously (Fuller-Bicer et al., 2009). Two breeding pairs of Cacna2d1$^{+/-}$ mice were purchased from Medical Research Council (Harwell Didcot, Oxfordshire, UK). Cacna2d1$^{-/-}$ mice and Cacna2d1$^{+/+}$ (wild-type) littermates were obtained by breeding the Cacna2d1$^{+/-}$ heterozygous mice.

Under isoflurane-induced anesthesia, the rat was placed prone on a stereotaxic frame, and a small puncture was made in the atlanto-occipital membrane of the cisterna magna. A catheter (PE-10 tubing) was then inserted such that the caudal tip reached the lumbar enlargement of the spinal cord (Chen and Pan, 2006a; Chen et al., 2007). The rostral end of the catheter was then exteriorized and closed the wound with sutures. The animals were allowed to recover for at least 5 days before intrathecal injections. Those rats displaying neurological deficits (e.g., paralysis) or poor grooming were promptly killed with $CO_2$ inhalation.

Morphine treatment and drug delivery: To induce opioid analgesic tolerance, morphine sulfate (West Ward Pharmaceuticals, Eatontown, N.J.) was injected intraperitoneally at 5 mg/kg (in rats) or 10 mg/kg (in mice) twice a day for 8 consecutive day (Chen et al., 2007; Zhao et al., 2012). Gabapentin was obtained from Tocris Bioscience (Ellisville, Mo.). The α2δ-1Tat peptide and scrambled control peptide were synthesized by Bio Basic Inc. (Marham, Ontario, Canada) and validated by using liquid chromatography and mass spectrometry. The α2δ-1Tat peptide and Tat-fused scrambled control peptide were dissolved in saline and injected intrathecally, followed by a 10 µl saline flush 20 min before morphine administration on each testing day. Gabapentin was dissolved in saline and injected intraperitoneally before morphine administration on each testing day.

Western immunoblotting: Western blotting was used to quantify the α2δ-1 protein level in the dorsal spinal cord and DRG. Spinal cord and DRG tissues at L5-L6 levels were collected and homogenized in 300 µl radioimmunoprecipitation assay buffer (50 mM Tris-HCl (pH 7.4), 150 mM NaCl, 1 mM $Na_3VO_4$, 1 mM EDTA, 1 mM NaF, 1% Nonidet P-40, and 0.25% sodium-deoxycholate) with the protease inhibitor cocktail (Sigma-Aldrich). The samples were homogenized with lysis buffer on ice for 30 min, and centrifuged at 13,000×g for 30 min at 4° C. The supernatant was carefully collected, and its protein concentration was measured. The protein samples extracted from spinal cord and DRG tissues were subjected to 12% sodium dodecyl sulfate-polyacrylamide gel and transferred to a polyvinylidene difluoride membrane. The blots were probed with rabbit anti-α2δ-1 antibody (#ACC-015, 1:500, Alomone Labs, Jerusalem, Israel) or rabbit anti-GAPDH antibody (#14C10, 1:5000, Cell Signaling Technology, Danvers, Mass.). The protein bands were detected with ECL kit (Thermo Fisher Scientific, Waltham, Mass.), and protein band intensity was visualized and quantified using the Odyssey Fc Imager (LI-COR Biosciences, Lincoln, Nebr.).

Coimmunoprecipitation using spinal cord membrane extracts: Spinal cord tissues at the L5 and L6 levels were collected and homogenized in ice-cold hypotonic buffer (20 mM Tris [pH 7.4], 1 mM $MgCl_2$, and 1 mM $CaCl_2$) containing the protease inhibitor cocktail (Sigma-Aldrich, St. Louis, Mo.) for extracting membrane proteins. The unbroken cells and nuclei were removed by centrifugation at 300×g for 5 min, and the supernatant was centrifuged for 20 min at 21,000×g. The pellets were re-suspended and solubilized in immunoprecipitation buffer (50 mM Tris [pH7.4], 250 mM NaCl, 1 mM $Na_3VO_4$, 10 mM N-ethylmaleimide, 20 mM NaF, 1 mM phenylmethylsulfonyl fluoride, 2 mM benzamide, 10% glycerol, and 0.5% NP-40) containing the protease inhibitor cocktail (Sigma-Aldrich), and the soluble fraction was incubated at 4° C. overnight with Protein A/G beads (#16-2δ6, Millipore, Darmstadt, Germany) prebound to mouse anti-GluN1 (#75-272, 1:1,000, NeuroMab, Davis, Calif.). Protein A/G beads prebound to mouse IgG were used as a control. All samples were washed 3 times with immunoprecipitation buffer and then immunoblotted. The following antibodies were selected for immunoblotting: rabbit anti-α2δ-1 (#C5105, 1:1,000, Sigma-Aldrich; #ACC-015, Alomone Labs, Jerusalem, Israel) and rabbit anti-GluN1 (#G8913, 1:1000, Sigma-Aldrich).

Spinal cord synaptosome preparation: The spinal cord tissues at the L5 and L6 levels were collected and homogenized using glass-Teflon homogenizer in 10 volumes of ice-cold HEPES-buffered sucrose (0.32 M sucrose, 4 mM HEPES, and 1 mM EGTA at pH 7.4) containing the protease inhibitor cocktail (Sigma-Aldrich). The homogenate was centrifuged at 1,000×g at 4° C. for 10 min to remove sediment including large debris and nuclei. To obtain the crude synaptosomal fraction, then the supernatant was centrifuged at 10,000×g for 15 min. The synaptosomal pellet was lysed in 9 volumes of ice-cold HEPES-buffer with the protease inhibitor cocktail for 30 min. The lysate was centrifuged at 25,000×g at 4° C. for 20 min to obtain the synaptosomal membrane fraction. After measuring the protein concentration, thirty μg of proteins were used for Western Blotting analysis. The following antibodies were selected for immunoblotting: rabbit anti-α2δ-1 (#ACC-015, Alomone Labs, Jerusalem, Israel), rabbit anti-GluN1 (#G8913, 1:1000, Sigma-Aldrich), and mouse anti-PSD95 (#75-348, 1:1,000, NeuroMab, Davis, Calif.).

Spinal cord slice preparation and electrophysiological recordings: The lumbar spinal cord was rapidly removed through laminectomy from the animals anesthetized with isoflurane. The spinal cord tissues were immediately placed in ice-cold sucrose artificial cerebrospinal fluid presaturated with 95% $O_2$ and 5% $CO_2$. The fluid contained (in mM) 234 sucrose, 3.6 KCl, 1.2 $MgCl_2$, 2.5 $CaCl_2$, 1.2 $NaH_2PO_4$, 25.0 $NaHCO_3$, and 12.0 glucose. The spinal cord tissue was then placed in a shallow groove formed in an agar block and glued onto the stage of a vibratome (Leica, Germany). Transverse slices (400 μm thick) of the spinal cords were cut in ice-cold sucrose artificial cerebrospinal and preincubated in Krebs solution oxygenated with 95% $O_2$ and 5% $CO_2$ at 34° C. for at least 1 h before being transferred to the recording chamber. The Krebs solution contained (in mM) 117.0 NaCl, 3.6 KCl, 2.5 $CaCl_2$, 1.2 $MgCl_2$, 1.2 $NaH_2PO_4$, 11.0 glucose, and 25.0 $NaHCO_3$. The spinal cord slices in a recording chamber were perfused with Krebs solution at 5.0 ml/min at 34° C. The lamina II outer neurons were visualized and selected for recording because they predominantly receive nociceptive input and are mostly glutamate-releasing excitatory neurons (Li et al., 2002; Santos et al., 2007; Zhou et al., 2010).

Excitatory postsynaptic currents (EPSCs) were recorded using whole-cell voltage-clamp techniques. The impedance of the glass electrode was 4-7 MΩ when the pipette was filled with the internal solution containing 135.0 mM potassium gluconate, 2.0 mM $MgCl_2$, 0.5 mM $CaCl_2$, 5.0 mM KCl, 5.0 mM HEPES, 5.0 mM EGTA and 5.0 mM ATP-Mg, 0.5 mM Na-GTP, and 10 mM QX314 (280-300 mosM, adjusted to pH 7.25 with 1.0 M KOH). EPSCs were evoked from the dorsal root using a bipolar tungsten electrode connected to a stimulator (0.5 ms, 0.6 mA and 0.1 Hz). Monosynaptic EPSCs were recorded on the basis of the constant latency and absence of conduction failure of evoked EPSCs in response to a 20-Hz electrical stimulation, as described previously (Li et al., 2002; Zhou et al., 2010). To measure the paired-pulse ratio (PPR), two EPSCs were evoked by a pair of stimuli administered at 50-ms intervals, and the ratio of the amplitudes of the second synaptic response to the first was used to obtain PPR (Xie et al., 2016). Miniature EPSCs (mEPSCs) were recorded at a holding potential of −60 mV in the presence of 10 μM bicuculline, 2 μM strychnine, and 1 μM tetrodotoxin. The input resistance was monitored, and the recording was abandoned if the input resistance changed more than 15%. All signals were recorded using an amplifier (MultiClamp700B; Axon Instruments Inc., Union City, Calif.), filtered at 1-2 kHz, and digitized at 10 kHz.

All drugs were prepared in artificial cerebrospinal fluid before the recording and delivered via syringe pumps reach to their final concentrations. Tetrodotoxin citrate (TTX) and 2-amino-5-phosphonopentanoic acid (AP5) was purchased from Hello Bio Inc. (Princeton, N.J.).

Behavioral assessment of nociception: To quantify the mechanical nociceptive threshold in rats and mice, the paw pressure (Randall-Selitto) test was conducted on the left hindpaw using an analgesiometer (Ugo Basile, Varese, Italy). To activate the device, a foot pedal was pressed which applied a constantly increasing force on a linear scale. When the animals withdraw the paw or vocalize, the pedal was immediately released, and the scale of the withdrawal threshold was recorded (Chen et al., 2014). A maximum of 400 g (in rats) or 200 g (in mice) of pressure was used as a cutoff to avoid potential tissue injury to the rats or mice, respectively.

To assess the thermal sensitivity of rats, rats were placed on the glass surface of a thermal testing apparatus (IITC Life Sciences, Woodland Hills, Calif.) and allowed to acclimate for 30 min before testing. The temperature of the glass surface was maintained at a constant 30° C. A mobile radiant heat source located under the glass was focused onto the hindpaw of each rat. The paw withdrawal latency was recorded with a timer, and the hindpaw was tested twice to obtain the average. A cut-off of 30 s was used to prevent potential tissue damage (Chen and Pan, 2006b; Li et al., 2016).

An incremental hot plate analgesia meter (IITC Life Sciences) was used to determine the thermal sensitivity of mice. Mice were placed individually in the observation chamber on the plate, which had been preheated to 30° C. for 60 min. To measure heat sensitivity, the plate was heated at a rate of 6° C./min until the mice showed nocifensive behaviors such as paw shaking (Laumet et al., 2015). After the threshold temperature was recorded, the mice were immediately removed from the plate. The heat threshold measurement was repeated 30 min later, and the average of the 2 recorded temperatures was considered as the heat threshold.

Data analysis: At least three animals were used for each recording protocol, and only one neuron was recorded from each spinal cord slice. The amplitude of the evoked EPSCs was quantified by averaging 6 consecutive EPSCs using Clampfit 10.0 software (Axon Instruments). The mEPSCs were analyzed off-line using the peak detection MiniAnalysis Program (Synaptosoft, Leonia, N.J.). The Kolmogorov-Smirnov tests were used to compare the cumulative probability of the amplitude and inter-event interval of mEPSCs. The two-tailed Student t test was used to compare two groups, and one-way analysis of the variance (ANOVA) followed by the Dunnett's post hoc test was used to determine the differences between more than two groups. Two-way ANOVA analysis was used to compare the behavioral data between the experimental groups. The investigators performing the behavioral and electrophysiological experiments were blinded to the treatment. All statistical analyses were performed using Prism 6 software (GraphPad Software Inc., La Jolla, Calif.). $P<0.05$ was considered to be statistically different.

Figures 47A, 47B, 47C, 47D, 47E, 47F:
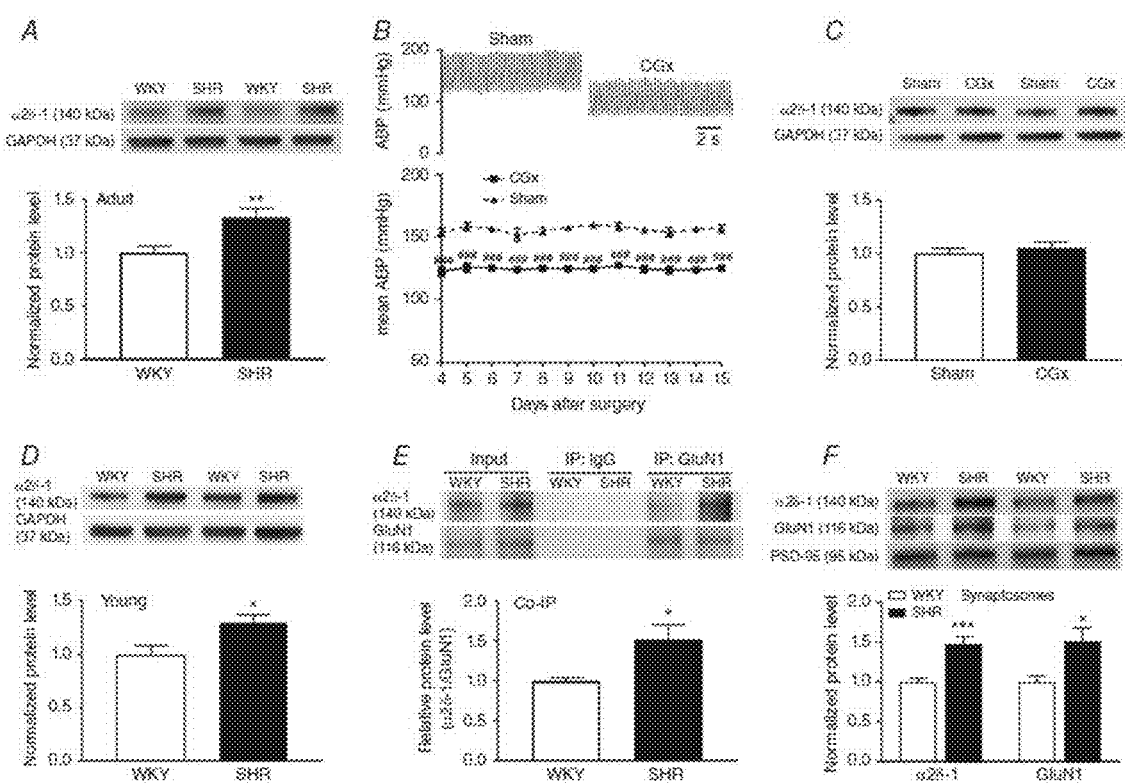

Example 11—α2δ-1 Couples to NMDA Receptors in the Hypothalamus to Sustain Sympathetic Vasomotor Activity in Hypertension α2δ-1 is upregulated in the PVN in SHRs: Immunoblotting was used to determine the α2δ-1 protein levels in the PVN in WKY rats and SHRs. The α2δ-1 protein level in the PVN was significantly greater in SHRs than in WKY rats (P=0.0074, $t_{12}$=3.217, n=7 rats in each group) (FIG. 47A). To determine whether the higher α2δ-1 protein level in the PVN of SHRs was secondary to elevated ABP in SHRs, CGx was performed to lower ABP in SHRs and then measured α2δ-1 protein levels in their PVNs. CGx substantially lowered ABP in SHRs, as measured by radio telemetry, compared to the sham group (n=6 rats in each group) (FIG. 47B). Immunoblotting showed that lowering ABP did not significantly alter the α2δ-1 protein level in the PVN in SHRs (FIG. 47C). In addition, the α2δ-1 protein level in the PVN was significantly higher in 4-week-old SHRs than in age-matched WKY rats (P=0.027, $t_{10}$=2.584, n=6 rats in each group) (FIG. 47D). These data suggest that α2δ-1 upregulation in the PVN in SHRs is independent of ABP changes.

α2δ-1 physically interacts with NMDARs in the hypothalamus in SHRs: It was shown that α2δ-1 physically interacts with NMDARs in the spinal cord (Chen et al. 2018). To determine whether α2δ-1 and NMDARs interact in the hypothalamus, co-immunoprecipitation analyses was conducted using total proteins extracted from the PVN_ of SHRs and WKY rats. The anti-GluN1 antibody co-precipitated with α2δ-1 in the hypothalamic tissues obtained from these rats, whereas the irrelevant IgG did not co-precipitate with α2δ-1 (FIG. 47E). Furthermore, the α2δ-1-GluN1 complex level in the hypothalamus was much higher in SHRs than in WKY rats (P=0.0204, $t_{10}$=2.752, n=6 rats in each group) (FIG. 47E). These results indicate that α2δ-1 forms a protein complex in the hypothalamus and that the α2δ-1-NMDAR interaction is enhanced in SHRs.

Figures 48A, 48B, 48C, 48D, 48E, 48F:
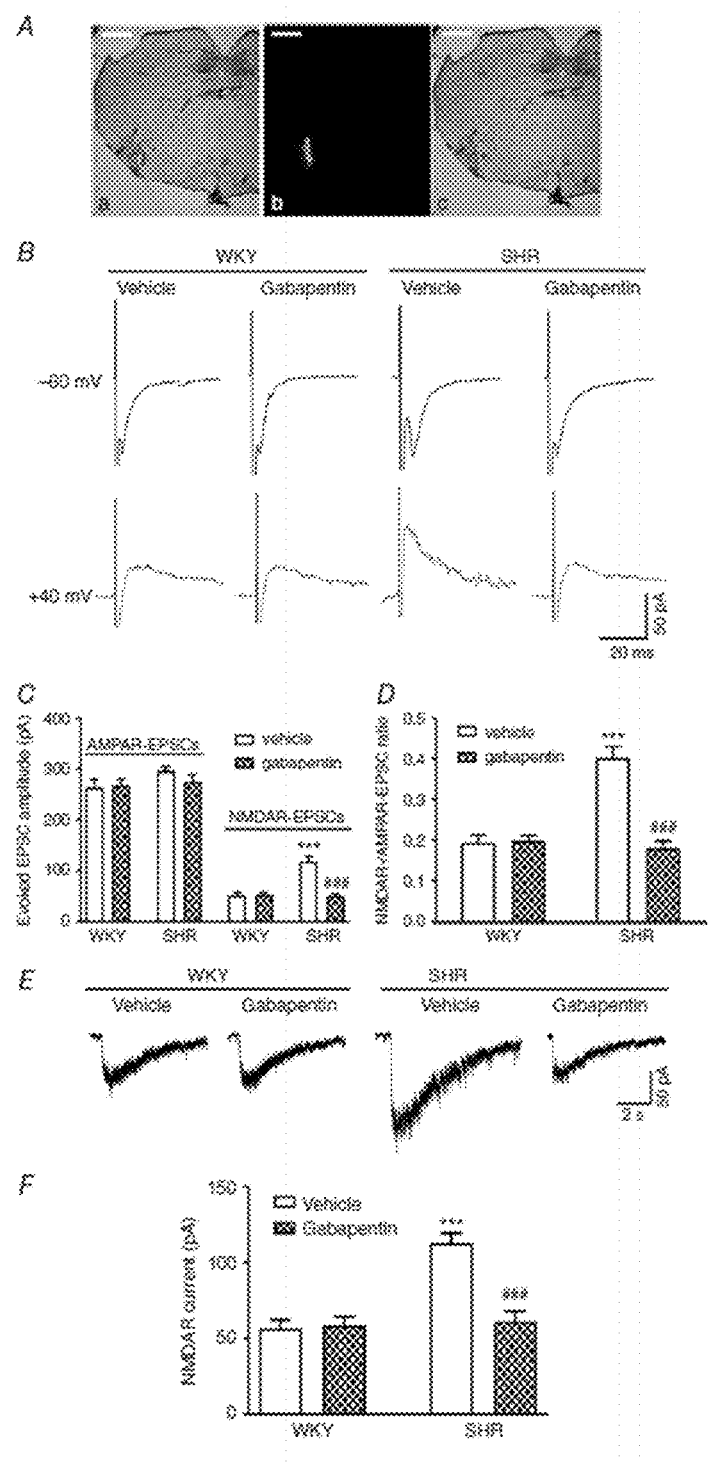

Synaptic α2δ-1-bound NMDARs are increased in the hypothalamus in SHRs: α2δ-1 primarily increases NMDAR activity by promoting synaptic targeting of NMDARs in the spinal cord after nerve injury. It was next determined whether α2δ-1-NMDAR complexes are increased at synaptic sites in the hypothalamus of SHRs. Immunoblotting of isolated synaptosomes showed that the protein levels of both α2δ-1 (P=0.0009, $t_{10}$=4.655) and GluN1 (P=0.0189, $t_{10}$=2.797), an obligatory subunit of NMDARs, were much higher in SHRs than in WKY rats (n=6 independent experiments, each tissue sample was pooled from two rats) (FIG. 47F). These data suggest that the prevalence of α2δ-1-bound NMDARs at the synaptic site in the hypothalamus is increased in SHRs.

α2δ-1 is indispensable for enhanced postsynaptic NMDAR activity of PVN presympathetic neurons in SHRs: It was then determined whether α2δ-1 plays a role in regulating synaptic NMDAR activity of RVLM-projecting PVN neurons in SHRs. The hypothalamic slices from WKY rats and SHRs were treated with either vehicle (aCSF) or gabapentin (100 μmol L-1), an α2δ-1-inhibitory ligand, for 60 min before electrophysiological recording. The amplitude of evoked NMDAR-EPSCs of labelled RVLM-projecting PVN neurons was significantly larger in SHRs (n=8 neurons) than in WKY rats (n=9 neurons) (P<0.0001, $F_{3,30}$=25.69) (FIG. 48A-C). Gabapentin treatment completely normalized the amplitude of evoked NMDAR-EPSCs of labelled PVN neurons in SHRs but had no effect in WKY rats (FIGS. 48B and C). By contrast, gabapentin did not significantly alter the amplitude of evoked AMPAR-EPSCs of labelled PVN neurons in WKY rats or SHRs. The ratio of NMDAR-EPSCs to AMPAR-EPSCs in vehicle-treated slices was significantly higher in SHRs than in WKY rats (WKY, n=9 neurons; SHR, n=8 neurons; P<0.0001, $F_{3,30}$=26.52) (FIG. 48B-D). Gabapentin treatment also restored the ratio of NMDAR-EPSCs to AMPAR-EPSCs in SHRs to the level in WKY rats, although it had no such effect in WKY rats (FIG. 48B-D).

Figures 49A, 49B, 49C, 49D:
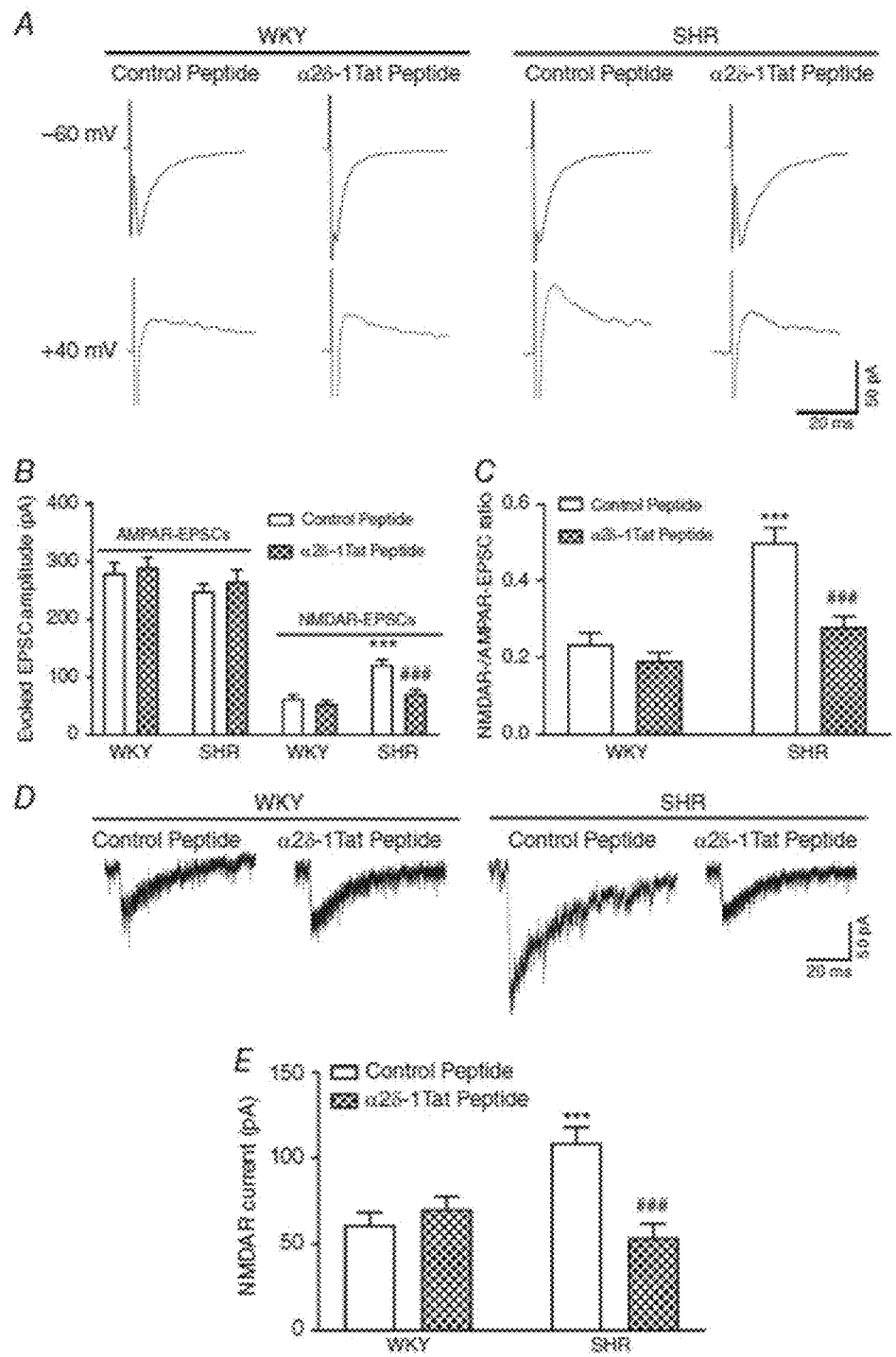

To directly determine the role of α2δ-1 in increased postsynaptic NMDAR activity of PVN presympathetic neurons in SHRs, the effect of gabapentin was examined on NMDAR currents elicited by puff application of NMDA (100 μmol L-1) directly to labelled PVN neurons. In vehicle-treated slices, puff NMDA induced a significantly larger current of labelled-neurons in SHRs than in WKY rats (WKY, n=11 neurons; SHR, n=12 neurons; P<0.0001, $F_{3,41}$=20.68) (FIGS. 48E and F). Treatment with gabapentin completely restored the puff NMDA currents of labelled PVN neurons in SHRs to the levels in WKY rats (FIGS. 48E and F). These results suggest that α2δ-1 is critically involved in increased postsynaptic NMDAR activity of PVN presympathetic neurons in SHRs.

α2δ-1-bound NMDARs are essential for increased postsynaptic NMDAR activity of PVN presympathetic neurons in SHRs: The C-terminus of α2δ-1 is essential for its interaction with NMDARs, and a 30-amino-acid peptide (VSGLNPSLWSIFGLQFILLWLVSGSRHYLW; SEQ ID NO:1) mimicking the transmembrane C-terminus of α2δ-1 fused with Tat protein (YGRKKRRQRRR; SEQ ID NO:2, α2δ-1Tat peptide) effectively interrupts the α2δ-1-NMDAR interaction. Pretreatment with a Tat-fused scrambled control peptide (FGLGWQPWSLSFYLVWSGLILSVLHLIRSN; SEQ ID NO:3, 1 µmol L-1, 60 min) did not affect the evoked AMPAR-EPSCs, evoked NMDAR-EPSCs or the ratio of NMDAR-EPSCs to AMPAR-EPSCs of labelled PVN neurons from WKY rats (n=10 neurons) or SHRs (n=9 neurons) (FIG. 49A-C). By contrast, α2δ-1Tat peptide (1 µmol L-1, 60 min) fully normalized the amplitude of evoked NMDAR-EPSCs of labelled PVN neurons in SHRs (n=9 neurons in each group) (FIGS. 49A and B). However, α2δ-1Tat peptide had no effect on the amplitude of evoked NMDAR-EPSCs of labelled PVN neurons in WKY rats (FIGS. 49A and B). Also, α2δ-1Tat peptide had no effect on the amplitude of evoked AMPAR-EPSCs of labelled PVN neurons in WKY rats or SHRs (FIGS. 49A and B). α2δ-1Tat peptide normalized the ratio of NMDAR-EPSCs to AMPAR-EPSCs in SHRs to the level in WKY rats (FIG. 49C), although it had no effect on the ratio of NMDAR-EPSCs to AMPAR-EPSCs in WKY rats.

Figures 50A, 50B, 50C, 50D, 50E, 50F:
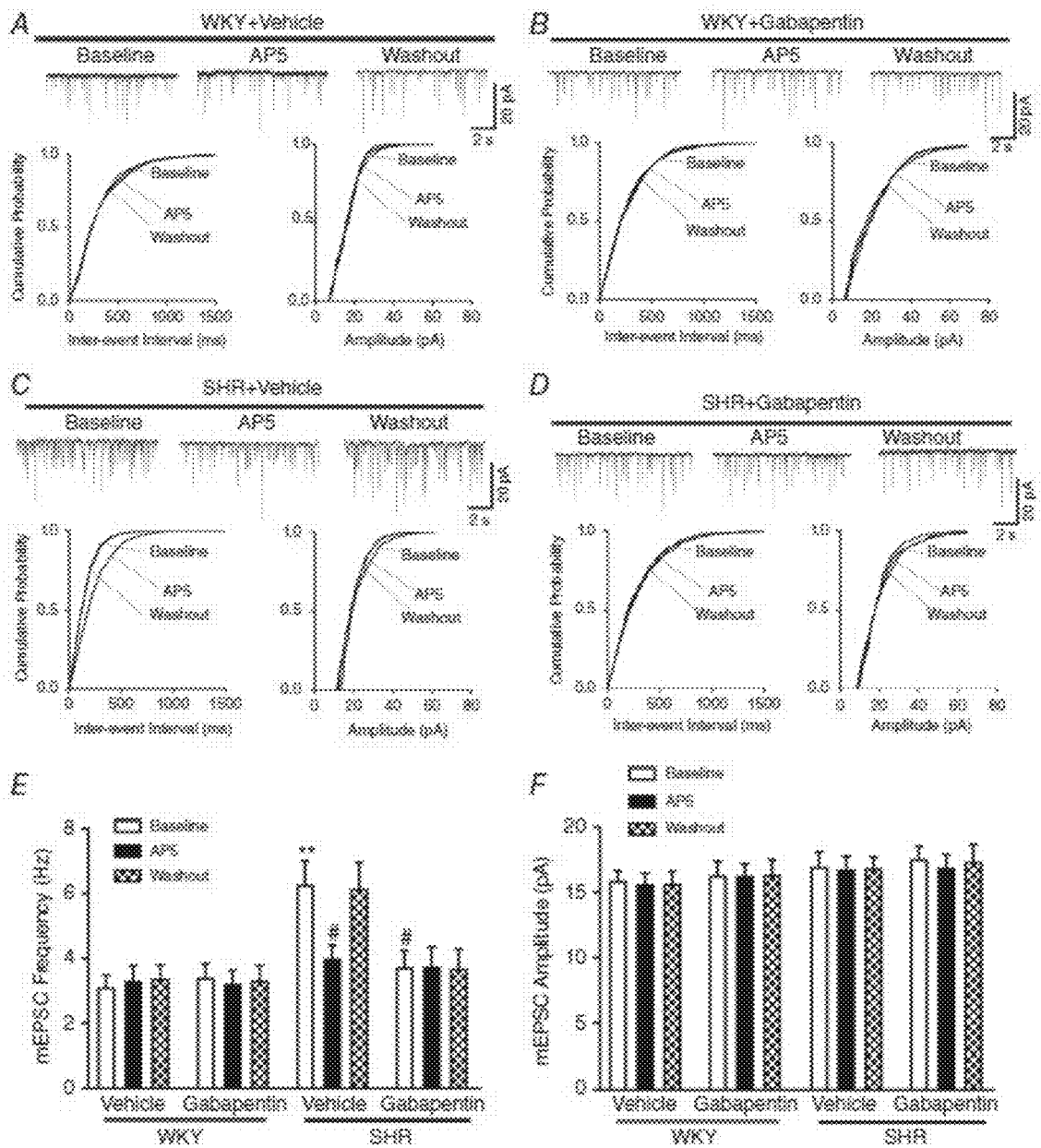
Figures 51A, 51B, 51C, 51D, 51E, 51F:
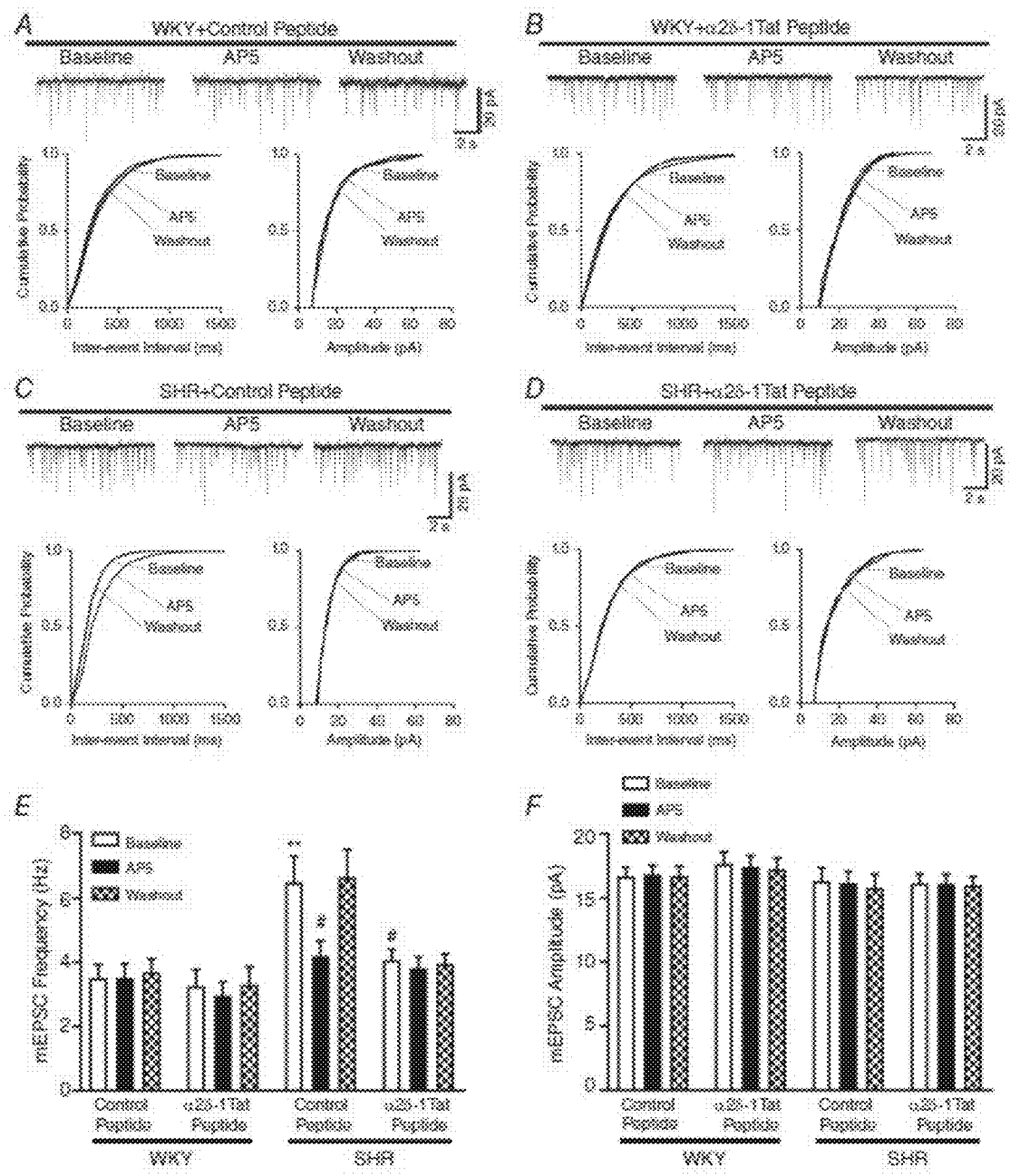
Figures 52A, 52B, 52C, 52D, 52E:
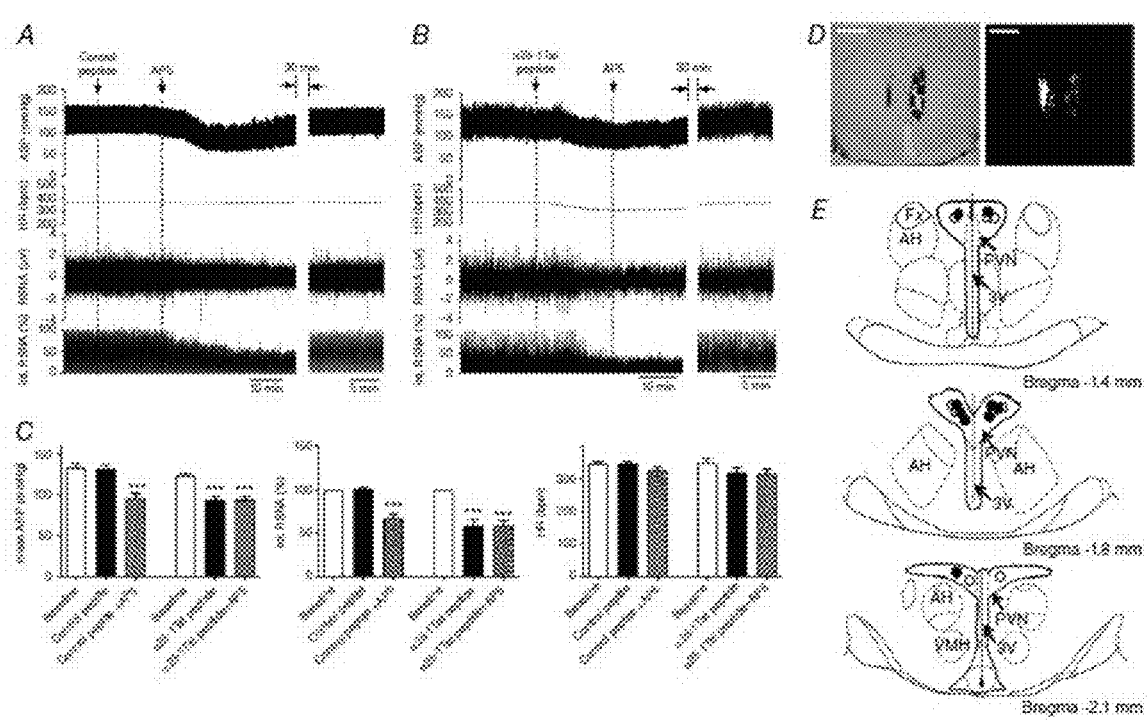

Furthermore, treatment with α2δ-1Tat peptide had no effect on the amplitude of puff NMDA currents in WKY rats. However, α2δ-1Tat peptide restored the amplitude of puff NMDA currents of labelled PVN neurons in SHRs (n=11 neurons) to the level in WKY rats (n=8 neurons) (FIGS. 49D and E). By contrast, treatment with the Tat-fused control peptide had no effect on the amplitude of puff NMDA currents in WKY (n=8 neurons) or SHRs (n=11 neurons) (FIGS. 49D and E). These data indicate that α2δ-1-bound NMDARs are crucial for increased post-synaptic NMDAR activity of PVN presympathetic neurons in SHR.

α2δ-1 is required for tonic activation of presynaptic NMDARs of PVN presympathetic neurons in SHRs: Presynaptic NMDARs in the PVN are normally latent, although they are tonically activated to augment glutamate release from presynaptic terminals in SHRs. To determine whether α2δ-1 contributes to increased presynaptic NMDAR activity in the PVN in SHRs, mEPSCs were recorded, which reflect quantal release of glutamate from pre-synaptic terminals. The baseline frequency of mEPSCs of labelled PVN neurons was significantly higher in SHRs than in WKY rats (WKY, n=10 neurons; SHR, n=11 neurons; P=0.0012, $F_{5,57}$=6.607) (FIG. 50), whereas the amplitude of mEPSCs did not differ significantly between the two groups. To confirm that the increase in the frequency of mEPSCs in SHRs is mediated by NMDARs, a specific NMDAR antagonist, AP5 (50 µmol L-1), was applied. AP5 application readily normalized the frequency of mEPSCs of labelled PVN neurons in SHRs to the level in WKY rats (FIG. 50C-E), whereas it had no effect in WKY rats (FIG. 50A-E). Gabapentin (100 µmol L-1, 60 min) treatment fully restored the baseline frequency of mEPSCs of labelled PVN neurons in SHRs without changing their amplitude (n=11 neurons) (FIG. 50D-F). Subsequent bath application of AP5 no longer had any effect on the frequency of mEPSCs of labelled PVN neurons in SHR brain slices pretreated with gabapentin. By contrast, gabapentin had no effect on the frequency or amplitude of mEPSCs of labelled PVN neurons in WKY rats (FIGS. 50B, E and F). These findings suggest that α2δ-1 is obligatory for tonic activation of presynaptic NMDARs of PVN presympathetic neurons in SHRs.

α2δ-1-bound NMDARs mediate increased synaptic glutamate release to PVN presympathetic neurons in SHRs: α2δ-1Tat peptide was next used to determine whether α2δ-1-bound NMDARs are responsible for the increased pre-synaptic NMDAR activity in SHRs. Pretreatment with α2δ-1Tat peptide (1 µmol L-1, 60 min) completely normalized the baseline frequency of mEPSCs of labelled PVN neurons in SHRs to the level in WKY rats (SHR control peptide, n 9 neurons; SHR α2δ-1Tat peptide, n 10 neurons) (FIG. 51A-E). However, α2δ-1Tat peptide had no effect on the frequency or amplitude of mEPSCs in WKY rats. After treatment with α2δ-1Tat peptide, further application of AP5 (50 µmol L-1) no longer had any effect on mEPSCs of labelled PVN neurons in brain slices from SHRs (FIG. 51D-E). Treatment with the Tat-fused control peptide had no effect on the frequency or amplitude of mEPSCs of labelled PVN neurons in brain slices from WKY rats (n=12 neurons) or SHRs (n=9 neurons) (FIGS. 51A, C, E and F). These data indicate that α2δ-1-bound NMDARs are required for tonic activation of presynaptic NMDARs of PVN presympathetic neurons in SHRs.

α2δ-1-bound NMDARs in the PVN maintain heightened sympathetic vasomotor tone in SHRs: Because gabapentin-andpregabalin bind to both α2δ-1 and α2δ-2, α2δ-1Tat peptide was used to determine whether α2δ-1-bound NMDARs in the PVN play a role in heightened sympathetic vasomotor tone in SHRs. It was shown that microinjection of AP5 into the PVN has no effect on the basal sympathetic vasomotor activity in normotensive WKY rats. Microinjection of α2δ-1Tat peptide (50 pmol, 50 nL) bilaterally into the PVN significantly decreased the ABP (P<0.0001, $F_{2,24}$=15.67) and RSNA (P<0.0001, $F_{2,24}$=20.20) in SHRs (n=9 rats) (FIG. 52A-C). The effect of α2δ-1Tat peptide on the mean ABP and RSNA lasted for more than 60 min. In SHRs microinjected with α2δ-1Tat peptide, subsequent microinjection of AP5 (1.0 nmol, 50 nL) into the PVN failed to further decrease ABP and RSNA (FIG. 52A-C).

By contrast, AP5 microinjection into the PVN significantly decreased ABP and RSNA in the SHRs subjected to a prior microinjection of Tat-fused control peptide (50 pmol, 50 nL; n 9 rats) (FIG. 52). These results suggest that α2δ-1-bound NMDARs in the PVN contribute to maintaining elevated sympathetic vasomotor tone in SHRs. The present study reveals that the direct interaction between α2δ-1 and NMDARs in the brain is of high pathophysiological relevance in dysregulation of the autonomic nervous hypertension development. Consistent with this notion, it was found that the α2δ-1 protein level in the PVN was significantly higher in 4-week-old prehypertensive SHRs than in age-matched WKY rats. In the spinal cord, nerve injury-induced α2δ-1 upregulation promotes its interaction with NMDARs and the synaptic expression of α2δ-1-bound NMDARs. Consistent with this concept is the finding in the present study that α2δ-1 interacted with NMDARs in the hypothalamus and that the physical association between α2δ-1 and NMDARs was enhanced in SHRs. In addition, it was show that the protein level of α2δ-1 and NMDARs in the hypothalamic synaptosomes was substantially increased in SHRs. Taken together, these biochemical data suggest that the prevalence of α2δ-1-bound NMDARs in the hypothalamus is increased in SHRs, which potentiates the synaptic trafficking of α2δ-1-NMDAR complexes in this hypertension model.

Example 12—Materials and Methods

Immunoblotting: Rats were anaesthetized with 2-3% isoflurane and then decapitated. The brain was quickly removed and placed in ice-cold artificial CSF (aCSF) saturated with 95% O2 and 5% CO2. Hypothalamic slices were sectioned 1.08-2.12 mm caudal to the bregma, and hypothalamic tissues containing the PVN were micropunched bilaterally with a slice punch (0.5 mm diameter) following stereotactic co-ordinates: 0.5 mm lateral to the midline and 6.5-9.0 mm ventral to the surface of the cortex. The tissues were frozen in liquid nitrogen and then transferred to a freezer at 80° C.

TABLE 3

Arterial blood pressure of 13-week-old WKY rats and SHRs.

|  | WKY | SHR |
|---|---|---|
| SAP | 108.7 ± 2.88 | 178.57 ± 2.38*** |
| DAP | 75.57 ± 2.11 | 126.09 ± 2.57*** |
| MAP | 86.61 ± 2.10 | 143.58 ± 2.16*** |

Blood pressure was measured using a tail-cuff system.
SAP, systolic blood pressure; DAP, diastolic blood pressure; MAP, mean arterial blood pressure.
WKY rats, n = 30 rats; SHRs, n = 35 rats.
***P < 0.001 compared to the WKY group.

Total proteins were extracted with a RIPA lysis/extraction buffer (Thermo Fisher Scientific, Waltham, Mass., USA) in the presence of a mixture containing protease inhibitor cocktail (Sigma-Aldrich, St Louis, Mo., USA). The PVN tissues were homogenized and then subjected to centrifugation at 16,000 g for 10 min to obtain the supernatant. For synaptosome isolation, the hypothalamic tissues (pooled from two rats per sample) were homogenized using 10 volumes of ice-cold Hepes-buffered sucrose solution (0.32 mol $L^{-1}$ sucrose, 1 mmol $L^{-1}$ EGTA and 4 mmol $L^{-1}$ Hepes at pH, 7.4) containing the protease inhibitor cocktail. The homogenates were centrifuged at 2000 g for 10 min at 4° C. to remove the nuclei and large debris. The supernatant was centrifuged at 20,000 g for 30 min to obtain the crude synaptosomes. The synaptosomal pellets were subjected to lysis via hypoosmotic shock in nine volumes of ice-cold Hepes buffer with the protease inhibitor cocktail for 30 min. The lysates were centrifuged at 25,000 g for 45 min at 4° C. to obtain the synaptosomal fraction (Chen et al. 2018), which was then dissolved in sodium dodecyl sulphate sample buffer at a final concentration of 0.25 μg $μL^{-1}$ for immunoblotting. The protein concentration was determined by bicinchoninic acid assay.

The samples were subjected to 4-15% Tris-HCl SDS-PAGE (#456-1086; Bio-Rad, Hercules, Calif., USA) and then transferred to a polyvinylidene difluoride membrane (EMD Millipore, Burlington, Mass., USA). The membranes were treated with 5% non-fat dry milk in Tris-buffered saline solution at 25° C. for 1 h, and then incubated in Tris-buffered saline solution supplemented with 0.1% Triton X-100, 1% BSA and rabbit anti-GluN1 (#G8913; dilution 1:2000; Sigma-Aldrich), rabbit anti-α2δ-1 (#C0515; dilution 1:500; Sigma-Aldrich), rabbit anti-GAPDH antibody (#ab37168; dilution 1:1000; Abcam, Cambridge, Mass., USA) or mouse anti-PSD-95 (#75-348; dilution 1:1000; NeuroMab, Davis, Calif., USA) antibody overnight at 4° C. The membrane was washed three times and then incubated with horseradish peroxidase-conjugated anti-rabbit or anti-mouse IgG antibody (dilution 1:7500; Jackson ImmunoResearch, West Grove, Pa., USA) for 1 h at room temperature. An ECL kit (Thermo Fisher Scientific) was used to detect the protein band, which was visualized and quantified with the Odyssey Fc Imager (LI-COR Biosciences, Lincoln, Nebr., USA) and normalized to the GAPDH or PSD-95 (a synaptic protein) band on the same blot.

Co-immunoprecipitation: Rat hypothalamic slices containing the PVN were sectioned 1.08-2.12 mm caudal to the bregma. The tissues were dissected and homogenized in ice-cold IP lysis buffer (#87788; Thermo Fisher Scientific; 25 mmol $L^{-1}$ Tris-HCl, pH 7.4, 150 mmol $L^{-1}$ NaCl, 1% NP-40, 1 mmol $L^{-1}$ EDTA, 5% glycerol and the protease inhibitor cocktail) and incubated on ice for 30 min for total protein preparation. The lysates were centrifuged for 15 min at 16,000 g to obtain the supernatants. The protein sample were quantified and incubated at 4° C. overnight with Protein G beads (#16-266; EMD Millipore) prebound to rabbit anti-GluN1 antibody (#G8913; dilution 1:100; Sigma-Aldrich). Protein G beads prebound to rabbit IgG were used as controls. Samples were washed three times with immunoprecipitation buffer and then immuno-blotted with mouse anti-α2δ-1 antibody (#sc-271697; dilution 1:500; Santa Cruz Biotechnology, Santa Cruz, Calif., USA). The protein bands were detected using immuno-blotting analysis.

Retrograde labelling of RVLM-projecting PVN presympathetic neurons: Retrograde labelling was performed to identify RVLM-projecting PVN neurons as described previously. The rats were anaesthetized with 2-3% isoflurane and placed in a stereotactic frame. A small piece of skull was removed and a microinjection pipette (tip diameter, 20-30 μm) filled with fluorescent microsphere suspension (FluoSpheres, 0.04 μm; Molecular Probes, Invitrogen, Eugene, Oreg., USA) was advanced into the RVLM in accordance with the stereotactic co-ordinates: 12.5-13.0 mm caudal to the bregma, 1.9-2.0 mm lateral to the midline and 7.5-8.0 mm ventral to the dura. The FluoSpheres were pressure-injected (Nanoject II Microinjectors; Drummond Scientific Company, Broomall, Pa., USA) into the RVLM bilaterally in two separate 50 nL injections using a micromanipulator. The tracer injection was monitored through a surgical microscope. The rats were returned to their home cages for 3-5 days to allow the FluoSpheres to be transported into the PVN. The animals were inspected daily for motor activity, signs of infection, and food and water intake.

Brain slice preparation: The rats were rapidly decapitated under 2-3% isoflurane anaesthesia. The brain was quickly removed and sliced in an ice-cold aCSF solution containing (in mmol L-1) 126 NaCl, 3 KCl, 1.5 MgCl2, 2.4 $CaCl_2$), 1.2 NaH2PO4, 10 glucose and 26 NaHCO3 saturated with 95% O2 and 5% CO2. Coronal hypothalamic slices (300 μm thick) containing the PVN were obtained from FluoSphere-injected rats using a vibrating microtome (VT1000 S; Leica Biosystems Inc., Buffalo Grove, Ill., USA). The slices were incubated in the aCSF at 34° C. for at least 1 h before recording. To confirm the injection sites of the FluoSpheres, the RVLM was sectioned at the injection level and viewed under a microscope immediately after the rat was killed. Data were excluded from the analysis if either of the injection sites were not located within the RVLM.

Electrophysiological recordings: The labelled PVN neurons were identified under an upright microscope (BX51WI; Olympus, Tokyo, Japan) with epifluorescence and infrared differential interference contrast optics. Whole-cell, patch clamp recordings were performed in FluoSphere-labelled PVN neurons. The hypothalamic slices were continuously perfused with aCSF (saturated by 95% $O_2$ and 5% $CO_2$; speed, 3.0 mL min=) at 34° C. maintained by an inline solution heater.

The miniature EPSCs (mEPSCs) were recorded in the presence of 1 μmol L-1 tetrodotoxin and 20 μmol L-1 bicuculline at a holding potential of −60 mV (Li et al. 2003; Ye et al. 2011). The recording glass pipette (4-8 MΩ) was filled with internal solution containing (in mmol L-1) 135.0 potassium gluconate, 5.0 tetraethylammonium, 2.0 MgCl2, 0.5 CaCl2), 5.0 Hepes, 5.0 EGTA, 5.0 Mg-ATP and 0.5 Na-GTP (adjusted to pH 7.2-7.4 with 1 mol L-1 KOH; 290-300 mosmol L-1). A sodium channel blocker, lidocaine N-ethyl bromide (10.0 mmol L-1), was included in the pipette solution to block the firing activity of the recorded neuron.

The evoked EPSCs were elicited by electrical stimulation (0.2 ms, 0.8-1.0 mA at 0.2 Hz) through a bipolar tungsten electrode connected to a stimulator. The tip of the stimulation electrode was placed on the ventral side 150 μm from the recorded neuron. The internal solution contained (in mmol L-1): 110.0 Cs2SO4, 2.0 MgCl2, 0.1 CaCl2), 10.0 Hepes, 1.1 EGTA, 0.3 Na2-GTP and 2.0 Mg-ATP, adjusted to pH 7.25 with 1.0 mol L-1 CsOH (270-290 mosm). Evoked α-amino-3-hydroxy-5-methyl-4-isoxazolepropionic acid receptor (AMPAR)-EPSCs were recorded at a holding potential of 60 mV in the presence of 10 μmol L-1 bicuculline, and evoked NMDAR-EPSCs were recorded at a holding potential of 40 μmV in the presence of 10 μmol L-1 bicuculline and 10 μmol L-1 6,7-dinitroquinoxaline-2,3-dione. It was shown that the evoked NMDAR-EPSCs at 40 mV were abolished by the NMDAR specific antagonist, AP5, whereas the evoked AMPAR-EPSCs at −60 mV were completed blocked by the AMPAR antagonist 6,7-dinitroquinoxaline-2,3-dione. The amplitude of AMPAR-EPSCs recorded in labelled PVN neurons at a holding potential of −60 mV is similar in WKY rats and SHRs. Therefore, AMPAR-EPSCs were used to normalize the NMDAR-EPSCs elicited under the same stimulation intensity (0.8 mA) in the present study.

To record postsynaptic NMDAR currents, NMDA (100 μmol $L^{-1}$) was puffed directly onto the recorded neuron at a holding potential of −60 mV using a positive pressure system (4 psi, 50 ms; Toohey Company, Fairfield, N.J., USA). The puff pipette (10 μm tip diameter) was placed 150 μm away from the recorded neuron. Because NMDARs are voltage-dependently blocked by $Mg2+$ at a negative holding potential and co-activated by glycine, puff NMDA-induced currents were recorded in $Mg2+$-free aCSF in the presence of 10 μmol L-1 glycine and 1 μmol L-1 tetrodotoxin. Although puff application of NMDA can also result in presynaptic release of glutamate, the currents elicited by presynaptic glutamate release are very small and negligible compared to currents produced by a large amount of puff glutamate receptor agonists. Therefore, the current elicited by puff application of NMDA is generally considered to be a measure of postsynaptic NMDAR activity.

PVN microinjection and recording of renal sympathetic nerve activity: Rats were anaesthetized via i.p. administration of a mixture of α-chloralose (60 mg kg-1) and urethane (800 mg kg-1) and mechanically ventilated with trachea cannulation. The arterial blood pressure (ABP) was monitored via a catheter placed in the left femoral artery, and heart rate (HR) was extracted from the pulsatile pressure wave. A retroperitoneal incision was made, and a branch of the left renal postganglionic sympathetic nerve was isolated under a surgical microscope. The renal sympathetic nerve was cut distally to ensure that afferent activity was not recorded. The ABP, HR and renal sympathetic nerve activity (RSNA) were recorded using a 1401-PLUS analogue-to-digital converter and Spike2 system (Cambridge Electronic Design, Cambridge, UK). After the brain was exposed, a microinjection pipette (tip diameter 20-30 μm) was advanced into the PVN in accordance with the stereotactic co-ordinates: 1.6-2.0 mm caudal to the bregma, 0.5 mm lateral to the midline and 7.0-7.5 mm ventral to the dura. The microinjection was performed using a Nanoject II (Drummond Scientific Company) and monitored using a surgical microscope as described previously (Li & Pan, 2006, 2007; Qiao et al. 2017). AP5 (1.0 nmol, 50 nL) was microinjected into the PVN to observe the change in ABP and RSNA in the presence of α2δ-1Tat peptide (50 pmol, 50 nL; Bio Basic, Markham, Ontario, Canada) or Tat-fused control peptide (50 pmol, 50 nL). At the end of each experiment, the electrical background noise was measured after the proximal end of renal nerve was crushed at the end of each experiment. To determine the location of the injection site and diffusion of the drugs in the PVN, 5% rhodamine-labelled fluorescent microspheres (0.04 μm; Molecular Probes) were included in the injection solution. Rats were excluded from the data analysis if the microinjections were misplaced outside the PVN.

Celiac ganglionectomy and ABP measurement using telemetry: Celiac ganglionectomy (CGx) or sham surgery was performed aseptically in SHRs anaesthetized with 2-3% isoflurane as described previously. The celiac ganglion area was exposed through a midline laparotomy and identified within the area near the superior mesenteric artery and celiac artery. For rats undergoing CGx, the celiac plexus and all visible nerves were dissected and removed as completely as possible. In sham control rats, the celiac ganglion plexus was exposed but not disrupted. A Millar catheter (Millar, Houston, Tex., USA) attached to the transmitter was inserted into the abdominal aorta for continuous monitoring of ABP, and the transmitter body was implanted in an abdominal cavity. The rats were housed individually, and the ABP was measured in freely moving rats by using a telemetry system (Telemetry Research Ltd., Houston, Tex., USA). The ABP data were recorded continuously after surgery and analysed with a data acquisition system (LabChart; AD Instruments, Sydney, Australia). Two weeks after CGx or sham surgery, the rats were anaesthetized with 2-3% isoflurane and then decapitated. The brain tissues of rats were harvested for immunoblotting analysis.

Statistical analysis: For electrophysiological recording experiments, only one neuron in each brain slice was recorded, and at least four animals were used for each recording protocol. Data are presented as the mean SEM. The amplitude and frequency of mEPSCs were analysed offline with peak detection software (MiniAnalysis; Synaptosoft Inc., Decatur, Ga., USA). The cumulative probabilities of the amplitude and inter-event interval were compared using the Kolmogorov-Smirnov test. Clampfit, version 10.2 (Molecular Devices, Sunnyvale, Calif., USA) was used to determine the peak amplitude of evoked EPSCs and puff NMDA currents. The mean ABP, RSNA and HR were analysed using Spike2 software. The mean ABP was derived from the pulsatile ABP and calculated as the diastolic pressure plus one-third of the pulse pressure. RSNA was rectified and integrated offline after subtracting the background noise, which was recorded after the proximal end of renal nerve was crushed at the end of each experiment. The integrated RSNA value was calculated and derived from the raw RSNA with an integrating time of 1.0 s using Spike2 software. Control values were obtained by averaging the signal over a 60 s period immediately before PVN microinjection. Response values after each intervention were averaged over 30 s when the maximal responses occurred. A two-tailed Student's t test was used to compare two groups and one-way ANOVA followed by the Dunnett's and Tukey's post hoc tests was used to compare more than two groups. Statistical analyses were performed using Prism, version 7 (GraphPad Software Inc., La Jolla, Calif.). $P<0.05$ was considered statistically significant.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alexander et al., *Proc. Nat. Acad. Sci. USA,* 85:5092-5096, 1988.
Anhut, H. et al. The International Gabapentin Study Group. Epilepsia 35, 795-801 (1994).
Ausubel et al., *Current Protocols in Molecular Biology,* Greene Publ. Assoc. Inc. & John Wiley & Sons, Inc., MA, 1996.
Baichwal and Sugden, *In: Gene Transfer,* Kucherlapati (Ed.), Plenum Press, N.Y., 117-148, 1986.
Bashir, Z. I., Nature 349, 156-8 (1991).
Blomer et al., *J. Virol.,* 71(9):6641-6649, 1997.
Bodanszky et al., *J. Antibiot.,* 29(5):549-53, 1976.
Brown, J. T. & Randall, A. Synapse 55, 262-9 (2005).
Chaplan, S. R., J Pharmacol Exp Ther 280, 829-38 (1997).
Chen, S. R., J Pharmacol Exp Ther 350, 301-12 (2014).
Cohen et al., *J. Med. Chem.,* 33:883-894, 1990.
Cole, R. L. et al. J Comp Neurol 491, 246-69 (2005).
Coupar et al., *Gene,* 68:1-10, 1988.
Davies, A. et al., Trends Pharmacol Sci 28, 220-8 (2007).
Dolphin, A. C. Nat Rev Neurosci 13, 542-55 (2012).
Dworkin, R. H. et al. Mayo Clin Proc 85, S3-14 (2010).
Ercolani et al., *J. Biol. Chem.,* 263:15335-15341,1988.
Eroglu, C. et al. Cell 139, 380-92 (2009).
European Patent Publication No. EP 266,032
Field, M. J. et al. Proc Natl Acad Sci USA 103, 17537-42 (2006).
Fischer, *Med. Res. Rev.,* 27(6):755-796, 2007.
Friedmann, *Science,* 244:1275-1281, 1989.
Fuller-Bicer, G. A. et al. Am J Physiol Heart Circ Physiol 297, H117-24 (2009).
Gee, N. S. et al. J Biol Chem 271, 5768-76 (1996).
Hoppa, M. B., Nature 486, 122-5 (2012).
Horwich et al. *J. Virol.,* 64:642-650, 1990.
International Patent Publication No. PCT/US99/11913
International Patent Publication No. WO 2008/121767
Jackson, *Seminars in Oncology,* 24:L164-172, 1997.
Johnson et al., *In: Biotechnology And Pharmacy,* Pezzuto et al. (Eds.), Chapman and Hall, N Y, 1993.
Jones et al., *J. Med. Chem.,* 39:904-917, 1996.
Kim, S. H. & Chung, J. M. Pain 50, 355-63 (1992).
Lab. Press, 2001.
Lana, B. et al. Sci Rep 6, 24531 (2016).
Laughlin et al., *J. Virol.,* 60(2):515-524, 1986.
Laumet, G. et al. Nat Neurosci 18, 1746-55 (2015).
Lebkowski et al., *Mol. Cell. Biol.,* 8(10):3988-3996, 1988.
Li, C. Y., et al. J Neurosci 24, 8494-9 (2004).
Li, L. et al. Cell Rep 15, 1376-83 (2016).
Li, L. et al. Mol Pharmacol 86, 760-72 (2014).
Luo, Z. D. et al. J Neurosci 21, 1868-75 (2001).
Macejak and Sarnow, *Nature,* 353:90-94, 1991.
Mann et al., *Cell,* 33:153-159, 1983.
Marais, E., Mol Pharmacol 59, 1243-8 (2001).
McLaughlin et al., *J. Virol.,* 62(6):1963-1973, 1988.
Merrifield, *J. Am. Chem. Soc.,* 85:2149-2154, 1963.
Minskaia and Ryan, 2013
Muller, C. S. et al. Proc Natl Acad Sci USA 107, 14950-7, 2010.
Muzyczka, *Curr. Topics Microbiol. Immunol.,* 158:97-129, 1992.
Naldini et al., *Science,* 272(5259):263-267, 1996.
Navia et al., *Curr. Opin. Struct. Biol.,* 2:202-210, 1992.
Nicolas and Rubinstein, In: *Vectors: A survey of molecular cloning vectors and their uses,* Rodriguez and Denhardt, eds., Stoneham: Butterworth, pp. 494-513, 1988.
Nicoll, R. A. & Malenka, R. C. Nature 377, 115-8 (1995).
Paskind et al., *Virology,* 67:242-248, 1975.
Patel, R. et al. J Neurosci 33, 16412-26 (2013).
Pelletier and Sonenberg, *Nature,* 334(6180):320-325, 1988.
Quitsche et al., *J. Biol. Chem.,* 264:9539-9545, 1989.
Richards et al., *Cell,* 37:263-272, 1984.
Ridgeway, *In: Vectors: A Survey of Molecular Cloning Vectors and Their Uses,* Rodriguez et al. (Eds.), Stoneham: Butterworth, 467-492, 1988.
Rock, D. M., Epilepsy Res 16, 89-98 (1993).
Roux et al., *Proc. Natl. Acad. Sci. USA,* 86:9079-9083, 1989.
Rowbotham, M., JAMA 280, 1837-42 (1998).
Sambrook and Russell, *Molecular Cloning: A Laboratory Manual,* 3rd Ed. Cold Spring Harbor
Schafmeister et al., *Journal of the American Chemical Society,* 122(24): p. 5891-5892, 2000.
Schumacher, T. B., Epilepsia 39, 355-63 (1998).
Schwarze, S. R., Science 285, 1569-72 (1999).
Sirrieh, R. E., J Biol Chem 288, 22555-64 (2013).
Temin, *In: Gene Transfer,* Kucherlapati (Ed.), NY, Plenum Press, 149-188, 1986.
Tratschin et al., *Mol. Cell. Biol.,* 4:2072-2081, 1984.
U.S. Pat. No. 5,994,136
U.S. Pat. No. 4,682,195
U.S. Pat. No. 4,683,202
U.S. Pat. No. 4,797,368
U.S. Pat. No. 5,139,941
U.S. Pat. No. 5,440,013
U.S. Pat. No. 5,446,128
U.S. Pat. No. 5,475,085
U.S. Pat. No. 5,618,914
U.S. Pat. No. 5,645,897
U.S. Pat. No. 5,670,155
U.S. Pat. No. 5,674,976
U.S. Pat. No. 5,705,629
U.S. Pat. No. 5,710,245
U.S. Pat. No. 5,840,833
U.S. Pat. No. 5,859,184
U.S. Pat. No. 5,889,155
U.S. Pat. No. 5,925,565
U.S. Pat. No. 5,928,906
U.S. Pat. No. 5,929,237
U.S. Pat. No. 5,935,819
U.S. Pat. No. 6,013,516
U.S. Pat. No. 6,740,320
U.S. Pat. No. 7,183,059
U.S. Pat. No. 7,192,713
U.S. Patent Publication No. 2005/02506890
U.S. Patent Publication No. 2006/0008848
Walensky et al., *Science* 305:1466-1470, 2004.

Wang, M., et al. Biochem J 342, 313-20 (1999).
Wiser, O. et al. FEBS Lett 379, 15-20 (1996).
Woolf & Decosterd, *Pain Supp.*, 6, S141-5147, 1999.
Woolf and Mannion, *Lancet,* 353, 1959-1964, 1999.
Zhou, H. Y. et al. J Biol Chem 287, 33853-64 (2012).
Zufferey et al., *Nat. Biotechnol.,* 15(9):871-875, 1997.

What is claimed is:

1. An isolated peptide comprising amino acid sequence SEQ ID NO:1, wherein said peptide is fused to a cell-penetrating peptide and said peptide acts as an α2δ-1 C-terminal domain mimetic and blocks binding of α2δ-1 to a glutamate receptor.

2. The peptide of claim 1, wherein the peptide comprises at least 30, 35, 40, 45 or 50 residues.

3. The peptide of claim 1, wherein the peptide contains no more than 30, 35, 40, 45 or 50 residues.

4. The peptide of claim 1, wherein the cell penetrating peptide is TAT.

5. The peptide of claim 1, wherein the cell-penetrating peptide comprises the sequence of SEQ ID NO:2.

6. The peptide of claim 5, wherein said peptide comprises the sequence of SEQ ID NO:4.

7. The peptide of claim 5, wherein said peptide consists of the sequence of SEQ ID NO:4.

8. The peptide of claim 1, wherein the peptide is further defined as a linear peptide.

9. The peptide of claim 1, wherein the peptide is further defined as a cyclic peptide.

10. A pharmaceutical composition comprising (a) a peptide of claim 1 that acts as an α2δ-1 C-terminal domain mimetic and blocks binding of α2δ-1 to a glutamate receptor and (b) a pharmaceutically acceptable carrier, buffer or diluent.

11. A method for treating pain and/or epileptic seizures in a subject comprising administering an effective amount of a α2δ-1 C-terminal domain peptide mimetic of claim 1 to the subject, wherein the α2δ-1 C-terminal domain peptide mimetic blocks binding of α2δ-1 to a glutamate receptor.

12. The method of claim 11, wherein the pain is neuropathic pain.

13. The method of claim 12, wherein the neuropathic pain is chronic neuropathic pain.

14. The method of claim 13, wherein the chronic neuropathic pain is chemotherapy-induced neuropathic pain.

15. The method of claim 11, wherein the subject has opioid-induced analgesic tolerance.

16. A method for treating brain injury comprising ischemia and/or reperfusion in a subject comprising administering an effective amount of a α2δ-1 C-terminal domain peptide mimetic of claim 1 to the subject, wherein the α2δ-1 C-terminal domain peptide mimetic blocks binding of α2δ-1 to a glutamate receptor.

17. The method of claim 16, wherein the ischemia and/or reperfusion is associated with ischemic stroke.

* * * * *

```
                              SEQUENCE LISTING

<160> NUMBER OF SEQ ID NOS: 67

<210> SEQ ID NO 1
<211> LENGTH: 30
<212> TYPE: PRT
<213> ORGANISM: Artificial Sequence
<220> FEATURE:
<223> OTHER INFORMATION: Peptide

<400> SEQUENCE: 1

Val Ser Gly Leu Asn Pro Ser Leu Trp Ser Ile Phe Gly Leu Gln Phe
1               5                   10                  15

Ile Leu Leu Trp Leu Val Ser Gly Ser Arg His Tyr Leu Trp
            20                  25                  30

<210> SEQ ID NO 2
<211> LENGTH: 11
<212> TYPE: PRT
<213> ORGANISM: Artificial Sequence
<220> FEATURE:
<223> OTHER INFORMATION: TAT peptide

<400> SEQUENCE: 2

Tyr Gly Arg Lys Lys Arg Arg Gln Arg Arg Arg
1               5                   10

<210> SEQ ID NO 3
<211> LENGTH: 30
<212> TYPE: PRT
<213> ORGANISM: Artificial Sequence
<220> FEATURE:
<223> OTHER INFORMATION: Control peptide

<400> SEQUENCE: 3

Phe Gly Leu Gly Trp Gln Pro Trp Ser Leu Ser Phe Tyr Leu Val Trp
1               5                   10                  15

Ser Gly Leu Ile Leu Ser Val Leu His Leu Ile Arg Ser Asn
            20                  25                  30

<210> SEQ ID NO 4
<211> LENGTH: 41
<212> TYPE: PRT
<213> ORGANISM: Artificial Sequence
<220> FEATURE:
<223> OTHER INFORMATION: a2d1 peptide

<400> SEQUENCE: 4

Tyr Gly Arg Lys Lys Arg Arg Gln Arg Arg Val Ser Gly Leu Asn
1               5                   10                  15

Pro Ser Leu Trp Ser Ile Phe Gly Leu Gln Phe Ile Leu Leu Trp Leu
            20                  25                  30

Val Ser Gly Ser Arg His Tyr Leu Trp
        35                  40

<210> SEQ ID NO 5
<211> LENGTH: 34
<212> TYPE: PRT
<213> ORGANISM: Artificial Sequence
<220> FEATURE:
<223> OTHER INFORMATION: Peptide
```

```
<400> SEQUENCE: 5

Gln Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Pro
            20                  25                  30

Val Glu

<210> SEQ ID NO 6
<211> LENGTH: 16
<212> TYPE: PRT
<213> ORGANISM: Artificial Sequence
<220> FEATURE:
<223> OTHER INFORMATION: Peptide

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Peptide

<400> SEQUENCE: 7

Arg Arg Met Lys Trp Lys Lys
1               5

<210> SEQ ID NO 8
<211> LENGTH: 16
<212> TYPE: PRT
<213> ORGANISM: Artificial Sequence
<220> FEATURE:
<223> OTHER INFORMATION: Peptide

<400> SEQUENCE: 8

Arg Arg Trp Arg Arg Trp Trp Arg Arg Trp Trp Arg Arg Trp Arg Arg
1               5                   10                  15

<210> SEQ ID NO 9
<211> LENGTH: 18
<212> TYPE: PRT
<213> ORGANISM: Artificial Sequence
<220> FEATURE:
<223> OTHER INFORMATION: Peptide

<400> SEQUENCE: 9

Arg Gly Gly Arg Leu Ser Tyr Ser Arg Arg Arg Phe Ser Thr Ser Thr
1               5                   10                  15

Gly Arg

<210> SEQ ID NO 10
<211> LENGTH: 11
<212> TYPE: PRT
<213> ORGANISM: Artificial Sequence
<220> FEATURE:
<223> OTHER INFORMATION: Peptide

<400> SEQUENCE: 10

Tyr Gly Arg Lys Lys Arg Arg Gln Arg Arg Arg
1               5                   10
```

```
<210> SEQ ID NO 11
<211> LENGTH: 9
<212> TYPE: PRT
<213> ORGANISM: Artificial Sequence
<220> FEATURE:
<223> OTHER INFORMATION: Peptide

<400> SEQUENCE: 11

Arg Lys Lys Arg Arg Gln Arg Arg Arg
1               5

<210> SEQ ID NO 12
<211> LENGTH: 11
<212> TYPE: PRT
<213> ORGANISM: Artificial Sequence
<220> FEATURE:
<223> OTHER INFORMATION: Peptide

<400> SEQUENCE: 12

Tyr Ala Arg Ala Ala Ala Arg Gln Ala Arg Ala
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Peptide

<400> SEQUENCE: 13

Arg Arg Arg Arg Arg Arg Arg Arg
1               5

<210> SEQ ID NO 14
<211> LENGTH: 8
<212> TYPE: PRT
<213> ORGANISM: Artificial Sequence
<220> FEATURE:
<223> OTHER INFORMATION: Peptide

<400> SEQUENCE: 14

Lys Lys Lys Lys Lys Lys Lys Lys
1               5

<210> SEQ ID NO 15
<211> LENGTH: 27
<212> TYPE: PRT
<213> ORGANISM: Artificial Sequence
<220> FEATURE:
<223> OTHER INFORMATION: Peptide
<220> FEATURE:
<221> NAME/KEY: misc_feature
<222> LOCATION: (25)..(25)
<223> OTHER INFORMATION: Xaa can be any naturally occurring amino acid

<400> SEQUENCE: 15

Gly Trp Thr Leu Asn Ser Ala Gly Tyr Leu Leu Gly Lys Ile Asn Leu
1               5                   10                  15

Lys Ala Leu Ala Ala Leu Ala Lys Xaa Ile Leu
            20                  25

<210> SEQ ID NO 16
<211> LENGTH: 18
<212> TYPE: PRT
<213> ORGANISM: Artificial Sequence
<220> FEATURE:
<223> OTHER INFORMATION: Peptide
```

```
<400> SEQUENCE: 16

Leu Leu Ile Leu Leu Arg Arg Arg Ile Arg Lys Gln Ala Asn Ala His
1               5                   10                  15

Ser Lys

<210> SEQ ID NO 17
<211> LENGTH: 16
<212> TYPE: PRT
<213> ORGANISM: Artificial Sequence
<220> FEATURE:
<223> OTHER INFORMATION: Peptide

<400> SEQUENCE: 17

Ser Arg Arg His His Cys Arg Ser Lys Ala Lys Arg Ser Arg His His
1               5                   10                  15

<210> SEQ ID NO 18
<211> LENGTH: 11
<212> TYPE: PRT
<213> ORGANISM: Artificial Sequence
<220> FEATURE:
<223> OTHER INFORMATION: Peptide

<400> SEQUENCE: 18

Asn Arg Ala Arg Arg Asn Arg Arg Arg Val Arg
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Peptide

<400> SEQUENCE: 19

Arg Gln Leu Arg Ile Ala Gly Arg Arg Leu Arg Gly Arg Ser Arg
1               5                   10                  15

<210> SEQ ID NO 20
<211> LENGTH: 13
<212> TYPE: PRT
<213> ORGANISM: Artificial Sequence
<220> FEATURE:
<223> OTHER INFORMATION: Peptide

<400> SEQUENCE: 20

Lys Leu Ile Lys Gly Arg Thr Pro Ile Lys Phe Gly Lys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Peptide

<400> SEQUENCE: 21

Arg Arg Ile Pro Asn Arg Arg Pro Arg Arg
1               5                   10

<210> SEQ ID NO 22
<211> LENGTH: 18
<212> TYPE: PRT
<213> ORGANISM: Artificial Sequence
<220> FEATURE:
<223> OTHER INFORMATION: Peptide
```

```
<400> SEQUENCE: 22

Lys Leu Ala Leu Lys Leu Ala Leu Lys Ala Leu Lys Ala Ala Leu Lys
1               5                   10                  15

Leu Ala

<210> SEQ ID NO 23
<211> LENGTH: 14
<212> TYPE: PRT
<213> ORGANISM: Artificial Sequence
<220> FEATURE:
<223> OTHER INFORMATION: Peptide

<400> SEQUENCE: 23

Lys Leu Ala Lys Leu Ala Lys Lys Leu Ala Lys Leu Ala Lys
1               5                   10

<210> SEQ ID NO 24
<211> LENGTH: 27
<212> TYPE: PRT
<213> ORGANISM: Artificial Sequence
<220> FEATURE:
<223> OTHER INFORMATION: Peptide

<400> SEQUENCE: 24

Gly Ala Leu Phe Leu Gly Phe Leu Gly Ala Ala Gly Ser Thr Asn Gly
1               5                   10                  15

Ala Trp Ser Gln Pro Lys Lys Lys Arg Lys Val
            20                  25

<210> SEQ ID NO 25
<211> LENGTH: 21
<212> TYPE: PRT
<213> ORGANISM: Artificial Sequence
<220> FEATURE:
<223> OTHER INFORMATION: Peptide

<400> SEQUENCE: 25

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 26
<211> LENGTH: 23
<212> TYPE: PRT
<213> ORGANISM: Artificial Sequence
<220> FEATURE:
<223> OTHER INFORMATION: Peptide

<400> SEQUENCE: 26

Gly Ala Leu Phe Leu Gly Trp Leu Gly Ala Ala Gly Ser Thr Met Gly
1               5                   10                  15

Ala Lys Lys Lys Arg Lys Val
            20

<210> SEQ ID NO 27
<211> LENGTH: 23
<212> TYPE: PRT
<213> ORGANISM: Artificial Sequence
<220> FEATURE:
<223> OTHER INFORMATION: Peptide
```

```
<400> SEQUENCE: 27

Met Gly Leu Gly Leu His Leu Leu Val Leu Ala Ala Ala Leu Gln Gly
1               5                   10                  15

Ala Lys Ser Lys Arg Lys Val
            20

<210> SEQ ID NO 28
<211> LENGTH: 26
<212> TYPE: PRT
<213> ORGANISM: Artificial Sequence
<220> FEATURE:
<223> OTHER INFORMATION: Peptide

<400> SEQUENCE: 28

Ala Ala Val Ala Leu Leu Pro Ala Val Leu Leu Ala Leu Leu Ala Pro
1               5                   10                  15

Ala Ala Ala Asn Tyr Lys Lys Pro Lys Leu
            20                  25

<210> SEQ ID NO 29
<211> LENGTH: 28
<212> TYPE: PRT
<213> ORGANISM: Artificial Sequence
<220> FEATURE:
<223> OTHER INFORMATION: Peptide

<400> SEQUENCE: 29

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 30
<211> LENGTH: 24
<212> TYPE: PRT
<213> ORGANISM: Artificial Sequence
<220> FEATURE:
<223> OTHER INFORMATION: Peptide

<400> SEQUENCE: 30

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 31
<211> LENGTH: 26
<212> TYPE: PRT
<213> ORGANISM: Artificial Sequence
<220> FEATURE:
<223> OTHER INFORMATION: Peptide
<220> FEATURE:
<221> NAME/KEY: misc_feature
<222> LOCATION: (24)..(24)
<223> OTHER INFORMATION: Xaa can be any naturally occurring amino acid

<400> SEQUENCE: 31

Asp Pro Lys Gly Asp Pro Lys Gly Val Thr Val Thr Val Thr Val Thr
1               5                   10                  15

Val Thr Gly Lys Gly Asp Pro Xaa Pro Asp
            20                  25
```

```
<210> SEQ ID NO 32
<211> LENGTH: 14
<212> TYPE: PRT
<213> ORGANISM: Artificial Sequence
<220> FEATURE:
<223> OTHER INFORMATION: Peptide

<400> SEQUENCE: 32

Pro Pro Pro Pro Pro Pro Pro Pro Pro Pro Pro Pro Pro Pro
1               5                   10

<210> SEQ ID NO 33
<211> LENGTH: 18
<212> TYPE: PRT
<213> ORGANISM: Artificial Sequence
<220> FEATURE:
<223> OTHER INFORMATION: Peptide

<400> SEQUENCE: 33

Val Arg Leu Pro Pro Pro Val Arg Leu Pro Pro Pro Val Arg Leu Pro
1               5                   10                  15

Pro Pro

<210> SEQ ID NO 34
<211> LENGTH: 10
<212> TYPE: PRT
<213> ORGANISM: Artificial Sequence
<220> FEATURE:
<223> OTHER INFORMATION: Peptide

<400> SEQUENCE: 34

Pro Arg Pro Leu Pro Pro Pro Arg Pro Gly
1               5                   10

<210> SEQ ID NO 35
<211> LENGTH: 30
<212> TYPE: PRT
<213> ORGANISM: Artificial Sequence
<220> FEATURE:
<223> OTHER INFORMATION: Peptide

<400> SEQUENCE: 35

Ser Val Arg Arg Arg Pro Arg Pro Pro Tyr Leu Pro Arg Pro Arg Pro
1               5                   10                  15

Pro Pro Phe Phe Pro Pro Arg Leu Pro Pro Arg Ile Pro Pro
            20                  25                  30

<210> SEQ ID NO 36
<211> LENGTH: 21
<212> TYPE: PRT
<213> ORGANISM: Artificial Sequence
<220> FEATURE:
<223> OTHER INFORMATION: Peptide

<400> SEQUENCE: 36

Thr Arg Ser Ser Arg Ala Gly Leu Gln Phe Pro Val Gly Arg Val His
1               5                   10                  15

Arg Leu Leu Arg Lys
            20

<210> SEQ ID NO 37
<211> LENGTH: 23
<212> TYPE: PRT
<213> ORGANISM: Artificial Sequence
<220> FEATURE:
<223> OTHER INFORMATION: Peptide
```

-continued

<400> SEQUENCE: 37

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 38
<211> LENGTH: 37
<212> TYPE: PRT
<213> ORGANISM: Artificial Sequence
<220> FEATURE:
<223> OTHER INFORMATION: Peptide

<400> SEQUENCE: 38

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Gly Gln Ala
            20                  25                  30

Thr Gln Ile Ala Lys
            35

<210> SEQ ID NO 39
<211> LENGTH: 28
<212> TYPE: PRT
<213> ORGANISM: Artificial Sequence
<220> FEATURE:
<223> OTHER INFORMATION: Peptide

<400> SEQUENCE: 39

Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
            20                  25

<210> SEQ ID NO 40
<211> LENGTH: 26
<212> TYPE: PRT
<213> ORGANISM: Artificial Sequence
<220> FEATURE:
<223> OTHER INFORMATION: Peptide

<400> SEQUENCE: 40

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 41
<211> LENGTH: 14
<212> TYPE: PRT
<213> ORGANISM: Artificial Sequence
<220> FEATURE:
<223> OTHER INFORMATION: Peptide

<400> SEQUENCE: 41

Ile Asn Leu Lys Ala Leu Ala Ala Leu Ala Lys Lys Ile Leu
1               5                   10

<210> SEQ ID NO 42
<211> LENGTH: 33
<212> TYPE: PRT
<213> ORGANISM: Artificial Sequence
<220> FEATURE:
<223> OTHER INFORMATION: Peptide

<400> SEQUENCE: 42

Gly Phe Phe Ala Leu Ile Pro Lys Ile Ile Ser Ser Pro Leu Pro Lys
1               5                   10                  15

Thr Leu Leu Ser Ala Val Gly Ser Ala Leu Gly Gly Ser Gly Gly Gln
            20                  25                  30

Glu

<210> SEQ ID NO 43
<211> LENGTH: 15
<212> TYPE: PRT
<213> ORGANISM: Artificial Sequence
<220> FEATURE:
<223> OTHER INFORMATION: Peptide

<400> SEQUENCE: 43

Leu Ala Lys Trp Ala Leu Lys Gln Gly Phe Ala Lys Leu Lys Ser
1               5                   10                  15

<210> SEQ ID NO 44
<211> LENGTH: 27
<212> TYPE: PRT
<213> ORGANISM: Artificial Sequence
<220> FEATURE:
<223> OTHER INFORMATION: Peptide
<220> FEATURE:
<221> NAME/KEY: misc_feature
<222> LOCATION: (23)..(23)
<223> OTHER INFORMATION: Xaa can be any naturally occurring amino acid

<400> SEQUENCE: 44

Ser Met Ala Gln Asp Ile Ile Ser Thr Ile Gly Asp Leu Val Lys Trp
1               5                   10                  15

Ile Ile Gln Thr Val Asn Xaa Phe Thr Lys Lys
            20                  25

<210> SEQ ID NO 45
<211> LENGTH: 41
<212> TYPE: PRT
<213> ORGANISM: Artificial Sequence
<220> FEATURE:
<223> OTHER INFORMATION: Peptide

<400> SEQUENCE: 45

Leu Leu Gly Asp Phe Phe Arg Lys Ser Lys Glu Lys Ile Gly Lys Glu
1               5                   10                  15

Phe Lys Arg Ile Val Gln Arg Ile Lys Gln Arg Ile Lys Asp Phe Leu
            20                  25                  30

Ala Asn Leu Val Pro Arg Thr Glu Ser
        35                  40

<210> SEQ ID NO 46
<211> LENGTH: 20
<212> TYPE: PRT
<213> ORGANISM: Artificial Sequence
<220> FEATURE:
<223> OTHER INFORMATION: Peptide

<400> SEQUENCE: 46

Leu Lys Lys Leu Leu Lys Lys Leu Leu Lys Lys Leu Leu Lys Lys Leu
1               5                   10                  15

Leu Lys Lys Leu
            20

```
<210> SEQ ID NO 47
<211> LENGTH: 18
<212> TYPE: PRT
<213> ORGANISM: Artificial Sequence
<220> FEATURE:
<223> OTHER INFORMATION: Peptide

<400> SEQUENCE: 47

Lys Leu Lys Leu Lys Leu Lys Leu Lys Leu Lys Leu Lys Leu Lys Leu
1               5                   10                  15

Lys Leu

<210> SEQ ID NO 48
<211> LENGTH: 18
<212> TYPE: PRT
<213> ORGANISM: Artificial Sequence
<220> FEATURE:
<223> OTHER INFORMATION: Peptide

<400> SEQUENCE: 48

Pro Ala Trp Arg Lys Ala Phe Arg Trp Ala Trp Arg Met Leu Lys Lys
1               5                   10                  15

Ala Ala

<210> SEQ ID NO 49
<211> LENGTH: 19
<212> TYPE: RNA
<213> ORGANISM: Artificial Sequence
<220> FEATURE:
<223> OTHER INFORMATION: siRNA

<400> SEQUENCE: 49
caagcaacga aguugucua                                               19

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
cgagcatgat gagacacctg                                              20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
ttgatggcac ataggctgag                                              20

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
cgagcatgat gagacacctg                                              20
```

```
<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
caggttccga ttgtccttgt                                                   20

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
tgccactcag aagactgtgg                                                   20

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
ttcagctctg ggatgacctt                                                   20

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
acgccaactg gttgaaattg                                                   20

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
cttgcaaaat cttccctcca                                                   20

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
gggtgtgaac cacgagaaat                                                   20

<210> SEQ ID NO 59
<211> LENGTH: 20
<212> TYPE: DNA
<213> ORGANISM: Artificial Sequence
<220> FEATURE:
<223> OTHER INFORMATION: Primer
```

<400> SEQUENCE: 59
ccttccacaa tgccaaagtt                                                  20

<210> SEQ ID NO 60
<211> LENGTH: 23
<212> TYPE: DNA
<213> ORGANISM: Artificial Sequence
<220> FEATURE:
<223> OTHER INFORMATION: Primer

<400> SEQUENCE: 60
ggacctattc agtggatggc ttg                                              23

<210> SEQ ID NO 61
<211> LENGTH: 26
<212> TYPE: DNA
<213> ORGANISM: Artificial Sequence
<220> FEATURE:
<223> OTHER INFORMATION: Primer

<400> SEQUENCE: 61
ccattggtct tcccagaaca tctaga                                           26

<210> SEQ ID NO 62
<211> LENGTH: 25
<212> TYPE: DNA
<213> ORGANISM: Artificial Sequence
<220> FEATURE:
<223> OTHER INFORMATION: Primer

<400> SEQUENCE: 62
cggctgctac aaaaggagac acact                                            25

<210> SEQ ID NO 63
<211> LENGTH: 23
<212> TYPE: DNA
<213> ORGANISM: Artificial Sequence
<220> FEATURE:
<223> OTHER INFORMATION: Primer

<400> SEQUENCE: 63
cggccacagt ctgaggtatc ttc                                              23

<210> SEQ ID NO 64
<211> LENGTH: 23
<212> TYPE: DNA
<213> ORGANISM: Artificial Sequence
<220> FEATURE:
<223> OTHER INFORMATION: Primer

<400> SEQUENCE: 64
ggctcagaag atcagacgac gtc                                              23

<210> SEQ ID NO 65
<211> LENGTH: 23
<212> TYPE: DNA
<213> ORGANISM: Artificial Sequence
<220> FEATURE:
<223> OTHER INFORMATION: Primer

<400> SEQUENCE: 65
ttgagaagag actcgaaacc agg                                              23

```
<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
gacatgccgc ctggagaaac                                               20

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
agcccaggat gccctttagt                                               20
```